US011046959B2

(12) United States Patent
Schiller et al.

(10) Patent No.: US 11,046,959 B2
(45) Date of Patent: Jun. 29, 2021

(54) COMPOSITIONS COMPRISING TALENS AND METHODS OF TREATING HIV

(71) Applicant: THE BOARD OF REGENTS OF THE NEVADA SYSTEM OF HIGHER EDUCATION ON BEHALF OF THE UNIVERSITY OF NEVADA, LA, Las Vegas, NV (US)

(72) Inventors: Martin R. Schiller, Henderson, NV (US); Christy L. Strong, Henderson, NV (US)

(73) Assignee: The Board Of Regents Of The Nevada System Of Higher Education On Behalf Of The University Of Nevada, Las Vegas, Las Vegas, NV (US)

( * ) Notice: Subject to any disclaimer, the term of this patent is extended or adjusted under 35 U.S.C. 154(b) by 325 days.

(21) Appl. No.: 15/562,962

(22) PCT Filed: Mar. 30, 2016

(86) PCT No.: PCT/US2016/025037
§ 371 (c)(1),
(2) Date: Sep. 29, 2017

(87) PCT Pub. No.: WO2016/161004
PCT Pub. Date: Oct. 6, 2016

(65) Prior Publication Data
US 2018/0112219 A1    Apr. 26, 2018

Related U.S. Application Data

(60) Provisional application No. 62/140,048, filed on Mar. 30, 2015, provisional application No. 62/265,232, filed on Dec. 9, 2015.

(51) Int. Cl.
| | | |
|---|---|---|
| *C12N 15/113* | (2010.01) | |
| *A61K 31/18* | (2006.01) | |
| *C12P 19/34* | (2006.01) | |
| *A61K 45/06* | (2006.01) | |
| *A61K 31/7105* | (2006.01) | |
| *C12N 9/22* | (2006.01) | |
| *A61K 31/7088* | (2006.01) | |
| *A61P 31/18* | (2006.01) | |
| *A61K 38/03* | (2006.01) | |
| *A61K 48/00* | (2006.01) | |

(52) U.S. Cl.
CPC ...... *C12N 15/1132* (2013.01); *A61K 31/7088* (2013.01); *A61K 31/7105* (2013.01); *A61K 38/03* (2013.01); *A61K 45/06* (2013.01); *A61K 48/0066* (2013.01); *A61K 48/0075* (2013.01); *A61P 31/18* (2018.01); *C12N 9/22* (2013.01); *C12P 19/34* (2013.01); *C12Y 301/21004* (2013.01); *C07K 2319/09* (2013.01); *C07K 2319/80* (2013.01)

(58) Field of Classification Search
None
See application file for complete search history.

(56) References Cited

U.S. PATENT DOCUMENTS

| | | |
|---|---|---|
| 4,703,004 A | 10/1987 | Hopp et al. |
| 4,851,341 A | 7/1989 | Hopp et al. |
| 5,587,455 A | 12/1996 | Berger et al. |
| 5,696,237 A | 12/1997 | FitzGerald et al. |
| 5,767,260 A | 6/1998 | Whitlow et al. |
| 5,856,456 A | 1/1999 | Whitlow et al. |
| 5,914,254 A | 6/1999 | Mascarenhas et al. |
| 5,981,177 A | 11/1999 | Demirjian et al. |
| 5,994,104 A | 11/1999 | Anderson et al. |
| 2011/0145940 A1* | 6/2011 | Voytas ............... C12N 9/22 800/13 |
| 2014/0072961 A1 | 3/2014 | Schiller et al. |
| 2015/0056237 A1 | 2/2015 | Pavlakis et al. |

FOREIGN PATENT DOCUMENTS

| | | |
|---|---|---|
| WO | WO-98/36087 A1 | 8/1998 |
| WO | WO-2016/161004 A1 | 10/2016 |

OTHER PUBLICATIONS

Aubert, M. et al., Successful Targeting and Disruption of an Integrated Reported Lentivirus using the Engineered Homing Endonuclease Y2 I-Anil. PloS One. 2011; 6(2):e16825 (12 pages).
Aza, A. et al., DNA Expansion Generated by Human Polμ on Iterative Sequences. Nucleic Acids Res. 2013; 41(1):253-63.
Bedell, V.M. et al., In Vivo Genome Editing Using a High-Efficiency TALEN System. Nature. 2012; 491(7422):114-8.
Berg, J. et al., HeLa-LAV, an Epithelial Cell Line Stably Infected with HIV-1. J Virol Methods. 1991; 34(2):173-80.
Beumer, K.J. et al., Comparing Zinc Finger Nucleases and Transcription Activator-Like Effector Nucleases for Gene Targeting in Drosophilia. G3 (Bethesda). 2013; 3(10):1717-25.
Bloom, K. et al., Inactivation of Hepatitis B Virus Replication in Cultured Cells and In Vivo with Engineered Transcription Activator-Like Effector Nucleases. Mol Ther. 2013; 21(10):1889-97.

(Continued)

*Primary Examiner* — Stacy B Chen
(74) *Attorney, Agent, or Firm* — Ballard Spahr LLP

(57) ABSTRACT

Disclosed herein, are compositions and methods for the treatment of human immunodeficiency virus infection. The compositions comprise engineered transcription activator like effector nucleases (TALENs) comprising a TALE DNA binding domain flanked by two spacer sequences, and a FokI nuclease catalytic domain. Also, described herein, are methods of using TALENs to cleave nucleic acids; and methods of administering the TALENs to subjects at risk for or having an HIV infection.

11 Claims, 57 Drawing Sheets
Specification includes a Sequence Listing.

(56) References Cited

OTHER PUBLICATIONS

Boch, J. et al., Breaking the Code of DNA Binding Specificity of TAL-type III Effectors. Science. 2009; 326(5959):1509-12.

Cade, L. et al., Highly Efficient Generation of Heritable Zebrafish Gene Mutations Using Homo- and Heterodimeric TALENs. Nucleic Acid Res. 2012; 40(16):8001-10.

Chen, S. et al., A Large-scale In vivo Analysis Reveals that TALENs are Significantly More Mutagenic Than ZFNs Generated Using Context-Dependent Assembly. Nucleic Acid Res. 2013; 41(4):2769-78.

Chun, T.W. et al., In vivo Fate of HIV-1-infected T Cells: Quantitative Analysis of the Transition to Stable Latency. Nat Med. 1995; 1(12):1284-90.

Chun, T.W. et al., Rebound of Plasma Viremia Following Cessation of Antiretroviral Therapy Despite Profoundly Low Levels of HIV Reservoir: Implications for Eradication. AIDS. 2010; 24(18): 2803-8.

Colin, L. and Van Lint, C., Molecular Control of HIV-1 Postintegration Latency: Implications for the Development of New Therapeutic Strategies. Retrovirology. 2009; 6:111 (29 pages).

Das, A.T. et al., The TAR Hairpin of Human Immunodeficiency Virus Type 1 Can Be Deleted When Not Required for Tat-Mediated Activation of Transcription. J Virol. 2007; 81(14):7742-8.

Dhamija et al., Epigenetic Regulation of HIV-1 Persistence and Evolving Strategies for Virus Eradication. Subcell Biochem. 2012; 61:479-505.

Dueva, R. and Iliakis, G., Alternative Pathways of Non-Homologous End Joining (NHEJ) in Genomic Instability and Cancer. Transl Cancer Res. 2013; 2:163-77.

Ebina, H. et al., Harnessing the CRISPR/Cas9 System to Disrupt Latent HIV-1 Provirus. Sci Rep. 2013; 3:2510 (7 pages).

Ebina, H. et al., A High Excision Potential of TALENs for Integrated DNA of HIV-based Lentiviral Vector. PLoS One. 2015; 10(3):e0120047 (15 pages).

Frank, S. et al., A Modified TALEN-based System for Robust Generation of Knock-out Human Pluripotent Stem Cell Lines and Disease Models. BMC Genomics. 2013; 14:773 (9 pages).

Fu, Y. et al., High Frequency Off-Target Mutagenesis Induced by CRISPR-Cas Nucleases in Human Cells. Nat Biotechnol. 2013; 31(9):822-26.

Gaj, T. et al., Targeted Gene Knockout by Direct Delivery of ZFN Proteins. Nat Methods. 2012; 9(8):805-7.

Grabarz, A. et al., Initiation of DNA Double Strand Break Repaid: Signaling and Single-Stranded Resection Dictate the Choice Between Homologous Recombination, Non-Homologous End-Joining and Alternative End-Joining. Am J Cancer Res. 2012; 2(3):249-68.

Guilinger, J.P. et al., Broad Specificity Profiling of TALENs Results in Engineered Nucleases with Improved DNA-cleavage Specificity. Nature Methods. 2014; 11(4):429-35.

Guirouilh-Barbat, J. et al., Defects in XRCC4 and KU80 Differentially Affect the Joining of Distal Nonhomologous Ends. Proc Natl Acad Sci U.S.A. 2007; 104(52):20902-7.

Hauber, I. et al., Highly Significant Antiviral Activity of HIV-1 LTR-Specific Tre-Recombinase in Humanized Mice. PLoS Pathog. 2013; 9(9):e1003587 (20 pages).

Hu, W. et al., RNA-directed Gene Editing Specifically Eradicates latent and Prevents New HIV-1 Infection. Proc Natl Acad Sci U.S.A. 2014; 111(31):11461-6.

Kauder, S.E. et al., Epigenetic Regulation of HIV-I Latency by Cytosine Methylation. PLoS Pathog. 2009; 5(6):e1000495 (15 pages).

Leitner, T. et al., HIV Sequence Compendium. 2005 Los Alamos, NM: Theoretical Biology and Biophysics Group, Los Alamos National Laboratory (2005).

Liu, J. et al., Efficient and Specific Modifications of the *Drosophila* Genome by Means of an Easy TALEN Strategy. J Genet Genomics. 2012; 39(5):209-15.

Ma, K. et al., Efficient Targeting of FATS at a Common Fragile Site in Mice Through TALEN-Mediated Double-Hit Genome Modification. Biotechnol Lett. 2014; 36(3):471-9.

Ma, A.C. et al., High Efficiency In Vivo Genome Engineering with a Simplified 15-RVD GoldyTALEN Design. PLoS One. 2013; 8(5):e65259.

Mahfouz, M.M. et al., De Novo-engineered Transcription Activator-Like Effector (TALE) Hybrid Nuclease with Novel DNA Binding Specificity Created Double-Strand Breaks. Proc Natl Acad Sci U.S.A. 2011; 108(6):2623-8.

Mariyanna, L. et al., Excision of HIV-1 Proviral DNA by Recombinant Cell Permeable Tre-Recombinase. PLoS One. 2012; 7(2):e31576 (10 pages).

Martin, M.J. et al., A Specific N-Terminal Extension of the 8 kDa Domain is Required for DNA End-Bridging by Human Polµ and Polλ. Nucleic Acids Res. 2013; 41(19):9105-16.

Matreyek, K.A. et al., Viral Latency and Potential Eradication of HIV-1. Expert Rev Anti Infect Ther. 2012; 10(8):855-7.

Miller, J.C. et al., A TALE Nuclease Architecture for Efficient Genome Editing. Nat Biotechnol. 2011; 29(2):143-8.

Mukherjee, S. and Thrasher, A.J., Gene Therapy for PIDs: Progress, Pitfalls and Prospects. Gene. 2013. 525(2):174-81.

Ousterout, D.G. et al., Reading Frame Correction by Targeted Genome Editing Restores Dystrophin Expression in Cells from Duchenne Muscular Dystrophy Patients. Mol Ther. 2013; 21(9):1718-26.

Parent, M. et al., Poly(ADP-ribose) Polymerase-1 Is a Negative Regulator of HIV-1 Transcription through Competitive Binding to TAR RNA with Tat-Positive Transcription Elongation Factor b (p-TEFb) Complex. J Biol Chem. 2005; 280(1):448-57.

Pennisi, E., The CRISPR Craze. Science. 2013; 341(6148): 833-6.

Peterson, C.W. et al., Combinatorial Anti-HIV Gene Therapy: Using a Multi-Pronged Approach to Reach Beyond HAART. Gene Ther. 2013; 20(7):695-02.

Qiu, Z. et al., High-Efficiency and Heritable Gene Targeting in Mouse by Transcription Activator-Like Effector Nucleases. Nucleic Acid Res. 2013; 41(11):e120.

Qu, X. et al., Zinc-Finger-Nucleases Mediate Specific and Efficient Excision of HIV-1 Proviral DNA from Infected and Latently Infected Human T Cells. Nucleic Acid Res. 2013; 41(16):7771-82.

Reyon, D. et al., Engineering Designer Transcription Activator-Like Effector Nucleases (TALENs) by Real or Real-Fast Assembly. Curr Protoc Mol Biol. 2012; Chapter 12: Unit 12.15.

Sambrook et al., Molecular Cloning: A Laboratory Manual Second Edition Cold Spring Harbor Laboratory Press, Cold Spring Harbor, NY (1989).

Schiffer, J.T. et al., Targeted DNA Mutagenesis for the Cure of Chronic Viral Infections. J Virol. 2012; 86(17):8920-36.

Schneider, C.A. et al., NIH Image to ImageJ: 25 Years of Image Analysis. Nat Methods. 2012; 9(7):671-5.

Scholze, H. and Boch, J., TAL Effector-DNA Specificity. Virulence. 2010; 1(5):428-32.

Sgarbanti, M. and Battistini, A., Therapeutics for HIV-1 Reactivation from Latency. Curr Opin Virol. 2013; 3(4):394-401.

Shan, L. and Siliciano, R.F., From Reactivation of Latent HIV-1 to Elimination of the Latent Reservoir: the Presence of Multiple Barriers to Viral Eradication. BioEssays. 2013; 35(6):544-52.

Shen, L. et al., Dose-response Curve Slope Sets Class-Specific Limits on Inhibitory Potential of Anti-HIV Drugs. Nat Med. 2008; 14(7): 762-6.

Sievers, F. et al., Fast, Scalable Generation of High-Quality Protein Multiple Sequence Alignments Using Clustal Omega. Mol Syst Biol. 2011; 7:539.

Sigal, A. and Baltimore, D., As Good As It Gets? The Problem of HIV Persistence Despite Antiretroviral Drugs. Cell Host Microbe. 2012; 12(2):132-8.

Stone, D. et al., Targeted Gene Disruption to Cure HIV. Curr Opin HIV AIDS. 2013; 8(3):217-23.

Strong, C.L. et al., Damaging the Integrated HIV Proviral DNA with TALENs. PLoS One. 2015; 10(5):e0125652 (20 pages).

Valton, J. et al., Overcoming Transcription Activator-Like Effector (TALE) DNA Binding Domain Sensitivity to Cytosine Methylation. J Biol Chem. 2012; 287(46):38427-32.

Weber, N.D. et al., TALENs Targeting HBV: Designer Endonuclease Therapies for Viral Infections. Mol Ther. 2013; 21(10):1819-20.

(56) References Cited

OTHER PUBLICATIONS

Wei, C. et al., Talen or Cas9—Rapid, Efficient and Specific Choices for Genome Modifications. J Genet Genomics. 2013; 40(6):281-9.
Zhou, Y. et al., Kinetics of Human Immunodeficiency Virus Type 1 Decay Following Entry into Resting CD4+ T Cells. J Virol. 2005; 79(4):2199-210.
International Search Report and Written Opinion dated on Sep. 8, 2016 by the International Searching Authority for Patent Application No. PCT/US2016/025037, which was filed on Mar. 30, 2016 and published as WO 2016/161004 on Oct. 6, 2016 (Inventor—Schiller et al.; Applicant—Board of Regents of the Nevada System of Higher Education on Behalf of the University of Nevada, LA; (15 pages).
International Preliminary Report on Patentability dated Oct. 3, 2017 by the International Searching Authority for Patent Application No. PCT/US2016/025037, which was filed on Mar. 30, 2016 and published as WO 2016/161004 on Oct. 6, 2016 (Inventor—Schiller et al.; Applicant—Board of Regents of the Nevada System of Higher Education on Behalf of the University of Nevada, LA; (11 pages).

\* cited by examiner

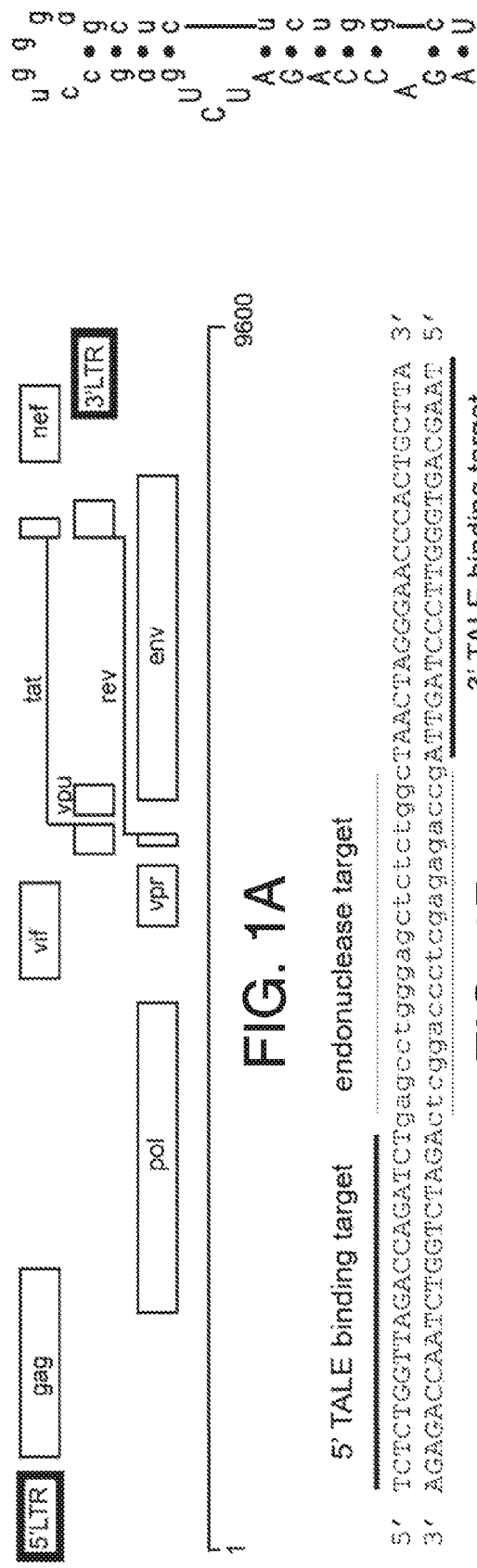

```
                     5' TALEN binding site                                                    3' TALEN binding site
WT:   CTTTTTGCCTGTACTGGTCTCTCTCTGGTTAGACCAGATTTGAGCCTGGGAGCTCTCTGCCTAACTAGGGAACCCACT
1-6:  CTTTTTatatgcagcatct----------------------------------------------------------
1-23: CTTTTTGCCTGTACTGGTCTCTCTCTGGTTAGACCAGATTT--------GAGCTCTGGCTAACTAGGGAACCCACT         -22/+13
A-06: CTTTTTGCCTGTACTGGTCTCTCTCTGGTTAGAC-AGATC-cAGCCcGGGAGCTCTGGCTAACTAGGGAACCCACT         -8
B-02: CTTTTTGCCTGTACTGGTCTCTCTCTGGTCTGG-------------------------CTAgCTAGGGAACCCACT         -6/+3
C-11: CTTTTTGCCTGTACTGGTCTCTCTCTGGTTAGACCAGATTTGAGCCTGGGAGCgctc--TggCTAGGGAACCCACT         -33/+1
D-01: CTTTTTGCCTGTACTGGTCTCTCTCTGGTTAGACCAGATTTGAGCCTGGGAGCTCTC--TggCTAGGGAACCCACT         -10/+6
D-08: CTTTTTGCCTGTACTGGTCTCTCTCTGGTTAGACCAGATTTGAGCCTGGgatctctc--GGGAACCCACT               -6/+2
G-08: CTTTTTGCCTGTACTGGTCTCTCTCTGGTTAGACCAGATTTGAGCCTGGG---------CTAgCTAGGGAACCCACT        -18/+7
D-09: CTTTTTGCCTGTACTGGTCTCTCTCTGGTTAGACCAGATTTGAGCCTGGG---------CTAACTAGGGAACCCACT        -11/+1
G-11: CTTTTTGCCTGTACTGGTCTCTCTCTGGTTAGACCAGATTTGAGCCTGGG---------CTAACTAGGGAACCCACT        -11
```

FIG. 3D

Table 1. Sequences.

| SEQ ID NO: | Sequence | Name |
|---|---|---|
| 1 | tctctggttagaccagatct | HIV-1 HXB2 accession number K03455; nucleotide positions 459-478; (5' TALE binding target, Fig. 1B) |
| 2 | taactagggaacccact | HIV HXB2 accession number K03455; nucleotide positions 499-515 (3' TALE binding target) |
| 3 | taagcactgggttccctagtta | 3' TALE binding target |
| 4 | TCTCTAGTCAGACCAGATCA | 5'TALE binding mutant 1 |
| 5 | TCTCTAGTCAGACCAGATCC | 5'TALE binding mutant 2 |
| 6 | TCTCTTGTCAGACCAGATCA | 5'TALE binding mutant 3 |
| 7 | TCTCTTGTCAGACCAGATCC | 5'TALE binding mutant 4 |
| 8 | PKKKRKV | NLS |
| 9 | gagcctgggagctctctggc | Spacer sequence, Fig. 1B |
| 10 | ctcggaccctcgagagaccg | Spacer sequence, Fig. 1B |
| 11 | GTCGCGGGATCCCAACTAGTCAAAAGTGAACTGGAGGAGAAGAAATCTGAACTTCGTCATAAATTGAAATATGTGCCTCATGAATATATTGAATTAATTGAAATTGCCAGAAATCCCACTCAGGATAGAATTCTTGAAATGAAGGTAATGGAATTTTTTATGAAAGTTTATGGATATAGAGGTCAGCATTTGGGTGGATCAAGGAAACCGGACGGAGCAATTTATACTGTCGGATCTCCTATTGATTACGGTGTGATCGTGGATACTAAAGCTTATAGCGGAGGTTATAATCTGCCAATTGGCCAAGCAGATGAAATGCAGCGATATGTCGAAGAAATCAAACACGAGCACAAACATCTGAACCCTAATGAATGGTGGAAAGTCTATCCATCTTCTGTAACGGAATTTAAGTTTTTATTTGTGAGTGGTCACTTTAAAGGAAACTACAAAGCTCAGCTTACACGATTAAATCATATCACTAATTGTAATGGAGCTGTTCTTAGTGTAGAAGAGCTTTTAATTGGTGGAGAAATGATTAAAGCCGGCACATTAACCTTAGAGGAAGTCAGACGGAAATTTAATAACGGCGAGATAAACTTTTAAGGGCCCTTCGAAGGTAAGCCTATCCCTAACCCTCTCCTCGGTCTCGATTCTACGCGTACCGGTCATCAT | T256/T258 5'TALEN FokI Gblock ELD.Sharkey |
| 12 | GTCGCGGGATCCCAACTAGTCAAAAGTGAACTGGAGGAGAAGAAATCTGAACTTCGTC | T278 3'TALEN FokI Gblock (672bps) |

FIG. 15

| | | |
|---|---|---|
| | *ATAAATTGAAATATGTGCCTCATGAATATA*<br>*TTGAATTAATTGAAATTGCCAGAAAT*CCCA<br>*CTCAGGATAGAATTCTTGAAATGAAGGTAA*<br>*TGGAATTTTTTATGAAAGTTTATGGATATA*<br>*GAGGT*GAG*CATTTGGGTGGATCAAGGAAA*<br>*CCGGACGGAGCAATTTATACTGTCGGATCT*<br>*CCTATTGATTACGGTGTGATCGTGGATACT*<br>*AAAGCTTATAGCGGAGGTTATAATCTGCCA*<br>*ATTGGCCAAGCAGATGAAATGCAACGATA*<br>*TGTC*AAG*GAAAATCAAACACGAAACAAAC*<br>*ATATCAACCCTAATGAATGGTGGAAAGTCT*<br>*ATCCATCTTCTGTAACGGAATTTAAGTTTT*<br>*TATTTGTGAGTGGTCACTTTAAAGGAAACT*<br>*ACAAAGCTCAGCTTACACGATTAAAT*CGA<br>AG*ACTAATTGTAATGGAGCTGTTCTTAGTG*<br>*TAGAAGAGCTTTTAATTGGTGGAGAAATGA*<br>*TTAAAGCCGGCACATTAACCTTAGAGGAA*<br>*GTCAGACGGAAATTTAATAACGGCGAGAT*<br>*AAACTTTTAA*GGGCCCTTCGAAGGTAAGC<br>CTATCCCTAACCCTCTCCTCGGTCTCGATT<br>CTACGCGTACCGGTCATCAT | KKR.Sharkey |
| 13 | VAGSQLVKSELEEKKSELRHKL<br>KYVPHEYIELIEIARNPTQDRIL<br>E Met KV Met EEE Met KVYGYRGEH<br>LGGSRKPDGAIYTVGSPIDYGVI<br>VDTKAYSGGYNLPIGQADE Met E<br>RYVEENQTRDKHLNPNEWWKV<br>YPSSVTEFKFLFVSGHFKGNYK<br>AQLTRLNHITNCNGAVLSVEEL<br>LIGGE Met IKAGTLTLEEVRRKF<br>NNGEINF Stop GPFEGKPIPNPLL<br>GLDSTRTGHH | T256/T258 5' TALEN FokI<br>ELD Sharkey Amino Acid<br>Sequence; shaded portion<br>refers to the protein coding<br>region open reading frame |
| 14 | VAGSQLVKSELEEKKSELRHKL<br>KYVPHEYIELIEIARNPTQDRIL<br>E Met KV Met EEE Met KVYGYRGEH<br>LGGSRKPDGAIYTVGSPIDYGVI<br>VDTKAYSGGYNLPIGQADE Met E<br>QRYVKENQTRNKHINPNEWWK<br>VYPSSVTEFKFLFVSGHFKGNY<br>KAQLTRLNRKTNCNGAVLSVEE<br>LLIGGE Met IKAGTLTLEEVRRK<br>FNNGEINF Stop GPFEGKPIPNPLL<br>GLDSTRTGHH | T278 3' TALEN FokI KKR<br>Sharkey Amino Acid<br>Sequence; shaded portion<br>refers to the protein coding<br>region open reading frame |
| 15 | CAGCTGGATCCTGATTGGCAG | forward primer<br>U3BamHI75F |
| 16 | GGGTGCGAGAGCGTCGACGACGG | reverse primer<br>GagSalI804Rev |
| 17 | CAGGCTCNNATCTGGTCNNNCNA | randomized reverse primer;<br>Random5'siteRev |
| 18 | CTCTNGNNNGACCAGATNNGAGC | randomized forward primer; |

FIG. 15 CONT.

| | | |
|---|---|---|
| 19 | GGCATGCTCGAGCTCAGATGCTGCATAT | Random5'siteFor forward primer pBSNY5For |
| 20 | CATGCCTCTAGAAGTGGGTTCCCTAGC | 21 |
| 21 | ATGGACTACAAAGACCATGACGGTGAT TATAAAGATCATGACATCGATTACAAG GATGACGATGACAAGATGGCCCCaagaa gaagaggaaggtgggcattcaccgcggggtacctatggtggacttg aggacactcggttattcgcaacagcaacaggagaaaatcaagccta aggtcaggagcaccgtcgcgcaacaccacgaggcgctgtgggg catggcttcactcatgcgcatattgtcgcgcttcacagcaccctgcg gcgcttgggacggtggctgtcaaataccaagatatgattgcggccct gcccgaagccacgcacgaggcaattgtaggggtcggtaaacagtg gtcgggagcgcgagcacttgaggcgctgctgactgtggcgggtga gcttaggggcctccgctccagctcgacaccgggcagctgctgaa gatcgcgaagagaggggagtaacagcggtagaggcagtgcacg cctggcgcaatgcgctcaccggggccccctt*GAACCTGAC CCCAGACCAGGTAGTCGCAATCGCGTCAC ATGACGGGGGAAAGCAAGCCCTGGAAAC CGTGCAAAGGTTGTTGCCGGTCCTTTGTC AAGACCACGGCCTTACACCGGAGCAAGTC GTGGCCATTGCAAGCAATGGGGGTGGCAAA CAGGCTCTTGAGACGGTTCAGAGACTTCTCC CAGTTCTCTGTCAAGCCCACGGGCTGACTC CCGATCAAGTTGTAGCGATTGCGTCGCAT GACGGAGGGAAACAAGCATTGGAGACTG TCCAACGGCTCCTTCCCGTGTTGTGTCAA GCCCACGGTTTGACGCCTGCACAAGTGGTC GCCATCGCCTCGAATGGCGGCGGTAAGCAG GCGCTGGAAACAGTACAGCGCCTGCTGCCT GTACTGTGCCAGGATCATGGA*ctgacccagacca ggtagtcgcaatcgcgaacaataatggggaaagcaagccctg gaaaccgtgcaaaggttgttgccggtcctttgtcaagaccacgg ccttacaccggagcaagtcgtggccattgcaaataataacggtg gcaaacaggctcttgagacggttcagagacttctcccagttctct gtcaagcccacggg*CTGACTCCCGATCAAGTTGTA GCGATTGCGTCCAACGGTGGAGGGAAACAA GCATTGGAGACTGTCCAACGGCTCCTTCCC GTGTTGTGTCAAGCCCACGGTTTGACGCCTG CACAAGTGGTCGCCATCGCCTCGAATGGCG GCGGTAAGCAGGCGCTGGAAACAGTACAGC GCCTGCTGCCTGTACTGTGCCAGGATCATG GA*ctgactcccgatcaagttgtagcgattgcgtcgaacattggagg gaaacagcattggagactgtccaacggctccttcccgtgttgtgtca agcccacggtcttacaccggagcaagtcgtggccattgcaaata ataacggtggcaaacaggctcttgagacggttcagagacttctc ccagttctctgtcaagcccacgggctgactcccgatcaagttgtag cgattgcgtcgaacattggaggaaacagcattggagactgtcca acggctccttcccgtgttgtgtcaagcccacggt*TTGACGCC** | 5'TALEN.ELD.Sharkey DNA sequence (From start codon to stop codon) |

FIG. 15 CONT.

| | | |
|---|---|---|
| | TGCACAAGTGGTCGCCATCGCCAGCCATG<br>ATGGCGGTAAGCAGGCGCTGGAAACAGT<br>ACAGCGCCTGCTGCCTGTACTGTGCCAGG<br>ATCATGGACTGACCCCAGACCAGGTAGTC<br>GCAATCGCGTCACATGACGGGGGAAAGC<br>AAGCCCTGGAAACCGTGCAAAGGTTGTTG<br>CCGGTCCTTTGTCAAGACCACGGCcttacaccgg<br>agcaagtcgtggccattgcaagcaacatcggtcgcaaacaggctc<br>ttgagacggttcagagacttctcccagttctctgtcaagcccacgggc<br>tgactcccgatcaagtgtagcgattgcgaataacaatggaggg<br>aaacaagcattggagactgtccaacggctccttcccgtgttgtgt<br>caagcccacggtTTGACGCCTGCACAAGTGGTC<br>GCCATCGCCTCCAATATTGGCGGTAAGCA<br>GGCGCTGGAAACAGTACAGCGCCTGCTGC<br>CTGTACTGTGCCAGGATCATGGACTGACC<br>CCAGACCAGGTAGTCGCAATCGCGTCAAAC<br>GGAGGGGGAAAGCAAGCCCTGGAAACCGTG<br>CAAAGGTTGTTGCCGGTCCTTTGTCAAGACC<br>ACGGCCTTACACCGGAGCAAGTCGTGGCC<br>ATTGCATCCCACGACGGTGGCAAACAGGC<br>TCTTGAGACGGTTCAGAGACTTCTCCCAG<br>TTCTCTGTCAAGCCCACGGGctgacaccgaaca<br>ggtggtcgccattgcttctaatgggggaggacggccagccttggag<br>tccatcgtagcccaattgtccaggcccgatcccgcgttggctgcgtta<br>acgaatgaccatctggtggcgttggcatgtcttggtggacgacccgc<br>gctcgatgcagtcaaaaggggtctgcctcatgctcccgcattgatca<br>aaagaaccaaccggcggattcccgagagaacttcccatcgagtcgc<br>gGGATCCCAACTAGTCAAAAGTGAACTGG<br>AGGAGAAGAAATCTGAACTTCGTCATAAAT<br>TGAAATATGTGCCTCATGAATATATTGAAT<br>TAATTGAAATTGCCAGAAATCCCACTCAGG<br>ATAGAATTCTTGAAATGAAGGTAATGGAAT<br>TTTTTATGAAAGTTTATGGATATAGAGGTC<br>AGCATTTGGGTGGATCAAGGAAACCGGAC<br>GGAGCAATTTATACTGTCGGATCTCCTATT<br>GATTACGGTGTGATCGTGGATACTAAAGCT<br>TATAGCGGAGGTTATAATCTGCCAATTGGC<br>CAAGCAGATGAAATGCAGCGATATGTCGA<br>AGAAAATCAAACACGACACAAACATCTGA<br>ACCCTAATGAATGGTGGAAAGTCTATCCAT<br>CTTCTGTAACGGAATTTAAGTTTTTATTTG<br>TGAGTGGTCACTTTAAAGGAAACTACAAAG<br>CTCAGCTTACACGATTAAATCATATCACTA<br>ATTGTAATGGAGCTGTTCTTAGTGTAGAAG<br>AGCTTTTAATTGGTGGAGAAATGATTAAAG<br>CCGGCACATTAACCTTAGAGGAAGTCAGA<br>CGGAAATTTAATAACGGCGAGATAAACTTT<br>TAA | |
| 22 | ATGGACTACAAAGACCATGACGGTGAT<br>TATAAAGATCATGACATCGATTACAAG | JDS78 (with<br>5'TALEN.ELD.Sharkey) |

FIG. 15 CONT.

GATGACGATGACAAGATGGCCCCaagaa
gaagaggaaggtgggcattcaccgcgggtacctatggtggacttg
aggacactcggttattcgcaacagcaacaggagaaaatcaagccta
aggtcaggagcaccgtcgcgcaacaccacgaggcgcttgtgggg
catggcttcactcatgcgcatattgtcgcgctttcacagcacctgcg
gcgcttgggacggtggctgtcaaataccaagatatgattgcggcct
gcccgaagccacgcacgaggcaattgtaggggtcggtaaacagtg
gtcgggagcgcgagcacttgaggcgctgctgactgtggcgggtga
gcttaggggcctccgctccagctcgacaccgggcagctgctgaa
gatcgcgaagagaggggagtaacagcggtagaggcagtgcacg
cctggcgcaatgcgctcaccggggcccccttGAACCTGAC
CCCAGACCAGGTAGTCGCAATCGCGTCAC
ATGACGGGGAAAGCAAGCCCTGGAAAC
CGTGCAAAGGTTGTTGCCGGTCCTTTGTC
AAGACCACGGCCTTACACCGGAGCAAGTC
GTGGCCATTGCAAGCAATGGGGGTGGCAAA
CAGGCTCTTGAGACGGTTCAGAGACTTCTCC
CAGTTCTCTGTCAAGCCCACGGGCTGACTC
CCGATCAAGTTGTAGCGATTGCGTCGCAT
GACGGAGGGAAACAAGCATTGGAGACTG
TCCAACGGCTCCTTCCCGTGTTGTGTCAA
GCCCACGGTTTGACGCCTGCACAAGTGGTC
GCCATCGCCTCGAATGGCGGCGGTAAGCAG
GCGCTGGAAACAGTACAGCGCCTGCTGCCT
GTACTGTGCCAGGATCATGGActgacccagacca
ggtagtcgcaatcgcgaacaataatgggggaaagcaagccctg
gaaaccgtgcaaaggttgttgccggtcctttgtcaagaccacgg
ccttacaccggagcaagtcgtggccattgcaaataataacggtg
gcaaacaggctcttgagacggttcagagacttctcccagttctct
gtcaagcccacgggCTGACTCCCGATCAAGTTGTA
GCGATTGCGTCCAACGGTGGAGGGAAACAA
GCATTGGAGACTGTCCAACGGCTCCTTCCC
GTGTTGTGTCAAGCCCACGGTTTGACGCCTG
CACAAGTGGTCGCCATCGCCTCGAATGGCG
GCGGTAAGCAGGCGCTGGAAACAGTACAGC
GCCTGCTGCCTGTACTGTGCCAGGATCATG
GActgactcccgatcaagttgtagcgattgcgtcgaacattggag
gaaacaagcattggagactgtccaacggctccttcccgtgttgtgtca
agcccacggtcttacaccggagcaagtcgtggccattgcaaata
ataacggtggcaaacaggctcttgagacggttcagagacttctc
ccagttctctgtcaagcccacgggctgactcccgatcaagttgtag
cgattgcgtcgaacattggagggaaacaagcattggagactgtca
acggctccttcccgtgttgtcaagcccacggTTGACGCC
TGCACAAGTGGTCGCCATCGCCAGCCATG
ATGGCGGTAAGCAGGCGCTGGAAACAGT
ACAGCGCCTGCTGCCTGTACTGTGCCAGG
ATCATGGACTGACCCCAGACCAGGTAGTC
GCAATCGCGTCACATGACGGGGAAAGC
AAGCCCTGGAAACCGTGCAAAGGTTGTTG
CCGGTCCTTTGTCAAGACCACGGCcttacacgg

FIG. 15 CONT.

gagcaagtcgtggccattgcaagcaacatcggtggcaaacaggctc
ttgagacggttcagagacttctcccagtctctgtcaagcccacgggc
tgactcccgatcaagttgtagcgattgcgaataacaatggaggg
aaacaagcattggagactgtccaacggctccttcccgtgttgtgt
caagcccacggtTTGACGCCTGCACAAGTGGTC
GCCATCGCCTCCAATATTGGCGGTAAGCA
GGCGCTGGAAACAGTACAGCGCCTGCTGC
CTGTACTGTGCCAGGATCATGGACTGACC
CCAGACCAGGTAGTCGCAATCGCGTCAAAC
GGAGGGGGAAAGCAAGCCCTGGAAACCGTG
CAAAGGTTGTTGCCGGTCCTTTGTCAAGACC
ACGGCCTTACACCGGAGCAAGTCGTGGCC
ATTGCATCCCACGACGGTGGCAAACAGGC
TCTTGAGACGGTTCAGAGACTTCTCCCAG
TTCTCTGTCAAGCCCACGGGctgacaccgaaca
ggtggtcgccattgcttctaatgggggaggacggccagccttggag
tccatcgtagcccaattgtccaggcccgatcccgcgttggctgcgtta
acgaatgaccatctggtggcgttggcatgtcttggtggacgacccgc
gctcgatgcagtcaaaaagggtctgcctcatgctcccgcattgatca
aaagaaccaaccggcggattcccgagagaacttcccatcgagtcgc
gGGATCCCAACTAGTCAAAAGTGAACTGG
AGGAGAAGAAATCTGAACTTCGTCATAAAT
TGAAATATGTGCCTCATGAATATATTGAAT
TAATTGAAATTGCCAGAAATCCACTCAGG
ATAGAATTCTTGAAATGAAGGTAATGGAAT
TTTTTATGAAAGTTTATGGATATAGAGGTC
AGCATTTGGGTGGATCAAGGAAACCGGAC
GGAGCAATTTATACTGTCGGATCTCCTATT
GATTACGGTGTGATCGTGGATACTAAAGCT
TATAGCGGAGGTTATAATCTGCCAATTGGC
CAAGCAGATGAAATGCAGCGATATGTCGA
AGAAAATCAAACACGAGACAAACATCTGA
ACCCTAATGAATGGTGGAAAGTCTATCCAT
CTTCTGTAACGGAATTTAAGTTTTTATTTG
TGAGTGGTCACTTTAAAGGAAACTACAAAG
CTCAGCTTACACGATTAAATCATATCACTA
ATTGTAATGGAGCTGTTCTTAGTGTAGAAG
AGCTTTTAATTGGTGGAGAAATGATTAAAG
CCGGCACATTAACCTTAGAGGAAGTCAGA
CGGAAATTTAATAACGGCGAGATAAACTTT
TAA
GGGCCCTTCGAAGGTAAGCCTATCCCT
AACCCTCTCCTCGGTCTCGATTCTACGC
GTACCGGTCATCATCACCATCACCATT
GAGTTTAAACCCGCTGATCAGCCTCGA
CTGTGCCTTCTAGTTGCCAGCCATCTGT
TGTTTGCCCCTCCCCGTGCCTTCCTTG
ACCCTGGAAGGTGCCACTCCCACTGTC
CTTTCCTAATAAAATGAGGAAATTGCAT
CGCATTGTCTGAGTAGGTGTCATTCTAT

FIG. 15 CONT.

```
TCTGGGGGGTGGGGTGGGGCAGGACA
GCAAGGGGGAGGATTGGGAAGACAATA
GCAGGCATGCTGGGGATGCGGTGGGCT
CTATGGCTTCTGAGGCGGAAAGAACCA
GCTGGGGCTCTAGGGGGTATCCCCACG
CGCCCTGTAGCGGCGCATTAAGCGCGG
CGGGTGTGGTGGTTACGCGCAGCGTGA
CCGCTACACTTGCCAGCGCCTAGCGC
CCGCTCCTTTCGCTTTCTTCCCTTCCTT
TCTCGCCACGTTCGCCGGCTTTCCCCG
TCAAGCTCTAAATCGGGGCATCCCTTT
AGGGTTCCGATTTAGTGCTTTACGGCA
CCTCGACCCCAAAAAACTTGATTAGGG
TGATGGTTCACGTAGTGGGCCATCGCC
CTGATAGACGGTTTTTCGCCCTTTGAC
GTTGGAGTCCACGTTCTTTAATAGTGG
ACTCTTGTTCCAAACTGGAACAACACTC
AACCCTATCTCGGTCTATTCTTTTGATT
TATAAGGGATTTTGGGGATTTCGGCCT
ATTGGTTAAAAAATGAGCTGATTTAACA
AAAATTTAACGCGAATTAATTCTGTGGA
ATGTGTGTCAGTTAGGGTGTGGAAAGT
CCCCAGGCTCCCCAGGCAGGCAGAAGT
ATGCAAAGCATGCATCTCAATTAGTCA
GCAACCAGGTGTGGAAAGTCCCCAGGC
TCCCCAGCAGGCAGAAGTATGCAAAGC
ATGCATCTCAATTAGTCAGCAACCATA
GTCCCGCCCCTAACTCCGCCCATCCCG
CCCCTAACTCCGCCCAGTTCCGCCCAT
TCTCCGCCCCATGGCTGACTAATTTTTT
TTATTTATGCAGAGGCCGAGGCCGCCT
CTGCCTCTGAGCTATTCCAGAAGTAGT
GAGGAGGCTTTTTTGGAGGCCTAGGCT
TTTGCAAAAAGCTCCCGGGAGCTTGTA
TATCCATTTTCGGATCTGATCAGCACGT
GTTGACAATTAATCATCGGCATAGTATA
TCGGCATAGTATAATACGACAAGGTGA
GGAACTAAACCATGGCCAAGCCTTTGT
CTCAAGAAGAATCCACCCTCATTGAAA
GAGCAACGGCTACAATCAACAGCATCC
CCATCTCTGAAGACTACAGCGTCGCCA
GCGCAGCTCTCTCTAGCGACGGCCGCA
TCTTCACTGGTGTCAATGTATATCATTT
TACTGGGGGACCTTGTGCAGAACTCGT
GGTGCTGGGCACTGCTGCTGCTGCGGC
AGCTGGCAACCTGACTTGTATCGTCGC
GATCGGAAATGAGAACAGGGGCATCTT
GAGCCCCTGCGGACGGTGTCGACAGGT
GCTTCTCGATCTGCATCCTGGGATCAA
AGCGATAGTGAAGGACAGTGATGGACA
```

FIG. 15 CONT.

```
GCCGACGGCAGTTGGGATTCGTGAATT
GCTGCCCTCTGGTTATGTGTGGGAGGG
CTAAGCACTTCGTGGCCGAGGAGCAGG
ACTGACACGTGCTACGAGATTTCGATT
CCACCGCCGCCTTCTATGAAAGGTTGG
GCTTCGGAATCGTTTTCCGGGACGCCG
GCTGGATGATCCTCCAGCGCGGGGATC
TCATGCTGGAGTTCTTCGCCCACCCCA
ACTTGTTTATTGCAGCTTATAATGGTTA
CAAATAAAGCAATAGCATCACAAATTTC
ACAAATAAAGCATTTTTTTCACTGCATT
CTAGTTGTGGTTTGTCCAAACTCATCAA
TGTATCTTATCATGTCTGTATACCGTCG
ACCTCTAGCTAGAGCTTGGCGTAATCA
TGGTCATAGCTGTTTCCTGTGTGAAATT
GTTATCCGCTCACAATTCCACACAACAT
ACGAGCCGGAAGCATAAAGTGTAAAGC
CTGGGGTGCCTAATGAGTGAGCTAACT
CACATTAATTGCGTTGCGCTCACTGCC
CGCTTTCCAGTCGGGAAACCTGTCGTG
CCAGCTGCATTAATGAATCGGCCAACG
CGCGGGGAGAGGCGGTTTGCGTATTGG
GCGCTCTTCCGCTTCCTCGCTCACTGA
CTCGCTGCGCTCGGTCGTTCGGCTGCG
GCGAGCGGTATCAGCTCACTCAAAGGC
GGTAATACGGTTATCCACAGAATCAGG
GGATAACGCAGGAAAGAACATGTGAGC
AAAAGGCCAGCAAAAGGCCAGGAACCG
TAAAAGGCCGCGTTGCTGGCGTTTTT
CCATAGGCTCCGCCCCCCTGACGAGCA
TCACAAAAATCGACGCTCAAGTCAGAG
GTGGCGAAACCCGACAGGACTATAAAG
ATACCAGGCGTTTCCCCCTGGAAGCTC
CCTCGTGCGCTCTCCTGTTCCGACCCT
GCCGCTTACCGGATACCTGTCCGCCTT
TCTCCCTTCGGGAAGCGTGGCGCTTTC
TCAATGCTCACGCTGTAGGTATCTCAG
TTCGGTGTAGGTCGTTCGCTCCAAGCT
GGGCTGTGTGCACGAACCCCCCGTTCA
GCCCGACCGCTGCGCCTTATCCGGTAA
CTATCGTCTTGAGTCCAACCCGGTAAG
ACACGACTTATCGCCACTGGCAGCAGC
CACTGGTAACAGGATTAGCAGAGCGAG
GTATGTAGGCGGTGCTACAGAGTTCTT
GAAGTGGTGGCCTAACTACGGCTACAC
TAGAAGGACAGTATTTGGTATCTGCGC
TCTGCTGAAGCCAGTTACCTTCGGAAA
AAGAGTTGGTAGCTCTTGATCCGGCAA
ACAAACCACCGCTGGTAGCGGTGGTTT
TTTTGTTTGCAAGCAGCAGATTACGCG
```

FIG. 15 CONT.

| | | |
|---|---|---|
| | CAGAAAAAAGGATCTCAAGAAGATCC<br>TTTGATCTTTTCTACGGGGTCTGACGCT<br>CAGTGGAACGAAAACTCACGTTAAGGG<br>ATTTTGGTCATGAGATTATCAAAAGG<br>ATCTTCACCTAGATCCTTTTAAATTAAA<br>AATGAAGTTTTAAATCAATCTAAAGTAT<br>ATATGAGTAAACTTGGTCTGACAGTTA<br>CCAATGCTTAATCAGTGAGGCACCTAT<br>CTCAGCGATCTGTCTATTTCGTTCATCC<br>ATAGTTGCCTGACTCCCCGTCGTGTAG<br>ATAACTACGATACGGGAGGGCTTACCA<br>TCTGGCCCCAGTGCTGCAATGATACCG<br>CGAGACCCACGCTCACCGGCTCCAGAT<br>TTATCAGCAATAAACCAGCCAGCCGGA<br>AGGGCCGAGCGCAGAAGTGGTCCTGCA<br>ACTTTATCCGCTCCATCCAGTCTATTA<br>ATTGTTGCCGGGAAGCTAGAGTAAGTA<br>GTTCGCCAGTTAATAGTTTGCGCAACG<br>TTGTTGCCATTGCTACAGGCATCGTGG<br>TGTCACGCTCGTCGTTTGGTATGGCTT<br>CATTCAGCTCCGGTTCCCAACGATCAA<br>GGCGAGTTACATGATCCCCCATGTTGT<br>GCAAAAAAGCGGTTAGCTCCTTCGGTC<br>CTCCGATCGTTGTCAGAAGTAAGTTGG<br>CCGCAGTGTTATCACTCATGGTTATGG<br>CAGCACTGCATAATTCTCTTACTGTCAT<br>GCCATCCGTAAGATGCTTTTCTGTGACT<br>GGTGAGTACTCAACCAAGTCATTCTGA<br>GAATAGTGTATGCGGCGACCGAGTTGC<br>TCTTGCCCGGCGTCAATACGGGATAAT<br>ACCGCGCCACATAGCAGAACTTTAAAA<br>GTGCTCATCATTGGAAAACGTTCTTCG<br>GGGCGAAAACTCTCAAGGATCTTACCG<br>CTGTTGAGATCCAGTTCGATGTAACCC<br>ACTCGTGCACCCAACTGATCTTCAGCA<br>TCTTTTACTTTCACCAGCGTTTCTGGGT<br>GAGCAAAAACAGGAAGGCAAAATGCCG<br>CAAAAAAGGGAATAAGGGCGACACGGA<br>AATGTTGAATACTCATACTCTTCCTTTT<br>TCAATATTATTGAAGCATTTATCAGGGT<br>TATTGTCTCATGAGCGGATACATATTTG<br>AATGTATTTAGAAAAATAAACAAATAG<br>GGGTTCCGCGCACATTTCCCCGAAAAG<br>TGCCACCTGACGTC | |
| 23 | GACGGATCGGGAGATCTCCCGATCCCC<br>TATGGTCGACTCTCAGTACAATCTGCTC<br>TGATGCCGCATAGTTAAGCCAGTATCT<br>GCTCCCTGCTTGTGTGTTGGAGGTCGC<br>TGAGTAGTGCGCGAGCAAAATTTAAGC<br>TACAACAAGGCAAGGCTTGACCGACAA | JDS78 |

FIG. 15 CONT.

```
TTGCATGAAGAATCTGCTTAGGGTTAG
GCGTTTTGCGCTGCTTCGCGATGTACG
GGCCAGATATACGCGTTGACATTGATT
ATTGACTAGTTATTAATAGTAATCAATT
ACGGGGTCATTAGTTCATAGCCCATAT
ATGGAGTTCCGCGTTACATAACTTACG
GTAAATGGCCCGCCTGGCTGACCGCCC
AACGACCCCGCCCATTGACGTCAATA
ATGACGTATGTTCCCATAGTAACGCCA
ATAGGGACTTTCCATTGACGTCAATGG
GTGGACTATTTACGGTAAACTGCCCAC
TTGGCAGTACATCAAGTGTATCATATG
CCAAGTACGCCCCTATTGACGTCAAT
GACGGTAAATGGCCCGCTGGCATTAT
GCCCAGTACATGACCTTATGGGACTTT
CCTACTTGGCAGTACATCTACGTATTAG
TCATCGCTATTACCATGGTGATGCGGT
TTTGGCAGTACATCAATGGGCGTGGAT
AGCGGTTTGACTCACGGGGATTTCCAA
GTCTCCACCCCATTGACGTCAATGGGA
GTTTGTTTTGGCACCAAAATCAACGGG
ACTTTCCAAAATGTCGTAACAACTCCGC
CCCATTGACGCAAATGGGCGGTAGGCG
TGTACGGTGGGAGGTCTATATAAGCAG
AGCTCTCTGGCTAACTAGAGAACCCAC
TGCTTACTGGCTTATCGAAATTAATACG
ACTCACTATAGGGAGACCCAAGCTGGC
TAGCaccATGGACTACAAAGACCATGAC
GGTGATTATAAAGATCATGACATCGAT
TACAAGGATGACGATGACAAGATGGCC
CCCAAGAAGAAGAGGAAGGTGGGCATT
CACCGCGGGGTACCTATGGTGGACTTG
AGGACACTCGGTTATTCGCAACAGCAA
CAGGAGAAAATCAAGCCTAAGGTCAGG
AGCACCGTCGCGCAACACCACGAGGCG
CTTGTGGGGCATGGCTTCACTCATGCG
CATATTGTCGCGCTTTCACAGCACCCT
GCGGCGCTTGGGACGGTGGCTGTCAAA
TACCAAGATATGATTGCGGCCCTGCCC
GAAGCCACGCACGAGGCAATTGTAGGG
GTCGGTAAACAGTGGTCGGGAGCGCGA
GCACTTGAGGCGCTGCTGACTGTGGCG
GGTGAGCTTAGGGGCCTCCGCTCCAG
CTCGACACCGGGCAGCTGCTGAAGATC
GCGAAGAGAGGGGAGTAACAGCGGT
AGAGGCAGTGCACGCCTGGCGCAATGC
GCTCACCGGGGCCCCCTTGAACAGAGA
CGATTAATGCGTCTCGCTGACACCCGA
ACAGGTGGTCGCCATTGCTTCTAATGG
GGGAGGACGGCCAGCCTTGGAGTCCAT
```

FIG. 15 CONT.

```
CGTAGCCCAATTGTCCAGGCCCGATCC
CGCGTTGGCTGCGTTAACGAATGACCA
TCTGGTGGCGTTGGCATGTCTTGGTGG
ACGACCCGCGCTCGATGCAGTCAAAAA
GGGTCTGCCTCATGCTCCGCATTGAT
CAAAAGAACCAACCGGCGGATTCCCGA
GAGAACTTCCCATCGAGTCGCGGGATC
CCAACTAGTCAAAAGTGAACTGGAGGA
GAAGAAATCTGAACTTCGTCATAAATT
GAAATATGTGCCTCATGAATATATTGAA
TTAATTGAAATTGCCAGAAATTCCACTC
AGGATAGAATTCTTGAAATGAAGGTAA
TGGAATTTTTTATGAAAGTTTATGGATA
TAGAGGTAAACATTTGGGTGGATCAAG
GAAACCGGACGGAGCAATTTATACTGT
CGGATCTCCTATTGATTACGGTGTGAT
CGTGGATACTAAAGCTTATAGCGGAGG
TTATAATCTGCCAATTGGCCAAGCAGA
TGAAATGCAACGATATGTCGAAGAAAA
TCAAACACGAAACAAACATATCAACCC
TAATGAATGGTGGAAAGTCTATCCATC
TTCTGTAACGGAATTTAAGTTTTTATTT
GTGAGTGGTCACTTTAAAGGAAACTAC
AAAGCTCAGCTTACACGATTAAATCATA
TCACTAATTGTAATGGAGCTGTTCTTAG
TGTAGAAGAGCTTTTAATTGGTGGAGA
AATGATTAAAGCCGGCACATTAACCTT
AGAGGAAGTCAGACGGAAATTTAATAA
CGGCGAGATAAACTTTTAAGGGCCCTT
CGAAGGTAAGCCTATCCCTAACCCTCT
CCTCGGTCTCGATTCTACGCGTACCGG
TCATCATCACCATCACCATTGAGTTTAA
ACCCGCTGATCAGCCTCGACTGTGCCT
TCTAGTTGCCAGCCATCTGTTGTTTGCC
CCTCCCCCGTGCCTTCCTTGACCCTGG
AAGGTGCCACTCCCACTGTCCTTTCCTA
ATAAAATGAGGAAATTGCATCGCATTG
TCTGAGTAGGTGTCATTCTATTCTGGG
GGGTGGGGTGGGGCAGGACAGCAAGG
GGGAGGATTGGGAAGACAATAGCAGGC
ATGCTGGGGATGCGGTGGGCTCTATGG
CTTCTGAGGCGGAAAGAACCAGCTGGG
GCTCTAGGGGTATCCCCACGCGCCCT
GTAGCGGCGCATTAAGCGCGGCGGGTG
TGGTGGTTACGCGCAGCGTGACCGCTA
CACTTGCCAGCGCCCTAGCGCCCGCTC
CTTTCGCTTTCTTCCCTTCCTTTCTCGC
CACGTTCGCCGGCTTTCCCCGTCAAGC
TCTAAATCGGGGCATCCCTTTAGGGTT
CCGATTTAGTGCTTTACGGCACCTCGA
```

FIG. 15 CONT.

```
CCCCAAAAAACTTGATTAGGGTGATGG
TTCACGTAGTGGGCCATCGCCCTGATA
GACGGTTTTTCGCCCTTTGACGTTGGA
GTCCACGTTCTTTAATAGTGGACTCTTG
TTCCAAACTGGAACAACACTCAACCCT
ATCTCGGTCTATTCTTTTGATTTATAAG
GGATTTTGGGGATTTCGGCCTATTGGT
TAAAAAATGAGCTGATTTAACAAAAATT
TAACGCGAATTAATTCTGTGGAATGTG
TGTCAGTTAGGGTGTGGAAAGTCCCA
GGCTCCCAGGCAGGCAGAAGTATGCA
AAGCATGCATCTCAATTAGTCAGCAAC
CAGGTGTGGAAAGTCCCCAGGCTCCCC
AGCAGGCAGAAGTATGCAAAGCATGCA
TCTCAATTAGTCAGCAACCATAGTCCC
GCCCTAACTCCGCCCATCCCGCCCCT
AACTCCGCCCAGTTCCGCCCATTCTCC
GCCCCATGGCTGACTAATTTTTTTATT
TATGCAGAGGCCGAGGCCGCCTCTGCC
TCTGAGCTATTCCAGAAGTAGTGAGGA
GGCTTTTTTGGAGGCCTAGGCTTTTGC
AAAAAGCTCCGGGAGCTTGTATATCC
ATTTTCGGATCTGATCAGCACGTGTTG
ACAATTAATCATCGGCATAGTATATCG
GCATAGTATAATACGACAAGGTGAGGA
ACTAAACCATGGCCAAGCCTTTGTCTC
AAGAAGAATCCACCCTCATTGAAAGAG
CAACGGCTACAATCAACAGCATCCCCA
TCTCTGAAGACTACAGCGTCGCCAGCG
CAGCTCTCTAGCGACGGCCGCATCT
TCACTGGTGTCAATGTATATCATTTTAC
TGGGGGACCTTGTGCAGAACTCGTGGT
GCTGGGCACTGCTGCTGCTGCGGCAGC
TGGCAACCTGACTTGTATCGTCGCGAT
CGGAAATGAGAACAGGGGCATCTTGAG
CCCCTGCGGACGGTGTCGACAGGTGCT
TCTCGATCTGCATCCTGGGATCAAAGC
GATAGTGAAGGACAGTGATGGACAGCC
GACGGCAGTTGGGATTCGTGAATTGCT
GCCCTCTGGTTATGTGTGGGAGGGCTA
AGCACTTCGTGGCCGAGGAGCAGGACT
GACACGTGCTACGAGATTTCGATTCCA
CCGCCGCCTTCTATGAAAGGTTGGGCT
TCGGAATCGTTTCCGGGACGCCGGCT
GGATGATCCTCCAGCGCGGGGATCTCA
TGCTGGAGTTCTTCGCCCACCCCAACT
TGTTTATTGCAGCTTATAATGGTTACAA
ATAAAGCAATAGCATCACAAATTTCACA
AATAAAGCATTTTTTTCACTGCATTCTA
GTTGTGGTTTGTCCAAACTCATCAATGT
```

FIG. 15 CONT.

```
ATCTTATCATGTCTGTATACCGTCGACC
TCTAGCTAGAGCTTGGCGTAATCATGG
TCATAGCTGTTTCCTGTGTGAAATTGTT
ATCCGCTCACAATTCCACACAACATAC
GAGCCGGAAGCATAAAGTGTAAAGCCT
GGGGTGCCTAATGAGTGAGCTAACTCA
CATTAATTGCGTTGCGCTCACTGCCCG
CTTTCCAGTCGGGAAACCTGTCGTGCC
AGCTGCATTAATGAATCGGCCAACGCG
CGGGGAGAGGCGGTTTGCGTATTGGGC
GCTCTTCCGCTTCCTCGCTCACTGACTC
GCTGCGCTCGGTCGTTCGGCTGCGGCG
AGCGGTATCAGCTCACTCAAAGGCGGT
AATACGGTTATCCACAGAATCAGGGGA
TAACGCAGGAAAGAACATGTGAGCAAA
AGGCCAGCAAAAGGCCAGGAACCGTAA
AAAGGCCGCGTTGCTGGCGTTTTTCCA
TAGGCTCCGCCCCCCTGACGAGCATCA
CAAAAATCGACGCTCAAGTCAGAGGTG
GCGAAACCCGACAGGACTATAAAGATA
CCAGGCGTTTCCCCCTGGAAGCTCCCT
CGTGCGCTCTCCTGTTCCGACCCTGCC
GCTTACCGGATACCTGTCCGCCTTTCTC
CCTTCGGGAAGCGTGGCGCTTTCTCAA
TGCTCACGCTGTAGGTATCTCAGTTCG
GTGTAGGTCGTTCGCTCCAAGCTGGGC
TGTGTGCACGAACCCCCCGTTCAGCCC
GACCGCTGCGCCTTATCCGGTAACTAT
CGTCTTGAGTCCAACCCGGTAAGACAC
GACTTATCGCCACTGGCAGCAGCCACT
GGTAACAGGATTAGCAGAGCGAGGTAT
GTAGGCGGTGCTACAGAGTTCTTGAAG
TGGTGGCCTAACTACGGCTACACTAGA
AGGACAGTATTTGGTATCTGCGCTCTG
CTGAAGCCAGTTACCTTCGGAAAAAGA
GTTGGTAGCTCTTGATCCGGCAAACAA
ACCACCGCTGGTAGCGGTGGTTTTTTT
GTTTGCAAGCAGCAGATTACGCGCAGA
AAAAAAGGATCTCAAGAAGATCCTTTG
ATCTTTTCTACGGGGTCTGACGCTCAG
TGGAACGAAAACTCACGTTAAGGGATT
TTGGTCATGAGATTATCAAAAAGGATC
TTCACCTAGATCCTTTTAAATTAAAAAT
GAAGTTTTAAATCAATCTAAAGTATATA
TGAGTAAACTTGGTCTGACAGTTACCA
ATGCTTAATCAGTGAGGCACCTATCTC
AGCGATCTGTCTATTTCGTTCATCCATA
GTTGCCTGACTCCCCGTCGTGTAGATA
ACTACGATACGGGAGGGCTTACCATCT
GGCCCCAGTGCTGCAATGATACCGCGA
```

FIG. 15 CONT.

| | | |
|---|---|---|
| | GACCCACGCTCACCGGCTCCAGATTTA<br>TCAGCAATAAACCAGCCAGCCGGAAGG<br>GCCGAGCGCAGAAGTGGTCCTGCAACT<br>TTATCCGCCTCCATCCAGTCTATTAATT<br>GTTGCCGGGAAGCTAGAGTAAGTAGTT<br>CGCCAGTTAATAGTTTGCGCAACGTTG<br>TTGCCATTGCTACAGGCATCGTGGTGT<br>CACGCTCGTCGTTTGGTATGGCTTCATT<br>CAGCTCCGGTTCCAACGATCAAGGCG<br>AGTTACATGATCCCCATGTTGTGCAA<br>AAAAGCGGTTAGCTCCTTCGGTCCTCC<br>GATCGTTGTCAGAAGTAAGTTGGCCGC<br>AGTGTTATCACTCATGGTTATGGCAGC<br>ACTGCATAATTCTCTTACTGTCATGCCA<br>TCCGTAAGATGCTTTTCTGTGACTGGT<br>GAGTACTCAACCAAGTCATTCTGAGAA<br>TAGTGTATGCGGCGACCGAGTTGCTCT<br>TGCCCGGCGTCAATACGGGATAATACC<br>GCGCCACATAGCAGAACTTTAAAAGTG<br>CTCATCATTGGAAAACGTTCTTCGGGG<br>CGAAAACTCTCAAGGATCTTACCGCTG<br>TTGAGATCCAGTTCGATGTAACCCACT<br>CGTGCACCCAACTGATCTTCAGCATCTT<br>TTACTTTCACCAGCGTTTCTGGGTGAG<br>CAAAAACAGGAAGGCAAAATGCCGCAA<br>AAAAGGGAATAAGGGCGACACGGAAAT<br>GTTGAATACTCATACTCTTCCTTTTTCA<br>ATATTATTGAAGCATTTATCAGGGTTAT<br>TGTCTCATGAGCGGATACATATTTGAAT<br>GTATTTAGAAAAATAAACAAATAGGGG<br>TTCCGCGCACATTTCCCCGAAAAGTGC<br>CACCTGACGTC | |
| 24 | ATGGACTACAAAGACCATGACGGTGAT<br>TATAAAGATCATGACATCGATTACAAG<br>GATGACGATGACAAGATGGCCCCCaagaa<br>gaagaggaaggtgggcattcaccgcggggtacctatggtggactg<br>aggacactcggttattcgcaacagcaacaggagaaaatcaagccta<br>aggtcaggagcacgtcgcgcaacaccacgaggcgcttgtgggg<br>catggcttcactcatgcgcatattgtcgcgctttcacagcacccctgcg<br>gcgcttgggacggtggctgtcaaataccaagatatgattgcggccct<br>gcccgaagccacgcacgaggcaattgtaggggtcggtaaacagtg<br>gtcgggagcgcgagcacttgagcgcgctgctgactgtggcgggtga<br>gcttaggggcctccgctccagctcgacaccgggcagctgctgaa<br>gatcgcgaagagaggggagtaacagcggtagaggcagtgcacg<br>cctggcgcaatgcgctcaccggggccccttgaacctgacccag<br>accaggtagtcgcaatcgcgtcgaacattggggaaagcaagccct<br>ggaaaccgtgcaaaggttgttgccgatccttgtcaagaccacggcc<br>ttacaccggagcaagtcgtggccattgcaagcacatcggtgcaa<br>acaggcttgagacggtcagagactctcccagttctgtcaagc<br>ccacgggctgactcccgatcaagttgtagcgattgcgaataaca | 3'TALEN (in JDS70)<br>Constructs T278 |

FIG. 15 CONT.

atggagggaaacaagcattggagactgtccaacggctccttccc
gtgttgtgtcaagcccacggtTTGACGCCTGCACAA
GTGGTCGCCATCGCCAGCCATGATGGCGG
TAAGCAGGCGCTGGAAACAGTACAGCGC
CTGCTGCCTGTACTGTGCCAGGATCATGG
Actgaccccagaccaggtagtcgcaatcgcgtcgaacattggggg
aaagcaagccctggaaaccgtgcaaaggttgttgccggtccttgtc
aagaccacggccttacaccggagcaagtcgtggccattgcaaat
aataacggtggcaaacaggctcttgagacggttcagagacttct
cccagttctctgtcaagcccacgggCTGACTCCCGATC
AAGTTGTAGCGATTGCGTCCAACGGTGGAG
GGAAACAAGCATTGGAGACTGTCCAACGGC
TCCTTCCCGTGTTGTGTCAAGCCCACGGTttg
acgcctgcacaagtggtcgccatcgccaacaacaacggcggta
agcaggcgctggaaacagtacagcgcctgctgcctgtactgtgc
caggatcatggactgaccccagaccaggtagtcgcaatcgcga
acaataatgggggaaagcaagccctggaaaccgtgcaaaggt
tgttgccggtcctttgtcaagaccacggccttacaccggagcaa
gtcgtggccattgcaaataataacggtggcaaacaggctcttga
gacggttcagagacttctcccagttctctgtcaagcccacgggC
TGACTCCCGATCAAGTTGTAGCGATTGCGTC
CAACGGTGGAGGGAAACAAGCATTGGAGAC
TGTCCAACGGCTCCTTCCCGTGTTGTGTCAA
GCCCACGGTTTGACGCCTGCACAAGTGGTC
GCCATCGCCTCGAATGGCGGCGGTAAGCAG
GCGCTGGAAACAGTACAGCGCCTGCTGCCT
GTACTGTGCCAGGATCATGGACTGACCCCA
GACCAGGTAGTCGCAATCGCGTCACATGA
CGGGGAAAGCAAGCCCTGGAAACCGTG
CAAAGGTTGTTGCCGGTCCTTTGTCAAGA
CCACGGCCTTACACCGGAGCAAGTCGTGG
CCATTGCATCCCACGACGGTGGCAAACAG
GCTCTTGAGACGGTTCAGAGACTTCTCCC
AGTTCTCTGTCAAGCCCACGGGCTGACTC
CCGATCAAGTTGTAGCGATTGCGTCGCAT
GACGGAGGGAAACAAGCATTGGAGACTG
TCCAACGGCTCCTTCCCGTGTTGTGTCAA
GCCCACGGTTTGACGCCTGCACAAGTGGTC
GCCATCGCCTCGAATGGCGGCGGTAAGCAG
GCGCTGGAAACAGTACAGCGCCTGCTGCCT
GTACTGTGCCAGGATCATGGActgaccccagacca
ggtagtcgcaatcgcgtcgaacattgggggaaagcaagccctgga
aaccgtgcaaaggttgttgccggtcctttgtcaagaccacggccta
caccggagcaagtcgtggccattgcaaataataacggtggcaa
acaggctcttgagacggttcagagacttctcccagttctctgtca
agcccacgggCTGACTCCCGATCAAGTTGTAGC
GATTGCGTCCAACGGTGGAGGGAAACAAGC
ATTGGAGACTGTCCAACGGCTCCTTCCCGTG
TTGTGTCAAGCCCACGGTTTGACGCCTGCAC
AAGTGGTCGCCATCGCCTCGAATGGCGGCG

FIG. 15 CONT.

| | | |
|---|---|---|
| | *GTAAGCAGGCGCTGGAAACAGTACAGCGCC* *TGCTGCCTGTACTGTGCCAGGATCATGGA*ctg acaccegaacaggtggtcgccattgcttctaacatcggaggacggc cagcctiggagtccatcgtagccaattgtccaggcccgatcccgcg ttggctgcgttaacgaatgaccatctggtgcgttggcatgtcttgt ggacgacccgcgctcgatgcagtcaaaaagggtctgcctcatgctc ccgcattgatcaaaagaaccaaccggcggattcccgagagaacttc ccatcgagtcgcggga*TCCCAACTAGTCAAAAGTG AACTGGAGGAGAAGAAATCTGAACTTCGT CATAAATTGAAATATGTGCCTCATGAATAT ATTGAATTAATTGAAATTGCCAGAAATTCC ACTCAGGATAGAATTCTTGAAATGAAGGTA ATGGAATTTTTTATGAAAGTTTATGGATAT AGAGGTAAACATTTGGGTGGATCAAGGAA ACCGGACGGAGCAATTTATACTGTCGGAT CTCCTATTGATTACGGTGTGATCGTGGATA CTAAAGCTTATAGCGGAGGTTATAATCTGC CAATTGGCCAAGCAGATGAAATGCAACGA TATGTCGAAGAAATCAAACACGAAACAAA CATATCAACCCTAATGAATGGTGGAAAGTC TATCCATCTTCTGTAACGGAATTTAAGTTT TTATTTGTGAGTGGTCACTTTAAAGGAAAC TACAAAGCTCAGCTTACACGATTAAATCAT ATCACTAATTGTAATGGAGCTGTTCTTAGT GTAGAAGAGCTTTTAATTGGTGGAGAAAT GATTAAAGCCGGCACATTAACCTTAGAGG AAGTCAGACGGAAATTTAATAACGGCGAG ATAAACTTTTAA* | |
| 25 | GACGGATCGGGAGATCTCCCGATCCCCTA TGGTCGACTCTCAGTACAATCTGCTCTGA TGCCGCATAGTTAAGCCAGTATCTGCTCC CTGCTTGTGTGTTGGAGGTCGCTGAGTAG TGCGCGAGCAAAATTTAAGCTACAACAA GGCAAGGCTTGACCGACAATTGCATGAA GAATCTGCTTAGGGTTAGGCGTTTTGCGC TGCTTCGCGATGTACGGGCCAGATATACG CGTTGACATTGATTATTGACTAGTTATTA ATAGTAATCAATTACGGGGTCATTAGTTC ATAGCCCATATATGGAGTTCCGCGTTACA TAACTTACGGTAAATGGCCCGCCTGGCTG ACCGCCCAACGACCCCCGCCCATTGACGT CAATAATGACGTATGTTCCCATAGTAACG CCAATAGGGACTTTCCATTGACGTCAATG GGTGGACTATTTACGGTAAACTGCCCACT TGGCAGTACATCAAGTGTATCATATGCCA AGTACGCCCCCTATTGACGTCAATGACGG TAAATGGCCCGCCTGGCATTATGCCCAGT ACATGACCTTATGGGACTTTCCTACTTGG CAGTACATCTACGTATTAGTCATCGCTAT TACCATGGTGATGCGGTTTTGGCAGTACA | JDS70 |

FIG. 15 CONT.

```
TCAATGGGCGTGGATAGCGGTTTGACTCA
CGGGGATTTCCAAGTCTCCACCCCATTGA
CGTCAATGGGAGTTTGTTTTGGCACCAAA
ATCAACGGGACTTTCCAAAATGTCGTAAC
AACTCCGCCCCATTGACGCAAATGGGCGG
TAGGCGTGTACGGTGGGAGGTCTATATAA
GCAGAGCTCTCTGGCTAACTAGAGAACCC
ACTGCTTACTGGCTTATCGAAATTAATAC
GACTCACTATAGGGAGACCCAAGCTGGCT
AGCaccATGGACTACAAAGACCATGACGG
TGATTATAAAGATCATGACATCGATTACA
AGGATGACGATGACAAGATGGCCCCCAA
GAAGAAGAGGAAGGTGGGCATTCACCGC
GGGGTACCTATGGTGGACTTGAGGACACT
CGGTTATTCGCAACAGCAACAGGAGAAA
ATCAAGCCTAAGGTCAGGAGCACCGTCGC
GCAACACCACGAGGCGCTTGTGGGGCAT
GGCTTCACTCATGCGCATATTGTCGCGCT
TTCACAGCACCCTGCGGCGCTTGGGACGG
TGGCTGTCAAATACCAAGATATGATTGCG
GCCCTGCCCGAAGCCACGCACGAGGCAA
TTGTAGGGGTCGGTAAACAGTGGTCGGGA
GCGCGAGCACTTGAGGCGCTGCTGACTGT
GGCGGGTGAGCTTAGGGGGCCTCCGCTCC
AGCTCGACACCGGGCAGCTGCTGAAGATC
GCGAAGAGAGGGGGAGTAACAGCGGTAG
AGGCAGTGCACGCCTGGCGCAATGCGCTC
ACCGGGGCCCCCTTGAACAGAGACGATTA
ATGCGTCTCGctgacacccgaacaggtggtcgccattgctt
ctaacatcggaggacggccagccttggagtccatcgtagcccaatt
gtccaggcccgatcccgcgttggctgccgttaacgaatgaccatctgg
tggccttggcatgtcttggtggacgacccgcgctcgatgcagtcaaa
aagggtctgcctcatgctcccgcattgatcaaaagaaccaaccggc
ggattcccgagagaacttcccatcgagtcgcgggaTCCAAC
TAGTCAAAAGTGAACTGGAGGAGAAGAA
ATCTGAACTTCGTCATAAATTGAAATATG
TGCCTCATGAATATATTGAATTAATTGAA
ATTGCCAGAAATTCCACTCAGGATAGAAT
TCTTGAAATGAAGGTAATGGAATTTTTA
TGAAAGTTTATGGATATAGAGGTAAACAT
TTGGGTGGATCAAGGAAACCGGACGGAG
CAATTTATACTGTCGGATCTCCTATTGATT
ACGGTGTGATCGTGGATACTAAAGCTTAT
AGCGGAGGTTATAATCTGCCAATTGGCCA
AGCAGATGAAATGCAACGATATGTCGAA
GAAAATCAAACACGAAACAAACATATCA
ACCCTAATGAATGGTGGAAAGTCTATCCA
TCTTCTGTAACGGAATTTAAGTTTTTATTT
GTGACTGGTCACTTTAAACGGAAAACTACAA
AGCTCAGCTTACACGATTAAATCATATCA
```

FIG. 15 CONT.

```
CTAATTGTAATGGAGCTGTTCTTAGTGTA
GAAGAGCTTTTAATTGGTGGAGAAATGAT
TAAAGCCGGCACATTAACCTTAGAGGAA
GTCAGACGGAAATTTAATAACGGCGAGA
TAAACTTTTAAGGGCCCTTCGAAGGTAAG
CCTATCCCTAACCCTCTCCTCGGTCTCGAT
TCTACGCGTACCGGTCATCATCACCATCA
CCATTGAGTTTAAACCCGCTGATCAGCCT
CGACTGTGCCTTCTAGTTGCCAGCCATCT
GTTGTTTGCCCCTCCCCCGTGCCTTCCTTG
ACCCTGGAAGGTGCCACTCCCACTGTCCT
TTCCTAATAAAATGAGGAAATTGCATCGC
ATTGTCTGAGTAGGTGTCATTCTATTCTGG
GGGGTGGGGTGGGGCAGGACAGCAAGGG
GGAGGATTGGGAAGACAATAGCAGGCAT
GCTGGGGATGCGGTGGGCTCTATGGCTTC
TGAGGCGGAAAGAACCAGCTGGGGCTCT
AGGGGGTATCCCCACGCGCCCTGTAGCGG
CGCATTAAGCGCGGCGGGTGTGGTGGTTA
CGCGCAGCGTGACCGCTACACTTGCCAGC
GCCCTAGCGCCCGCTCCTTTCGCTTTCTTC
CCTTCCTTTCTCGCCACGTTCGCCGGCTTT
CCCCGTCAAGCTCTAAATCGGGGCATCCC
TTTAGGGTTCCGATTTAGTGCTTTACGGC
ACCTCGACCCCAAAAAACTTGATTAGGGT
GATGGTTCACGTAGTGGGCCATCGCCCTG
ATAGACGGTTTTTCGCCCTTTGACGTTGG
AGTCCACGTTCTTTAATAGTGGACTCTTGT
TCCAAACTGGAACAACACTCAACCCTATC
TCGGTCTATTCTTTTGATTTATAAGGGATT
TTGGGGATTTCGGCCTATTGGTTAAAAAA
TGAGCTGATTTAACAAAAATTTAACGCGA
ATTAATTCTGTGGAATGTGTGTCAGTTAG
GGTGTGGAAAGTCCCCAGGCTCCCCAGGC
AGGCAGAAGTATGCAAAGCATGCATCTC
AATTAGTCAGCAACCAGGTGTGGAAAGTC
CCCAGGCTCCCCAGCAGGCAGAAGTATGC
AAAGCATGCATCTCAATTAGTCAGCAACC
ATAGTCCCGCCCCTAACTCCGCCCATCCC
GCCCCTAACTCCGCCCAGTTCCGCCCATT
CTCCGCCCCATGGCTGACTAATTTTTTTTA
TTTATGCAGAGGCCGAGGCCGCCTCTGCC
TCTGAGCTATTCCAGAAGTAGTGAGGAGG
CTTTTTTGGAGGCCTAGGCTTTTGCAAAA
AGCTCCCGGGAGCTTGTATATCCATTTTC
GGATCTGATCAGCACGTGTTGACAATTAA
TCATCGGCATAGTATATCGGCATAGTATA
ATACGACAAGGTGAGGAACTAAACCATG
GCCAAGCCTTTGTCTCAAGAAGAATCCAC
CCTCATTGAAAGAGCAACGGCTACAATCA
```

FIG. 15 CONT.

```
ACAGCATCCCCATCTCTGAAGACTACAGC
GTCGCCAGCGCAGCTCTCTCTAGCGACGG
CCGCATCTTCACTGGTGTCAATGTATATC
ATTTTACTGGGGGACCTTGTGCAGAACTC
GTGGTGCTGGGCACTGCTGCTGCTGCGGC
AGCTGGCAACCTGACTTGTATCGTCGCGA
TCGGAAATGAGAACAGGGGCATCTTGAG
CCCCTGCGGACGGTGTCGACAGGTGCTTC
TCGATCTGCATCCTGGGATCAAAGCGATA
GTGAAGGACAGTGATGGACAGCCGACGG
CAGTTGGGATTCGTGAATTGCTGCCCTCT
GGTTATGTGTGGGAGGGCTAAGCACTTCG
TGGCCGAGGAGCAGGACTGACACGTGCT
ACGAGATTTCGATTCCACCGCCGCCTTCT
ATGAAAGGTTGGGCTTCGGAATCGTTTTC
CGGGACGCCGGCTGGATGATCCTCCAGCG
CGGGGATCTCATGCTGGAGTTCTTCGCCC
ACCCCAACTTGTTTATTGCAGCTTATAAT
GGTTACAAATAAAGCAATAGCATCACAA
ATTTCACAAATAAAGCATTTTTTTCACTGC
ATTCTAGTTGTGGTTTGTCCAAACTCATCA
ATGTATCTTATCATGTCTGTATACCGTCGA
CCTCTAGCTAGAGCTTGGCGTAATCATGG
TCATAGCTGTTTCCTGTGTGAAATTGTTAT
CCGCTCACAATTCCACACAACATACGAGC
CGGAAGCATAAAGTGTAAAGCCTGGGGT
GCCTAATGAGTGAGCTAACTCACATTAAT
TGCGTTGCGCTCACTGCCCGCTTTCCAGTC
GGGAAACCTGTCGTGCCAGCTGCATTAAT
GAATCGGCCAACGCGCGGGGAGAGGCGG
TTTGCGTATTGGGCGCTCTTCCGCTTCCTC
GCTCACTGACTCGCTGCGCTCGGTCGTTC
GGCTGCGGCGAGCGGTATCAGCTCACTCA
AAGGCGGTAATACGGTTATCCACAGAATC
AGGGGATAACGCAGGAAAGAACATGTGA
GCAAAAGGCCAGCAAAAGGCCAGGAACC
GTAAAAGGCCGCGTTGCTGGCGTTTTTC
CATAGGCTCCGCCCCCCTGACGAGCATCA
CAAAAATCGACGCTCAAGTCAGAGGTGG
CGAAACCCGACAGGACTATAAAGATACC
AGGCGTTTCCCCCTGGAAGCTCCCTCGTG
CGCTCTCCTGTTCCGACCCTGCCGCTTACC
GGATACCTGTCCGCCTTTCTCCCTTCGGG
AAGCGTGGCGCTTTCTCAATGCTCACGCT
GTAGGTATCTCAGTTCGGTGTAGGTCGTT
CGCTCCAAGCTGGGCTGTGTGCACGAACC
CCCCGTTCAGCCCGACCGCTGCGCCTTAT
CCGGTAACTATCGTCTTGAGTCCAACCCG
GTAAGACACGACTTATCGCCACTGGCAGC
AGCCACTGGTAACAGGATTAGCAGAGCG
```

FIG. 15 CONT.

| | AGGTATGTAGGCGGTGCTACAGAGTTCTT<br>GAAGTGGTGGCCTAACTACGGCTACACTA<br>GAAGGACAGTATTTGGTATCTGCGCTCTG<br>CTGAAGCCAGTTACCTTCGGAAAAAGAGT<br>TGGTAGCTCTTGATCCGGCAAACAAACCA<br>CCGCTGGTAGCGGTGGTTTTTTTGTTTGCA<br>AGCAGCAGATTACGCGCAGAAAAAAGG<br>ATCTCAAGAAGATCCTTTGATCTTTTCTAC<br>GGGGTCTGACGCTCAGTGGAACGAAAAC<br>TCACGTTAAGGGATTTTGGTCATGAGATT<br>ATCAAAAGGATCTTCACCTAGATCCTTT<br>TAAATTAAAAATGAAGTTTTAAATCAATC<br>TAAAGTATATATGAGTAAACTTGGTCTGA<br>CAGTTACCAATGCTTAATCAGTGAGGCAC<br>CTATCTCAGCGATCTGTCTATTTCGTTCAT<br>CCATAGTTGCCTGACTCCCCGTCGTGTAG<br>ATAACTACGATACGGGAGGGCTTACCATC<br>TGGCCCCAGTGCTGCAATGATACCGCGAG<br>ACCCACGCTCACCGGCTCCAGATTTATCA<br>GCAATAAACCAGCCAGCCGGAAGGGCCG<br>AGCGCAGAAGTGGTCCTGCAACTTTATCC<br>GCCTCCATCCAGTCTATTAATTGTTGCCG<br>GGAAGCTAGAGTAAGTAGTTCGCCAGTTA<br>ATAGTTTGCGCAACGTTGTTGCCATTGCT<br>ACAGGCATCGTGGTGTCACGCTCGTCGTT<br>TGGTATGGCTTCATTCAGCTCCGGTTCCC<br>AACGATCAAGGCGAGTTACATGATCCCCC<br>ATGTTGTGCAAAAAAGCGGTTAGCTCCTT<br>CGGTCCTCCGATCGTTGTCAGAAGTAAGT<br>TGGCCGCAGTGTTATCACTCATGGTTATG<br>GCAGCACTGCATAATTCTCTTACTGTCAT<br>GCCATCCGTAAGATGCTTTTCTGTGACTG<br>GTGAGTACTCAACCAAGTCATTCTGAGAA<br>TAGTGTATGCGGCGACCGAGTTGCTCTTG<br>CCCGGCGTCAATACGGGATAATACCGCGC<br>CACATAGCAGAACTTTAAAAGTGCTCATC<br>ATTGGAAAACGTTCTTCGGGGCGAAAACT<br>CTCAAGGATCTTACCGCTGTTGAGATCCA<br>GTTCGATGTAACCCACTCGTGCACCCAAC<br>TGATCTTCAGCATCTTTACTTTCACCAGC<br>GTTTCTGGGTGAGCAAAAACAGGAAGGC<br>AAAATGCCGCAAAAAAGGGAATAAGGGC<br>GACACGGAAATGTTGAATACTCATACTCT<br>TCCTTTTTCAATATTATTGAAGCATTTATC<br>AGGGTTATTGTCTCATGAGCGGATACATA<br>TTTGAATGTATTTAGAAAAATAAACAAAT<br>AGGGGTTCCGCGCACATTTCCCCGAAAAG<br>TGCCACCTGACGTC | |
| 26 | GACGGATCGGGAGATCTCCCGATCCCCTA<br>TGGTCGACTCTCAGTACAATCTGCTCTGA | JDS70 (with 3'TALEN) |

FIG. 15 CONT.

```
TGCCGCATAGTTAAGCCAGTATCTGCTCC
CTGCTTGTGTGTTGGAGGTCGCTGAGTAG
TGCGCGAGCAAAATTTAAGCTACAACAA
GGCAAGGCTTGACCGACAATTGCATGAA
GAATCTGCTTAGGGTTAGGCGTTTTGCGC
TGCTTCGCGATGTACGGGCCAGATATACG
CGTTGACATTGATTATTGACTAGTTATTA
ATAGTAATCAATTACGGGGTCATTAGTTC
ATAGCCCATATATGGAGTTCCGCGTTACA
TAACTTACGGTAAATGGCCCGCCTGGCTG
ACCGCCCAACGACCCCGCCCATTGACGT
CAATAATGACGTATGTTCCCATAGTAACG
CCAATAGGGACTTTCCATTGACGTCAATG
GGTGGACTATTTACGGTAAACTGCCCACT
TGGCAGTACATCAAGTGTATCATATGCCA
AGTACGCCCCCTATTGACGTCAATGACGG
TAAATGGCCCGCCTGGCATTATGCCCAGT
ACATGACCTTATGGGACTTTCCTACTTGG
CAGTACATCTACGTATTAGTCATCGCTAT
TACCATGGTGATGCGGTTTTGGCAGTACA
TCAATGGGCGTGGATAGCGGTTTGACTCA
CGGGGATTTCCAAGTCTCCACCCCATTGA
CGTCAATGGGAGTTTGTTTTGGCACCAAA
ATCAACGGGACTTTCCAAAATGTCGTAAC
AACTCCGCCCCATTGACGCAAATGGGCGG
TAGGCGTGTACGGTGGGAGGTCTATATAA
GCAGAGCTCTCTGGCTAACTAGAGAACCC
ACTGCTTACTGGCTTATCGAAATTAATAC
GACTCACTATAGGGAGACCCAAGCTGGCT
AGCaccATGGACTACAAAGACCATGACG
GTGATTATAAAGATCATGACATCGATTA
CAAGGATGACGATGACAAGATGGCCCC
Caagaagaagaggaaggtgggcattcaccgcggggtacctatgg
tggacttgaggacactcggttattcgcaacagcaacaggagaaaatc
aagcctaaggtcaggagcaccgtcgcgcaacaccacgaggcgctt
gtggggcatggcttcactcatgcgcatattgtcgcgctttcacagcac
cctgcggcgcttgggacggtggctgtcaaataccaagatatgattgc
ggccctgcccgaagccacgcacgaggcaattgtaggggtcggtaa
acagtggtcgggagcgcgagcacttgaggcgctgctgactgtggc
gggtgagcttaggggcctccgctccagctcgacaccgggcagct
gctgaagatcgcgaagagaggggagtaacagcggtagaggcag
tgcacgcctggcgcaatgcgctcaccggggccccttgaacctgac
cccagaccaggtagtcgcaatcgcgtcgaacattggggaaagca
agccctggaaaccgtgcaaaggttgttgccggtccttgtcaagacc
acggccttacaccggagcaagtcgtggccattgcaagcaacatcgg
tggcaaacaggctcttgagacggttcagagacttctcccagttctctg
tcaagcccacgggctgactcccgatcaagttgtagcgattgcga
ataacaatggagggaaacaagcattggagactgtccaacggct
ccttcccgtgttgtgtcaagcccacggtTTGACGCCTGC
ACAAGTGGTCGCCATCGCCAGCCATGATG
```

```
GCGGTAAGCAGGCGCTGGAAACAGTACA
GCGCCTGCTGCCTGTACTGTGCCAGGATC
ATGGActgacccagaccaggtagtcgcaatcgcgtcgaacat
tgggggaaagcaagccctggaaaccgtgcaaaggttgttgccggt
cctttgtcaagaccacggccttacaccggagcaagtcgtggccat
tgcaaataataacggtggcaaacaggctcttgagacggttcag
agacttctcccagttctctgtcaagcccacgggCTGACTCC
CGATCAAGTTGTAGCGATTGCGTCCAACGGT
GGAGGGAAACAAGCATTGGAGACTGTCCAA
CGGCTCCTTCCCGTGTTGTGTCAAGCCCAC
GGTttgacgcctgcacaagtggtcgccatcgccaacaacaac
ggcggtaagcaggcgctggaaacagtacagcgcctgctgcctg
tactgtgccaggatcatggactgacccagaccaggtagtcgca
atcgcgaacaataatgggggaaagcaagccctggaaaccgtg
caaaggttgttgccggtcctttgtcaagaccacggccttacaccg
gagcaagtcgtggccattgcaaataataacggtggcaaacagg
ctcttgagacggttcagagacttctcccagttctctgtcaagccca
cgggCTGACTCCCGATCAAGTTGTAGCGATTG
CGTCCAACGGTGGAGGGAAACAAGCATTGG
AGACTGTCCAACGGCTCCTTCCCGTGTTGTG
TCAAGCCCACGGTTTGACGCCTGCACAAGT
GGTCGCCATCGCCTCGAATGGCGGCGGTAA
GCAGGCGCTGGAAACAGTACAGCGCCTGCT
GCCTGTACTGTGCCAGGATCATGGACTGAC
CCAGACCAGGTAGTCGCAATCGCGTCAC
ATGACGGGGGAAAGCAAGCCCTGGAAAC
CGTGCAAAGGTTGTTGCCGGTCCTTTGTC
AAGACCACGGCCTTACACCGGAGCAAGT
CGTGGCCATTGCATCCCACGACGGTGGCA
AACAGGCTCTTGAGACGGTTCAGAGACTT
CTCCCAGTTCTCTGTCAAGCCCACGGGCT
GACTCCCGATCAAGTTGTAGCGATTGCGT
CGCATGACGGAGGGAAACAAGCATTGGA
GACTGTCCAACGGCTCCTTCCCGTGTTGT
GTCAAGCCCACGGTTTGACGCCTGCACAAG
TGGTCGCCATCGCCTCGAATGGCGGCGGTA
AGCAGGCGCTGGAAACAGTACAGCGCCTGC
TGCCTGTACTGTGCCAGGATCATGGActgacc
cagaccaggtagtcgcaatcgcgtcgaacattgggggaaagcaag
ccctggaaaccgtgcaaaggttgttgccggtcctttgtcaagaccac
ggccttacaccggagcaagtcgtggccattgcaaataataacg
gtggcaaacaggctcttgagacggttcagagacttctcccagttc
tctgtcaagcccacgggCTGACTCCCGATCAAGTTG
TAGCGATTGCGTCCAACGGTGGAGGGAAAC
AAGCATTGGAGACTGTCCAACGGCTCCTTCC
CGTGTTGTGTCAAGCCCACGGTTTGACGCCT
GCACAAGTGGTCGCCATCGCCTCGAATGGC
GGCGGTAAGCAGGCGCTGGAAACAGTACAG
CGCCTGCTGCCTGTACTGTGCCAGGATCAT
GGActgacacccgaacaggtggtcgccattgcttctaacatcgga
```

FIG. 15 CONT.

ggacggccagccttggagtccatcgtagcccaattgtccaggcccg
atcccgcgttggctgcgttaacgaatgaccatctggtggcgttggcat
gtcttggtggacgacccgcgctcgatgcagtcaaaaagggtctgcc
tcatgctcccgcattgatcaaaagaaccaaccggcggattcccgag
agaactcccatcgagtcgcggga*TCCCAACTAGTCAA*
*AAGTGAACTGGAGGAGAAGAAATCTGAAC*
*TTCGTCATAAATTGAAATATGTGCCTCATG*
*AATATATTGAATTAATTGAAATTGCCAGAA*
*ATTCCACTCAGGATAGAATTCTTGAAATGA*
*AGGTAATGGAATTTTTTATGAAAGTTTATG*
*GATATAGAGGTAAACATTTGGGTGGATCA*
*AGGAAACCGGACGGAGCAATTTATACTGT*
*CGGATCTCCTATTGATTACGGTGTGATCGT*
*GGATACTAAAGCTTATAGCGGAGGTTATAA*
*TCTGCCAATTGGCCAAGCAGATGAAATGC*
*AACGATATGTCGAAGAAATCAAACACGA*
*AACAAACATATCAACCCTAATGAATGGTGG*
*AAAGTCTATCCATCTTCTGTAACGGAATTT*
*AAGTTTTTATTTGTGAGTGGTCACTTTAAA*
*GGAAACTACAAAGCTCAGCTTACACGATTA*
*AATCATATCACTAATTGTAATGGAGCTGTT*
*CTTAGTGTAGAAGAGCTTTTAATTGGTGGA*
*GAAATGATTAAAGCCGGCACATTAACCTTA*
*GAGGAAGTCAGACGGAAATTTAATAACGG*
*CGAGATAAACTTTT*AAGGGCCCTTCGAAG
GTAAGCCTATCCCTAACCCTCTCCTCGGT
CTCGATTCTACGCGTACCGGTCATCATCA
CCATCACCATTGAGTTTAAACCCGCTGAT
CAGCCTCGACTGTGCCTTCTAGTTGCCAG
CCATCTGTTGTTTGCCCCTCCCCCGTGCCT
TCCTTGACCCTGGAAGGTGCCACTCCCAC
TGTCCTTTCCTAATAAAATGAGGAAATTG
CATCGCATTGTCTGAGTAGGTGTCATTCT
ATTCTGGGGGGTGGGGTGGGGCAGGACA
GCAAGGGGGAGGATTGGGAAGACAATAG
CAGGCATGCTGGGGATGCGGTGGGCTCTA
TGGCTTCTGAGGCGGAAAGAACCAGCTG
GGGCTCTAGGGGGTATCCCCACGCGCCCT
GTAGCGGCGCATTAAGCGCGGCGGGTGT
GGTGGTTACGCGCAGCGTGACCGCTACAC
TTGCCAGCGCCCTAGCGCCCGCTCCTTTC
GCTTTCTTCCCTTCCTTTCTCGCCACGTTC
GCCGGCTTTCCCCGTCAAGCTCTAAATCG
GGGCATCCCTTTAGGGTTCCGATTTAGTG
CTTTACGGCACCTCGACCCCAAAAAACTT
GATTAGGGTGATGGTTCACGTAGTGGGCC
ATCGCCCTGATAGACGGTTTTTCGCCCTTT
GACGTTGGAGTCCACGTTCTTTAATAGTG
GACTCTTGTTCCAAACTGGAACAACACTC
AACCCTATCTCGGTCTATTCTTTTGATTTA

FIG. 15 CONT.

```
TAAGGGATTTTGGGGATTTCGGCCTATTG
GTTAAAAAATGAGCTGATTTAACAAAAAT
TTAACGCGAATTAATTCTGTGGAATGTGT
GTCAGTTAGGGTGTGGAAAGTCCCCAGGC
TCCCCAGGCAGGCAGAAGTATGCAAAGC
ATGCATCTCAATTAGTCAGCAACCAGGTG
TGGAAAGTCCCCAGGCTCCCCAGCAGGCA
GAAGTATGCAAAGCATGCATCTCAATTAG
TCAGCAACCATAGTCCCGCCCCTAACTCC
GCCCATCCGCCCCTAACTCCGCCCAGTT
CCGCCCATTCTCCGCCCCATGGCTGACTA
ATTTTTTTATTTATGCAGAGGCCGAGGC
CGCCTCTGCCTCTGAGCTATTCCAGAAGT
AGTGAGGAGGCTTTTTGGAGGCCTAGGC
TTTTGCAAAAAGCTCCCGGGAGCTTGTAT
ATCCATTTTCGGATCTGATCAGCACGTGT
TGACAATTAATCATCGGCATAGTATATCG
GCATAGTATAATACGACAAGGTGAGGAA
CTAAACCATGGCCAAGCCTTTGTCTCAAG
AAGAATCCACCCTCATTGAAAGAGCAAC
GGCTACAATCAACAGCATCCCCATCTCTG
AAGACTACAGCGTCGCCAGCGCAGCTCTC
TCTAGCGACGGCCGCATCTTCACTGGTGT
CAATGTATATCATTTTACTGGGGGACCTT
GTGCAGAACTCGTGGTGCTGGGCACTGCT
GCTGCTGCGGCAGCTGGCAACCTGACTTG
TATCGTCGCGATCGGAAATGAGAACAGG
GGCATCTTGAGCCCCTGCGGACGGTGTCG
ACAGGTGCTTCTCGATCTGCATCCTGGA
TCAAAGCGATAGTGAAGGACAGTGATGG
ACAGCCGACGGCAGTTGGGATTCGTGAAT
TGCTGCCCTCTGGTTATGTGTGGGAGGGC
TAAGCACTTCGTGGCCGAGGAGCAGGACT
GACACGTGCTACGAGATTTCGATTCCACC
GCCGCCTTCTATGAAAGGTTGGGCTTCGG
AATCGTTTTCCGGGACGCCGGCTGGATGA
TCCTCCAGCGCGGGATCTCATGCTGGAG
TTCTTCGCCCACCCCAACTTGTTTATTGCA
GCTTATAATGGTTACAAATAAAGCAATAG
CATCACAAATTTCACAAATAAAGCATTTT
TTTCACTGCATTCTAGTTGTGGTTTGTCCA
AACTCATCAATGTATCTTATCATGTCTGTA
TACCGTCGACCTCTAGCTAGAGCTTGGCG
TAATCATGGTCATAGCTGTTTCCTGTGTG
AAATTGTTATCCGCTCACAATTCCACACA
ACATACGAGCCGGAAGCATAAAGTGTAA
AGCCTGGGGTGCCTAATGAGTGAGCTAAC
TCACATTAATTGCGTTGCGCTCACTGCCC
GCTTTCCAGTCGGGAAACCTGTCGTGCCA
GCTGCATTAATGAATCGGCCAACGCGCGG
```

FIG. 15 CONT.

```
GGAGAGGCGGTTTGCGTATTGGGCGCTCT
TCCGCTTCCTCGCTCACTGACTCGCTGCGC
TCGGTCGTTCGGCTGCGGCGAGCGGTATC
AGCTCACTCAAAGGCGGTAATACGGTTAT
CCACAGAATCAGGGGATAACGCAGGAAA
GAACATGTGAGCAAAAGGCCAGCAAAAG
GCCAGGAACCGTAAAAAGGCCGCGTTGC
TGGCGTTTTTCCATAGGCTCCGCCCCCTG
ACGAGCATCACAAAATCGACGCTCAAG
TCAGAGGTGGCGAAACCCGACAGGACTA
TAAAGATACCAGGCGTTTCCCCCTGGAAG
CTCCCTCGTGCGCTCTCCTGTTCCGACCCT
GCCGCTTACCGGATACCTGTCCGCCTTTCT
CCCTTCGGGAAGCGTGGCGCTTTCTCAAT
GCTCACGCTGTAGGTATCTCAGTTCGGTG
TAGGTCGTTCGCTCCAAGCTGGGCTGTGT
GCACGAACCCCCCGTTCAGCCCGACCGCT
GCGCCTTATCCGGTAACTATCGTCTTGAG
TCCAACCCGGTAAGACACGACTTATCGCC
ACTGGCAGCAGCCACTGGTAACAGGATTA
GCAGAGCGAGGTATGTAGGCGGTGCTAC
AGAGTTCTTGAAGTGGTGGCCTAACTACG
GCTACACTAGAAGGACAGTATTTGGTATC
TGCGCTCTGCTGAAGCCAGTTACCTTCGG
AAAAAGAGTTGGTAGCTCTTGATCCGGCA
AACAAACCACCGCTGGTAGCGGTGGTTTT
TTTGTTTGCAAGCAGCAGATTACGCGCAG
AAAAAAAGGATCTCAAGAAGATCCTTTG
ATCTTTTCTACGGGGTCTGACGCTCAGTG
GAACGAAAACTCACGTTAAGGGATTTTGG
TCATGAGATTATCAAAAAGGATCTTCACC
TAGATCCTTTTAAATTAAAAATGAAGTTT
TAAATCAATCTAAAGTATATATGAGTAAA
CTTGGTCTGACAGTTACCAATGCTTAATC
AGTGAGGCACCTATCTCAGCGATCTGTCT
ATTTCGTTCATCCATAGTTGCCTGACTCCC
CGTCGTGTAGATAACTACGATACGGGAGG
GCTTACCATCTGGCCCCAGTGCTGCAATG
ATACCGCGAGACCCACGCTCACCGGCTCC
AGATTTATCAGCAATAAACCAGCCAGCCG
GAAGGGCCGAGCGCAGAAGTGGTCCTGC
AACTTTATCCGCCTCCATCCAGTCTATTAA
TTGTTGCCGGGAAGCTAGAGTAAGTAGTT
CGCCAGTTAATAGTTTGCGCAACGTTGTT
GCCATTGCTACAGGCATCGTGGTGTCACG
CTCGTCGTTTGGTATGGCTTCATTCAGCTC
CGGTTCCCAACGATCAAGGCGAGTTACAT
GATCCCCCATGTTGTGCAAAAAGCGGTT
AGCTCCTTCGGTCCTCCGATCGTTGTCAG
AAGTAAGTTGGCCGCAGTGTTATCACTCA
```

FIG. 15 CONT.

| | | |
|---|---|---|
| | TGGTTATGGCAGCACTGCATAATTCTCTT<br>ACTGTCATGCCATCCGTAAGATGCTTTTCT<br>GTGACTGGTGAGTACTCAACCAAGTCATT<br>CTGAGAATAGTGTATGCGGCGACCGAGTT<br>GCTCTTGCCCGGCGTCAATACGGGATAAT<br>ACCGCGCCACATAGCAGAACTTTAAAAGT<br>GCTCATCATTGGAAAACGTTCTTCGGGGC<br>GAAAACTCTCAAGGATCTTACCGCTGTTG<br>AGATCCAGTTCGATGTAACCCACTCGTGC<br>ACCCAACTGATCTTCAGCATCTTTTACTTT<br>CACCAGCGTTTCTGGGTGAGCAAAAACAG<br>GAAGGCAAAATGCCGCAAAAAGGGAAT<br>AAGGGCGACACGGAAATGTTGAATACTC<br>ATACTCTTCCTTTTTCAATATTATTGAAGC<br>ATTTATCAGGGTTATTGTCTCATGAGCGG<br>ATACATATTTGAATGTATTTAGAAAAATA<br>AACAAATAGGGGTTCCGCGCACATTTCCC<br>CGAAAAGTGCCACCTGACGTC | |
| 27 | ATGGACTACAAAGACCATGACGGTGAT<br>TATAAAGATCATGACATCGATTACAAG<br>GATGACGATGACAAGATGGCCCCCaagaa<br>gaagaggaaggtgggcattcaccgcggggtacctatggtggacttg<br>aggacactcggttattcgcaacagcaacaggagaaaatcaagccta<br>aggtcaggagcaccgtcgcgcaacaccacgaggcgcttgtgggg<br>catggcttcactcatgcgcatattgtcgcgctttcacagcaccctgcg<br>gcgcttgggacggtggctgtcaaataccaagatatgattgcggccct<br>gcccgaagccacgcacgaggcaattgtaggggtcggtaaacagtg<br>gtcgggagcgcgagcacttgaggcgctgctgactgtgcggggtga<br>gcttaggggcctccgctccagctcgacaccgggcagctgctgaa<br>gatcgcgaagagaggggagtaacagcggtagaggcagtgcacg<br>cctggcgcaatgcgctcaccggggccccccttgaacctgacccag<br>accaggtagtcgcaatcgcgtcgaacattgggggaaagcaagccct<br>ggaaaccgtgcaaaggttgttgccggtcctttgtcaagaccacggcc<br>ttacaccggagcaagtcgtggccattgcaagcaacatcggtgcaa<br>acaggctcttgagacggttcagagacttctcccagttctctgtcaagc<br>ccacgggctgactcccgatcaagttgtagcgattgcgaataaca<br>atggagggaaacaagcattggagactgtcaacggctccttccc<br>gtgttgtgtcaagcccacggtTTGACGCCTGCACAA<br>GTGGTCGCCATCGCCAGCCATGATGGCGG<br>TAAGCAGGCGCTGGAAACAGTACAGCGC<br>CTGCTGCCTGTACTGTGCCAGGATCATGG<br>Actgacccagaccaggtagtcgcaatcgcgtcgaacattggggg<br>aaagcaagccctggaaaccgtgcaaaggttgttgccggtcctttgtc<br>aagaccacggccttacaccggagcaagtcgtggccattgcaaat<br>aatggtggcaaacaggctcttgagacggttcagagacttct<br>cccagtctctgtcaagcccacggg*CTGACTCCCGATC<br>AAGTTGTAGCGATTGCGTCAACGGTGGAG<br>GGAAACAAGCATTGGAGACTGTCAACGGC<br>TCCTTCCCGTGTTGTGTCAAGCCCACGGT*ttg<br>acgcctgcacaagtggtcgccatcgccaacaacaacggcggta | 3'TALEN.KKR.Sharkey<br>DNA sequence (From start<br>codon to stop codon) |

FIG. 15 CONT.

agcaggcgctggaaacagtacagcgcctgctgcctgtactgtgc
caggatcatggactgacccagaccaggtagtcgcaatcgcga
acaataatggggaaagcaagccctggaaaccgtgcaaaggt
tgttgccggtcctttgtcaagaccacggccttacaccggagcaa
gtcgtggccattgcaaataataacggtggcaaacaggctcttga
gacggttcagagacttctcccagttctctgtcaagcccacgggC
TGACTCCCGATCAAGTTGTAGCGATTGCGTC
CAACGGTGGAGGGAAACAAGCATTGGAGAC
TGTCCAACGGCTCCTTCCCGTGTTGTGTCAA
GCCCACGGTTTGACGCCTGCACAAGTGGTC
GCCATCGCCTCGAATGGCGGCGGTAAGCAG
GCGCTGGAAACAGTACAGCGCCTGCTGCCT
GTACTGTGCCAGGATCATGGACTGACCCCA
GACCAGGTAGTCGCAATCGCGTCACATGA
CGGGGAAAGCAAGCCCTGGAAACCGTG
CAAAGGTTGTTGCCGGTCCTTTGTCAAGA
CCACGGCCTTACACCGGAGCAAGTCGTGG
CCATTGCATCCCACGACGGTGGCAAACAG
GCTCTTGAGACGGTTCAGAGACTTCTCCC
AGTTCTCTGTCAAGCCCACGGGCTGACTC
CCGATCAAGTTGTAGCGATTGCGTCGCAT
GACGGAGGGAAACAAGCATTGGAGACTG
TCCAACGGCTCCTTCCCGTGTTGTGTCAA
GCCCACGGTTTGACGCCTGCACAAGTGGTC
GCCATCGCCTCGAATGGCGGCGGTAAGCAG
GCGCTGGAAACAGTACAGCGCCTGCTGCCT
GTACTGTGCCAGGATCATGGActgacccagacca
ggtagtcgcaatcgcgtcgaacattggggaaagcaagccctgga
aaccgtgcaaaggttgttgccggtcctttgtcaagaccacggccta
caccggagcaagtcgtggccattgcaaataataacggtggcaa
acaggctcttgagacggttcagagacttctcccagttctctgtca
agcccacgggCTGACTCCCGATCAAGTTGTAGC
GATTGCGTCCAACGGTGGAGGGAAACAAGC
ATTGGAGACTGTCCAACGGCTCCTTCCCGTG
TTGTGTCAAGCCCACGGTTTGACGCCTGCAC
AAGTGGTCGCCATCGCCTCGAATGGCGGCG
GTAAGCAGGCGCTGGAAACAGTACAGCGCC
TGCTGCCTGTACTGTGCCAGGATCATGGActg
acacccgaacaggtggtcgccattgcttctaacatcggaggacggc
cagcctggagtccatcgtagcccaattgtccaggcccgatcccgcg
ttggctgcgttaacgaatgaccatctggtggcgttggcatgtcttggt
ggacgacccgcgctcgatgcagtcaaaaagggtctgcctcatgctc
ccgcattgatcaaaagaaccaaccggcggattcccgagagaactc
ccatcgagtcgcgGGATCCCAACTAGTCAAAAGT
GAACTGGAGGAGAAGAAATCTGAACTTCG
TCATAAATTGAAATATGTGCCTCATGAATA
TATTGAATTAATTGAAATTGCCAGAAATCC
CACTCAGGATAGAATTCTTGAAATGAAGGT
AATGGAATTTTTTATGAAAGTTTATGGATA
TAGAGGTCACCATTTGGGTGGATCAAGGA

FIG. 15 CONT.

| | | |
|---|---|---|
| | *AACCGGACGGAGCAATTTATACTGTCGGA TCTCCTATTGATTACGGTGTGATCGTGGAT ACTAAAGCTTATAGCGGAGGTTATAATCTG CCAATTGGCCAAGCAGATGAAATGCAACG ATATGTCAAGGAAAATCAAACACGAAACA AACATATCAACCCTAATGAATGGTGGAAAG TCTATCCATCTTCTGTAACGGAATTTAAGT TTTTATTTGTGAGTGGTCACTTTAAAGGAA ACTACAAAGCTCAGCTTACACGATTAAATC GGAAGACTAATTGTAATGGAGCTGTTCTTA GTGTAGAAGAGCTTTTAATTGGTGGAGAA ATGATTAAAGCCGGCACATTAACCTTAGAG GAAGTCAGACGGAAATTTAATAACGGCGA GATAAACTTTTAA* | |
| 28 | GACGGATCGGGAGATCTCCCGATCCCCTA TGGTCGACTCTCAGTACAATCTGCTCTGA TGCCGCATAGTTAAGCCAGTATCTGCTCC CTGCTTGTGTGTTGGAGGTCGCTGAGTAG TGCGCGAGCAAAATTTAAGCTACAACAA GGCAAGGCTTGACCGACAATTGCATGAA GAATCTGCTTAGGGTTAGGCGTTTTGCGC TGCTTCGCGATGTACGGGCCAGATATACG CGTTGACATTGATTATTGACTAGTTATTA ATAGTAATCAATTACGGGGTCATTAGTTC ATAGCCCATATATGGAGTTCCGCGTTACA TAACTTACGGTAAATGGCCCGCCTGGCTG ACCGCCCAACGACCCCCGCCCATTGACGT CAATAATGACGTATGTTCCCATAGTAACG CCAATAGGGACTTTCCATTGACGTCAATG GGTGGACTATTTACGGTAAACTGCCCACT TGGCAGTACATCAAGTGTATCATATGCCA AGTACGCCCCCTATTGACGTCAATGACGG TAAATGGCCCGCCTGGCATTATGCCCAGT ACATGACCTTATGGGACTTTCCTACTTGG CAGTACATCTACGTATTAGTCATCGCTAT TACCATGGTGATGCGGTTTTGGCAGTACA TCAATGGGCGTGGATAGCGGTTTGACTCA CGGGGATTTCCAAGTCTCCACCCCATTGA CGTCAATGGGAGTTTGTTTTGGCACCAAA ATCAACGGGACTTTCCAAAATGTCGTAAC AACTCCGCCCCATTGACGCAAATGGGCGG TAGGCGTGTACGGTGGGAGGTCTATATAA GCAGAGCTCTCTGGCTAACTAGAGAACCC ACTGCTTACTGGCTTATCGAAATTAATAC GACTCACTATAGGGAGACCCAAGCTGGCT AGCaccATGGACTACAAAGACCATGACG GTGATTATAAAGATCATGACATCGATTA CAAGGATGACGATGACAAGATGGCCCC Caagaagaagaggaaggtggcattcaccgcggggtacctatgg tggacttgaggacactcggttattcgcaacagcaacaggagaaaatc | JDS70 (with 3'TALEN.KKR.Sharkey) | aagcctaaggtcaggagcaccgtcgcgcaacaccacgaggcgctt
gtggggcatggcttcactcatgcgcatattgtcgcgctttcacagcac
cctgcgcgcttgggacggtggctgtcaaataccaagatatgattgc
ggccctgcccgaagccacgcacgaggcaattgtaggggtcggtaa
acagtggtcgggagcgcgagcacttgaggcgctgctgactgtggc
gggtgagcttaggggcctccgctccagctcgacaccgggcagct
gctgaagatcgcgaagagaggggagtaacagcggtagaggcag
tgcacgcctggcgcaatgcgctcaccggggcccccttgaacctgac
cccagaccaggtagtcgcaatcgcgtcgaacattgggggaaagca
agccctggaaaccgtgcaaaggttgttgccggtcctttgtcaagacc
acggccttacaccggagcaagtcgtggccattgcaagcaacatcgg
tgcaaacaggctcttgagacggttcagagacttctcccagttctctg
tcaagcccacgggctgactcccgatcaagttgtagcgattgcga
ataacaatggagggaaacaagcattggagactgtccaacggct
ccttcccgtgttgtgtcaagcccacggtTTGACGCCTGC
ACAAGTGGTCGCCATCGCCAGCCATGATG
GCGGTAAGCAGGCGCTGGAAACAGTACA
GCGCCTGCTGCCTGTACTGTGCCAGGATC
ATGGActgacccagaccaggtagtcgcaatcgcgtcgaacat
tgggggaaagcaagccctggaaaccgtgcaaaggttgttgccggt
cctttgtcaagaccacggccttacaccggagcaagtcgtggccat
tgcaaataataacggtggcaaacaggctcttgagacggttcag
agacttctcccagttctctgtcaagcccacggg*CTGACTCC*
*CGATCAAGTTGTAGCGATTGCGTCCAACGGT*
*GGAGGGAAACAAGCATTGGAGACTGTCCAA*
*CGGCTCCTTCCCGTGTTGTGTCAAGCCCAC*
*GGT*ttgacgcctgcacaagtggtcgccatcgccaacaacaac
ggcggtaagcaggcgctggaaacagtacagcgcctgctgcctg
tactgtgccaggatcatggactgacccagaccaggtagtcgca
atcgcgaacaataatgggggaaagcaagccctggaaaccgtg
caaaggttgttgccggtcctttgtcaagaccacggccttacaccg
gagcaagtcgtggccattgcaaataataacggtggcaaacagg
ctcttgagacggttcagagacttctcccagttctctgtcaagccca
cggg*CTGACTCCCGATCAAGTTGTAGCGATTG*
*CGTCCAACGGTGGAGGGAAACAAGCATTGG*
*AGACTGTCCAACGGCTCCTTCCCGTGTTGTG*
*TCAAGCCCACGGTTTGACGCCTGCACAAGT*
*GGTCGCCATCGCCTCGAATGGCGGCGGTAA*
*GCAGGCGCTGGAAACAGTACAGCGCCTGCT*
*GCCTGTACTGTGCCAGGATCATGGA*CTGAC
CCCAGACCAGGTAGTCGCAATCGCGTCAC
ATGACGGGGAAAGCAAGCCCTGGAAAC
CGTGCAAAGGTTGTTGCCGGTCCTTTGTC
AAGACCACGGCCTTACACCGGAGCAAGT
CGTGGCCATTGCATCCCACGACGGTGGCA
AACAGGCTCTTGAGACGGTTCAGAGACTT
CTCCCAGTTCTCTGTCAAGCCCACGGGCT
GACTCCCGATCAAGTTGTAGCGATTGCGT
CGCATGACGGAGGGAAACAAGCATTGGA
GACTGTCCAACGGCTCCTTCCCGTGTTGT

FIG. 15 CONT.

GTCAAGCCCACGGTTTGACGCCTGCACAAG
TGGTCGCCATCGCCTCGAATGGCGGCGGTA
AGCAGGCGCTGGAAACAGTACAGCGCCTGC
TGCCTGTACTGTGCCAGGATCATGGActgacc
cagaccaggtagtcgcaatcgcgtcgaacattgggggaaagcaag
ccctggaaaccgtgcaaaggttgttgccggtcctttgtcaagaccac
ggccttacaccggagcaagtcgtggccattgcaaataataacg
gtggcaaacaggctcttgagacggttcagagacttctcccagttc
tctgtcaagcccacgggCTGACTCCCGATCAAGTTG
TAGCGATTGCGTCCAACGGTGGAGGGAAAC
AAGCATTGGAGACTGTCCAACGGCTCCTTCC
CGTGTTGTGTCAAGCCCACGGTTTGACGCCT
GCACAAGTGGTCGCCATCGCCTCGAATGGC
GGCGGTAAGCAGGCGCTGGAAACAGTACAG
CGCCTGCTGCCTGTACTGTGCCAGGATCAT
GGActgacacccgaacaggtggtcgccattgcttctaacatcgga
ggacggccagccttggagtccatcgtagcccaattgtccaggcccg
atcccgcgttggctgcgttaacgaatgaccatctggtggcgttggcat
gtcttggtggacgacccgcgctcgatgcagtcaaaaagggtctgcc
tcatgctcccgcattgatcaaaagaaccaaccggcggattcccgag
agaacttccatcgagtcgcgGGATCCCAACTAGTCA
AAAGTGAACTGGAGGAGAAGAAATCTGAA
CTTCGTCATAAATTGAAATATGTGCCTCAT
GAATATATTGAATTAATTGAAATTGCCAGA
AATCCCACTCAGGATAGAATTCTTGAAATG
AAGGTAATGGAATTTTTTATGAAAGTTTAT
GGATATAGAGGTGAGCATTTGGGTGGATC
AAGGAAACCGGACGGAGCAATTTATACTG
TCGGATCTCCTATTGATTACGGTGTGATCG
TGGATACTAAAGCTTATAGCGGAGGTTATA
ATCTGCCAATTGGCCAAGCAGATGAAATG
CAACGATATGTCAAGGAAAATCAAACACG
AAACAAACATATCAACCCTAATGAATGGTG
GAAAGTCTATCCATCTTCTGTAACGGAATT
TAAGTTTTTATTTGTGAGTGGTCACTTTAA
AGGAAACTACAAAGCTCAGCTTACACGATT
AAATCGGAAGACTAATTGTAATGGAGCTG
TTCTTAGTGTAGAAGAGCTTTTAATTGGTG
GAGAAATGATTAAAGCCGGCACATTAACCT
TAGAGGAAGTCAGACGGAAATTTAATAAC
GGCGAGATAAACTTTTAAGGGCCCTTCGA
AGGTAAGCCTATCCCTAACCCTCTCCTCG
GTCTCGATTCTACGCGTACCGGTCATCAT
CACCATCACCATTGAGTTTAAACCCGCTG
ATCAGCCTCGACTGTGCCTTCTAGTTGCC
AGCCATCTGTTGTTTGCCCCTCCCCCGTGC
CTTCCTTGACCCTGGAAGGTGCCACTCCC
ACTGTCCTTTCCTAATAAAATGAGGAAAT
TGCATCGCATTGTCTGAGTAGGTGTCATT
CTATTCTGGGGGGTGGGGTGGGGCAGGA

FIG. 15 CONT.

```
CAGCAAGGGGGAGGATTGGGAAGACAAT
AGCAGGCATGCTGGGGATGCGGTGGGCT
CTATGGCTTCTGAGGCGGAAAGAACCAGC
TGGGCTCTAGGGGGTATCCCCACGCGCC
CTGTAGCGGCGCATTAAGCGCGGCGGGTG
TGGTGGTTACGCGCAGCGTGACCGCTACA
CTTGCCAGCGCCCTAGCGCCCGCTCCTTT
CGCTTTCTTCCCTTCCTTTCTCGCCACGTT
CGCCGGCTTTCCCCGTCAAGCTCTAAATC
GGGGCATCCCTTTAGGGTTCCGATTTAGT
GCTTTACGGCACCTCGACCCCAAAAAACT
TGATTAGGGTGATGGTTCACGTAGTGGGC
CATCGCCCTGATAGACGGTTTTTCGCCCTT
TGACGTTGGAGTCCACGTTCTTTAATAGT
GGACTCTTGTTCCAAACTGGAACAACACT
CAACCCTATCTCGGTCTATTCTTTTGATTT
ATAAGGGATTTTGGGGATTTCGGCCTATT
GGTTAAAAAATGAGCTGATTTAACAAAA
ATTTAACGCGAATTAATTCTGTGGAATGT
GTGTCAGTTAGGGTGTGGAAAGTCCCCAG
GCTCCCCAGGCAGGCAGAAGTATGCAAA
GCATGCATCTCAATTAGTCAGCAACCAGG
TGTGGAAAGTCCCCAGGCTCCCCAGCAGG
CAGAAGTATGCAAAGCATGCATCTCAATT
AGTCAGCAACCATAGTCCCGCCCCTAACT
CCGCCCATCCCGCCCCTAACTCCGCCCAG
TTCCGCCCATTCTCCGCCCCATGGCTGACT
AATTTTTTTTATTTATGCAGAGGCCGAGG
CCGCCTCTGCCTCTGAGCTATTCCAGAAG
TAGTGAGGAGGCTTTTTTGGAGGCCTAGG
CTTTTGCAAAAAGCTCCCGGGAGCTTGTA
TATCCATTTTCGGATCTGATCAGCACGTG
TTGACAATTAATCATCGGCATAGTATATC
GGCATAGTATAATACGACAAGGTGAGGA
ACTAAACCATGGCCAAGCCTTTGTCTCAA
GAAGAATCCACCCTCATTGAAAGAGCAA
CGGCTACAATCAACAGCATCCCCATCTCT
GAAGACTACAGCGTCGCCAGCGCAGCTCT
CTCTAGCGACGGCCGCATCTTCACTGGTG
TCAATGTATATCATTTTACTGGGGACCT
TGTGCAGAACTCGTGGTGCTGGGCACTGC
TGCTGCTGCGGCAGCTGGCAACCTGACTT
GTATCGTCGCGATCGGAAATGAGAACAG
GGGCATCTTGAGCCCCTGCGGACGGTGTC
GACAGGTGCTTCTCGATCTGCATCCTGGG
ATCAAAGCGATAGTGAAGGACAGTGATG
GACAGCCGACGGCAGTTGGGATTCGTGA
ATTGCTGCCCTCTGGTTATGTGTGGGAGG
GCTAAGCACTTCGTGGCCGAGGAGCAGG
ACTGACACGTGCTACGAGATTTCGATTCC
```

FIG. 15 CONT.

```
ACCGCCGCCTTCTATGAAAGGTTGGGCTT
CGGAATCGTTTTCCGGGACGCCGGCTGGA
TGATCCTCCAGCGCGGGGATCTCATGCTG
GAGTTCTTCGCCCACCCCAACTTGTTTATT
GCAGCTTATAATGGTTACAAATAAAGCAA
TAGCATCACAAATTTCACAAATAAAGCAT
TTTTTTCACTGCATTCTAGTTGTGGTTTGT
CCAAACTCATCAATGTATCTTATCATGTCT
GTATACCGTCGACCTCTAGCTAGAGCTTG
GCGTAATCATGGTCATAGCTGTTTCCTGT
GTGAAATTGTTATCCGCTCACAATTCCAC
ACAACATACGAGCCGGAAGCATAAAGTG
TAAAGCCTGGGGTGCCTAATGAGTGAGCT
AACTCACATTAATTGCGTTGCGCTCACTG
CCCGCTTTCCAGTCGGGAAACCTGTCGTG
CCAGCTGCATTAATGAATCGGCCAACGCG
CGGGGAGAGGCGGTTTGCGTATTGGGCGC
TCTTCCGCTTCCTCGCTCACTGACTCGCTG
CGCTCGGTCGTTCGGCTGCGGCGAGCGGT
ATCAGCTCACTCAAAGGCGGTAATACGGT
TATCCACAGAATCAGGGGATAACGCAGG
AAAGAACATGTGAGCAAAAGGCCAGCAA
AAGGCCAGGAACCGTAAAAAGGCCGCGT
TGCTGGCGTTTTTCCATAGGCTCCGCCCCC
CTGACGAGCATCACAAAAATCGACGCTCA
AGTCAGAGGTGGCGAAACCCGACAGGAC
TATAAAGATACCAGGCGTTTCCCCCTGGA
AGCTCCCTCGTGCGCTCTCCTGTTCCGACC
CTGCCGCTTACCGGATACCTGTCCGCCTTT
CTCCCTTCGGGAAGCGTGGCGCTTTCTCA
ATGCTCACGCTGTAGGTATCTCAGTTCGG
TGTAGGTCGTTCGCTCCAAGCTGGGCTGT
GTGCACGAACCCCCCGTTCAGCCCGACCG
CTGCGCCTTATCCGGTAACTATCGTCTTG
AGTCCAACCCGGTAAGACACGACTTATCG
CCACTGGCAGCAGCCACTGGTAACAGGAT
TAGCAGAGCGAGGTATGTAGGCGGTGCT
ACAGAGTTCTTGAAGTGGTGGCCTAACTA
CGGCTACACTAGAAGGACAGTATTTGGTA
TCTGCGCTCTGCTGAAGCCAGTTACCTTC
GGAAAAAGAGTTGGTAGCTCTTGATCCGG
CAAACAAACCACCGCTGGTAGCGGTGGTT
TTTTTGTTTGCAAGCAGCAGATTACGCGC
AGAAAAAAAGGATCTCAAGAAGATCCTT
TGATCTTTTCTACGGGGTCTGACGCTCAG
TGGAACGAAAACTCACGTTAAGGGATTTT
GGTCATGAGATTATCAAAAGGATCTTCA
CCTAGATCCTTTTAAATTAAAAATGAAGT
TTTAAATCAATCTAAAGTATATATGAGTA
AACTTGGTCTGACAGTTACCAATGCTTAA
```

FIG. 15 CONT.

| | | |
|---|---|---|
| | TCAGTGAGGCACCTATCTCAGCGATCTGT<br>CTATTTCGTTCATCCATAGTTGCCTGACTC<br>CCCGTCGTGTAGATAACTACGATACGGGA<br>GGGCTTACCATCTGGCCCCAGTGCTGCAA<br>TGATACCGCGAGACCCACGCTCACCGGCT<br>CCAGATTTATCAGCAATAAACCAGCCAGC<br>CGGAAGGGCCGAGCGCAGAAGTGGTCCT<br>GCAACTTTATCCGCCTCCATCCAGTCTATT<br>AATTGTTGCCGGGAAGCTAGAGTAAGTAG<br>TTCGCCAGTTAATAGTTTGCGCAACGTTG<br>TTGCCATTGCTACAGGCATCGTGGTGTCA<br>CGCTCGTCGTTTGGTATGGCTTCATTCAGC<br>TCCGGTTCCCAACGATCAAGGCGAGTTAC<br>ATGATCCCCATGTTGTGCAAAAAGCGG<br>TTAGCTCCTTCGGTCCTCCGATCGTTGTCA<br>GAAGTAAGTTGGCCGCAGTGTTATCACTC<br>ATGGTTATGGCAGCACTGCATAATTCTCT<br>TACTGTCATGCCATCCGTAAGATGCTTTTC<br>TGTGACTGGTGAGTACTCAACCAAGTCAT<br>TCTGAGAATAGTGTATGCGGCGACCGAGT<br>TGCTCTTGCCCGGCGTCAATACGGGATAA<br>TACCGCGCCACATAGCAGAACTTTAAAAG<br>TGCTCATCATTGGAAAACGTTCTTCGGGG<br>CGAAAACTCTCAAGGATCTTACCGCTGTT<br>GAGATCCAGTTCGATGTAACCCACTCGTG<br>CACCCAACTGATCTTCAGCATCTTTTACTT<br>TCACCAGCGTTTCTGGGTGAGCAAAAACA<br>GGAAGGCAAAATGCCGCAAAAAAGGGAA<br>TAAGGGCGACACGGAAATGTTGAATACTC<br>ATACTCTTCCTTTTTCAATATTATTGAAGC<br>ATTTATCAGGGTTATTGTCTCATGAGCGG<br>ATACATATTTGAATGTATTTAGAAAAATA<br>AACAAATAGGGGTTCCGCGCACATTTCCC<br>CGAAAAGTGCCACCTGACGTC | |
| 29 | GACGGATCGGGAGATCTCCCGATCCCC<br>TATGGTCGACTCTCAGTACAATCTGCTC<br>TGATGCCGCATAGTTAAGCCAGTATCT<br>GCTCCCTGCTTGTGTGTTGGAGGTCGC<br>TGAGTAGTGCGCGAGCAAAATTTAAGC<br>TACAACAAGGCAAGGCTTGACCGACAA<br>TTGCATGAAGAATCTGCTTAGGGTTAG<br>GCGTTTTGCGCTGCTTCGCGATGTACG<br>GGCCAGATATACGCGTTGACATTGATT<br>ATTGACTAGTTATTAATAGTAATCAATT<br>ACGGGGTCATTAGTTCATAGCCCATAT<br>ATGGAGTTCCGCGTTACATAACTTACG<br>GTAAATGGCCCGCCTGGCTGACCGCCC<br>AACGACCCCCGCCCATTGACGTCAATA<br>ATGACGTATGTTCCCATAGTAACGCCA<br>ATAGGGACTTTCCATTGACGTCAATGG | JDS78 (with 5'TALEN) |

FIG. 15 CONT.

GTGGACTATTTACGGTAAACTGCCCAC
TTGGCAGTACATCAAGTGTATCATATG
CCAAGTACGCCCCTATTGACGTCAAT
GACGGTAAATGGCCCGCCTGGCATTAT
GCCCAGTACATGACCTTATGGGACTTT
CCTACTTGGCAGTACATCTACGTATTAG
TCATCGCTATTACCATGGTGATGCGGT
TTTGGCAGTACATCAATGGGCGTGGAT
AGCGGTTTGACTCACGGGGATTTCCAA
GTCTCCACCCCATTGACGTCAATGGGA
GTTTGTTTTGGCACCAAAATCAACGGG
ACTTTCCAAAATGTCGTAACAACTCCGC
CCCATTGACGCAAATGGGCGGTAGGCG
TGTACGGTGGGAGGTCTATATAAGCAG
AGCTCTCTGGCTAACTAGAGAACCCAC
TGCTTACTGGCTTATCGAAATTAATACG
ACTCACTATAGGGAGACCCAAGCTGGC
TAGCacc*ATGGACTACAAAGACCATGACGGT*
*GATTATAAAGATCATGACATCGATTACAAGGA*
*TGACGATGACAAGATGGCCCCC*aagaagaagag
gaaggtgggcatcaccgcggggtacctatggtggacttgaggac
actcggttattcgcatcagcaacaggagataatcaagcctaagg
tcaggagcaccgtcgcgcaacaccacgaggcgcttgtggggcat
ggcttcactcatgcgcatattgtcgcgcttcacagcaccctgcggc
gcttgggacggtggctgtcaaatacccaagatatgattgcggccctg
cccgaagccacgcacgaggcaattgtaggggtcggtaaacagt
ggtcgggagcgcgagcacttgaggcgctgctgactgtggcgggt
gagcttaggggggcctccgctccagctcgacaccgggcagctgct
gaagatcgcgaagagaggggagtaacagcggtagaggcagt
gcacgcctggcgcaatgcgctcaccggggccccctt*GAACCT*
*GACCCCAGACCAGGTAGTCGCAATCGCGTC*
*ACATGACGGGGAAAGCAAGCCCTGGAAAC*
*CGTGCAAAGGTTGTTGCCGGTCCTTTGTCAA*
*GACCACGGCCTTACACCGGAGCAAGTCGTG*
*GCCATTGCAAGCAATGGGGGTGGCAAACAG*
*GCTCTTGAGACGGTTCAGAGACTTCTCCAG*
*TTCTCTGTCAAGCCCACGGGCTGACTCCCGA*
*TCAAGTTGTAGCGATTGCGTCGCATGACGGA*
*GGGAAACAAGCATTGGAGACTGTCCAACGG*
*CTCCTTCCCGTGTTGTGTCAAGCCCACGGTT*
*TGACGCCTGCACAAGTGGTCGCCATCGCCT*
*CGAATGGCGGCGGTAAGCAGGCGCTGGAAA*
*CAGTACAGCGCCTGCTGCCTGTACTGTGCC*
*AGGATCATGGA*ctgacccagaccaggtagtcgcaatcg
cgaacaataatgggggaaagcaagccctggaaaccgtgcaaa
ggttgttgccggtccttgtcaagaccacggcctacaccggagca
agtcgtggccattgcaaataataacggtggcaaacaggctcttga
gacggtcagagacttctcccagttctctgtcaagcccacggg*CT*
*GACTCCCGATCAAGTTGTAGCGATTGCGTCC*
*AACGGTGGAGGGAAACAAGCATTGGAGACT*

FIG. 15 CONT.

```
GTCCAACGGCTCCTTCCCGTGTTGTGTCAAG
CCCACGGTTTGACGCCTGCACAAGTGGTCG
CCATCGCCTCGAATGGCGGCGGTAAGCAGG
CGCTGGAAACAGTACAGCGCCTGCTGCCTG
TACTGTGCCAGGATCATGGActgactcccgatcaag
tgtagcgattgcgtcgaacattggagggaaacaagcattggaga
ctgtccaacggctccttcccgtgttgtgtcaagcccacggtcttaca
ccggagcaagtcgtggccattgcaaataataacggtggcaaaca
ggctcttgagacggtcagagacttctcccagttctgtcaagccc
acgggctgactcccgatcaagttgtagcgattgcgtcgaacattgg
agggaaacaagcattggagactgtccaacggctccttcccgtgtt
gtgtcaagcccacggtTTGACGCCTGCACAAGTGGT
CGCCATCGCCAGCCATGATGGCGGTAAGCA
GGCGCTGGAAACAGTACAGCGCCTGCTGCC
TGTACTGTGCCAGGATCATGGACTGACCCCA
GACCAGGTAGTCGCAATCGCGTCACATGAC
GGGGGAAAGCAAGCCCTGGAAACCGTGCAA
AGGTTGTTGCCGGTCCTTTGTCAAGACCACG
GCcttacaccggagcaagtcgtggccattgaagcaacatcggt
ggcaaacaggctcttgagacggtcagagacttctcccagttctct
gtcaagcccacgggctgactcccgatcaagttgtagcgattgcga
ataacaatggagggaaacaagcattggagactgtccaacggctc
cttcccgtgttgtgtcaagcccacggttgacgcctgcacaagtggt
cgccatcgcctccaatattggcgggtaagcaggcgctggaaacagt
acagcgctgctgcctgtactgtgccaggatcatggaCTGACC
CCAGACCAGGTAGTCGCAATCGCGTCAAAC
GGAGGGGGAAAGCAAGCCCTGGAAACCGTG
CAAAGGTTGTTGCCGGTCCTTTGTCAAGACC
ACGGCCTTACACCGGAGCAAGTCGTGGCCA
TTGCATCCCACGACGGTGGCAAACAGGCTC
TTGAGACGGTTCAGAGACTTCTCCCAGTTCT
CTGTCAAGCCCACGGGctgacaccccgaacaggtggtc
gccattgcttctaatgggggaggacggccagccttggagtccatc
gtagcccaatgtccaggcccgatcccgcgttggctgcgttaacga
atgaccatctggtggcgttggcatgtcttggtggacgacccgcgct
cgatgcagtcaaaatagggtctgcctcatgctcccgcattgatcaa
aagaaccaaccggcggattcccgagagaacttcccatcgagtcg
cgggaTCCCAACTAGTCAAAAGTGAACTGGAG
GAGAAGAAATCTGAACTTCGTCATAAATTGAA
ATATGTGCCTCATGAATATATTGAATTAATTG
AAATTGCCAGAAATTCCACTCAGGATAGAATT
CTTGAAATGAAGGTAATGGAATTTTTTATGAA
AGTTTATGGATATAGAGGTAAACATTTGGGT
GGATCAAGGAAACCGGACGGAGCAATTTATA
CTGTCGGATCTCCTATTGATTACGGTGTGAT
CGTGGATACTAAAGCTTATAGCGGAGGTTAT
AATCTGCCAATTGGCCAAGCAGATGAAATGC
AACGATATGTCGAAGAAAATCAAACACGAAA
CAAACATATCAACCCTAATGAATGGTGGAAA
GTCTATCCATCTTCTGTAACGGAATTTAAGTT
```

FIG. 15 CONT.

*TTTATTTGTGAGTGGTCACTTTAAAGGAAACT*
*ACAAAGCTCAGCTTACACGATTAAATCATATC*
*ACTAATTGTAATGGAGCTGTTCTTAGTGTAGA*
*AGAGCTTTTAATTGGTGGAGAAATGATTAAA*
*GCCGGCACATTAACCTTAGAGGAAGTCAGAC*
*GGAAATTTAATAACGGCGAGATAAACTTTTA*
AGGGCCCTTCGAAGGTAAGCCTATCCC
TAACCCTCTCCTCGGTCTCGATTCTACG
CGTACCGGTCATCATCACCATCACCATT
GAGTTTAAACCCGCTGATCAGCCTCGA
CTGTGCCTTCTAGTTGCCAGCCATCTGT
TGTTTGCCCCTCCCCGTGCCTTCCTTG
ACCCTGGAAGGTGCCACTCCCACTGTC
CTTTCCTAATAAAATGAGGAAATTGCAT
CGCATTGTCTGAGTAGGTGTCATTCTAT
TCTGGGGGGTGGGGTGGGGCAGGACA
GCAAGGGGGAGGATTGGGAAGACAATA
GCAGGCATGCTGGGGATGCGGTGGGCT
CTATGGCTTCTGAGGCGGAAAGAACCA
GCTGGGGCTCTAGGGGGTATCCCCACG
CGCCCTGTAGCGGCGCATTAAGCGCGG
CGGGTGTGGTGGTTACGCGCAGCGTGA
CCGCTACACTTGCCAGCGCCCTAGCGC
CCGCTCCTTTCGCTTTCTTCCCTTCCTT
TCTCGCCACGTTCGCCGGCTTTCCCCG
TCAAGCTCTAAATCGGGGCATCCCTTT
AGGGTTCCGATTAGTGCTTTACGGCAC
CTCGACCCCAAAAAACTTGATTAGGGT
GATGGTTCACGTAGTGGGCCATCGCCC
TGATAGACGGTTTTTCGCCCTTTGACGT
TGGAGTCCACGTTCTTTAATAGTGGAC
TCTTGTTCCAAACTGGAACAACACTCAA
CCCTATCTCGGTCTATTCTTTTGATTTA
TAAGGGATTTTGGGGATTTCGGCCTAT
TGGTTAAAAATGAGCTGATTTAACAA
AAATTTAACGCGAATTAATTCTGTGGAA
TGTGTGTCAGTTAGGGTGTGGAAAGTC
CCCAGGCTCCCCAGGCAGGCAGAAGTA
TGCAAAGCATGCATCTCAATTAGTCAG
CAACCAGGTGTGGAAAGTCCCCAGGCT
CCCCAGCAGGCAGAAGTATGCAAAGCA
TGCATCTCAATTAGTCAGCAACCATAGT
CCCGCCCCTAACTCCGCCCATCCCGCC
CCTAACTCCGCCCAGTTCCGCCCATTCT
CCGCCCCATGGCTGACTAATTTTTTTA
TTTATGCAGAGGCCGAGGCCGCCTCTG
CCTCTGAGCTATTCCAGAAGTAGTGAG
GAGGCTTTTTTGGAGGCCTAGGCTTTT
GCAAAAAGCTCCCGGGAGCTTGTATAT
CCATTTTCGGATCTGATCAGCACGTGTT

FIG. 15 CONT.

```
GACAATTAATCATCGGCATAGTATATC
GGCATAGTATAATACGACAAGGTGAGG
AACTAAACCATGGCCAAGCCTTTGTCT
CAAGAAGAATCCACCCTCATTGAAAGA
GCAACGGCTACAATCAACAGCATCCCC
ATCTCTGAAGACTACAGCGTCGCCAGC
GCAGCTCTCTAGCGACGGCCGCATC
TTCACTGGTGTCAATGTATATCATTTTA
CTGGGGACCTTGTGCAGAACTCGTGG
TGCTGGGCACTGCTGCTGCGGCAG
CTGGCAACCTGACTTGTATCGTCGCGA
TCGGAAATGAGAACAGGGGCATCTTGA
GCCCCTGCGGACGGTGTCGACAGGTGC
TTCTCGATCTGCATCCTGGGATCAAAG
CGATAGTGAAGGACAGTGATGGACAGC
CGACGGCAGTTGGGATTCGTGAATTGC
TGCCCTCTGGTTATGTGTGGGAGGGCT
AAGCACTTCGTGGCCGAGGAGCAGGAC
TGACACGTGCTACGAGATTTCGATTCC
ACCGCCGCCTTCTATGAAAGGTTGGGC
TTCGGAATCGTTTTCCGGGACGCCGGC
TGGATGATCCTCCAGCGCGGGGATCTC
ATGCTGGAGTTCTTCGCCCACCCCAAC
TTGTTTATTGCAGCTTATAATGGTTACA
AATAAAGCAATAGCATCACAAATTTCAC
AAATAAAGCATTTTTTTCACTGCATTCT
AGTTGTGGTTTGTCCAAACTCATCAATG
TATCTTATCATGTCTGTATACCGTCGAC
CTCTAGCTAGAGCTTGGCGTAATCATG
GTCATAGCTGTTTCCTGTGTGAAATTGT
TATCCGCTCACAATTCCACACAACATAC
GAGCCGGAAGCATAAAGTGTAAAGCCT
GGGGTGCCTAATGAGTGAGCTAACTCA
CATTAATTGCGTTGCGCTCACTGCCCG
CTTTCCAGTCGGGAAACCTGTCGTGCC
AGCTGCATTAATGAATCGGCCAACGCG
CGGGGAGAGGCGGTTTGCGTATTGGGC
GCTCTTCCGCTTCCTCGCTCACTGACTC
GCTGCGCTCGGTCGTTCGGCTGCGGCG
AGCGGTATCAGCTCACTCAAAGGCGGT
AATACGGTTATCCACAGAATCAGGGGA
TAACGCAGGAAAGAACATGTGAGCAAA
AGGCCAGCAAAAGGCCAGGAACCGTAA
AAAGGCCGCGTTGCTGGCGTTTTTCCA
TAGGCTCCGCCCCCTGACGAGCATCA
CAAAAATCGACGCTCAAGTCAGAGGTG
GCGAAACCCGACAGGACTATAAAGATA
CCAGGCGTTTCCCCCTGGAAGCTCCCT
CGTGCGCTCTCCTGTTCCGACCCTGCC
GCTTACCGGATACCTGTCCGCCTTTCTC
```

FIG. 15 CONT.

| | | |
|---|---|---|
| | ACTGATCTTCAGCATCTTTTACTTTCAC CAGCGTTTCTGGGTGAGCAAAAACAGG AAGGCAAAATGCCGCAAAAAGGGAAT AAGGGCGACACGGAAATGTTGAATACT CATACTCTTCCTTTTTCAATATTATTGA AGCATTTATCAGGGTTATTGTCTCATGA GCGGATACATATTTGAATGTATTTAGAA AAATAAACAAATAGGGGTTCCGCGCAC ATTTCCCCGAAAAGTGCCACCTGACGT C | |
| 30 | ATGGACTACAAAGACCATGACGGTGAT TATAAGATCATGACATCGATTACAAG GATGACGATGACAAGATGGCCCCaagaa gaagaggaaggtgggcattcaccgcggggtacctatggtggacttg aggacactcggttattcgcaacagcaacaggagaaaatcaagccta aggtcaggagcaccgtcgcgcaacaccacgaggcgcttgtgggg catggcttcactcatgcgcatattgtcgcgctttcacagcaccctgcg gcgcttgggacggtggctgtcaaataccaagatatgattgcggccct gcccgaagccacgcacgaggcaattgtaggggtcggtaaacagtg gtcgggagcgcgagcacttgaggcgctgctgactgtggcgggtga gcttaggggggcctccgctccagctcgacaccggcagctgctgaa gatcgcgaagagagggggagtaacagcggtagaggcagtgcacg cctggcgcaatgcgctcaccggggcccccttGAACCTGAC CCCAGACCAGGTAGTCGCAATCGCGTCAC ATGACGGGGAAAGCAAGCCCTGGAAAC CGTGCAAAGGTTGTTGCCGGTCCTTTGTC AAGACCACGGCCTTACACCGGAGCAAGTC GTGGCCATTGCAAGCAATGGGGGTGGCAAA CAGGCTCTTGAGACGGTTCAGAGACTTCTCC CAGTTCTCTGTCAAGCCCACGGGCTGACTC CCGATCAAGTTGTAGCGATTGCGTCGCAT GACGGAGGGAAACAAGCATTGGAGACTG TCCAACGGCTCCTTCCCGTGTTGTGTCAA GCCCACGGTTTGACGCCTGCACAAGTGGTC GCCATCGCCTCGAATGGCGGCGGTAAGCAG GCGCTGGAAACAGTACAGCGCCTGCTGCCT GTACTGTGCCAGGATCATGGActgacccagacca ggtagtcgcaatcgcgaacaataatgggggaaagcaagccctg gaaaccgtgcaaaggttgttgccggtccttgtcaagaccacgg ccttacaccggagcaagtcgtggccattgcaaataataacggtg gcaaacaggctcttgagacggttcagagacttctcccagttctct gtcaagcccacgggCTGACTCCCGATCAAGTTGTA GCGATTGCGTCCAACGGTGGAGGGAAACAA GCATTGGAGACTGTCCAACGGCTCCTTCCC GTGTTGTGTCAAGCCCACGGTTTGACGCCTG CACAAGTGGTCGCCATCGCCTCGAATGGCG GCGGTAAGCAGGCGCTGGAAACAGTACAGC GCCTGCTGCCTGTACTGTGCCAGGATCATG GActgactcccgatcaagttgtagcgattgcgtcgaacattggagg gaacaagcattggagactgtccaacggctccttcccgtgttgtgtca | 5'TALEN (in JDS78) Constructs T256/T258 |

FIG. 15 CONT.

agccacggtcttacaccggagcaagtcgtggccattgcaaata
ataacggtggcaaacaggctcttgagacggttcagagacttctc
ccagttctctgtcaagcccacggg*ctgactcccgatcaagttgtag
cgattgcgtcgaacattggagggaaacaagcattggagactgtcca
acggctccttcccgtgttgtcaagcccacgg*TTGACGCC
TGCACAAGTGGTCGCCATCGCCAGCCATG
ATGGCGGTAAGCAGGCGCTGGAAACAGT
ACAGCGCCTGCTGCCTGTACTGTGCCAGG
ATCATGGACTGACCCCAGACCAGGTAGTC
GCAATCGCGTCACATGACGGGGAAAGC
AAGCCCTGGAAACCGTGCAAAGGTTGTTG
CCGGTCCTTTGTCAAGACCACGGC*cttacaccg
gagcaagtcgtggccattgcaagcaacatcgtggcaaacaggctc
ttgagacggttcagagacttctcccagtctctgtcaagcccacgggc
**tgactcccgatcaagttgtagcgattgcgaataacaatggaggg
aaacaagcattggagactgtccaacggctccttcccgtgttgtgt
caagcccacgg**tttgacgcctgcacaagtggtcgccatcgcctca
atattggcggtaagcaggcgctggaaacagtacagcgctgctgcc
tgtactgtgccaggatcatgga*CTGACCCCAGACCAGG
TAGTCGCAATCGCGTCAAACGGAGGGGGAA
AGCAAGCCCTGGAAACCGTGCAAAGGTTGTT
GCCGGTCCTTTGTCAAGACCACGGCCTTAC
ACCGGAGCAAGTCGTGGCCATTGCATCCC
ACGACGGTGGCAAACAGGCTCTTGAGAC
GGTTCAGAGACTTCTCCCAGTTCTCTGTC
AAGCCCACGGC*ctgacacccgaacaggtggtcgccattg
cttctaatgggggaggacggccagccttggagtccatcgtagccca
attgtccaggcccgatcccgcgttggctgcgttaacgaatgaccatct
ggtggcgttggcatgtcttggtggacgacccgcgctcgatgcagtc
aaaaagggtctgcctcatgctcccgcattgatcaaaagaaccaaccg
gcggattcccgagagaacttccatcgagtcgcggga*TCCCA
ACTAGTCAAAAGTGAACTGGAGGAGAAGA
AATCTGAACTTCGTCATAAATTGAAATATG
TGCCTCATGAATATATTGAATTAATTGAAA
TTGCCAGAAATTCCACTCAGGATAGAATTC
TTGAAATGAAGGTAATGGAATTTTTTATGA
AAGTTTATGGATATAGAGGTAAACATTTGG
GTGGATCAAGGAAACCGGACGGAGCAATT
TATACTGTCGGATCTCCTATTGATTACGGT
GTGATCGTGGATACTAAAGCTTATAGCGG
AGGTTATAATCTGCCAATTGGCCAAGCAGA
TGAAATGCAACGATATGTCGAAGAAAATCA
AACACGAAACAAACATATCAACCCTAATGA
ATGGTGGAAAGTCTATCCATCTTCTGTAAC
GGAATTTAAGTTTTATTTGTGAGTGGTCA
CTTTAAAGGAAACTACAAAGCTCAGCTTAC
ACGATTAAATCATATCACTAATTGTAATGG
AGCTGTTCTTAGTGTAGAAGAGCTTTTAAT
TGGTGGAGAAATGATTAAAGCCGGCACAT
TAACCTTAGAGGAAGTCAGACGGAAATTTA*

FIG. 15 CONT.

| | *ATAACGGCGAGATAAACTTTTAA* | |
|---|---|---|
| 31 | GAACCTGACCCCAGACCAGGTAGTCGCA<br>ATCGCGTCACATGACGGGGGAAAGCAAG<br>CCCTGGAAACCGTGCAAAGGTTGTTGCCG<br>GTCCTTTGTCAAGACCACGGCCTTACACC<br>GGAGCAAGTCGTGGCCATTGCAAGCAAT<br>GGGGGTGGCAAACAGGCTCTTGAGACGG<br>TTCAGAGACTTCTCCCAGTTCTCTGTCAA<br>GCCCACGGGCTGACTCCCGATCAAGTTGT<br>AGCGATTGCGTCGCATGACGGAGGGAAA<br>CAAGCATTGGAGACTGTCCAACGGCTCCT<br>TCCCGTGTTGTGTCAAGCCCACGGTTTGA<br>CGCCTGCACAAGTGGTCGCCATCGCCTCG<br>AATGGCGGCGGTAAGCAGGCGCTGGAAA<br>CAGTACAGCGCCTGCTGCCTGTACTGTGC<br>CAGGATCATGGACTGACCCCAGACCAGGT<br>AGTCGCAATCGCGAACAATTCGGGGGA<br>AAGCAAGCCCTGGAAACCGTGCAAAGGT<br>TGTTGCCGGTCCTTTGTCAAGACCACGGC<br>CTTACACCGGAGCAAGTCGTGGCCATTGC<br>AAATAATAACGGTGGCAAACAGGCTCTTG<br>AGACGGTTCAGAGACTTCTCCCAGTTCTC<br>TGTCAAGCCCACGGGCTGACTCCCGATCA<br>AGTTGTAGCGATTGCGTCCAACGGTGGAG<br>GGAAACAAGCATTGGAGACTGTCCAACG<br>GCTCCTTCCCGTGTTGTGTCAAGCCCACG<br>GTTTGACGCCTGCACAAGTGGTCGCCATC<br>GCCTCGAATTCGGGCGGTAAGCAGGCGC<br>TGGAAACAGTACAGCGCCTGCTGCCTGTA<br>CTGTGCCAGGATCATGGACTGACCCCAGA<br>CCAGGTAGTCGCAATCGCGTCGAACATTG<br>GGGGAAAGCAAGCCCTGGAAACCGTGCA<br>AAGGTTGTTGCCGGTCCTTTGTCAAGACC<br>ACGGCCTTACACCGGAGCAAGTCGTGGCC<br>ATTGCAAATAATAACGGTGGCAAACAGG<br>CTCTTGAGACGGTTCAGAGACTTCTCCCA<br>GTTCTCTGTCAAGCCCACGGGCTGACTCC<br>CGATCAAGTTGTAGCGATTGCGTCGAACA<br>TTGGAGGGAAACAAGCATTGGAGACTGT<br>CCAACGGCTCCTTCCCGTGTTGTGTCAAG<br>CCCACGGTTTGACGCCTGCACAAGTGGTC<br>GCCATCGCCAGCCATGATGGCGGTAAGCA<br>GGCGCTGGAAACAGTACAGCGCCTGCTGC<br>CTGTACTGTGCCAGGATCATGGACTGACC<br>CCAGACCAGGTAGTCGCAATCGCGTCACA<br>TGACGGGGGAAAGCAAGCCCTGGAAACC<br>GTGCAAAGGTTGTTGCCGGTCCTTTGTCA<br>AGACCACGGCCTTACACCGGAGCAAGTC<br>GTGGCCATTGCAAGCAACATCGGTGGCAA<br>ACAGGCTCTTGAGACGGTTCAGAGACTTC | TALE component of mutant clone; does not include FokI; T259 mutant |

FIG. 15 CONT.

```
TCCCAGTTCTCTGTCAAGCCCACGGGCTG
ACTCCCGATCAAGTTGTAGCGATTGCGAA
TAACAATGGAGGGAAACAAGCATTGGAG
ACTGTCCAACGGCTCCTTCCCGTGTTGTGT
CAAGCCCACGGTTTGACGCCTGCACAAGT
GGTCGCCATCGCCTCCAATATTGGCGGTA
AGCAGGCGCTGGAAACAGTACAGCGCCT
GCTGCCTGTACTGTGCCAGGATCATGGAC
TGACCCCAGACCAGGTAGTCGCAATCGCG
TCAAACGGAGGGGGAAAGCAAGCCCTGG
AAACCGTGCAAAGGTTGTTGCCGGTCCTT
TGTCAAGACCACGGCCTTACACCGGAGCA
AGTCGTGGCCATTGCATCCAATTCGGTG
GCAAACAGGCTCTTGAGACGGTTCAGAG
ACTTCTCCCAGTTCTCTGTCAAGCCCACG
GG
```

FIG. 15 CONT.

SEQUENCE LISTING

```
<160> NUMBER OF SEQ ID NOS: 55

<210> SEQ ID NO 1
<211> LENGTH: 20
<212> TYPE: DNA
<213> ORGANISM: Human immunodeficiency virus

<400> SEQUENCE: 1
tctctggtta gaccagatct                                              20

<210> SEQ ID NO 2
<211> LENGTH: 17
<212> TYPE: DNA
<213> ORGANISM: Human immunodeficiency virus

<400> SEQUENCE: 2
taactaggga acccact                                                 17

<210> SEQ ID NO 3
<211> LENGTH: 22
<212> TYPE: DNA
```

```
<213> ORGANISM: Artificial Sequence
<220> FEATURE:
<223> OTHER INFORMATION: 3' TALE binding target

<400> SEQUENCE: 3
taagcactgg gttccctagt ta                                              22

<210> SEQ ID NO 4
<211> LENGTH: 20
<212> TYPE: DNA
<213> ORGANISM: Artificial Sequence
<220> FEATURE:
<223> OTHER INFORMATION: 5' TALE binding mutant

<400> SEQUENCE: 4
tctctagtca gaccagatca                                                 20

<210> SEQ ID NO 5
<211> LENGTH: 20
<212> TYPE: DNA
<213> ORGANISM: Artificial Sequence
<220> FEATURE:
<223> OTHER INFORMATION: 5' TALE binding mutant

<400> SEQUENCE: 5
tctctagtca gaccagatcc                                                 20

<210> SEQ ID NO 6
<211> LENGTH: 20
<212> TYPE: DNA
<213> ORGANISM: Artificial Sequence
<220> FEATURE:
<223> OTHER INFORMATION: 5' TALE binding mutant

<400> SEQUENCE: 6
tctcttgtca gaccagatca                                                 20

<210> SEQ ID NO 7
<211> LENGTH: 20
<212> TYPE: DNA
<213> ORGANISM: Artificial Sequence
<220> FEATURE:
<223> OTHER INFORMATION: 5'TALE binding mutant

<400> SEQUENCE: 7
tctcttgtca gaccagatcc                                                 20

<210> SEQ ID NO 8
<211> LENGTH: 7
<212> TYPE: PRT
<213> ORGANISM: Artificial Sequence
<220> FEATURE:
<223> OTHER INFORMATION: Nuclear localization signal (NLS)

<400> SEQUENCE: 8

Pro Lys Lys Lys Arg Lys Val
1               5

<210> SEQ ID NO 9
<211> LENGTH: 20
<212> TYPE: DNA
<213> ORGANISM: Artificial Sequence
<220> FEATURE:
<223> OTHER INFORMATION: Spacer sequence

<400> SEQUENCE: 9
```

```
gagcctggga gctctctggc                                                  20

<210> SEQ ID NO 10
<211> LENGTH: 20
<212> TYPE: DNA
<213> ORGANISM: Artificial Sequence
<220> FEATURE:
<223> OTHER INFORMATION: Spacer sequence

<400> SEQUENCE: 10
ctcggaccct cgagagaccg                                                  20

<210> SEQ ID NO 11
<211> LENGTH: 672
<212> TYPE: DNA
<213> ORGANISM: Artificial Sequence
<220> FEATURE:
<223> OTHER INFORMATION: T256/T258 5'TALEN FokI Gblock ELD.Sharkey

<400> SEQUENCE: 11
gtcgcgggat cccaactagt caaaagtgaa ctggaggaga agaaatctga acttcgtcat       60
aaattgaaat atgtgcctca tgaatatatt gaattaattg aaattgccag aaatcccact     120
caggatagaa ttcttgaaat gaaggtaatg gaattttta tgaaagttta tggatataga     180
ggtgagcatt tgggtggatc aaggaaaccg gacggagcaa tttatactgt cggatctcct     240
attgattacg gtgtgatcgt ggatactaaa gcttatagcg gaggttataa tctgccaatt     300
ggccaagcag atgaaatgga gcgatatgtc gaagaaaatc aaacacgaga caaacatctg     360
aaccctaatg aatggtggaa agtctatcca tcttctgtaa cggaatttaa gttttattt    420 gtgagtggtc actttaaagg aaactacaaa gctcagctta cacgattaaa tcatatcact     480
aattgtaatg gagctgttct tagtgtagaa gagcttttaa ttggtggaga aatgattaaa     540
gccggcacat taaccttaga ggaagtcaga cggaaattta ataacggcga gataaacttt     600
taagggccct tcgaaggtaa gcctatccct aaccctctcc tcggtctcga ttctacgcgt     660
accggtcatc at                                                        672

<210> SEQ ID NO 12
<211> LENGTH: 672
<212> TYPE: DNA
<213> ORGANISM: Artificial Sequence
<220> FEATURE:
<223> OTHER INFORMATION: T278 3'TALEN FokI Gblock (672bps) KKR.Sharkey

<400> SEQUENCE: 12
gtcgcgggat cccaactagt caaaagtgaa ctggaggaga agaaatctga acttcgtcat       60
aaattgaaat atgtgcctca tgaatatatt gaattaattg aaattgccag aaatcccact     120
caggatagaa ttcttgaaat gaaggtaatg gaattttta tgaaagttta tggatataga     180
ggtgagcatt tgggtggatc aaggaaaccg gacggagcaa tttatactgt cggatctcct     240
attgattacg gtgtgatcgt ggatactaaa gcttatagcg gaggttataa tctgccaatt     300
ggccaagcag atgaaatgca acgatatgtc aaggaaaatc aaacacgaaa caacatatc     360 aaccctaatg aatggtggaa agtctatcca tcttctgtaa cggaatttaa gttttattt    420 gtgagtggtc actttaaagg aaactacaaa gctcagctta cacgattaaa tcggaagact     480
aattgtaatg gagctgttct tagtgtagaa gagcttttaa ttggtggaga aatgattaaa     540
gccggcacat taaccttaga ggaagtcaga cggaaattta ataacggcga gataaacttt     600
taagggccct tcgaaggtaa gcctatccct aaccctctcc tcggtctcga ttctacgcgt     660
```
accggtcatc at					672

<210> SEQ ID NO 13
<211> LENGTH: 234
<212> TYPE: PRT
<213> ORGANISM: Artificial Sequence
<220> FEATURE:
<223> OTHER INFORMATION: T256/T258 5' TALEN FokI ELD Sharkey Amino Acid
      Sequence; shaded portion refers to the protein coding region open
      reading frame

<400> SEQUENCE: 13

Val Ala Gly Ser Gln Leu Val Lys Ser Glu Leu Glu Glu Lys Lys Ser
1               5                   10                  15

Glu Leu Arg His Lys Leu Lys Tyr Val Pro His Glu Tyr Ile Glu Leu
            20                  25                  30

Ile Glu Ile Ala Arg Asn Pro Thr Gln Asp Arg Ile Leu Glu Met Glu
        35                  40                  45

Thr Lys Val Met Glu Thr Glu Phe Phe Met Glu Thr Lys Val Tyr Gly
    50                  55                  60

Tyr Arg Gly Glu His Leu Gly Gly Ser Arg Lys Pro Asp Gly Ala Ile
65                  70                  75                  80

Tyr Thr Val Gly Ser Pro Ile Asp Tyr Gly Val Ile Val Asp Thr Lys
                85                  90                  95

Ala Tyr Ser Gly Gly Tyr Asn Leu Pro Ile Gly Gln Ala Asp Glu Met
            100                 105                 110

Glu Thr Glu Arg Tyr Val Glu Glu Asn Gln Thr Arg Asp Lys His Leu
        115                 120                 125

Asn Pro Asn Glu Trp Trp Lys Val Tyr Pro Ser Ser Val Thr Glu Phe
    130                 135                 140

Lys Phe Leu Phe Val Ser Gly His Phe Lys Gly Asn Tyr Lys Ala Gln
145                 150                 155                 160

Leu Thr Arg Leu Asn His Ile Thr Asn Cys Asn Gly Ala Val Leu Ser
                165                 170                 175

Val Glu Glu Leu Leu Ile Gly Gly Glu Met Glu Thr Ile Lys Ala Gly
            180                 185                 190

Thr Leu Thr Leu Glu Glu Val Arg Arg Lys Phe Asn Asn Gly Glu Ile
        195                 200                 205

Asn Phe Leu Gly Pro Phe Glu Gly Lys Pro Ile Pro Asn Pro Leu Leu
    210                 215                 220

Gly Leu Asp Ser Thr Arg Thr Gly His His
225                 230

<210> SEQ ID NO 14
<211> LENGTH: 234
<212> TYPE: PRT
<213> ORGANISM: Artificial Sequence
<220> FEATURE:
<223> OTHER INFORMATION: T278 3' TALEN FokI KKR Sharkey Amino Acid
      Sequence; shaded portion refers to the protein coding region open
      reading frame

<400> SEQUENCE: 14

Val Ala Gly Ser Gln Leu Val Lys Ser Glu Leu Glu Glu Lys Lys Ser
1               5                   10                  15

Glu Leu Arg His Lys Leu Lys Tyr Val Pro His Glu Tyr Ile Glu Leu
            20                  25                  30

Ile Glu Ile Ala Arg Asn Pro Thr Gln Asp Arg Ile Leu Glu Met Glu

```
            35                  40                  45
Thr Lys Val Met Glu Thr Glu Phe Phe Met Glu Thr Lys Val Tyr Gly
 50                  55                  60

Tyr Arg Gly Glu His Leu Gly Gly Ser Arg Lys Pro Asp Gly Ala Ile
 65                  70                  75                  80

Tyr Thr Val Gly Ser Pro Ile Asp Tyr Gly Val Ile Val Asp Thr Lys
                 85                  90                  95

Ala Tyr Ser Gly Gly Tyr Asn Leu Pro Ile Gly Gln Ala Asp Glu Met
                100                 105                 110

Glu Thr Gln Arg Tyr Val Lys Glu Asn Gln Thr Arg Asn Lys His Ile
            115                 120                 125

Asn Pro Asn Glu Trp Trp Lys Val Tyr Pro Ser Ser Val Thr Glu Phe
130                 135                 140

Lys Phe Leu Phe Val Ser Gly His Phe Lys Gly Asn Tyr Lys Ala Gln
145                 150                 155                 160

Leu Thr Arg Leu Asn Arg Lys Thr Asn Cys Asn Gly Ala Val Leu Ser
                165                 170                 175

Val Glu Glu Leu Leu Ile Gly Gly Glu Met Glu Thr Ile Lys Ala Gly
            180                 185                 190

Thr Leu Thr Leu Glu Glu Val Arg Arg Lys Phe Asn Asn Gly Glu Ile
        195                 200                 205

Asn Phe Leu Gly Pro Phe Glu Lys Pro Ile Pro Asn Pro Leu Leu
210                 215                 220

Gly Leu Asp Ser Thr Arg Thr Gly His His
225                 230

<210> SEQ ID NO 15
<211> LENGTH: 21
<212> TYPE: DNA
<213> ORGANISM: Artificial Sequence
<220> FEATURE:
<223> OTHER INFORMATION: forward primer U3BamHI75F

<400> SEQUENCE: 15
cagctggatc ctgattggca g                                              21

<210> SEQ ID NO 16
<211> LENGTH: 23
<212> TYPE: DNA
<213> ORGANISM: Artificial Sequence
<220> FEATURE:
<223> OTHER INFORMATION: reverse primer GagSalI804Rev

<400> SEQUENCE: 16
gggtgcgaga gcgtcgacga cgg                                            23

<210> SEQ ID NO 17
<211> LENGTH: 23
<212> TYPE: DNA
<213> ORGANISM: Artificial Sequence
<220> FEATURE:
<223> OTHER INFORMATION: randomized reverse primer; Random5'siteRev
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
```

```
<222> LOCATION: (22)..(22)
<223> OTHER INFORMATION: n is a, c, g, or t

<400> SEQUENCE: 17
caggctcnna tctggtcnnn cna                                              23

<210> SEQ ID NO 18
<211> LENGTH: 23
<212> TYPE: DNA
<213> ORGANISM: Artificial Sequence
<220> FEATURE:
<223> OTHER INFORMATION: randomized forward primer; Random5'siteFor
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 18
ctctngnnng accagatnng agc                                              23

<210> SEQ ID NO 19
<211> LENGTH: 28
<212> TYPE: DNA
<213> ORGANISM: Artificial Sequence
<220> FEATURE:
<223> OTHER INFORMATION: forward primer pBSNY5For

<400> SEQUENCE: 19
ggcatgctcg agctcagatg ctgcatat                                         28

<210> SEQ ID NO 20
<211> LENGTH: 27
<212> TYPE: DNA
<213> ORGANISM: Artificial Sequence
<220> FEATURE:
<223> OTHER INFORMATION: reverse primer pBSNY5Rev

<400> SEQUENCE: 20
catgcctcta gaagtgggtt ccctagc                                          27

<210> SEQ ID NO 21
<211> LENGTH: 3210
<212> TYPE: DNA
<213> ORGANISM: Artificial Sequence
<220> FEATURE:
<223> OTHER INFORMATION: 5'TALEN.ELD.Sharkey DNA sequence (From start
      codon to stop codon)

<400> SEQUENCE: 21
atggactaca aagaccatga cggtgattat aaagatcatg acatcgatta caaggatgac       60
gatgacaaga tggccccccaa gaagaagagg aaggtgggca ttcaccgcgg ggtacctatg     120
gtggacttga ggacactcgg ttattcgcaa cagcaacagg agaaaatcaa gcctaaggtc     180
aggagcaccg tcgcgcaaca ccacgaggcg cttgtggggc atggcttcac tcatgcgcat     240
attgtcgcgc tttcacagca ccctgcggcg cttgggacgg tggctgtcaa ataccaagat     300
atgattgcgg ccctgcccga agccacgcac gaggcaattg taggggtcgg taaacagtgg     360
tcgggagcgc gagcacttga ggcgctgctg actgtggcgg gtgagcttag ggggcctccg     420
```

| | | | |
|---|---|---|---|
| ctccagctcg | acaccgggca gctgctgaag atcgcgaaga gagggggagt aacagcggta | 480 |
| gaggcagtgc | acgcctggcg caatgcgctc accggggccc ccttgaacct gaccccagac | 540 |
| caggtagtcg | caatcgcgtc acatgacggg ggaaagcaag ccctggaaac cgtgcaaagg | 600 |
| ttgttgccgg | tcctttgtca agaccacggc cttacaccgg agcaagtcgt ggccattgca | 660 |
| agcaatgggg | gtggcaaaca ggctcttgag acggttcaga gacttctccc agttctctgt | 720 |
| caagcccacg | ggctgactcc cgatcaagtt gtagcgattc gtcgcatga cggagggaaa | 780 |
| caagcattgg | agactgtcca acggctcctt cccgtgttgt gtcaagccca cggtttgacg | 840 |
| cctgcacaag | tggtcgccat cgcctcgaat ggcggcggta agcaggcgct ggaaacagta | 900 |
| cagcgcctgc | tgcctgtact gtgccaggat catggactga ccccagacca ggtagtcgca | 960 |
| atcgcgaaca | ataatggggg aaagcaagcc tggaaaccg tgcaaaggtt gttgccggtc | 1020 |
| ctttgtcaag | accacggcct acaccggag caagtcgtgg ccattgcaaa taataacggt | 1080 |
| ggcaaacagg | ctcttgagac ggttcagaga cttctcccag ttctctgtca agcccacggg | 1140 |
| ctgactcccg | atcaagttgt agcgattgcg tccaacggtg agggaaaca agcattggag | 1200 |
| actgtccaac | ggctccttcc cgtgttgtgt caagcccacg gtttgacgcc tgcacaagtg | 1260 |
| gtcgccatcg | cctcgaatgg cggcggtaag caggcgctgg aaacagtaca gcgcctgctg | 1320 |
| cctgtactgt | gccaggatca tggactgact cccgatcaag ttgtagcgat gcgtcgaac | 1380 |
| attggaggga | aacaagcatt ggagactgtc caacggctcc ttcccgtgtt gtgtcaagcc | 1440 |
| cacggtctta | caccgagca agtcgtggcc attgcaaata ataacggtgg caaacaggct | 1500 |
| cttgagacgg | ttcagagact ctcccagtt ctctgtcaag cccacgggct gactcccgat | 1560 |
| caagttgtag | cgattgcgtc gaacattgga gggaaacaag cattggagac tgtccaacgg | 1620 |
| ctccttcccg | tgttgtgtca gcccacggt ttgacgcctg cacaagtggt cgccatcgcc | 1680 |
| agccatgatg | gcggtaagca ggcgctggaa acagtacagc gcctgctgcc tgtactgtgc | 1740 |
| caggatcatg | gactgacccc agaccaggta gtcgcaatcg cgtcacatga cggggggaaag | 1800 |
| caagccctgg | aaaccgtgca aaggttgttg ccggtccttt gtcaagacca cggccttaca | 1860 |
| ccggagcaag | tcgtggccat tgcaagcaac atcggtggca acaggctct tgagacggtt | 1920 |
| cagagacttc | tcccagttct ctgtcaagcc cacgggctga ctcccgatca agttgtagcg | 1980 |
| attgcgaata | caatggagg gaaacaagca ttggagactg tccaacggct ccttcccgtg | 2040 |
| ttgtgtcaag | cccacggttt gacgcctgca caagtggtcg ccatcgcctc caatattggc | 2100 |
| ggtaagcagg | cgctggaaac agtacagcgc ctgctgcctg tactgtgcca ggatcatgga | 2160 |
| ctgaccccag | accaggtagt cgcaatcgcg tcaaacggag ggggaaagca agccctggaa | 2220 |
| accgtgcaaa | ggttgttgcc ggtcctttgt caagaccacg ccttacacc ggagcaagtc | 2280 |
| gtggccattg | catcccacga cggtggcaaa caggctcttg agacggttca gagacttctc | 2340 |
| ccagttctct | gtcaagccca cgggctgaca cccgaacagg tggtcgccat tgcttctaat | 2400 |
| gggggaggac | ggccagcctt ggagtccatc gtagcccaat tgtccaggcc cgatcccgcg | 2460 |
| ttggctgcgt | taacgaatga ccatctggtg gcgttggcat gtcttggtgg acgaccgcg | 2520 |
| ctcgatgcag | tcaaaaaggg tctgcctcat gctcccgcat tgatcaaaag aaccaaccgg | 2580 |
| cggattcccg | agagaacttc ccatcgagtc gcgggatccc aactagtcaa aagtgaactg | 2640 |
| gaggagaaga | aatctgaact tcgtcataaa ttgaaatatg tgcctcatga atatattgaa | 2700 |
| ttaattgaaa | ttgccagaaa tcccactcag gatagaattc ttgaaatgaa ggtaatggaa | 2760 |

| | |
|---|---|
| tttttttatga aagtttatgg atatagaggt gagcatttgg gtggatcaag gaaaccggac | 2820 |
| ggagcaattt atactgtcgg atctcctatt gattacggtg tgatcgtgga tactaaagct | 2880 |
| tatagcggag gttataatct gccaattggc caagcagatg aaatggagcg atatgtcgaa | 2940 |
| gaaaatcaaa cacgagacaa acatctgaac cctaatgaat ggtggaaagt ctatccatct | 3000 |
| tctgtaacgg aatttaagtt tttatttgtg agtggtcact ttaaaggaaa ctacaaagct | 3060 |
| cagcttacac gattaaatca tatcactaat tgtaatggag ctgttcttag tgtagaagag | 3120 |
| cttttaattg gtggagaaat gattaaagcc ggcacattaa ccttagagga agtcagacgg | 3180 |
| aaatttaata acggcgagat aaacttttaa | 3210 |

```
<210> SEQ ID NO 22
<211> LENGTH: 7359
<212> TYPE: DNA
<213> ORGANISM: Artificial Sequence
<220> FEATURE:
<223> OTHER INFORMATION: JDS78 (with 5'TALEN.ELD.Sharkey)

<400> SEQUENCE: 22
```

| | |
|---|---|
| atggactaca aagaccatga cggtgattat aaagatcatg acatcgatta caaggatgac | 60 |
| gatgacaaga tggcccccaa gaagaagagg aaggtgggca ttcaccgcgg ggtacctatg | 120 |
| gtggacttga ggacactcgg ttattcgcaa cagcaacagg agaaaatcaa gcctaaggtc | 180 |
| aggagcaccg tcgcgcaaca ccacgaggcg cttgtggggc atggcttcac tcatgcgcat | 240 |
| attgtcgcgc tttcacagca ccctgcggcg cttgggacgg tggctgtcaa ataccaagat | 300 |
| atgattgcgc ccctgcccga agccacgcac gaggcaattg taggggtcgg taaacagtgg | 360 |
| tcgggagcgc gagcacttga ggcgctgctg actgtggcgg gtgagcttag ggggcctccg | 420 |
| ctccagctcg acaccgggca gctgctgaag atcgcgaaga gaggggggagt aacagcggta | 480 |
| gaggcagtgc acgcctggcg caatgcgctc accggggccc ccttgaacct gaccccagac | 540 |
| caggtagtcg caatcgcgtc acatgacggg ggaaagcaag ccctggaaac cgtgcaaagg | 600 |
| ttgttgccgg tcctttgtca agaccacggc cttacaccgg agcaagtcgt ggccattgca | 660 |
| agcaatgggg gtggcaaaca ggctcttgag acggttcaga gacttctccc agttctctgt | 720 |
| caagcccacg ggctgactcc cgatcaagtt gtagcgattg cgtcgcatga cggagggaaa | 780 |
| caagcattgg agactgtcca acggctcctt ccegtgttgt gtcaagccca cggtttgacg | 840 |
| cctgcacaag tggtcgccat cgcctcgaat ggcggcggta agcaggcgct ggaaacagta | 900 |
| cagcgcctgc tgcctgtact gtgccaggat catggactga ccccagacca ggtagtcgca | 960 |
| atcgcgaaca ataatggggg aaagcaagcc ctggaaaccg tgcaaaggtt gttgccggtc | 1020 |
| ctttgtcaag accacggcct tacaccggag caagtcgtgg ccattgcaaa taataacggt | 1080 |
| ggcaaacagg ctcttgagac ggttcagaga cttctcccag ttctctgtca gcccacgggg | 1140 |
| ctgactcccg atcaagttgt agcgattgcg tccaacggtg agggaaaca agcattggag | 1200 |
| actgtccaac ggctccttcc cgtgttgtgt caagcccacg gtttgacgcc tgcacaagtg | 1260 |
| gtcgccatcg cctcgaatgg cggcggtaag caggcgctgg aaacagtaca gcgcctgctg | 1320 |
| cctgtactgt gccaggatca tggactgact cccgatcaag ttgtagcgat tgcgtcgaac | 1380 |
| attggaggga acaagcatt ggagactgtc aacggctccc ttccegtgtt gtgtcaagcc | 1440 |
| cacggtctta caccggagca agtcgtggcc attgcaaata ataacggtgg caaacaggct | 1500 |
| cttgagacgt tcagagact tctcccagtt ctctgtcaag cccacgggct gactcccgat | 1560 |
| caagttgtag cgattgcgtc gaacattgga gggaaacaag cattggagac tgtccaacgg | 1620 |

```
ctccttcccg tgttgtgtca agcccacggt ttgacgcctg cacaagtggt cgccatcgcc   1680
agccatgatg gcggtaagca ggcgctggaa acagtacagc gcctgctgcc tgtactgtgc   1740
caggatcatg gactgacccc agaccaggta gtcgcaatcg cgtcacatga cggggggaaag  1800 caagccctgg aaaccgtgca aaggttgttg ccggtccttt gtcaagacca cggccttaca   1860
ccggagcaag tcgtggccat tgcaagcaac atcggtggca acaggctct tgagacggtt    1920 cagagacttc tcccagttct ctgtcaagcc cacgggctga ctcccgatca agttgtagcg   1980
attgcgaata caatggagg gaaacaagca ttggagactg tccaacggct ccttcccgtg    2040
ttgtgtcaag cccacggttt gacgcctgca caagtggtcg ccatcgcctc caatattggc   2100
ggtaagcagg cgctggaaac agtacagcgc ctgctgcctg tactgtgcca ggatcatgga   2160
ctgaccccag accaggtagt cgcaatcgcg tcaaacggag ggggaaagca agccctggaa   2220
accgtgcaaa ggttgttgcc ggtcctttgt caagaccacg ccttacacc ggagcaagtc    2280 gtggccattg catcccacga cggtggcaaa caggctcttg agacggttca gagacttctc   2340
ccagttctct gtcaagccca cgggctgaca cccgaacagg tggtcgccat tgcttctaat   2400
gggggaggac ggccagcctt ggagtccatc gtagcccaat tgtccaggcc cgatcccgcg   2460
ttggctgcgt taacgaatga ccatctggtg gcgttggcat gtcttggtgg acgacccgcg   2520
ctcgatgcag tcaaaaaggg tctgcctcat gctcccgcat tgatcaaaag aaccaaccgg   2580
cggattcccg agagaacttc ccatcgagtc gcgggatccc aactagtcaa aagtgaactg   2640
gaggagaaga aatctgaact tcgtcataaa ttgaaatatg tgcctcatga atatattgaa   2700
ttaattgaaa ttgccagaaa tcccactcag gatagaattc ttgaaatgaa ggtaatggaa   2760
ttttttatga agtttatgg atatagaggt gagcatttgg gtggatcaag gaaaccggac    2820
ggagcaattt atactgtcgg atctcctatt gattacggtg tgatcgtgga tactaaagct   2880
tatagcggag gttataatct gccaattggc caagcagatg aaatgagcg atatgtcgaa   2940 gaaaatcaaa cacgagacaa acatctgaac cctaatgaat ggtggaaagt ctatccatct   3000
tctgtaacgg aatttaagtt tttatttgtg agtggtcact ttaaaggaaa ctacaaagct   3060
cagcttacac gattaaatca tatcactaat tgtaatggag ctgttcttag tgtagaagag   3120
cttttaattg gtggagaaat gattaaagcc ggcacattaa ccttagagga agtcagacgg   3180
aaatttaata acgcgagat aaactttta gggcccttcg aaggtaagcc tatccctaac    3240
cctctcctcg gtctcgattc tacgcgtacc ggtcatcatc accatcacca ttgagtttaa   3300
acccgctgat cagcctcgac tgtgccttct agttgccagc catctgttgt ttgccctcc    3360 cccgtgcctt ccttgaccct ggaaggtgcc actcccactg tcctttccta ataaaatgag   3420
gaaattgcat cgcattgtct gagtaggtgt cattctattc tggggggtgg ggtggggcag   3480
gacagcaagg gggaggattg ggaagacaat agcaggcatg ctgggatgc ggtgggctct    3540 atggcttctg aggcggaaag aaccagctgg ggctctaggg ggtatcccca cgcgccctgt   3600
agcggcgcat taagcgcggc gggtgtggtg gttacgcgca gcgtgaccgc tacacttgcc   3660
agcgccctag cgcccgctcc tttcgctttc ttcccttcct ttctcgccac gttcgccggc   3720
tttccccgtc aagctctaaa tcggggcatc cctttagggt tccgatttag tgctttacgg   3780
cacctcgacc ccaaaaaact tgattagggt gatggttcac gtagtgggcc atcgccctga   3840
tagacggttt ttcgcccttt gacgttggag tccacgttct ttaatagtgg actcttgttc   3900
caaactggaa caacactcaa ccctatctcg gtctattctt ttgatttata agggatttg    3960
```

```
gggatttcgg cctattggtt aaaaaatgag ctgatttaac aaaaatttaa cgcgaattaa    4020
ttctgtggaa tgtgtgtcag ttagggtgtg aaagtcccc  aggctcccca ggcaggcaga    4080
agtatgcaaa gcatgcatct caattagtca gcaaccaggt gtggaaagtc cccaggctcc    4140
ccagcaggca gaagtatgca aagcatgcat ctcaattagt cagcaaccat agtcccgccc    4200
ctaactccgc ccatcccgcc cctaactccg cccagttccg cccattctcc gccccatggc    4260
tgactaattt tttttattta tgcagaggcc gaggccgcct ctgcctctga gctattccag    4320
aagtagtgag gaggcttttt tggaggccta ggcttttgca aaaagctccc gggagcttgt    4380
atatccattt tcggatctga tcagcacgtg ttgacaatta atcatcggca tagtatatcg    4440
gcatagtata atacgacaag gtgaggaact aaaccatggc caagcctttg tctcaagaag    4500
aatccaccct cattgaaaga gcaacggcta caatcaacag catccccatc tctgaagact    4560
acagcgtcgc cagcgcagct ctctctagcg acggccgcat cttcactggt gtcaatgtat    4620
atcattttac tgggggacct tgtgcagaac tcgtggtgct gggcactgct gctgctgcgg    4680
cagctggcaa cctgacttgt atcgtcgcga tcggaaatga gaacagggc  atcttgagcc    4740 cctgcggacg tgtcgacag  gtgcttctcg atctgcatcc tgggatcaaa gcgatagtga    4800
aggacagtga tggacagccg acggcagttg ggattcgtga attgctgccc tctggttatg    4860
tgtgggaggg ctaagcactt cgtggccgag gagcaggact gacacgtgct acgagatttc    4920
gattccaccg ccgccttcta tgaaaggttg gcttcggaa  tcgttttccg ggacgccggc    4980
tggatgatcc tccagcgcgg ggatctcatg ctggagttct cgcccacccc caacttgttt    5040
attgcagctt ataatggtta caaataaagc aatagcatca caaatttcac aaataaagca    5100 ttttttttcac tgcattctag ttgtggtttg tccaaactca tcaatgtatc ttatcatgtc    5160
tgtataccgt cgacctctag ctagagcttg gcgtaatcat ggtcatagct gtttcctgtg    5220
tgaaattgtt atccgctcac aattccacac aacatacgag ccggaagcat aaagtgtaaa    5280
gcctggggtg cctaatgagt gagctaactc acattaattg cgttgcgctc actgcccgct    5340
ttccagtcgg gaaacctgtc gtgccagctg cattaatgaa tcggccaacg cgcggggaga    5400
ggcggtttgc gtattgggcg ctcttccgct tcctcgctca ctgactcgct gcgctcggtc    5460
gttcggctgc ggcgagcggt atcagctcac tcaaaggcgg taatacggtt atccacagaa    5520 tcagggga ta acgcaggaaa gaacatgtga gcaaaaggcc agcaaaaggc caggaaccgt    5580
aaaaaggccg cgttgctggc gtttttccat aggctccgcc cccctgacga gcatcacaaa    5640
aatcgacgct caagtcagag gtggcgaaac ccgacaggac tataaagata ccaggcgttt    5700
ccccctggaa gctccctcgt gcgctctcct gttccgaccc tgccgcttac cggatacctg    5760
tccgcctttc tcccttcggg aagcgtggcg ctttctcaat gctcacgctg taggtatctc    5820
agttcggtgt aggtcgttcg ctccaagctg ggctgtgtgc acgaacccc  cgttcagccc    5880 gaccgctgcg ccttatccgg taactatcgt cttgagtcca acccggtaag acacgactta    5940
tcgccactgg cagcagccac tggtaacagg attagcagag cgaggtatgt aggcggtgct    6000
acagagttct tgaagtggtg gcctaactac ggctacacta aaggacagt  atttggtatc    6060 tgcgctctgc tgaagccagt taccttcgga aaaagagttg gtagctcttg atccggcaaa    6120
caaaccaccg ctggtagcgg tggttttttt gtttgcaagc agcagattac gcgcagaaaa    6180
aaaggatctc aagaagatcc tttgatcttt tctacggggt ctgacgctca gtggaacgaa    6240
aactcacgtt aagggatttt ggtcatgaga ttatcaaaaa ggatcttcac ctagatcctt    6300
ttaaattaaa aatgaagttt taaatcaatc taaagtatat atgagtaaac ttggtctgac    6360
```

```
agttaccaat gcttaatcag tgaggcacct atctcagcga tctgtctatt tcgttcatcc    6420
atagttgcct gactcccgt cgtgtagata actacgatac gggagggctt accatctggc    6480
cccagtgctg caatgatacc gcgagaccca cgctcaccgg ctccagattt atcagcaata   6540
aaccagccag ccggaagggc cgagcgcaga agtggtcctg caactttatc cgcctccatc   6600
cagtctatta attgttgccg ggaagctaga gtaagtagtt cgccagttaa tagtttgcgc   6660
aacgttgttg ccattgctac aggcatcgtg gtgtcacgct cgtcgtttgg tatggcttca   6720
ttcagctccg gttcccaacg atcaaggcga gttacatgat cccccatgtt gtgcaaaaaa   6780
gcggttagct ccttcggtcc tccgatcgtt gtcagaagta agttggccgc agtgttatca   6840
ctcatggtta tggcagcact gcataattct cttactgtca tgccatccgt aagatgcttt   6900
tctgtgactg gtgagtactc aaccaagtca ttctgagaat agtgtatgcg gcgaccgagt   6960
tgctcttgcc cggcgtcaat acgggataat accgcgccac atagcagaac tttaaaagtg   7020
ctcatcattg gaaaacgttc ttcggggcga aaactctcaa ggatcttacc gctgttgaga   7080
tccagttcga tgtaacccac tcgtgcaccc aactgatctt cagcatcttt tactttcacc   7140
agcgtttctg ggtgagcaaa aacaggaagg caaaatgccg caaaaaaggg aataagggcg   7200
acacggaaat gttgaatact catactcttc cttttttcaat attattgaag catttatcag   7260
ggttattgtc tcatgagcgg atacatattt gaatgtattt agaaaaataa acaaataggg   7320
gttccgcgca catttccccg aaaagtgcca cctgacgtc                          7359

<210> SEQ ID NO 23
<211> LENGTH: 6447
<212> TYPE: DNA
<213> ORGANISM: Artificial Sequence
<220> FEATURE:
<223> OTHER INFORMATION: JDS78

<400> SEQUENCE: 23
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
accatggact acaagacca tgacggtgat tataaagatc atgacatcga ttacaaggat    960
gacgatgaca agatggcccc caagaagaag aggaaggtgg gcattcaccg cggggtacct   1020
```

```
atggtggact tgaggacact cggttattcg caacagcaac aggagaaaat caagcctaag    1080
gtcaggagca ccgtcgcgca acaccacgag gcgcttgtgg ggcatggctt cactcatgcg    1140
catattgtcg cgctttcaca gcaccctgcg gcgcttggga cggtggctgt caaataccaa    1200
gatatgattc cggccctgcc cgaagccacg cacgaggcaa ttgtaggggt cggtaaacag    1260
tggtcgggag cgcgagcact tgaggcgctg ctgactgtgg cgggtgagct tagggggcct    1320
ccgctccagc tcgacaccgg gcagctgctg aagatcgcga agagagggg agtaacagcg    1380 gtagaggcag tgcacgcctg cgcaatgcg ctcaccgggg ccccttgaa cagagacgat    1440 taatgcgtct cgctgacacc cgaacaggtg gtcgccattg cttctaatgg gggaggacgg    1500
ccagccttgg agtccatcgt agcccaattg tccaggcccg atcccgcgtt ggctgcgtta    1560
acgaatgacc atctggtggc gttggcatgt cttggtggac gacccgcgct cgatgcagtc    1620
aaaaagggtc tgcctcatgc tcccgcattg atcaaaagaa ccaaccggcg gattcccgag    1680
agaacttccc atcgagtcgc gggatcccaa ctagtcaaaa gtgaactgga ggagaagaaa    1740
tctgaacttc gtcataaatt gaaatatgtg cctcatgaat atattgaatt aattgaaatt    1800
gccagaaatt ccactcagga tagaattctt gaaatgaagg taatggaatt ttttatgaaa    1860
gtttatggat atagaggtaa acatttgggt ggatcaagga aaccgacgg agcaatttat    1920 actgtcggat ctcctattga ttacggtgtg atcgtggata ctaaagctta tagcggaggt    1980
tataatctgc caattggcca agcagatgaa atgcaacgat atgtcgaaga aaatcaaaca    2040
cgaaacaaac atatcaaccc taatgaatgg tggaaagtct atccatcttc tgtaacggaa    2100
tttaagtttt tatttgtgag tggtcacttt aaaggaaact acaaagctca gcttacacga    2160
ttaaatcata tcactaattg taatggagct gttcttagtg tagaagagct tttaattggt    2220
ggagaaatga ttaaagccgg cacattaacc ttagaggaag tcagacgaa atttaataac    2280 ggcgagataa acttttaagg gcccttcgaa ggtaagccta tccctaaccc tctcctcggt    2340
ctcgattcta cgcgtaccgg tcatcatcac catcaccatt gagtttaaac ccgctgatca    2400
gcctcgactg tgccttctag ttgccagcca tctgttgttt gcccctcccc cgtgccttcc    2460
ttgaccctgg aaggtgccac tcccactgtc ctttcctaat aaaatgagga aattgcatcg    2520
cattgtctga gtaggtgtca ttctattctg ggggtgggg tgggcagga cagcaagggg    2580 gaggattggg aagacaatag caggcatgct ggggatgcgg tgggctctat ggcttctgag    2640
gcggaaagaa ccagctgggg ctctagggg tatccccacg cgccctgtag cggcgcatta    2700
agcgcggcgg gtgtggtggt tacgcgcagc gtgaccgcta cacttgccag cgccctagcg    2760
cccgctcctt tcgctttctt cccttccttt ctcgccacgt tcgccggctt tccccgtcaa    2820
gctctaaatc gggcatccc tttagggttc gatttagtg ctttacggca cctcgacccc    2880 aaaaacttg attagggtga tggttcacgt agtgggccat cgccctgata acggttttt    2940 cgcccttga cgttggagtc cacgttcttt aatagtggac tcttgttcca aactggaaca    3000
acactcaacc ctatctcggt ctattctttt gatttataag ggattttggg gatttcggcc    3060
tattggttaa aaaatgagct gatttaacaa aaatttaacg cgaattaatt ctgtggaatg    3120
tgtgtcagtt agggtgtgga agtccccag gctccccagg caggcagaag tatgcaaagc    3180
atgcatctca attagtcagc aaccaggtgt ggaaagtccc caggctcccc agcaggcaga    3240
agtatgcaaa gcatgcatct caattagtca gcaaccatag tcccgcccct aactccgccc    3300
atcccgcccc taactccgcc cagttccgcc cattctccgc cccatggctg actaattttt    3360
tttatttatg cagaggccga ggccgcctct gcctctgagc tattccagaa gtagtgagga    3420
```

```
ggcttttttg gaggcctagg cttttgcaaa aagctcccgg gagcttgtat atccattttc   3480
ggatctgatc agcacgtgtt gacaattaat catcggcata gtatatcggc atagtataat   3540
acgacaaggt gaggaactaa accatggcca agcctttgtc tcaagaagaa tccaccctca   3600
ttgaaagagc aacggctaca atcaacagca tccccatctc tgaagactac agcgtcgcca   3660
gcgcagctct ctctagcgac ggccgcatct tcactggtgt caatgtatat cattttactg   3720
ggggaccttg tgcagaactc gtggtgctgg gcactgctgc tgctgcggca gctggcaacc   3780
tgacttgtat cgtcgcgatc ggaaatgaga acaggggcat cttgagcccc tgcggacggt   3840
gtcgacaggt gcttctcgat ctgcatcctg ggatcaaagc gatagtgaag acagtgatg    3900 gacagccgac ggcagttggg attcgtgaat tgctgccctc tggttatgtg tgggagggct   3960
aagcacttcg tggccgagga gcaggactga cacgtgctac gagatttcga ttccaccgcc   4020
gccttctatg aaaggttggg cttcggaatc gttttccggg acgccggctg gatgatcctc   4080
cagcgcggga tctcatgct ggagttcttc gcccacccca acttgtttat tgcagcttat    4140
aatggttaca aataaagcaa tagcatcaca aatttcacaa ataaagcatt ttttttcactg  4200 cattctagtt gtggtttgtc caaactcatc aatgtatctt atcatgtctg tataccgtcg   4260
acctctagct agagcttggc gtaatcatgg tcatagctgt ttcctgtgtg aaattgttat   4320
ccgctcacaa ttccacacaa catacgagcc ggaagcataa agtgtaaagc ctggggtgcc   4380
taatgagtga gctaactcac attaattgcg ttgcgctcac tgcccgcttt ccagtcggga   4440
aacctgtcgt gccagctgca ttaatgaatc ggccaacgcg cggggagagg cggtttgcgt   4500
attgggcgct cttccgcttc ctcgctcact gactcgctgc gctcggtcgt tcggctgcgg   4560
cgagcggtat cagctcactc aaaggcggta atacggttat ccacagaatc agggataac    4620 gcaggaaaga acatgtgagc aaaaggccag caaaaggcca ggaaccgtaa aaaggccgcg   4680
ttgctggcgt ttttccatag gctccgcccc cctgacgagc atcacaaaaa tcgacgctca   4740
agtcagaggt ggcgaaaccc gacaggacta taaagatacc aggcgtttcc ccctggaagc   4800
tccctcgtgc gctctcctgt tccgaccctg ccgcttaccg gatacctgtc cgcctttctc   4860
ccttcgggaa gcgtggcgct ttctcaatgc tcacgctgta ggtatctcag ttcggtgtag   4920
gtcgttcgct ccaagctggg ctgtgtgcac gaaccccccg ttcagcccga ccgctgcgcc   4980
ttatccggta actatcgtct tgagtccaac ccggtaagac acgacttatc gccactggca   5040
gcagccactg gtaacaggat tagcagagcg aggtatgtag gcggtgctac agagttcttg   5100
aagtggtggc ctaactacgg ctacactaga aggacagtat ttggtatctg cgctctgctg   5160
aagccagtta ccttcggaaa aagagttggt agctcttgat ccggcaaaca accaccgct    5220 ggtagcggtg gttttttgt ttgcaagcag cagattacgc gcagaaaaaa aggatctcaa    5280
gaagatcctt tgatctttc tacggggtct gacgctcagt ggaacgaaaa ctcacgttaa    5340
gggattttgg tcatgagatt atcaaaaagg atcttcacct agatcctttt aaattaaaaa   5400
tgaagtttta aatcaatcta agtatatat gagtaaactt ggtctgacag ttaccaatgc    5460
ttaatcagtg aggcacctat ctcagcgatc tgtctatttc gttcatccat agttgcctga   5520
ctccccgtcg tgtagataac tacgatacgg gagggcttac catctggccc cagtgctgca   5580
atgataccgc gagacccacg ctcaccggct ccagatttat cagcaataaa ccagccagcc   5640
ggaagggccg agcgcagaag tggtcctgca actttatccg cctccatcca gtctattaat   5700
tgttgccggg aagctagagt aagtagttcg ccagttaata gtttgcgcaa cgttgttgcc   5760
```

```
attgctacag gcatcgtggt gtcacgctcg tcgtttggta tggcttcatt cagctccggt    5820
tcccaacgat caaggcgagt tacatgatcc cccatgttgt gcaaaaaagc ggttagctcc    5880
ttcggtcctc cgatcgttgt cagaagtaag ttggccgcag tgttatcact catggttatg    5940
gcagcactgc ataattctct tactgtcatg ccatccgtaa gatgcttttc tgtgactggt    6000
gagtactcaa ccaagtcatt ctgagaatag tgtatgcggc gaccgagttg ctcttgcccg    6060
gcgtcaatac gggataatac cgcgccacat agcagaactt taaaagtgct catcattgga    6120
aaacgttctt cggggcgaaa actctcaagg atcttaccgc tgttgagatc cagttcgatg    6180
taacccactc gtgcacccaa ctgatcttca gcatctttta ctttcaccag cgtttctggg    6240
tgagcaaaaa caggaaggca aaatgccgca aaaagggaa taagggcgac acggaaatgt    6300
tgaatactca tactcttcct ttttcaatat tattgaagca tttatcaggg ttattgtctc    6360
atgagcggat acatatttga atgtatttag aaaaataaac aaataggggt tccgcgcaca    6420
tttccccgaa aagtgccacc tgacgtc                                        6447
```

<210> SEQ ID NO 24
<211> LENGTH: 3414
<212> TYPE: DNA
<213> ORGANISM: Artificial Sequence
<220> FEATURE:
<223> OTHER INFORMATION: 3'TALEN (in JDS70) Constructs T278

<400> SEQUENCE: 24

```
atggactaca agaccatga cggtgattat aaagatcatg acatcgatta caaggatgac     60
gatgacaaga tggccccccaa gaagaagagg aaggtgggca ttcaccgcgg ggtacctatg    120
gtggacttga ggacactcgg ttattcgcaa cagcaacagg agaaaatcaa gcctaaggtc    180
aggagcaccg tcgcgcaaca ccacgaggcg cttgtggggc atggcttcac tcatgcgcat    240
attgtcgcgc tttcacagca ccctgcggcg cttgggacgg tggctgtcaa ataccaagat    300
atgattgcgg ccctgcccga agccacgcac gaggcaattg taggggtcgg taaacagtgg    360
tcgggagcgc gagcacttga ggcgctgctg actgtggcgg gtgagcttag ggggcctccg    420
ctccagctcg acaccgggca gctgctgaag atcgcgaaga gaggggggagt aacagcggta    480 gaggcagtgc acgcctggcg caatgcgctc accggggccc ccttgaacct gaccccagac    540
caggtagtcg caatcgcgtc gaacattggg ggaaagcaag ccctggaaac cgtgcaaagg    600
ttgttgccgg tcctttgtca agaccacggc cttacaccgg agcaagtcgt ggccattgca    660
agcaacatcg gtggcaaaca ggctcttgag acggttcaga acttctcccc agttctctgt    720
caagcccacg gctgactcc cgatcaagtt gtagcgattg cgaataacaa tggagggaaa    780
caagcattgg agactgtcca acggctcctt cccgtgttgt gtcaagccca cggtttgacg    840
cctgcacaag tggtcgccat cgccagccat gatggcggta agcaggcgct ggaaacagta    900 cagccgcctgc tgcctgtact gtgccaggat catggactga cccagacca ggtagtcgca    960 atcgcgtcga acattgggg aaagcaagcc ctggaaccg tgcaaaggtt gttgccggtc    1020
ctttgtcaag accacggcct tacaccggag caagtcgtgg ccattgcaaa taataacggt    1080
ggcaaacagg ctcttgagac ggttcagaga cttctcccag ttctctgtca gcccacgggg    1140
ctgactcccg atcaagttgt agcgattgcg tccaacggtg agggaaaca agcattggag    1200 actgtccaac ggctccttcc cgtgttgtgt caagcccacg gtttgacgcc tgcacaagtg    1260
gtcgccatcg ccaacaacaa cggcggtaag caggcgctgg aaacagtaca cgcctgctg    1320 cctgtactgt gccaggatca tggactgacc ccagaccagg tagtcgcaat cgcgaacaat    1380
```

```
aatgggggaa agcaagccct ggaaaccgtg caaaggttgt tgccggtcct ttgtcaagac   1440
cacggcctta caccggagca agtcgtggcc attgcaaata ataacggtgg caaacaggct   1500
cttgagacgg ttcagagact tctcccagtt ctctgtcaag cccacgggct gactcccgat   1560
caagttgtag cgattgcgtc caacggtgga gggaaacaag cattggagac tgtccaacgg   1620
ctccttcccg tgttgtgtca agcccacggt tgacgcctg cacaagtggt cgccatcgcc   1680
tcgaatggcg gcggtaagca ggcgctggaa acagtacagc gcctgctgcc tgtactgtgc   1740
caggatcatg gactgacccc agaccaggta gtcgcaatcg cgtcacatga cggggggaaag   1800 caagccctgg aaaccgtgca aaggttgttg ccggtccttt gtcaagacca cggccttaca   1860
ccggagcaag tcgtggccat tgcatcccac gacggtggca acaggctct gagacggtt   1920 cagagacttc tcccagttct ctgtcaagcc cacgggctga ctcccgatca agttgtagcg   1980
attgcgtcgc atgacggagg gaaacaagca ttggagactg tccaacggct ccttcccgtg   2040
ttgtgtcaag cccacggttt gacgcctgca caagtggtcg ccatcgcctc gaatggcggc   2100
ggtaagcagg cgctggaaac agtacagcgc ctgctgcctg tactgtgcca ggatcatgga   2160
ctgaccccag accaggtagt cgcaatcgcg tcgaacattg ggggaaagca agccctggaa   2220
accgtgcaaa ggttgttgcc ggtcctttgt caagaccacg ccttacacc ggagcaagtc   2280 gtggccattg caaataataa cggtggcaaa caggctcttg agacggttca gagacttctc   2340
ccagttctct gtcaagccca cgggctgact cccgatcaag ttgtagcgat tgcgtccaac   2400
ggtgagggga acaagcatt ggagactgtc aacggctcc ttcccgtgtt gtgtcaagcc   2460
cacggtttga cgcctgcaca agtggtcgcc atcgcctcga atgcggcgg taagcaggcg   2520 ctggaaacag tacagcgcct gctgcctgta ctgtgccagg atcatggact gacacccgaa   2580
caggtggtcg ccattgcttc taacatcgga ggacggccag ccttggagtc catcgtagcc   2640
caattgtcca ggcccgatcc cgcgttggct gcgttaacga atgaccatct ggtggcgttg   2700
gcatgtcttg gtggacgacc cgcgctcgat gcagtcaaaa agggtctgcc tcatgctccc   2760
gcattgatca aaagaaccaa ccggcggatt cccgagagaa cttcccatcg agtcgcggga   2820
tcccaactag tcaaaagtga actggaggag aagaaatctg aacttcgtca taaattgaaa   2880
tatgtgcctc atgaatatat tgaattaatt gaaattgcca gaaattccac tcaggataga   2940
attcttgaaa tgaaggtaat ggaattttt atgaaagttt atggatatag aggtaaacat   3000
ttgggtggat caaggaaacc ggacggagca atttatactg tcggatctcc tattgattac   3060
ggtgtgatcg tggatactaa agcttatagc ggaggttata atctgccaat ggccaagca   3120 gatgaaatgc aacgatatgt cgaagaaaat caaacacgaa acaaacatat caaccctaat   3180
gaatggtgga aagtctatcc atcttctgta acggaattta agttttattt tgtgagtggt   3240
cactttaaag gaaactacaa agctcagctt acacgattaa atcatatcac taattgtaat   3300
ggagctgttc ttagtgtaga agagctttta attggtggag aaatgattaa agccggcaca   3360
ttaaccttag aggaagtcag acggaaattt aataacggcg agataaactt ttaa         3414
```

<210> SEQ ID NO 25
<211> LENGTH: 6447
<212> TYPE: DNA
<213> ORGANISM: Artificial Sequence
<220> FEATURE:
<223> OTHER INFORMATION: JDS70

<400> SEQUENCE: 25

-continued

```
gacggatcgg gagatctccc gatccccstat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacgggtc attagttcat agcccatata    300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacccta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
accatggact acaaagacca tgacggtgat tataaagatc atgacatcga ttacaaggat   960
gacgatgaca agatggcccc caagaagaag aggaaggtgg gcattcaccg cggggtacct  1020
atggtggact tgaggacact cggttattcg caacagcaac aggagaaaat caagcctaag  1080
gtcaggagca ccgtcgcgca acaccacgag gcgcttgtgg ggcatggctt cactcatgcg  1140
catattgtcg cgctttcaca gcaccctgcg gcgcttggga cggtggctgt caaataccaa  1200
gatatgattg cggccctgcc cgaagccacg cacgaggcaa ttgtaggggt cggtaaacag  1260
tggtcgggag cgcgagcact tgaggcgctg ctgactgtgg cgggtgagct tagggggcct  1320
ccgctccagc tcgacaccgg gcagctgctg aagatcgcga agagaggggg agtaacagcg  1380
gtagaggcag tgcacgcctg gcgcaatgcg ctcaccgggg cccccttgaa cagagacgat  1440
taatgcgtct cgctgacacc cgaacaggtg gtcgccattg cttctaacat cggaggacgg  1500
ccagccttgg agtccatcgt agcccaattg tccaggcccg atcccgcgtt ggctgcgtta  1560
acgaatgacc atctggtggc gttggcatgt cttggtggac gacccgcgct cgatgcagtc  1620
aaaaagggtc tgcctcatgc tcccgcattg atcaaaagaa ccaaccggcg gattcccgag  1680
agaacttccc atcgagtcgc gggatcccaa ctagtcaaaa gtgaactgga ggagaagaaa  1740
tctgaacttc gtcataaatt gaaatatgtg cctcatgaat atattgaatt aattgaaatt  1800
gccagaaatt ccactcagga tagaattctt gaaatgaagg taatgaatt ttttatgaaa   1860
gtttatggat atagaggtaa acatttgggt ggatcaagga aaccggacgg agcaatttat  1920
actgtcggat ctcctattga ttacggtgtg atcgtggata ctaaagctta tagcggaggt  1980
tataatctgc caattggcca agcagatgaa atgcaacgat atgtcgaaga aaatcaaaca  2040
cgaaacaaac atatcaaccc taatgaatgg tggaaagtct atccatcttc tgtaacggaa  2100
tttaagtttt tatttgtgag tggtcacttt aaaggaaact acaaagctca gcttacacga  2160
ttaaatcata tcactaattg taatggagct gttcttagtg tagaagagct tttaattggt  2220
ggagaaatga ttaaagccgg cacattaacc ttagaggaag tcagacggaa atttaataac  2280
ggcgagataa acttttaagg gcccttcgaa ggtaagccta tccctaaccc tctcctcggt  2340
ctcgattcta cgcgtaccgg tcatcatcac catcaccatt gagtttaaac ccgctgatca  2400
```

```
gcctcgactg tgccttctag ttgccagcca tctgttgttt gccctcccc cgtgccttcc    2460 ttgaccctgg aaggtgccac tcccactgtc ctttcctaat aaaatgagga aattgcatcg    2520
cattgtctga gtaggtgtca ttctattctg ggggtgggg tggggcagga cagcaagggg    2580
gaggattggg aagacaatag caggcatgct ggggatgcgg tgggctctat ggcttctgag    2640
gcggaaagaa ccagctgggg ctctaggggg tatccccacg cgccctgtag cggcgcatta    2700
agcgcggcgg gtgtggtggt tacgcgcagc gtgaccgcta cacttgccag cgccctagcg    2760
cccgctcctt tcgctttctt cccttccttt ctcgccacgt tcgccggctt tccccgtcaa    2820
gctctaaatc gggcatccc tttagggttc cgatttagtg cttttacggca cctcgacccc    2880 aaaaaacttg attagggtga tggttcacgt agtgggccat cgccctgata cggttttt    2940 cgcccttga cgttggagtc cacgttcttt aatagtggac tcttgttcca aactggaaca    3000
acactcaacc ctatctcggt ctattctttt gatttataag ggattttggg gatttcggcc    3060
tattggttaa aaatgagct gatttaacaa aatttaacg cgaattaatt ctgtggaatg    3120
tgtgtcagtt agggtgtgga agtcccccag ctccccagg caggcagaag tatgcaaagc    3180
atgcatctca attagtcagc aaccaggtgt ggaaagtccc caggctcccc agcaggcaga    3240
agtatgcaaa gcatgcatct caattagtca gcaaccatag tcccgcccct aactccgccc    3300
atcccgcccc taactccgcc cagttccgcc cattctccgc cccatggctg actaattttt    3360
tttatttatg cagaggccga ggccgcctct gcctctgagc tattccagaa gtagtgagga    3420
ggcttttttg gaggcctagg cttttgcaaa aagctcccgg gagcttgtat atccatttttc    3480 ggatctgatc agcacgtgtt gacaattaat catcggcata gtatatcggc atagtataat    3540
acgacaaggt gaggaactaa accatggcca agctttgtc tcaagaagaa tccaccctca    3600
ttgaaagagc aacggctaca atcaacagca tccccatctc tgaagactac agcgtcgcca    3660
gcgcagctct ctctagcgac ggccgcatct tcactggtgt caatgtatat cattttactg    3720
ggggaccttg tgcagaactc gtggtgctgg cactgctgc tgctgcggca gctggcaacc    3780
tgacttgtat cgtcgcgatc ggaaatgaga acagggcat cttgagcccc tgcggacggt    3840
gtcgacaggt gcttctcgat ctgcatcctg ggatcaaagc gatagtgaag gacagtgatg    3900
gacagccgac ggcagttggg attcgtgaat tgctgccctc tggttatgtg tgggaggct    3960 aagcacttcg tggccgagga gcaggactga cacgtgctac gagatttcga ttccaccgcc    4020
gccttctatg aaaggttggg cttcggaatc gttttccggg acgccggctg gatgatcctc    4080
cagcgcgggg atctcatgct ggagttcttc gcccacccca acttgtttat tgcagcttat    4140
aatggttaca ataaagcaa tagcatcaca aatttcacaa ataaagcatt ttttcactg    4200 cattctagtt gtggtttgtc caaactcatc aatgtatctt atcatgtctg tataccgtcg    4260
acctctagct agagcttggc gtaatcatgg tcatagctgt ttcctgtgtg aaattgttat    4320
ccgctcacaa ttccacacaa catacgagcc ggaagcataa agtgtaaagc ctggggtgcc    4380
taatgagtga gctaactcac attaattgcg ttgcgctcac tgcccgcttt ccagtcggga    4440
aacctgtcgt gccagctgca ttaatgaatc ggccaacgcg cggggagagg cggtttgcgt    4500
attgggcgct cttccgcttc ctcgctcact gactcgctgc gctcggtcgt tcggctgcgg    4560
cgagcggtat cagctcactc aaaggcggta atacggttat ccacagaatc aggggataac    4620
gcaggaaaga acatgtgagc aaaaggccag caaaaggcca ggaaccgtaa aaaggccgcg    4680
ttgctggcgt ttttccatag gctccgcccc cctgacgagc atcacaaaaa tcgacgctca    4740
```

| | |
|---|---|
| agtcagaggt ggcgaaaccc gacaggacta taaagatacc aggcgtttcc ccctggaagc | 4800 |
| tccctcgtgc gctctcctgt tccgaccctg ccgcttaccg gatacctgtc cgcctttctc | 4860 |
| ccttcgggaa gcgtggcgct ttctcaatgc tcacgctgta ggtatctcag ttcggtgtag | 4920 |
| gtcgttcgct ccaagctggg ctgtgtgcac gaaccccccg ttcagcccga ccgctgcgcc | 4980 |
| ttatccggta actatcgtct tgagtccaac ccggtaagac acgacttatc gccactggca | 5040 |
| gcagccactg gtaacaggat tagcagagcg aggtatgtag gcggtgctac agagttcttg | 5100 |
| aagtggtggc ctaactacgg ctacactaga aggacagtat ttggtatctg cgctctgctg | 5160 |
| aagccagtta ccttcggaaa aagagttggt agctcttgat ccggcaaaca aaccaccgct | 5220 |
| ggtagcggtg gttttttgt ttgcaagcag cagattacgc gcagaaaaaa aggatctcaa | 5280 |
| gaagatcctt tgatctttc tacggggtct gacgctcagt ggaacgaaaa ctcacgttaa | 5340 |
| gggattttgg tcatgagatt atcaaaaagg atcttcacct agatcctttt aaattaaaaa | 5400 |
| tgaagtttta aatcaatcta agtatatat gagtaaactt ggtctgacag ttaccaatgc | 5460 |
| ttaatcagtg aggcacctat ctcagcgatc tgtctatttc gttcatccat agttgcctga | 5520 |
| ctccccgtcg tgtagataac tacgatacgg gagggcttac catctggccc cagtgctgca | 5580 |
| atgataccgc gagacccacg ctcaccggct ccagatttat cagcaataaa ccagccagcc | 5640 |
| ggaagggccg agcgcagaag tggtcctgca actttatccg cctccatcca gtctattaat | 5700 |
| tgttgccggg aagctagagt aagtagttcg ccagttaata gtttgcgcaa cgttgttgcc | 5760 |
| attgctacag gcatcgtggt gtcacgctcg tcgtttggta tggcttcatt cagctccggt | 5820 |
| tcccaacgat caaggcgagt tacatgatcc cccatgttgt gcaaaaaagc ggttagctcc | 5880 |
| ttcggtcctc cgatcgttgt cagaagtaag ttggccgcag tgttatcact catggttatg | 5940 |
| gcagcactgc ataattctct tactgtcatg ccatccgtaa gatgcttttc tgtgactggt | 6000 |
| gagtactcaa ccaagtcatt ctgagaatag tgtatgcggc gaccgagttg ctcttgcccg | 6060 |
| gcgtcaatac gggataatac cgcgccacat agcagaactt taaaagtgct catcattgga | 6120 |
| aaacgttctt cggggcgaaa actctcaagg atcttaccgc tgttgagatc cagttcgatg | 6180 |
| taacccactc gtgcacccaa ctgatcttca gcatctttta ctttcaccag cgtttctggg | 6240 |
| tgagcaaaaa caggaaggca aaatgccgca aaaagggaa taagggcgac acggaaatgt | 6300 |
| tgaatactca tactcttcct ttttcaatat tattgaagca tttatcaggg ttattgtctc | 6360 |
| atgagcggat acatatttga atgtatttag aaaaataaac aaataggggt tccgcgcaca | 6420 |
| tttccccgaa aagtgccacc tgacgtc | 6447 |

<210> SEQ ID NO 26
<211> LENGTH: 8466
<212> TYPE: DNA
<213> ORGANISM: Artificial Sequence
<220> FEATURE:
<223> OTHER INFORMATION: JDS70 (with 3'TALEN)

<400> SEQUENCE: 26

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
accatggact acaaagacca tgacggtgat tataaagatc atgacatcga ttacaaggat    960
gacgatgaca agatggcccc caagaagaag aggaaggtgg gcattcaccg cggggtacct   1020
atggtggact tgaggacact cggttattcg caacagcaac aggagaaaat caagcctaag   1080
gtcaggagca ccgtcgcgca acaccacgag gcgcttgtgg ggcatggctt cactcatgcg   1140
catattgtcg cgcttttcaca gcaccctgcg gcgcttggga cggtggctgt caaataccaa   1200
gatatgattg cggccctgcc cgaagccacg cacgaggcaa ttgtaggggt cggtaaacag   1260
tggtcgggag cgcgagcact tgaggcgctg ctgactgtgg cgggtgagct tagggggcct   1320
ccgctccagc tcgacaccgg gcagctgctg aagatcgcga agagaggggg agtaacagcg   1380
gtagaggcag tgcacgcctg cgcaatgcg ctcaccgggg cccccttgaa cctgacccca   1440
gaccaggtag tcgcaatcgc gtcgaacatt ggggaaagc aagccctgga aaccgtgcaa   1500
aggttgttgc cggtcctttg tcaagaccac ggccttacac cggagcaagt cgtggccatt   1560
gcaagcaaca tcggtggcaa acaggctctt gagacggttc agagacttct cccagttctc   1620
tgtcaagccc acgggctgac tcccgatcaa gttgtagcga ttgcgaataa caatggaggg   1680
aaacaagcat tggagactgt ccaacggctc cttcccgtgt tgtgtcaagc ccacggtttg   1740
acgcctgcac aagtggtcgc catcgccagc catgatggcg gtaagcaggc gctggaaaca   1800
gtacagcgcc tgctgcctgt actgtgccag gatcatggac tgacccccaga ccaggtagtc   1860 gcaatcgcgt cgaacattgg gggaaagcaa gccctggaaa ccgtgcaaag gttgttgccg   1920
gtcctttgtc aagaccacgg ccttacaccg gagcaagtcg tggccattgc aaataataac   1980
ggtggcaaac aggctcttga gacggttcag agacttctcc cagttctctg tcaagcccac   2040
gggctgactc ccgatcaagt tgtagcgatt gcgtccaacg gtggagggaa caagcattg    2100 gagactgtcc aacggctcct tcccgtgttg tgtcaagccc acggtttgac gcctgcacaa   2160
gtggtcgcca tcgccaacaa caacggcggt aagcaggcgc tggaaacagt acagcgcctg   2220
ctgcctgtac tgtgccagga tcatggactg accccagacc aggtagtcgc aatcgcgaac   2280
aataatgggg aaagcaagc cctggaaacc gtgcaaaggt tgttgccggt cctttgtcaa   2340
gaccacggcc ttacaccgga gcaagtcgtg gccattgcaa ataataacgg tggcaaacag   2400
gctcttgaga cggttcagag acttctccca gttctctgtc aagcccacgg ctgactccc   2460 gatcaagttg tagcgattgc gtccaacggt ggagggaaa agcattgga gactgtccaa   2520 cggctccttc ccgtgttgtg tcaagcccac ggtttgacgc ctgcacaagt ggtcgccatc   2580
gcctcgaatg gcggcggtaa gcaggcgctg gaaacagtac agcgcctgct gcctgtactg   2640
tgccaggatc atggactgac cccagaccag gtagtcgcaa tcgcgtcaca tgacggggga   2700
```

```
aagcaagccc tggaaaccgt gcaaaggttg ttgccggtcc tttgtcaaga ccacggcctt    2760
acaccggagc aagtcgtggc cattgcatcc cacgacggtg gcaaacaggc tcttgagacg    2820
gttcagagac ttctcccagt tctctgtcaa gcccacgggc tgactcccga tcaagttgta    2880
gcgattgcgt cgcatgacgg agggaaacaa gcattggaga ctgtccaacg gctccttccc    2940
gtgttgtgtc aagcccacgg tttgacgcct gcacaagtgg tcgccatcgc ctcgaatggc    3000
ggcggtaagc aggcgctgga aacagtacag cgcctgctgc ctgtactgtg ccaggatcat    3060
ggactgaccc cagaccaggt agtcgcaatc gcgtcgaaca ttgggggaaa gcaagccctg    3120
gaaaccgtgc aaaggttgtt gccggtcctt tgtcaagacc acggcttac accggagcaa    3180 gtcgtggcca ttgcaaataa taacggtggc aaacaggctc ttgagacggt tcagagactt    3240
ctcccagttc tctgtcaagc ccacgggctg actcccgatc aagttgtagc gattgcgtcc    3300
aacggtggag ggaaacaagc attggagact gtccaacggc tccttcccgt gttgtgtcaa    3360
gcccacggtt tgacgcctgc acaagtggtc gccatcgcct cgaatggcgg cggtaagcag    3420
gcgctggaaa cagtacagcg cctgctgcct gtactgtgcc aggatcatgg actgacaccc    3480
gaacaggtgg tcgccattgc ttctaacatc ggaggacggc cagccttgga gtccatcgta    3540
gcccaattgt ccaggcccga tcccgcgttg gctgcgttaa cgaatgacca tctggtggcg    3600
ttggcatgtc ttggtggacg acccgcgctc gatgcagtca aaagggtct gcctcatgct    3660 cccgcattga tcaaaagaac caaccggcgg attcccgaga aacttccca tcgagtcgcg    3720 ggatcccaac tagtcaaaag tgaactggag gagaagaaat ctgaacttcg tcataaattg    3780
aaatatgtgc ctcatgaata tattgaatta attgaaattg ccagaaattc cactcaggat    3840
agaattcttg aaatgaaggt aatggaattt tttatgaaag tttatggata tagaggtaaa    3900
catttgggtg gatcaaggaa accggacgga gcaatttata ctgtcggatc tcctattgat    3960
tacggtgtga tcgtggatac taaagcttat agcggaggtt ataatctgcc aattggccaa    4020
gcagatgaaa tgcaacgata tgtcgaagaa aatcaaacac gaaacaaaca tatcaacccc    4080
aatgaatggt ggaaagtcta tccatcttct gtaacggaat ttaagttttt atttgtgagt    4140
ggtcacttta aaggaaacta caaagctcag cttacacgat taaatcatat cactaattgt    4200
aatggagctg ttcttagtgt agaagagctt ttaattggtg gagaaatgat taaagccggc    4260
acattaacct tagaggaagt cagacggaaa tttaataacg gcgagataaa ctttaagggg    4320
cccttcgaag gtaagcctat ccctaaccct ctcctcggtc tcgattctac gcgtaccggt    4380
catcatcacc atcaccattg agtttaaacc cgctgatcag cctcgactgt gccttctagt    4440
tgccagccat ctgttgtttg cccctccccc gtgccttcct tgaccctgga aggtgccact    4500
cccactgtcc tttcctaata aaatgaggaa attgcatcgc attgtctgag taggtgtcat    4560
tctattctgg ggggtgggt ggggcaggac agcaagggg aggattggga agacaatagc    4620
aggcatgctg gggatgcggt gggctctatg gcttctgagg cggaaagaac cagctggggc    4680
tctagggggt atccccacgc gccctgtagc ggcgcattaa gcgcggcggg tgtggtggtt    4740
acgcgcagcg tgaccgctac acttgccagc gccctagcgc ccgctccttt cgctttcttc    4800
ccttcctttc tcgccacgtt cgccggcttt cccgtcaag ctctaaatcg ggcatccct    4860 ttagggttcc gatttagtgc tttacggcac ctcgacccca aaaaacttga ttagggtgat    4920
ggttcacgta gtgggccatc gccctgatag acgttttc gcccttgac gttggagtcc    4980 acgttcttta atagtggact cttgttccaa actggaacaa cactcaaccc tatctcggtc    5040
tattcttttg atttataagg gattttgggg atttcggcct attggttaaa aaatgagctg    5100
```

```
atttaacaaa aatttaacgc gaattaattc tgtggaatgt gtgtcagtta gggtgtggaa    5160
agtccccagg ctccccaggc aggcagaagt atgcaaagca tgcatctcaa ttagtcagca    5220
accaggtgtg gaaagtcccc aggctcccca gcaggcagaa gtatgcaaag catgcatctc    5280
aattagtcag caaccatagt cccgcccta actccgccca tcccgcccct aactccgccc    5340
agttccgccc attctccgcc ccatggctga ctaatttttt ttatttatgc agaggccgag    5400
gccgcctctg cctctgagct attccagaag tagtgaggag gcttttttgg aggcctaggc    5460
ttttgcaaaa agctcccggg agcttgtata tccattttcg gatctgatca gcacgtgttg    5520
acaattaatc atcggcatag tatatcggca tagtataata cgacaaggtg aggaactaaa    5580
ccatggccaa gcctttgtct caagaagaat ccaccctcat tgaaagagca acggctacaa    5640
tcaacagcat ccccatctct gaagactaca gcgtcgccag cgcagctctc tctagcgacg    5700
gccgcatctt cactggtgtc aatgtatatc attttactgg gggaccttgt gcagaactcg    5760
tggtgctggg cactgctgct gctgcggcag ctggcaacct gacttgtatc gtcgcgatcg    5820
gaaatgagaa cagggggcatc ttgagccccct gcggacggtg tcgacaggtg cttctcgatc    5880
tgcatcctgg gatcaaagcg atagtgaagg acagtgatgg acagccgacg gcagttggga    5940
ttcgtgaatt gctgccctct ggttatgtgt gggagggcta agcacttcgt ggccgaggag    6000
caggactgac acgtgctacg agatttcgat tccaccgccg ccttctatga aaggttgggc    6060
ttcggaatcg ttttccggga cgccggctgg atgatcctcc agcgcgggga tctcatgctg    6120
gagttcttcg cccaccccaa cttgtttatt gcagcttata atggttacaa ataaagcaat    6180
agcatcacaa atttcacaaa taaagcattt ttttcactgc attctagttg tggtttgtcc    6240
aaactcatca atgtatctta tcatgtctgt ataccgtcga cctctagcta gagcttggcg    6300
taatcatggt catagctgtt tcctgtgtga aattgttatc cgctcacaat tccacacaac    6360
atacgagccg aagcataaa gtgtaaagcc tggggtgcct aatgagtgag ctaactcaca    6420
ttaattgcgt tgcgctcact gcccgctttc cagtcgggaa acctgtcgtg ccagctgcat    6480
taatgaatcg gccaacgcgc ggggagaggc ggtttgcgta ttgggcgctc ttccgcttcc    6540
tcgctcactg actcgctgcg ctcggtcgtt cggctgcggc gagcggtatc agctcactca    6600
aaggcggtaa tacggttatc cacagaatca ggggataacg caggaaagaa catgtgagca    6660
aaaggccagc aaaaggccag gaaccgtaaa aaggccgcgt tgctggcgtt tttccatagg    6720
ctccgccccc ctgacgagca tcacaaaaat cgacgctcaa gtcagaggtg gcgaaacccg    6780
acaggactat aaagatacca ggcgtttccc cctggaagct ccctcgtgcg ctctcctgtt    6840
ccgaccctgc cgcttaccgg atacctgtcc gcctttctcc cttcgggaag cgtggcgctt    6900
tctcaatgct cacgctgtag gtatctcagt tcggtgtagg tcgttcgctc caagctgggc    6960
tgtgtgcacg aaccccccgt tcagcccgac cgctgcgcct tatccggtaa ctatcgtctt    7020
gagtccaacc cggtaagaca cgacttatcg ccactggcag cagccactgg taacaggatt    7080
agcagagcga ggtatgtagg cggtgctaca gagttcttga agtggtggcc taactacggc    7140
tacactagaa ggacagtatt tggtatctgc gctctgctga agccagttac cttcggaaaa    7200
agagttggta gctcttgatc cggcaaacaa accaccgctg gtagcggtgg ttttttgtt    7260 tgcaagcagc agattacgcg cagaaaaaaa ggatctcaag aagatccttt gatcttttct    7320
acggggtctg acgctcagtg gaacgaaaac tcacgttaag ggattttggt catgagatta    7380
tcaaaaagga tcttcaccta gatccttta aattaaaaat gaagttttaa atcaatctaa    7440
```

| | |
|---|---|
| agtatatatg agtaaacttg gtctgacagt taccaatgct taatcagtga ggcacctatc | 7500 |
| tcagcgatct gtctatttcg ttcatccata gttgcctgac tccccgtcgt gtagataact | 7560 |
| acgatacggg agggcttacc atctggcccc agtgctgcaa tgataccgcg agacccacgc | 7620 |
| tcaccggctc cagatttatc agcaataaac cagccagccg gaagggccga gcgcagaagt | 7680 |
| ggtcctgcaa ctttatccgc ctccatccag tctattaatt gttgccggga agctagagta | 7740 |
| agtagttcgc cagttaatag tttgcgcaac gttgttgcca ttgctacagg catcgtggtg | 7800 |
| tcacgctcgt cgtttggtat ggcttcattc agctccggtt cccaacgatc aaggcgagtt | 7860 |
| acatgatccc ccatgttgtg caaaaaagcg gttagctcct tcggtcctcc gatcgttgtc | 7920 |
| agaagtaagt tggccgcagt gttatcactc atggttatgg cagcactgca taattctctt | 7980 |
| actgtcatgc catccgtaag atgcttttct gtgactggtg agtactcaac caagtcattc | 8040 |
| tgagaatagt gtatgcggcg accgagttgc tcttgcccgg cgtcaatacg ggataatacc | 8100 |
| gcgccacata gcagaacttt aaaagtgctc atcattggaa aacgttcttc ggggcgaaaa | 8160 |
| ctctcaagga tcttaccgct gttgagatcc agttcgatgt aacccactcg tgcacccaac | 8220 |
| tgatcttcag catctttac tttcaccagc gtttctgggt gagcaaaaac aggaaggcaa | 8280 |
| aatgccgcaa aaaagggaat aagggcgaca cggaaatgtt gaatactcat actcttcctt | 8340 |
| tttcaatatt attgaagcat ttatcagggt tattgtctca tgagcggata catatttgaa | 8400 |
| tgtatttaga aaaataaaca aataggggtt ccgcgcacat ttccccgaaa agtgccacct | 8460 |
| gacgtc | 8466 |

<210> SEQ ID NO 27
<211> LENGTH: 3414
<212> TYPE: DNA
<213> ORGANISM: Artificial Sequence
<220> FEATURE:
<223> OTHER INFORMATION: 3'TALEN.KKR.Sharkey DNA sequence (From start codon to stop codon)

<400> SEQUENCE: 27

| | |
|---|---|
| atggactaca aagaccatga cggtgattat aaagatcatg acatcgatta caaggatgac | 60 |
| gatgacaaga tggcccccaa gaagaagagg aaggtgggca ttcaccgcgg ggtacctatg | 120 |
| gtggacttga ggacactcgg ttattcgcaa cagcaacagg agaaaatcaa gcctaaggtc | 180 |
| aggagcaccg tcgcgcaaca ccacgaggcg cttgtggggc atggcttcac tcatgcgcat | 240 |
| attgtcgcgc tttcacagca ccctgcggcg cttgggacgg tggctgtcaa ataccaagat | 300 |
| atgattgcgg ccctgcccga agccacgcac gaggcaattg taggggtcgg taaacagtgg | 360 |
| tcgggagcgc gagcacttga ggcgctgctg actgtggcgg gtgagcttag ggggcctccg | 420 |
| ctccagctcg acaccgggca gctgctgaag atcgcgaaga gaggggagt aacagcggta | 480 |
| gaggcagtgc acgcctggcg caatgcgctc accggggccc ccttgaacct gaccccagac | 540 |
| caggtagtcg caatcgcgtc gaacattggg ggaaagcaag ccctggaaac cgtgcaaagg | 600 |
| ttgttgccgg tcctttgtca agaccacggc cttacaccgg agcaagtcgt ggccattgca | 660 |
| agcaacatcg gtggcaaaca ggctcttgag acggttcaga acttctcccc agttctctgt | 720 |
| caagcccacg gctgactcc cgatcaagtt gtagcgattg caataacaa tggagggaaa | 780 |
| caagcattgg agactgtcca acggctcctt cccgtgttgt gtcaagccca cggtttgacg | 840 |
| cctgcacaag tggtcgccat cgccagccat gatggcggta agcaggcgct ggaaacagta | 900 |
| cagcgcctgc tgcctgtact gtgccaggat catggactga ccccagacca ggtagtcgca | 960 |

```
atcgcgtcga acattggggg aaagcaagcc ctggaaaccg tgcaaaggtt gttgccggtc    1020
ctttgtcaag accacggcct tacaccggag caagtcgtgg ccattgcaaa taataacggt    1080
ggcaaacagg ctcttgagac ggttcagaga cttctcccag ttctctgtca gcccacggg     1140 ctgactcccg atcaagttgt agcgattgcg tccaacggtg agggaaaca agcattggag     1200 actgtccaac ggctccttcc cgtgttgtgt caagcccacg gtttgacgcc tgcacaagtg    1260
gtcgccatcg ccaacaacaa cggcggtaag caggcgctgg aaacagtaca gcgcctgctg    1320
cctgtactgt gccaggatca tggactgacc ccagaccagg tagtcgcaat cgcgaacaat    1380
aatgggggaa agcaagccct ggaaaccgtg caaaggttgt tgccggtcct ttgtcaagac    1440
cacggcctta caccggagca agtcgtggcc attgcaaata taacggtgg caaacaggct    1500 cttgagacgg ttcagagact ctcccagtt ctctgtcaag cccacgggct gactcccgat    1560
caagttgtag cgattgcgtc caacggtgga gggaaacaag cattggagac tgtccaacgg    1620
ctccttcccg tgttgtgtca gcccacggt ttgacgcctg cacaagtggt cgccatcgcc    1680
tcgaatggcg gcggtaagca ggcgctgaa acagtacagc gcctgctgcc tgtactgtgc    1740
caggatcatg gactgacccc agaccaggta gtcgcaatcg cgtcacatga cgggggaaag   1800
caagccctgg aaaccgtgca aaggttgttg ccggtccttt gtcaagacca cggccttaca   1860
ccggagcaag tcgtggccat tgcatcccac gacggtggca acaggctct gagacggtt    1920 cagagacttc tcccagttct ctgtcaagcc cacgggctga ctcccgatca agttgtagcg   1980
attgcgtcgc atgacggagg gaaacaagca ttggagactg tccaacggct ccttcccgtg   2040
ttgtgtcaag cccacggttt gacgcctgca caagtggtcg ccatcgcctc gaatggcggc   2100
ggtaagcagg cgctggaaac agtacagcgc ctgctgcctg tactgtgcca ggatcatgga   2160
ctgaccccag accaggtagt cgcaatcgcg tcgaacattg ggggaaagca agccctggaa   2220
accgtgcaaa ggttgttgcc ggtcctttgt caagaccacg gccttacacc ggagcaagtc   2280
gtggccattg caataataa cggtggcaaa caggctcttg agacggttca gagacttctc    2340
ccagttctct gtcaagccca cgggctgact cccgatcaag ttgtagcgat gcgtccaac    2400 ggtgagggaa acaagcatt ggagactgtc caacggctcc ttcccgtgtt gtgtcaagcc    2460
cacggtttga cgcctgcaca gtggtcgcc atcgcctcga atggcggcgg taagcaggcg   2520
ctggaaacag tacagcgcct gctgcctgta ctgtgcagg atcatggact gacacccgaa    2580
caggtggtcg ccattgcttc taacatcgga ggacggccag ccttggagtc atcgtagcc    2640 caattgtcca ggcccgatcc cgcgttggct gcgttaacga atgaccatct ggtggcgttg   2700
gcatgtcttg gtggacgacc cgcgctcgat gcagtcaaaa agggtctgcc tcatgctccc   2760
gcattgatca aaagaaccaa ccggcggatt cccgagagaa cttcccatcg agtcgcggga   2820
tcccaactag tcaaaagtga actggaggag aagaaatctg aacttcgtca taaattgaaa   2880
tatgtgcctc atgaatatat tgaattaatt gaaattgcca gaaatcccac tcaggataga   2940
attcttgaaa tgaaggtaat ggaatttttt atgaaagttt atggatatag aggtgagcat   3000
ttgggtggat caaggaaacc ggacggagca atttatactg tcggatctcc tattgattac   3060
ggtgtgatcg tggatactaa agcttatagc ggaggttata atctgccaat ggccaagca    3120 gatgaaatgc aacgatatgt caaggaaaat caaacacgaa acaaacatat caaccctaat   3180
gaatggtgga agtctatcc atcttctgta acggaattta gttttttatt tgtgagtggt   3240
cactttaaag gaaactacaa agctcagctt acacgattaa atcggaagac taattgtaat   3300
ggagctgttc ttagtgtaga agagctttta attggtggag aaatgattaa agccggcaca   3360
```

<210> SEQ ID NO 28
<211> LENGTH: 8466
<212> TYPE: DNA
<213> ORGANISM: Artificial Sequence
<220> FEATURE:
<223> OTHER INFORMATION: JDS70 (with 3'TALEN.KKR.Sharkey)

<400> SEQUENCE: 28

```
ttaaccttag aggaagtcag acggaaattt aataacggcg agataaactt ttaa        3414
```

```
gacggatcgg gagatctccc gatccccat ggtcgactct cagtacaatc tgctctgatg     60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
accatggact acaaagacca tgacggtgat tataaagatc atgacatcga ttacaaggat   960
gacgatgaca agatggcccc caagaagaag aggaaggtgg gcattcaccg cggggtacct  1020
atggtggact tgaggacact cggttattcg caacagcaac aggagaaaat caagcctaag  1080
gtcaggagca ccgtcgcgca acaccacgag gcgcttgtgg ggcatggctt cactcatgcg  1140
catattgtcg cgctttcaca gcaccctgcg gcgcttggga cggtggctgt caaataccaa  1200
gatatgattg cggccctgcc cgaagccacg cacgaggcaa ttgtaggggt cggtaaacag  1260
tggtcgggag cgcgagcact tgaggcgctg ctgactgtgg cgggtgagct tagggggcct  1320
ccgctccagc tcgacaccgg gcagctgctg aagatcgcga agagagggg agtaacagcg  1380
gtagaggcag tgcacgcctg gcgcaatgcg ctcaccgggg ccccttgaa cctgaccca  1440
gaccaggtag tcgcaatcgc gtcgaacatt gggggaaagc aagccctgga aaccgtgcaa  1500
aggttgttgc cggtcctttg tcaagaccac ggccttacac cggagcaagt cgtggccatt  1560
gcaagcaaca tcgtggcaa acaggctctt gagacggttc agagacttct cccagttctc  1620
tgtcaagccc acgggctgac tcccgatcaa gttgtagcga ttgcgaataa caatggaggg  1680
aaacaagcat tggagactgt ccaacggctc cttcccgtgt tgtgtcaagc ccacggtttg  1740
acgcctgcac aagtggtcgc catcgccagc catgatggcg taagcaggc gctgaaaaca  1800
gtacagcgcc tgctgcctgt actgtgccag gatcatggac tgacccccaga ccaggtagtc  1860
gcaatcgcgt cgaacattgg gggaaagcaa gccctgaaa ccgtgcaaag gttgttgccg  1920
gtccttgtc aagaccacgg ccttacaccg gagcaagtcg tggccattgc aaataataac  1980
```

```
ggtggcaaac aggctcttga gacggttcag agacttctcc cagttctctg tcaagcccac    2040
gggctgactc ccgatcaagt tgtagcgatt gcgtccaacg gtggagggaa acaagcattg    2100
gagactgtcc aacggctcct tcccgtgttg tgtcaagccc acggtttgac gcctgcacaa    2160
gtggtcgcca tcgccaacaa caacggcggt aagcaggcgc tggaaacagt acagcgcctg    2220
ctgcctgtac tgtgccagga tcatggactg accccagacc aggtagtcgc aatcgcgaac    2280
aataatgggg gaaagcaagc cctggaaacc gtgcaaaggt tgttgccggt cctttgtcaa    2340
gaccacggcc ttacaccgga gcaagtcgtg gccattgcaa ataataacgg tggcaaacag    2400
gctcttgaga cggttcagag acttctccca gttctctgtc aagcccacgg gctgactccc    2460
gatcaagttg tagcgattgc gtccaacggt ggagggaaac aagcattgga gactgtccaa    2520 cggctcctlc ccgtgttgtg tcaagcccac ggtttgacgc ctgcacaagt ggtcgccatc    2580
gcctcgaatg gcggcggtaa gcaggcgctg aaaacagtac agcgcctgct gctgtactg    2640 tgccaggatc atggactgac cccagaccag gtagtcgcaa tcgcgtcaca tgacggggga    2700
aagcaagccc tggaaaccgt gcaaaggttg ttgccggtcc tttgtcaaga ccacggcctt    2760
acaccggagc aagtcgtggc cattgcatcc cacgacggtg gcaaacaggc tcttgagacg    2820
gttcagagac ttctcccagt tctctgtcaa gcccacgggc tgactcccga tcaagttgta    2880
gcgattgcgt cgcatgacgg agggaaacaa gcattggaga ctgtccaacg gctccttccc    2940
gtgttgtgtc aagcccacgg tttgacgcct gcacaagtgg tcgccatcgc ctcgaatggc    3000
ggcggtaagc aggcgctgga aacagtacag cgcctgctgc tgtactgtgc caggatcat    3060 ggactgaccc cagaccaggt agtcgcaatc gcgtcgaaca ttgggggaaa gcaagccctg    3120
gaaaccgtgc aaaggttgtt gccggtcctt tgtcaagacc acggcttac accggagcaa    3180 gtcgtggcca ttgcaaataa taacggtggc aaacaggctc ttgagacggt tcagagactt    3240
ctcccagttc tctgtcaagc ccacgggctg actcccgatc aagttgtagc gattgcgtcc    3300
aacggtggag ggaaacaagc attggagact gtccaacggc tccttcccgt gttgtgtcaa    3360
gcccacggtt tgacgcctgc acaagtggtc gccatcgcct cgaatggcgg cggtaagcag    3420
gcgctggaaa cagtacagcg cctgctgcct gtactgtgcc aggatcatgg actgacaccc    3480
gaacaggtgg tcgccattgc ttctaacatc ggaggacggc cagccttgga gtccatcgta    3540
gcccaattgt ccaggcccga tcccgcgttg gctgcgttaa cgaatgacca tctggtggcg    3600
ttggcatgtc ttggtggacg accgcgctc gatgcagtca aaaagggtct gcctcatgct    3660
cccgcattga tcaaaagaac caaccggcgg attcccgaga gaacttccca tcgagtcgcg    3720
ggatcccaac tagtcaaaag tgaactggag gagaagaaat ctgaacttcg tcataaattg    3780
aaatatgtgc ctcatgaata tattgaatta attgaaattg ccagaaatcc cactcaggat    3840
agaattcttg aaatgaaggt aatggaattt tttatgaaag tttatggata tagaggtgag    3900
catttgggtg gatcaaggaa accggacgga gcaatttata ctgtcggatc tcctattgat    3960
tacggtgtga tcgtggatac taaagcttat agcggaggtt ataatctgcc aattggccaa    4020
gcagatgaaa tgcaacgata tgtcaaggaa aatcaaacac gaaacaaaca tatcaacccct    4080 aatgaatggt ggaaagtcta tccatcttct gtaacgaat ttaagttttt atttgtgagt    4140
ggtcacttta aggaaactaa caaagctcag cttacacgat taaatcggaa gactaattgt    4200
aatggagctg ttcttagtgt agaagagctt ttaattggtg agaaaatgat taaagccggc    4260
acattaacct tagaggaagt cagacggaaa tttaataacg gcgagataaa cttttaaggg    4320
cccttcgaag gtaagcctat ccctaaccct ctcctcggtc tcgattctac gcgtaccggt    4380
```

```
catcatcacc atcaccattg agtttaaacc cgctgatcag cctcgactgt gccttctagt    4440
tgccagccat ctgttgtttg cccctccccc gtgccttcct tgaccctgga aggtgccact    4500
cccactgtcc tttcctaata aaatgaggaa attgcatcgc attgtctgag taggtgtcat    4560
tctattctgg ggggtggggt ggggcaggac agcaagggg aggattggga agacaatagc    4620
aggcatgctg gggatgcggt gggctctatg gcttctgagg cggaaagaac cagctggggc    4680 tctaggggt atccccacgc ccctgtagc ggcgcattaa gcgcggcggg tgtggtggtt    4740
acgcgcagcg tgaccgctac acttgccagc gccctagcgc ccgctccttt cgctttcttc    4800
ccttcctttc tcgccacgtt cgccggcttt ccccgtcaag ctctaaatcg ggcatccct    4860 ttagggttcc gatttagtgc tttacggcac ctcgacccca aaaaacttga ttagggtgat    4920
ggttcacgta gtgggccatc gccctgatag acggttttc gccctttgac gttggagtcc    4980
acgttcttta atagtggact cttgttccaa actggaacaa cactcaaccc tatctcggtc    5040
tattcttttg atttataagg attttgggg atttcggcct attggttaaa aaatgagctg    5100
atttaacaaa aatttaacgc gaattaattc tgtggaatgt gtgtcagtta gggtgtggaa    5160
agtccccagg ctccccaggc aggcagaagt atgcaaagca tgcatctcaa ttagtcagca    5220
accaggtgtg gaaagtcccc aggctcccca gcaggcagaa gtatgcaaag catgcatctc    5280
aattagtcag caaccatagt cccgcccta actccgccca tcccgcccct aactccgccc    5340
agttccgccc attctccgcc ccatggctga ctaattttt ttatttatgc agaggccgag    5400
gccgcctctg cctctgagct attccagaag tagtgaggag gctttttgg aggcctaggc    5460 ttttgcaaaa agctcccggg agcttgtata tccattttcg gatctgatca gcacgtgttg    5520
acaattaatc atcggcatag tatatcggca tagtataata cgacaaggtg aggaactaaa    5580
ccatggccaa gcctttgtct caagaagaat ccaccctcat tgaaagagca acggctacaa    5640
tcaacagcat ccccatctct gaagactaca gcgtcgccag cgcagctctc tctagcgacg    5700
gccgcatctt cactggtgtc aatgtatatc attttactgg gggaccttgt gcagaactcg    5760
tggtgctggg cactgctgct gctgcggcag ctggcaacct gacttgtatc gtcgcgatcg    5820
gaaatgagaa cagggggcatc ttgagcccct gcggacggtg tcgacaggtg cttctcgatc    5880
tgcatcctgg gatcaaagcg atagtgaagg acagtgatgg acagccgacg gcagttggga    5940
ttcgtgaatt gctgccctct ggttatgtgt gggagggcta agcacttcgt ggccgaggag    6000
caggactgac acgtgctacg agatttcgat tccaccgccg ccttctatga aggttgggc    6060 ttcggaatcg ttttccggga cgccggctgg atgatcctcc agcgcgggga tctcatgctg    6120
gagttcttcg cccaccccaa cttgtttatt gcagcttata atggttacaa ataaagcaat    6180
agcatcacaa atttcacaaa taaagcattt ttttcactgc attctagttg tggtttgtcc    6240
aaactcatca atgtatctta tcatgtctgt ataccgtcga cctctagcta gagcttggcg    6300
taatcatggt catagctgtt tcctgtgtga aattgttatc cgctcacaat tccacacaac    6360
atacgagccg gaagcataaa gtgtaaagcc tggggtgcct aatgagtgag ctaactcaca    6420
ttaattgcgt tgcgctcact gcccgctttc cagtcgggaa acctgtcgtg ccagctgcat    6480
taatgaatcg gccaacgcgc ggggagaggc ggtttgcgta ttgggcgctc ttccgcttcc    6540
tcgctcactg actcgctgcg ctcggtcgtt cggctgcggc gagcggtatc agctcactca    6600
aaggcggtaa tacggttatc cacagaatca ggggataacg caggaaagaa catgtgagca    6660
aaaggccagc aaaaggccag gaaccgtaaa aaggccgcgt tgctggcgtt tttccatagg    6720
```

```
ctccgccccc ctgacgagca tcacaaaaat cgacgctcaa gtcagaggtg gcgaaacccg    6780
acaggactat aaagatacca ggcgtttccc cctggaagct ccctcgtgcg ctctcctgtt    6840
ccgaccctgc cgcttaccgg atacctgtcc gcctttctcc cttcgggaag cgtggcgctt    6900
tctcaatgct cacgctgtag gtatctcagt tcggtgtagg tcgttcgctc caagctgggc    6960
tgtgtgcacg aaccccccgt tcagcccgac cgctgcgcct tatccggtaa ctatcgtctt    7020
gagtccaacc cggtaagaca cgacttatcg ccactggcag cagccactgg taacaggatt    7080
agcagagcga ggtatgtagg cggtgctaca gagttcttga agtggtggcc taactacggc    7140
tacactagaa ggacagtatt tggtatctgc gctctgctga agccagttac cttcggaaaa    7200
agagttggta gctcttgatc cggcaaacaa accaccgctg gtagcggtgg tttttttgtt    7260
tgcaagcagc agattacgcg cagaaaaaaa ggatctcaag aagatccttt gatcttttct    7320
acggggtctg acgctcagtg gaacgaaaac tcacgttaag ggattttggt catgagatta    7380
tcaaaaggga tcttcaccta gatcctttta aattaaaaat gaagttttaa atcaatctaa    7440
agtatatatg agtaaacttg gtctgacagt taccaatgct taatcagtga ggcacctatc    7500
tcagcgatct gtctatttcg ttcatccata gttgcctgac tccccgtcgt gtagataact    7560
acgatacggg agggcttacc atctggcccc agtgctgcaa tgataccgcg agacccacgc    7620
tcaccggctc cagatttatc agcaataaac cagccagccg aagggccga gcgcagaagt     7680
ggtcctgcaa ctttatccgc ctccatccag tctattaatt gttgccggga agctagagta    7740
agtagttcgc cagttaatag tttgcgcaac gttgttgcca ttgctacagg catcgtggtg    7800
tcacgctcgt cgtttggtat ggcttcattc agctccggtt cccaacgatc aaggcgagtt    7860
acatgatccc ccatgttgtg caaaaaagcg gttagctcct tcggtcctcc gatcgttgtc    7920
agaagtaagt tggccgcagt gttatcactc atggttatgg cagcactgca taattctctt    7980
actgtcatgc catccgtaag atgcttttct gtgactggtg agtactcaac caagtcattc    8040
tgagaatagt gtatgcggcg accgagttgc tcttgcccgg cgtcaatacg ggataatacc    8100
gcgccacata gcagaacttt aaaagtgctc atcattggaa aacgttcttc ggggcgaaaa    8160
ctctcaagga tcttaccgct gttgagatcc agttcgatgt aacccactcg tgcacccaac    8220
tgatcttcag catcttttac tttcaccagc gtttctgggt gagcaaaaac aggaaggcaa    8280
aatgccgcaa aaaagggaat aagggcgaca cggaaatgtt gaatactcat actcttcctt    8340
tttcaatatt attgaagcat ttatcagggt tattgtctca tgagcggata catatttgaa    8400
tgtatttaga aaaataaaca aataggggtt ccgcgcacat ttccccgaaa agtgccacct    8460
gacgtc                                                                8466
```

<210> SEQ ID NO 29
<211> LENGTH: 8261
<212> TYPE: DNA
<213> ORGANISM: Artificial Sequence
<220> FEATURE:
<223> OTHER INFORMATION: JDS78 (with 5'TALEN)

<400> SEQUENCE: 29

```
gacggatcgg gagatctccc gatccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
```

```
tggagttccg cgttacataa cttacggtaa atggcccgcc tggctgaccg cccaacgacc      360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
accatggact acaaagacca tgacggtgat tataaagatc atgacatcga ttacaaggat     960
gacgatgaca agatggcccc caagaagaag aggaaggtgg gcattcaccg cggggtacct    1020
atggtggact tgaggacact cggttattcg caacagcaac aggagaaaat caagcctaag    1080
gtcaggagca ccgtcgcgca acaccacgag gcgcttgtgg ggcatggctt cactcatgcg    1140
catattgtcg cgctttcaca gcaccctgcg gcgcttggga cggtggctgt caaataccaa    1200
gatatgattg cggccctgcc cgaagccacg cacgaggcaa ttgtaggggt cggtaaacag    1260
tggtcgggag cgcgagcact tgaggcgctg ctgactgtgg cgggtgagct taggggggcct    1320 ccgctccagc tcgacaccgg gcagctgctg aagatcgcga agagaggggg agtaacagcg    1380
gtagaggcag tgcacgcctg gcgcaatgcg ctcaccgggg cccccttgaa cctgacccca    1440
gaccaggtag tcgcaatcgc gtcacatgac ggggggaaagc aagccctgga aaccgtgcaa    1500
aggttgttgc cggtcctttg tcaagaccac ggccttacac cggagcaagt cgtggccatt    1560
gcaagcaatg ggggtggcaa acaggctctt gagacggttc agagacttct cccagttctc    1620
tgtcaagccc acgggctgac tcccgatcaa gttgtagcga ttgcgtcgca tgacggaggg    1680
aaacaagcat tggagactgt ccaacggctc cttcccgtgt tgtgtcaagc ccacggtttg    1740
acgcctgcac aagtggtcgc catcgcctcg aatggcggcg taagcaggc gctggaaaca    1800 gtacagcgcc tgctgcctgt actgtgccag gatcatggac tgaccccaga ccaggtagtc    1860
gcaatcgcga caataatggg ggaaagcaa gccctggaaa ccgtgcaaag gttgttgccg    1920
gtcctttgtc aagaccacgg ccttacaccg gagcaagtcg tggccattgc aaataataac    1980
ggtggcaaac aggctcttga gacggttcag agacttctcc cagttctctg tcaagcccac    2040
gggctgactc ccgatcaagt tgtagcgatt gcgtccaacg gtggagggaa acaagcattg    2100
gagactgtca acggctcct tcccgtgttg tgtcaagccc acggtttgac gcctgcacaa    2160
gtggtcgcca tcgcctcgaa tggcggcggt aagcaggcgc tggaaacagt acagcgcctg    2220
ctgcctgtac tgtgccagga tcatggactg actcccgatc aagttgtagc gattgcgtcg    2280
aacattggag ggaaacaagc attggagact gtccaacggc tccttcccgt gttgtgtcaa    2340
gcccacggtc ttacaccgga gcaagtcgtg ccattgcaa ataataacgg tggcaaacag    2400
gctcttgaga cggttcagag acttctccca gttctctgtc aagcccacgg gctgactccc    2460
gatcaagttg tagcgattgc gtcgaacatt ggagggaaac aagcattgga gactgtccaa    2520
cggctccttc ccgtgttgtg tcaagcccac ggtttgacgc ctgcacaagt ggtcgccatc    2580
gccagccatg atggcggtaa gcaggcgctg gaaacagtac agcgcctgct gcctgtactg    2640
```

```
tgccaggatc atggactgac cccagaccag gtagtcgcaa tcgcgtcaca tgacggggga     2700
aagcaagccc tggaaaccgt gcaaaggttg ttgccggtcc tttgtcaaga ccacggcctt     2760
acaccggagc aagtcgtggc cattgcaagc aacatcggtg gcaaacaggc tcttgagacg     2820
gttcagagac ttctcccagt tctctgtcaa gcccacgggc tgactcccga tcaagttgta     2880
gcgattgcga ataacaatgg agggaaacaa gcattggaga ctgtccaacg gctccttccc     2940
gtgttgtgtc aagcccacgg tttgacgcct gcacaagtgg tcgccatcgc ctccaatatt     3000
ggcggtaagc aggcgctgga aacagtacag cgcctgctgc ctgtactgtg ccaggatcat     3060
ggactgaccc cagaccaggt agtcgcaatc gcgtcaaacg gagggggaaa gcaagccctg     3120
gaaaccgtgc aaaggttgtt gccggtcctt tgtcaagacc acggcttac accggagcaa      3180 gtcgtggcca ttgcatccca cgacggtggc aaacaggctc ttgagacggt tcagagactt     3240
ctcccagttc tctgtcaagc ccacgggctg acacccgaac aggtggtcgc cattgcttct     3300
aatgggggag gacggccagc cttggagtcc atcgtagccc aattgtccag gcccgatccc     3360
gcgttggctg cgttaacgaa tgaccatctg gtggcgttgg catgtcttgg tggacgaccc     3420
gcgctcgatg cagtcaaaaa gggtctgcct catgctcccg cattgatcaa agaaccaac      3480 cggcggattc ccgagagaac ttcccatcga gtcgcgggat cccaactagt caaagtgaa      3540 ctggaggaga agaaatctga acttcgtcat aaattgaaat atgtgcctca tgaatatatt     3600
gaattaattg aaattgccag aaattccact caggatagaa ttcttgaaat gaaggtaatg     3660 gaattttta tgaaagttta tggatataga ggtaaacatt tgggtggatc aaggaaaccg      3720
gacggagcaa tttatactgt cggatctcct attgattacg gtgtgatcgt ggatactaaa     3780
gcttatagcg gaggttataa tctgccaatt ggccaagcag atgaaatgca acgatatgtc     3840
gaagaaaatc aaacacgaaa caaacatatc aaccctaatg aatggtggaa agtctatcca     3900
tcttctgtaa cggaatttaa gttttattt gtgagtggtc actttaaagg aaactacaaa      3960
gctcagctta cacgattaaa tcatatcact aattgtaatg gagctgttct tagtgtagaa     4020
gagcttttaa ttggtggaga aatgattaaa gccggcacat taaccttaga ggaagtcaga    4080
cggaaattta ataacggcga gataaacttt taagggccct tcgaaggtaa gcctatccct    4140
aaccctctcc tcggtctcga ttctacgcgt accggtcatc atcaccatca ccattgagtt    4200
taaacccgct gatcagcctc gactgtgcct tctagttgcc agccatctgt tgtttgcccc    4260
tcccccgtgc cttccttgac cctggaaggt gccactccca ctgtcctttc ctaataaaat    4320
gaggaaattg catcgcattg tctgagtagg tgtcattcta ttctgggggg tggggtgggg    4380
caggacagca aggggagga ttgggaagac aatagcaggc atgctgggga tgcggtgggc     4440
tctatggctt ctgaggcgga aagaaccagc tggggctcta gggggtatcc ccacgcgccc    4500
tgtagcggcg cattaagcgc ggcgggtgtg gtggttacgc gcagcgtgac cgctacactt    4560
gccagcgccc tagcgcccgc tccttttcgct ttcttccctt cctttctcgc cacgttcgcc   4620
ggctttcccc gtcaagctct aaatcggggc atccctttag ggttccgatt agtgctttac    4680
ggcacctcga ccccaaaaaa cttgattagg gtgatggttc acgtagtggg ccatcgccct    4740
gatagacggt tttcgccct tgacgttgg agtccacgtt ctttaatagt ggactcttgt      4800
tccaaactgg aacaacactc aaccctatct cggtctattc ttttgattta agggatttt     4860 tggggatttc ggcctattgg ttaaaaaatg agctgattta caaaaatttt aacgcgaatt    4920
aattctgtgg aatgtgtgtc agttagggtg tggaaagtcc ccaggctccc caggcaggca    4980
gaagtatgca aagcatgcat ctcaattagt cagcaaccag gtgtggaaag tccccaggct    5040
```

```
ccccagcagg cagaagtatg caaagcatgc atctcaatta gtcagcaacc atagtcccgc    5100
ccctaactcc gcccatcccg cccctaactc cgcccagttc cgcccattct ccgcccatg     5160 gctgactaat ttttttatt tatgcagagg ccgaggccgc ctctgcctct gagctattcc    5220
agaagtagtg aggaggcttt tttggaggcc taggcttttg caaaaagctc ccgggagctt    5280
gtatatccat tttcggatct gatcagcacg tgttgacaat taatcatcgg catagtatat    5340
cggcatagta taatacgaca aggtgaggaa ctaaaccatg ccaagcctt tgtctcaaga     5400 agaatccacc ctcattgaaa gagcaacggc tacaatcaac agcatcccca tctctgaaga    5460
ctacagcgtc gccagcgcag ctctctctag cgacggccgc atcttcactg tgtcaatgt     5520 atatcatttt actgggggac cttgtgcaga actcgtggtg ctgggcactg ctgctgctgc    5580
ggcagctggc aacctgactt gtatcgtcgc gatcggaaat gagaacaggg gcatcttgag    5640
cccctgcgga cggtgtcgac aggtgcttct cgatctgcat cctgggatca aagcgatagt    5700
gaaggacagt gatggacagc cgacggcagt tgggattcgt gaattgctgc cctctggtta    5760
tgtgtgggag ggctaagcac ttcgtggccg aggagcagga ctgacacgtg ctacgagatt    5820
tcgattccac cgccgccttc tatgaaaggt tgggcttcgg aatcgttttc cgggacgccg    5880
gctggatgat cctccagcgc ggggatctca tgctggagtt cttcgcccac cccaacttgt    5940
ttattgcagc ttataatggt tacaaataaa gcaatagcat cacaaatttc acaaataaag    6000 cattttttc actgcattct agttgtggtt tgtccaaact catcaatgta tcttatcatg     6060
tctgtatacc gtcgacctct agctagagct tggcgtaatc atggtcatag ctgtttcctg    6120
tgtgaaattg ttatccgctc acaattccac acaacatacg agccgaagc ataaagtgta     6180 aagcctgggg tgcctaatga gtgagctaac tcacattaat tgcgttgcgc tcactgcccg    6240
ctttccagtc gggaaacctg tcgtgccagc tgcattaatg aatcggccaa cgcgcgggga    6300
gaggcggttt gcgtattggg cgctcttccg cttcctcgct cactgactcg ctgcgctcgg    6360
tcgttcggct gcggcgagcg gtatcagctc actcaaaggc ggtaatacgg ttatccacag    6420
aatcagggga taacgcagga aagaacatgt gagcaaaagg ccagcaaaag gccaggaacc    6480
gtaaaaaggc cgcgttgctg cgttttttcc ataggctccg cccccctgac gagcatcaca    6540
aaaatcgacg ctcaagtcag aggtggcgaa acccgacagg actataaaga taccaggcgt    6600
ttccccctgg aagctccctc gtgcgctctc ctgttccgac cctgccgctt accggatacc    6660
tgtccgcctt tctcccttcg ggaagcgtgg cgctttctca atgctcacgc tgtaggtatc    6720
tcagttcggt gtaggtcgtt cgctccaagc tgggctgtgt gcacgaaccc cccgttcagc    6780
ccgaccgctg cgccttatcc ggtaactatc gtcttgagtc aacccggta agacacgact     6840 tatcgccact ggcagcagcc actggtaaca ggattagcag agcgaggtat gtaggcggtg    6900
ctacagagtt cttgaagtgg tggcctaact acggctacac tagaaggaca gtatttggta    6960
tctgcgctct gctgaagcca gttaccttcg gaaaaagagt tggtagctct tgatccggca    7020
aacaaaccac cgctggtagc ggtggttttt ttgtttgcaa gcagcagatt acgcgcagaa    7080
aaaaaggatc tcaagaagat cctttgatct tttctacggg gtctgacgct cagtggaacg    7140
aaaactcacg ttaagggatt ttggtcatga gattatcaaa aaggatcttc acctagatcc    7200
ttttaaatta aaaatgaagt tttaaatcaa tctaaagtat atatgagtaa acttggtctg    7260
acagttacca atgcttaatc agtgaggcac ctatctcagc gatctgtcta tttcgttcat    7320
ccatagttgc ctgactcccc gtcgtgtaga taactacgat acgggagggc ttaccatctg    7380
```

```
gccccagtgc tgcaatgata ccgcgagacc cacgctcacc ggctccagat ttatcagcaa    7440
taaaccagcc agccggaagg gccgagcgca gaagtggtcc tgcaacttta tccgcctcca    7500
tccagtctat taattgttgc cgggaagcta gagtaagtag ttcgccagtt aatagtttgc    7560
gcaacgttgt tgccattgct acaggcatcg tggtgtcacg ctcgtcgttt ggtatggctt    7620
cattcagctc cggttcccaa cgatcaaggc gagttacatg atcccccatg ttgtgcaaaa    7680
aagcggttag ctccttcggt cctccgatcg ttgtcagaag taagttggcc gcagtgttat    7740
cactcatggt tatggcagca ctgcataatt ctcttactgt catgccatcc gtaagatgct    7800
tttctgtgac tggtgagtac tcaaccaagt cattctgaga atagtgtatg cggcgaccga    7860
gttgctcttg cccggcgtca atacgggata ataccgcgcc acatagcaga actttaaaag    7920
tgctcatcat tggaaaacgt tcttcggggc gaaaactctc aaggatctta ccgctgttga    7980
gatccagttc gatgtaaccc actcgtgcac ccaactgatc ttcagcatct tttactttca    8040
ccagcgtttc tgggtgagca aaaacaggaa ggcaaaatgc cgcaaaaaag gaataagggg    8100
cgacacggaa atgttgaata ctcatactct tcctttttca atattattga agcatttatc    8160
agggttattg tctcatgagc ggatacatat ttgaatgtat ttagaaaaat aaacaaatag    8220
gggttccgcg cacatttccc cgaaaagtgc cacctgacgt c                        8261
```

<210> SEQ ID NO 30
<211> LENGTH: 3210
<212> TYPE: DNA
<213> ORGANISM: Artificial Sequence
<220> FEATURE:
<223> OTHER INFORMATION: 5'TALEN (in JDS78) Constructs T256/T258

<400> SEQUENCE: 30

```
atggactaca agaccatgga cggtgattat aaagatcatg acatcgatta caaggatgac      60
gatgacaaga tggcccccaa gaagaagagg aaggtgggca ttcaccgcgg ggtacctatg     120
gtggacttga ggacactcgg ttattcgcaa cagcaacagg agaaaatcaa gcctaaggtc     180
aggagcaccg tcgcgcaaca ccacgaggcg cttgtggggc atggcttcac tcatgcgcat     240
attgtcgcgc tttcacagca ccctgcggcg cttgggacgg tggctgtcaa ataccaagat     300
atgattgcgg ccctgcccga agccacgcac gaggcaattg tagggggtcgg taaacagtgg     360
tcgggagcgc gagcacttga ggcgctgctg actgtggcgg gtgagcttag ggggcctccg     420
ctccagctcg acaccgggca gctgctgaag atcgcgaaga gaggggggagt aacagcggta     480
gaggcagtgc acgcctggcg caatgcgctc accggggccc ccttgaacct gaccccagac     540
caggtagtcg caatcgcgtc acatgacggg ggaaagcaag ccctggaaac cgtgcaaagg     600
ttgttgccgg tcctttgtca agaccacggc cttacaccgg agcaagtcgt ggccattgca     660
agcaatgggg gtggcaaaca ggctcttgag acggttcaga gacttctccc agttctctgt     720
caagcccacg gctgactcc cgatcaagtt gtagcgattg cgtcgcatga cggagggaaa     780
caagcattgg agactgtcca acggctcctt ccgtgttgt gtcaagccca cggtttgacg     840
cctgcacaag tggtcgccat cgcctcgaat ggcggcggta agcaggcgct ggaaacagta     900
cagcgcctgc tgcctgtact gtgccaggat catggactga cccagacca ggtagtcgca     960
atcgcgaaca taatgggggg aaagcaagcc ctggaaaccg tgcaaaggtt gttgccggtc    1020
ctttgtcaag accacggcct tacaccggag caagtcgtgg ccattgcaaa taatacggt    1080
ggcaaacagg ctcttgagac ggttcagaga cttctcccag ttctctgtca gcccacgggt    1140
ctgactcccg atcaagttgt agcgattgcg tccaacggtg agggaaaaca agcattggag    1200
```

```
actgtccaac ggctccttcc cgtgttgtgt caagcccacg gtttgacgcc tgcacaagtg    1260
gtcgccatcg cctcgaatgg cggcggtaag caggcgctgg aaacagtaca gcgcctgctg    1320
cctgtactgt gccaggatca tggactgact cccgatcaag ttgtagcgat tgcgtcgaac    1380
attggaggga aacaagcatt ggagactgtc aacggctcc ttcccgtgtt gtgtcaagcc     1440
cacggtctta caccggagca agtcgtggcc attgcaaata taacggtgg caaacaggct     1500 cttgagacgg ttcagagact tctcccagtt ctctgtcaag cccacgggct gactcccgat    1560
caagttgtag cgattgcgtc gaacattgga gggaaacaag cattggagac tgtccaacgg    1620
ctccttcccg tgttgtgtca agcccacggt ttgacgcctg cacaagtggt cgccatcgcc    1680
agccatgatg gcggtaagca ggcgctggaa acagtacagc gcctgctgcc tgtactgtgc    1740
caggatcatg gactgacccc agaccaggta gtcgcaatcg cgtcacatga cggggggaaag   1800 caagccctgg aaaccgtgca aggttgttg ccggtccttt gtcaagacca cggccttaca    1860
ccggagcaag tcgtggccat tgcaagcaac atcggtggca acaggctct tgagacggtt    1920 cagagacttc tcccagttct ctgtcaagcc cacgggctga ctcccgatca agttgtagcg    1980
attgcgaata caatggagg gaaacaagca ttggagactg tccaacggct ccttcccgtg     2040
ttgtgtcaag cccacggttt gacgcctgca caagtggtcg ccatcgcctc caatattggc    2100
ggtaagcagg cgctggaaac agtacagcgc ctgctgcctg tactgtgcca ggatcatgga    2160
ctgaccccag accaggtagt cgcaatcgcg tcaaacggag ggggaaagca agccctggaa    2220
accgtgcaaa ggttgttgcc ggtcctttgt caagaccacg ccttacacc ggagcaagtc    2280 gtggccattg catcccacga cggtggcaaa caggctcttg agacggttca gagacttctc    2340
ccagttctct gtcaagccca cgggctgaca cccgaacagg tggtcgccat tgcttctaat    2400
gggggaggac ggccagcctt ggagtccatc gtagcccaat tgtccaggcc cgatcccgcg    2460
ttggctgcgt taacgaatga ccatctggtg gcgttggcat gtcttggtgg acgaccccgcg   2520 ctcgatgcag tcaaaaaggg tctgcctcat gctcccgcat tgatcaaaag aaccaaccgg    2580
cggattcccg agagaacttc ccatcgagtc gcgggatccc aactagtcaa aagtgaactg    2640
gaggagaaga atctgaact tcgtcataaa ttgaaatatg tgcctcatga atatattgaa     2700
ttaattgaaa ttgccagaaa ttccactcag gatagaattc ttgaaatgaa ggtaatggaa    2760 tttttatga aagtttatgg atatagaggt aaacatttgg gtggatcaag gaaaccggac     2820
ggagcaattt atactgtcgg atctcctatt gattacggtg tgatcgtgga tactaaagct    2880
tatagcggag gttataatct gccaattggc caagcagatg aaatgcaacg atatgtcgaa    2940
gaaaatcaaa cacgaaacaa acatatcaac cctaatgaat ggtggaaagt ctatccatct    3000
tctgtaacga aatttaagtt tttatttgtg agtggtcact ttaaaggaaa ctacaaagct    3060
cagcttacac gattaaatca tatcactaat tgtaatggag ctgttcttag tgtagaagag    3120 ctttttaattg gtgagaaat gattaaagcc ggcacattaa ccttagagga agtcagacgg    3180
aaatttaata acggcgagat aaactttta                                      3210
```

<210> SEQ ID NO 31
<211> LENGTH: 1840
<212> TYPE: DNA
<213> ORGANISM: Artificial Sequence
<220> FEATURE:
<223> OTHER INFORMATION: TALE component of mutant clone; does not include FokI; T259 mutant

<400> SEQUENCE: 31

```
gaacctgacc ccagaccagg tagtcgcaat cgcgtcacat gacggggaa agcaagccct      60
ggaaaccgtg caaaggttgt tgccggtcct ttgtcaagac cacggcctta caccggagca     120
agtcgtggcc attgcaagca atggggtgg caaacaggct cttgagacgg ttcagagact      180
tctcccagtt ctctgtcaag cccacgggct gactcccgat caagttgtag cgattgcgtc    240
gcatgacgga gggaaacaag cattggagac tgtccaacgg ctccttcccg tgttgtgtca    300
agcccacggt ttgacgcctg cacaagtggt cgccatcgcc tcgaatggcg gcggtaagca   360
ggcgctggaa acagtacagc gcctgctgcc tgtactgtgc caggatcatg gactgacccc    420
agaccaggta gtcgcaatcg cgaacaattc gggggaaag caagccctgg aaaccgtgca    480
aaggttgttg ccggtccttt gtcaagacca cggccttaca ccggagcaag tcgtggccat    540
tgcaaataat aacggtggca aacaggctct tgagacggtt cagagacttc tcccagttct    600
ctgtcaagcc cacgggctga ctcccgatca agttgtagcg attgcgtcca acggtggagg    660
gaaacaagca ttggagactg tccaacggct ccttcccgtg ttgtgtcaag cccacggttt    720
gacgcctgca caagtggtcg ccatcgcctc gaattcgggc ggtaagcagg cgctggaaac    780
agtacagcgc ctgctgcctg tactgtgcca ggatcatgga ctgacccccag accaggtagt   840
cgcaatcgcg tcgaacattg ggggaaagca agccctggaa accgtgcaaa ggttgttgcc    900
ggtcctttgt caagaccacg gccttacacc ggagcaagtc gtggccattg caaataataa    960
cggtggcaaa caggctcttg agacggttca gagacttctc ccagttctct gtcaagccca   1020
cgggctgact cccgatcaag ttgtagcgat tgcgtcgaac attggaggga acaagcatt    1080
ggagactgtc caacggctcc ttcccgtgtt gtgtcaagcc cacggtttga cgcctgcaca   1140
agtggtcgcc atcgccagcc atgatggcgg taagcaggcg ctggaaacag tacagcgcct   1200
gctgcctgta ctgtgccagg atcatggact gaccccagac caggtagtcg caatcgcgtc   1260
acatgacggg ggaaagcaag ccctggaaac cgtgcaaagg ttgttgccgg tcctttgtca   1320
agaccacggc cttacaccgg agcaagtcgt ggccattgca agcaacatcg gtggcaaaca   1380
ggctcttgag acggttcaga gacttctccc agttctctgt caagcccacg gctgactcc    1440
cgatcaagtt gtagcgattg cgaataacaa tggagggaaa caagcattgg agactgtcca   1500
acggctcctt cccgtgttgt gtcaagccca cggtttgacg cctgcacaag tggtcgccat   1560
cgcctccaat attggcggta agcaggcgct ggaaacagta cagcgcctgc tgcctgtact   1620
gtgccaggat catggactga ccccagacca ggtagtcgca atcgcgtcaa cggagggg    1680
aaagcaagcc ctggaaaccg tgcaaaggtt gttgccggtc ctttgtcaag accacggcct   1740
tacaccggag caagtcgtgg ccattgcatc caattcgggt ggcaaacagg ctcttgagac   1800
ggttcagaga cttctcccag ttctctgtca agcccacggg                         1840
```

<210> SEQ ID NO 32
<211> LENGTH: 62
<212> TYPE: DNA
<213> ORGANISM: Artificial Sequence
<220> FEATURE:
<223> OTHER INFORMATION: Synthetic contruct

<400> SEQUENCE: 32

```
tctctggtta gaccagatct gagcctggga gctctctggc taactaggga acccactgct      60
ta                                                                    62
```

<210> SEQ ID NO 33

```
<211> LENGTH: 62
<212> TYPE: DNA
<213> ORGANISM: Artificial Sequence
<220> FEATURE:
<223> OTHER INFORMATION: Synthtetic construct

<400> SEQUENCE: 33
taagcagtgg gttccctagt tagccagaga gctcccaggc tcagatctgg tctaaccaga      60
ga                                                                    62

<210> SEQ ID NO 34
<211> LENGTH: 32
<212> TYPE: RNA
<213> ORGANISM: Artificial Sequence
<220> FEATURE:
<223> OTHER INFORMATION: Synthetic construct

<400> SEQUENCE: 34
agaccagauc ugggccuggg ggcucucugg cu                                   32

<210> SEQ ID NO 35
<211> LENGTH: 77
<212> TYPE: DNA
<213> ORGANISM: Artificial Sequence
<220> FEATURE:
<223> OTHER INFORMATION: Synthetic construct

<400> SEQUENCE: 35 cttttgcct gtactgggtc tctctggtta gaccagattt gagcctggga gctctctggc      60
taactaggga acccact                                                    77

<210> SEQ ID NO 36
<211> LENGTH: 55
<212> TYPE: DNA
<213> ORGANISM: Artificial Sequence
<220> FEATURE:
<223> OTHER INFORMATION: Synthetic construct

<400> SEQUENCE: 36
cttttatatg cagcatctga gcctgggagc tctctggcta actagggaac ccact          55

<210> SEQ ID NO 37
<211> LENGTH: 69
<212> TYPE: DNA
<213> ORGANISM: Artificial Sequence
<220> FEATURE:
<223> OTHER INFORMATION: Synthetic construct

<400> SEQUENCE: 37 cttttttgcct gtactgggtc tctctggtta gaccagattt gagctctctg gctaactagg    60
gaacccact                                                             69

<210> SEQ ID NO 38
<211> LENGTH: 74
<212> TYPE: DNA
<213> ORGANISM: Artificial Sequence
<220> FEATURE:
<223> OTHER INFORMATION: Synthetic construct

<400> SEQUENCE: 38 cttttttgcct gtactgggtc tctccgttag acagatccag cccgggagct ctctggctaa    60
ctagggaacc cact                                                       74
```

```
<210> SEQ ID NO 39
<211> LENGTH: 45
<212> TYPE: DNA
<213> ORGANISM: Artificial Sequence
<220> FEATURE:
<223> OTHER INFORMATION: Synthetic construct

<400> SEQUENCE: 39 cttttttgcct gtactgggtc tctctggcta gctagggaac ccact        45

<210> SEQ ID NO 40
<211> LENGTH: 73
<212> TYPE: DNA
<213> ORGANISM: Artificial Sequence
<220> FEATURE:
<223> OTHER INFORMATION: Synthetic construct

<400> SEQUENCE: 40 cttttttcggt gtactgggtc tctctggtta gaccagattt gagcctggga gcgctctggc    60
tagggaaccc act                                                        73

<210> SEQ ID NO 41
<211> LENGTH: 73
<212> TYPE: DNA
<213> ORGANISM: Artificial Sequence
<220> FEATURE:
<223> OTHER INFORMATION: Synthetic construct

<400> SEQUENCE: 41 cttttttgcct gtactgggtc tctctggtta gaccagattt gagcctggga gctctctggc    60
tagggaaccc act                                                        73

<210> SEQ ID NO 42
<211> LENGTH: 67
<212> TYPE: DNA
<213> ORGANISM: Artificial Sequence
<220> FEATURE:
<223> OTHER INFORMATION: Synthetic construct

<400> SEQUENCE: 42 cttttttgcct gtactgggtc tctctggtta gaccagattt gagccctgga tctctcggga    60
acccact                                                               67

<210> SEQ ID NO 43
<211> LENGTH: 67
<212> TYPE: DNA
<213> ORGANISM: Artificial Sequence
<220> FEATURE:
<223> OTHER INFORMATION: Synthetic construct

<400> SEQUENCE: 43 cttttttgcct gtactgggtc tctctggtta gaccagattt gagcctgggc tagctaggga    60
acccact                                                               67

<210> SEQ ID NO 44
<211> LENGTH: 67
<212> TYPE: DNA
<213> ORGANISM: Artificial Sequence
<220> FEATURE:
<223> OTHER INFORMATION: Synthetic construct

<400> SEQUENCE: 44 cttttttgcct gtactgggtc tctctggtta gaccagattt gagcctgggc taactaggga    60
``` acccact 67

<210> SEQ ID NO 45
<211> LENGTH: 57
<212> TYPE: DNA
<213> ORGANISM: Artificial Sequence
<220> FEATURE:
<223> OTHER INFORMATION: Synthetic construct

<400> SEQUENCE: 45
tctctggtta gaccagattt gagcctggga gctctctggc taactaggga acccact       57

<210> SEQ ID NO 46
<211> LENGTH: 59
<212> TYPE: DNA
<213> ORGANISM: Artificial Sequence
<220> FEATURE:
<223> OTHER INFORMATION: Synthetic construct

<400> SEQUENCE: 46
tctctggtta gaccagattt gagcctggga gctctctctg gctaactagg gaacccact     59

<210> SEQ ID NO 47
<211> LENGTH: 49
<212> TYPE: DNA
<213> ORGANISM: Artificial Sequence
<220> FEATURE:
<223> OTHER INFORMATION: Synthetic construct

<400> SEQUENCE: 47
tctctggtta gaccagattt gagctctctg gctaactagg gaacccact              49

<210> SEQ ID NO 48
<211> LENGTH: 44
<212> TYPE: DNA
<213> ORGANISM: Artificial Sequence
<220> FEATURE:
<223> OTHER INFORMATION: Synthetic construct

<400> SEQUENCE: 48
tctctggtta gaccagattt ctctggctaa ctagggaacc cact                   44

<210> SEQ ID NO 49
<211> LENGTH: 53
<212> TYPE: DNA
<213> ORGANISM: Artificial Sequence
<220> FEATURE:
<223> OTHER INFORMATION: Synthetic construct

<400> SEQUENCE: 49
tctctggtta gaccagattt gagcctggac tctggctaac tagggaaccc act          53

<210> SEQ ID NO 50
<211> LENGTH: 62
<212> TYPE: DNA
<213> ORGANISM: Artificial Sequence
<220> FEATURE:
<223> OTHER INFORMATION: Synthetic construct

<400> SEQUENCE: 50
tctctggtta gaccagattt gagcctggga gcgctcctat ctggctaact agggaaccca   60
ct                                                                 62

<210> SEQ ID NO 51
<211> LENGTH: 45

```
<212> TYPE: DNA
<213> ORGANISM: Artificial Sequence
<220> FEATURE:
<223> OTHER INFORMATION: Synthetic construct

<400> SEQUENCE: 51
tctctggtta gaccagattt gagcctggga gctagggaac ccact            45

<210> SEQ ID NO 52
<211> LENGTH: 43
<212> TYPE: DNA
<213> ORGANISM: Artificial Sequence
<220> FEATURE:
<223> OTHER INFORMATION: Synthetic construct

<400> SEQUENCE: 52
tctctggtta gaccagattc tctggctaac tagggaaccc act              43

<210> SEQ ID NO 53
<211> LENGTH: 47
<212> TYPE: DNA
<213> ORGANISM: Artificial Sequence
<220> FEATURE:
<223> OTHER INFORMATION: Synthetic construct

<400> SEQUENCE: 53
tctctggtta gaccagattt gagcctggga gcgctaggga acccact          47

<210> SEQ ID NO 54
<211> LENGTH: 25
<212> TYPE: DNA
<213> ORGANISM: Artificial Sequence
<220> FEATURE:
<223> OTHER INFORMATION: Synthetic construct

<400> SEQUENCE: 54
tctctggcta gctagggaac ccact                                  25

<210> SEQ ID NO 55
<211> LENGTH: 27
<212> TYPE: DNA
<213> ORGANISM: Artificial Sequence
<220> FEATURE:
<223> OTHER INFORMATION: Synthetic construct

<400> SEQUENCE: 55
tctctctggc taactaggga acccact                                27
```

COMPOSITIONS COMPRISING TALENS AND METHODS OF TREATING HIV

CROSS-REFERENCE TO RELATED PATENT APPLICATIONS

This application is a national phase application of International Application No. PCT/US2016/025037 filed on Mar. 30, 2016 which claims the benefit of the filing dates of U.S. Provisional Application No. 62/140,048, which was filed on Mar. 30, 2015; and U.S. Provisional Application No. 62/265,232, which was filed on Dec. 9, 2015. The contents of these earlier filed applications are hereby incorporated by reference in their entirety.

The sequence listing submitted herewith as a text file named "37474_0040U3_SequenceListing," created on Jul. 31, 2020, and having a size of 98,304 bytes is hereby incorporated by reference pursuant to 37 C.F.R. § 1.52(e)(5).

STATEMENT REGARDING FEDERALLY FUNDED RESEARCH

This invention was made with government support under grant number P20-GM103440 and R25-DK078385 awarded by the National Institutes of Health. The government has certain rights in the invention.

BACKGROUND

Human immunodeficiency virus (HIV), the causative agent of Acquired Immunodeficiency Syndrome (AIDS), is a pathogenic retrovirus that integrates a proviral DNA copy of its genome into the genome of host cells. Three decades of research and development have produced many antiretroviral (ARV) drugs that, when combined in highly active antiretroviral therapy (HAART) can reduce the plasma viral load in infected patients, and even shut down viral production (Shen et al. (2008) Nat Med 14: 762-766). But even with chronic HAART treatment, an integrated copy of proviral HIV DNA remains in latent cells, which can re-establish viral production and cause a rebound, producing plasma viremia (Matreyek et al. (2012) Expert Rev Anti Infect Ther 10: 855-857).

The persistent latent HIV reservoir is a barrier to HIV treatment (Sigal and Baltimore, (2012) Cell Host Microbe 12: 132-138). The current strategy to address HIV latency is, while under HAART therapy, to reactivate latently infected cells so that they can be targeted by the immune system (Matreyek et al. (2012) Expert Rev Anti Infect Ther 10: 855-857; Dhamija et al. (2012) Subcell Biochem 61: 479-505; Sgarbanti and Battistini, (2013) Curr Opin Virol., 3(4):394-401; and Colin and Van Lint, (2009) Retrovirology 6: 111). A major problem with this approach is that specific reactivation of latent cells has not been achieved and non-specific reactivation of T-cells can lead to a cytokine storm (Shan and Siliciano, (2013) BioEssays News Rev Mol Cell Dev Biol 35: 544-552). Thus, new strategies to eradicate or damage the integrated HIV proviral DNA are needed.

SUMMARY

Provided herein are compositions and methods relating to treatment and prevention of retroviral infections.

Disclosed herein, are engineered transcription activator like effector nucleases (TALENs) comprising from the N-terminus to the C-terminus, a first spacer sequence a TALE DNA binding domain, a second spacer sequence, and a FokI nuclease catalytic domain fused to the C-terminus.

Disclosed herein, is a nucleic acid comprising a sequence encoding a TALEN, wherein the TALEN comprises from the N-terminus to the C-terminus, a first spacer sequence a TALE DNA binding domain, a second spacer sequence, and a FokI nuclease catalytic domain fused to the C-terminus.

Disclosed herein, are pharmaceutical compositions comprising vectors encoding one or more TALEN monomers, wherein the one or more TALEN monomers comprise from the N-terminus to the C-terminus, a first spacer sequence, a TALE DNA binding domain, a second spacer sequence, and a FokI nuclease catalytic domain fused to the C-terminus.

Disclosed herein, are methods of inactivating a retrovirus in a mammalian cell, the method comprising exposing the cell to a composition comprising an isolated nucleic acid encoding a gene editing complex comprising a TALEN, wherein the TALEN comprises a TALE DNA binding domain, wherein the TALE DNA binding domain provides sequence-specific binding to a predetermined nucleotide sequence to target a nucleic acid sequence in the retrovirus.

Disclosed herein, are methods of treating a subject having a human immunodeficiency virus infection, the method comprising: determining the nucleic acid sequence of the human immunodeficiency virus; and administering to the subject a pharmaceutical composition comprising a nucleic acid sequence encoding a TALEN, wherein the TALEN comprises from the N-terminus to the C-terminus, a first spacer sequence, a TALE DNA binding domain, a second spacer sequence, and a FokI nuclease catalytic domain fused to the C-terminus.

Disclosed herein, are kits comprising a predetermined amount of a composition comprising an isolated nucleic acid sequence comprising a sequence encoding a TALEN, wherein the TALEN comprises a TALE DNA binding domain providing a sequence-specific binding to a target nucleotide sequence in a human immunodeficiency virus, instructions, sterile fluid, syringe, and a sterile container.

Other features and advantages of the present compositions and methods are illustrated in the description below, the drawings, and the claims.

BRIEF DESCRIPTION OF THE DRAWINGS

FIGS. 1A-1D illustrate results from the HIV-1 genome conservation analysis to select TALEN sites. A. Schematic diagram of HIV-1 genome adapted from the LANL HIV website (Leitner et al. (2005) HIV Sequence Compendium, 2005 Los Alamos, N. Mex.: Theoretical Biology and Biophysics Group, Los Alamos National Laboratory). Bolded boxes are regions with HT-TALEN DNA targets, one of which is shown in B. B. 5' LTR DNA TALEN target sequence (SEQ ID NO: 32, upper sequence; and SEQ ID NO: 33, lower sequence). The TALE binding targets are indicated by black lines. The endonuclease target site sequence is in lower case font and indicated by grey lines. C. TAR RNA with partial 5' TALE binding site in upper-case font and endonuclease target site in lower-case font (SEQ ID NO: 34). D. HIV-1 DNA sequences (274,874 total) from the Los Alamos HIV Sequence Database were aligned with ClustalΩ to determine sequence conservation, which is presented in a position specific-scoring matrix (Sievers et al. (2011) Mol Syst Biol, 7:539; and Leitner et al. (2005) HIV Sequence Compendium, 2005 Los Alamos, N. Mex.: Theoretical Biology and Biophysics Group, Los Alamos National Laboratory). The most conserved contiguous regions were chosen as TALEN target sequences and are found in the TAR coding region (B) of the LTRs (226 sequences) (A).

FIGS. 3A-3D show HT-TALEN and NS-TALEN targeting HIV-1 LTR in cell culture. A. Schematic diagram of DNA GFP reporter to be targeted by HT-TALENs and NS-TALENs. The target DNA contains the 5' LTR of HIV-1 fused upstream of the coding region of d1EGFP. B. Western blot analysis of HeLa-tat-III/LTR/d1EGFP cells transfected with either the HT-TALEN pair or NS-TALEN pair. The blot was probed with anti-Flag and anti-Actin as a loading control. C. Dose-response plot based on quantification of flow cytometry analysis of GFP reporter expression. Transiently transfected HeLa-tat-III/LTR/d1EGFP samples were analyzed for GFP and mCherry expression. Cells with mCherry contained the transfected plasmids. Cells containing the functional HIV-1 LTR fused d1EGFP reporter expressed GFP. Samples were done in triplicate. Those samples not expressing GFP, only mCherry were compared. Standard deviations from triplicate samples are smaller than the symbols and not shown. Statistically significant differences between slopes for TALEN treatment and control indicated is by a * ($p<0.000001$); NS-TALEN and HT-TALENs were not significantly different ($p<0.08$). D. Sequences of genomic clones containing mutated target regions. Uppercase bolded font indicates designated 5' TALE and 3' TALE binding sites. Inserted nucleotides are in lower-case italicized font. A deletion is represented by dashes. Lengths of the insertions (+) and deletions (−) are at the right of each sequence. SEQ ID NOs: 35-44 are shown corresponding to WT through G-11.

FIG. 15 is a table showing examples of TALEN sequences. Key: sequences in lowercase refer to the DNA code for the N and C terminus of the TALE proteins; sequences in UPPERCASE refer to DNA sequences for HD monomers; sequences in UPPERCASE refer to DNA sequences for NG monomers; sequences in lowercase refer to DNA sequences for NN monomers; sequences in UPPERCASE refer to NS changes in DNA sequences; ATG in a gray box refers to the start codon; TAA in a gray box refers to the stop codon; GGATC, GGATCC or ACCGGT in a gray box refers to the restriction enzyme site; sequences in lowercase in a light gray box refer to DNA sequences for NI monomers, sequences in UPPERCASE refers to DNA sequence FokI catalytic protein; and sequences in UPPERCASE in a gray box refers to Sharkey. Heterodimer mutations; and UPPERCASE refers to FLAG tag sequence ×3; N=any nucleotide or amino acid sequence.

DETAILED DESCRIPTION

Figure 2A:
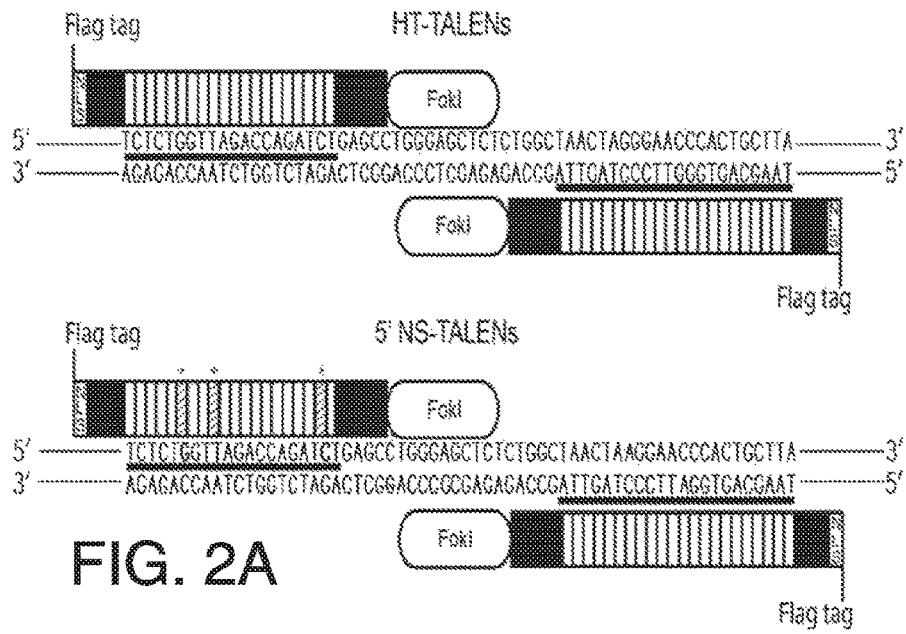
FIGS. 2A-2D demonstrate that HT-TALEN and NS-TALEN pairs cleave an HIV-1 DNA fragment in vitro. A. Schematic diagram representing HT-TALENs and NS-TALENs bound to their cognate DNA target sequence (thick lines). Relative locations of the FokI endonuclease, Flag epitope tag, and nuclear localization sequence (NLS) are indicated. Asterisks and grey boxes designate where a "NS" repeat variable diresidue (RVD) coded in a TALEN repeat was used in the 5' NS-TALEN construction. B. Western blot of in vitro transcription/translation reactions containing no expression plasmids, each TALEN alone, the HT-TALEN pair, or the NS-TALEN pair. C. Gel electrophoresis analysis of in vitro cleavage reactions containing no TALEN plasmids, the HT-TALEN pair, or the NS-TALEN pair. The HIV-1 target DNA fragment size is 747 bp, with expected on-target cleavage products of approximately 430 bp and 317 bp. Quantification of cleavage was performed using ImageJ software and is shown below the gel image. D. The HIV-1 target DNA fragment from (C) was mutated in the 5' TALE binding site to create a set of triple mutant templates (Mut-Mut4). The sequences of Mut1-Mut4 are depicted in bold, lowercase font and mutated positions are indicated by asterisks. Products from cleavage reactions containing either the HT-TALEN or NS-TALEN pairs incubated with the HIV-1 target templates were size fractionated by electrophoresis and quantified by densitometry with ImageJ (Schneider Rasband, and Eliceiri, (2012) Nat Methods, 9:671-675).

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

As used in the specification and in the claims, the term "comprising" can include the aspects "consisting of" and "consisting essentially of." "Comprising can also mean "including but not limited to."

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The phrase "nucleic acid" as used herein refers to a naturally occurring or synthetic oligonucleotide or polynucleotide, whether DNA or RNA or a DNA-RNA hybrid, single-stranded or double-stranded, sense or antisense, which is capable of hybridization to a complementary nucleic acid by Watson-Crick base-pairing. Nucleic acids as disclosed herein can also include nucleotide analogs (e.g., BrdU), and non-phosphodiester internucleoside linkages (e.g., peptide nucleic acid or thiodiester linkages). In particular, nucleic acids can include, without limitation, DNA, RNA, cDNA, gDNA, ssDNA, dsDNA or any combination thereof.

"Inhibit," "inhibiting," "inhibition," and "inactivate" are used herein to mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease, disorder or infection. The term "patient" includes human and veterinary subjects. In some aspects of the disclosed methods the "patient" has been diagnosed or identified with a need for treatment, for having an infection (e.g., HIV), such as, for example, prior to the administering step.

As used herein, the term "TALEN" refers to a nucleic acid encoding a protein comprising a TALE DNA binding domain fused to an endonuclease, resulting in a monomeric TALEN. A monomeric TALEN can be functional. A monomeric TALEN can be capable of dimerizing with another monomeric TALEN. Such dimerization can be a result of a homodimeric TALEN wherein both monomeric TALENs are the same (e.g., identical). Alternatively, the dimerization can be a result of the dimerization of two monomeric TALENs that are different. For example, two monomeric TALENs can be different when the repeat variable diresidues of each monomeric TALEN are different.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

INTRODUCTION

Integration of human immunodeficiency virus (HIV)-1 from HIV-1 infected cells using the genome editing tool with engineered nucleases, transcription activator-like effector nucleases (TALENs), can be inactivated. It is well known that HIV integrates its proviral DNA genome into the host genome, presenting barriers for virus eradication. Thus, an approach to eradicate or damage the integrated HIV proviral DNA was needed. Several new gene-editing technologies have emerged that can be used to damage integrated proviral DNA.

One strategy is genome editing with engineered nucleases (GEEN). There are four main technologies used for GEEN: (1) meganucleases; (2) zinc finger nucleases (ZFN); (3) transcription activator-like effector nucleases (TALENs); and (4) clustered regulatory interspaced short palindromic repeat (CRISPR)/Cas-based RNA-guided DNA endonucleases. The technologies catalyze double strand breaks in genomic DNA that are thought to be repaired in cells by endogenous nonhomologous end joining (NHEJ). These repairs can produce mistake insertions or deletions, introducing indels into the targeted DNA, thus mutating the genomic DNA.

Others have tested Tre recombinase, zinc finger nucleases, and CRISPR/Cas-9 in attempts to target the integrated HIV-1 proviral DNA in cells (Hauber et al. (2013) PLoS Pathog 9: e1003587; Qu et al. (2013) Nucleic Acids Res 41: 7771-7782; and Hu et al. (2014) Proc Natl Acad Sci USA 111: 11461-11466). One limitation of these GEEN approaches is that the HIV-1 proviral DNA has few long stretches with conserved nucleotides, thus GEEN treatment can be prone to HIV-1 escape mutations.

TALEN based technology was chosen over other GEEN technologies to mutate and thus inactivate the HIV-1 proviral DNA for many reasons. TALENs are the only GEEN in which the targeting construct can encode specific degeneracy for the DNA recognition site, and thus, can be engineered to inhibit escape mutations (Boch et al. (2009) Science 326: 1509-1512). TALENs also are reported to have damage efficiencies of >50% achieved in several systems (Cade et al. (2012) Nucleic Acids Res 40: 8001-8010; Qiu et al. (2013) Nucleic Acids Res 41: e120; and Chen et al. (2013) Nucleic Acids Res 41: 2769-27780). TALENs have flexibility in the target sequences, whereas meganucleases and ZFNs have a limited breadth (Mukherjee and Thrasher, (2013) Gene 525: 174-181; and Wei et al. (2013) J Genet Genomics Yi Chuan Xue Bao 40: 281-289). TALENs can be specific in some systems evaluated by exome sequencing with limited off-target editing and toxicity (Ousterout et al. (2013) Mol Ther J Am Soc Gene Ther 21: 1718-1726). ZFNs have reported off-target editing sites, as well as CRISPR/Cas where sites with multiple base pairs that differ from the guide RNA can be edited (Wei et al. (2013) J Genet Genomics Yi Chuan Xue Bao 40: 281-289; Pennisi (2013) Science 341: 833-836; and Fu et al. (2013) Nat Biotechnol 31: 822-82). Using TALENs for treating HIV latency is supported by recent publications (Stone et al. (2013) Curr Opin HIV AIDS 8: 217-223; and Weber et al. (2013) Mol Ther J Am Soc Gene Ther 21: 1819-1820). Further support for using this approach to treat HIV comes from a recent report where TALENs were effectively used to disable the episomal HBV genome and reduce viral load in cells and animals (Schiffer et al. (2012) J Virol 86: 8920-8936; and Bloom et al. (2013) Mol Ther J Am Soc Gene Ther 21: 1889-1897).

HIV-1 can persist due to latent cell reservoirs containing integrated HIV-1 proviral DNA, even with chronic HAART therapy. These reservoirs can remain inactive for years, not expressing viral proteins or producing infectious virus (Sigal and Baltimore (2012) Cell Host Microbe 12: 132-138). Upon activation, previously latent HIV-1 infected memory CD4+ T cells and other cell types can reseed viral infection (Chun et al. (1995) Nat Med 1: 1284-1290; and Zhou et al. (2005) J Virol 79: 2199-2210). Upon cessation of HAART therapy, viremia is reestablished in approximately 50 days (Chun T et al. (2010) AIDS Lond Engl 24: 2803-2808). In order to eradicate HIV-1 infection, the cells with integrated HIV-1 proviral DNA must be removed or damaged.

To address viral latency, GEEN technologies have been developed that could be used in combination with HAART therapy (Peterson et al. (2013) Gene Ther 20: 695-702). Tre recombinase and zinc finger nuclease were both previously used to edit an integrated copy of HIV-1 proviral DNA and CRISPR/CAS has been used to remove a GFP reporter flanked by the HIV-1 LTRs (Mariyanna et al. (2012) PLoS One 7: e31576; Ebina et al. (2013) Sci Rep 3:2510; and Aubert et al. (2011) PLoS One 6: e16825). TALENs were previously used to target the episomal Hepatitis B virus and can reduce viremia in cells and animal models (Bloom et al. (2013) Mol Ther 21: 1889-1897).

Described herein are custom TALEN pairs of HIV targeted-TALENs (HT-TALENs) that were engineered to specifically target a conserved region of the HIV-1 genome. A NS-TALEN was also designed, built and tested with some degenerate recognition to accommodate escape mutations in regions where viral genome mutations have been previously observed. As described herein, the engineered TALENs cleave a DNA template with the HIV-1 proviral target site in vitro. Briefly, a GFP reporter, under control of HIV-1 TAR, was inactivated by mutations introduced by transfection of TALEN plasmids. When infected cells containing the full-length integrated HIV-1 proviral DNA were transfected with TALENs, the TAR region accumulated indels. When one of these mutants was tested, the mutated HIV-1 proviral DNA was incapable of producing detectable Gag expression. TALEN variants engineered for degenerate recognition of select nucleotide positions also cleaved proviral DNA in vitro and the full-length integrated proviral DNA genome in living cells. These results suggest a design strategy for therapeutic considerations of incomplete target sequence conservation and acquired resistance mutations. As described herein, a new strategy was developed for damaging integrated HIV proviral DNA that can provide HIV-1 proviral DNA eradication. The results further show that both TALEN pairs can be used to damage the integrated HIV-1 proviral DNA in cultured cells infected with HIV-1. These data are the first demonstration that the full-length integrated HIV-1 proviral DNA can be mutated and protein expression negatively affected by introduction of TALENs, and thus inactivated in cells. The technology described herein is an alternative approach for treating viral latency as can serve as a covalent modification of the proviral DNA.

Compositions

Transcription activator-like effector nucleases (TALENs). TALENs are artificial endonucleases (i.e., restriction enzymes) and are produced by the fusion of a transcription activator-like effector (TALE) DNA binding domain with a DNA cleavage domain. TALENs can be engineered to bind any DNA sequence of interest. In an aspect, an engineered TALEN comprises from the N-terminus to the C-terminus, a first spacer, a TALE DNA binding domain, a second spacer, and a FokI nuclease catalytic domain fused to the C-terminus. The DNA cleavage domain cuts DNA strands and, so the fusion with a TALE DNA binding domain can be specific for a DNA sequence of interest to edit genomes by inducing double strand breaks. TALENs can function alone, in pairs, or in a plurality of pairs. For example, the TALE DNA binding domain can bind to targets positioned opposite of one another, across a spacer wherein the FokI domains come together to create the break in the DNA. In an aspect, TALE DNA binding domains can be designed for use in the disclosed TALENs. A single TALEN (also referred to herein as a monomeric TALEN or a TALEN monomer) comprises a TALE DNA binding domain and a FokI nuclease catalytic domain fused to the C-terminus. A TALEN can be engineered to be used in a TALEN pair (or also referred to herein as a pair of TALENs or TALEN pairs) designed to bind to a target nucleotide sequence configured from the N-terminus to the C-terminus on opposing strands of DNA. TALENs in a TALEN pair can have the same sequence or can be different in sequence.

Transcription activator-like effector (TALE). In an aspect, the TALE DNA binding domain comprises a protein sequence specific for binding to a target nucleotide sequence. The TALE DNA binding domains are derived from TALEs. TALEs are a class of specific DNA binding proteins found in *Xanthomonas* bacteria that upon binding to specific DNA sequences can activate the expression of target genes. TALE-like proteins can also found in other bacteria including but not limited to *Ralstonia* and *Burkholderia*. In an aspect, the target nucleotide sequence is in a retrovirus. The retrovirus can be a lentivirus, including, for example, a human immunodeficiency virus, a simian immunodeficiency virus, a feline immunodeficiency virus or a bovine immunodeficiency virus. In an aspect, the human immunodeficiency virus can be HIV-1 or HIV-2.

The target nucleotide sequence can include any sequence from any HIV (e.g., HIV-1 and HIV-2), and any circulating recombinant form thereof. HIV is known to be genetically variable and the multiple groups and subtypes have been described. HIV isolate DNA sequences are in the Los Alamos HIV sequence database (i.e., the sequence database website is www.hiv.lanl.gov). The compositions and methods described herein can be carried out to affect HIV from any group, subtype and circulating recombinant forms. Examples of HIV-1 groups include but are not limited to major group (sometimes called Group M) and the minor groups (e.g., N, O, and P). Examples of HIV-1 subtypes include but are not limited to, A, B, C, D, F, G, H, J and K. Examples of HIV-2 include but are not limited to A, B, C, F or G subtypes or groups, as well as any circulating recombinant forms.

In an aspect, the TALEN can be optimized for expression in a human cell. For example, the nucleic acid sequence can be codon optimized for efficient expression (e.g., transcription and/or translation) in mammalian cells, i.e., "humanized." Methods of codon optimization are well-known in the art. A humanized TALEN sequence can be, for example, TALEN binding sites (e.g., sequences) encompassing nucleotides corresponding to Genbank accession number K03455. Alternatively, the TALEN sequence can be inserted into a commercially available, for example, a vector such as JDS70, JDS71, JDS74 and JDS78 from Addgene (Cambridge, Mass.). Examples of such TALEN sequences are listed in FIG. 15. In some embodiments, the TALEN binding sites can have an amino acid sequence that is a variant or a fragment of the TALEN sequence of Genbank accession number K03455. The TALE nucleotide sequence can be modified to encode biologically active variants of a TALEN, and these variants can have or include, for example, an amino acid sequence that differs from a wild type TALEN by containing one or more mutations (e.g., an addition, deletion, or substitution mutation or a combination of such mutations). One or more substitution mutations can be a substitution (e.g., a conservative amino acid substitution). For example, a biologically active variant of a TALE polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type TALE polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the TALE amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one skilled in the art can consult a reference book or the worldwide web (a site is currently maintained by the California Institute of Technology and displays structures of non-natural amino acids that have been successfully incorporated into functional proteins). Examples of TALEN nucleotide sequences that can be modified to encode a biological variant of a TALEN are listed in FIG. 15.

The compositions disclosed herein can include a TALEN polypeptide encoded by any of the nucleic acid sequences described above. The terms "peptide," "polypeptide," and "protein" can be used herein interchangeably even though they may refer to peptide sequences of different sizes or lengths. A polypeptide of the present disclosure can include a fragment of a TALEN or a biologically active variant thereof, but it can also include additional amino acid residues as well. The biologically active variants will retain sufficient activity to cleave target DNA sequences.

The amino acid residues can be linked together by conventional peptide bonds or other types of covalent bonds (e.g., ester bond). The polypeptides can be modified by amidation, phosphorylation or glycosylation. A biologically active variant of a TALEN can include one or more structural modifications resulting from any combination of naturally occurring (e.g., in vivo) and synthetic modifications (i.e., made in vitro). Modifications of the present disclosure include but are not limited to amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

Polypeptides can be produced, isolated and purified by a variety of methods known to one skilled in the art. The final polypeptide composition can be confirmed by amino acid analysis after degradation of the peptide by amino acid sequencing or by FAB-MS methods or any other known standard technique. Polypeptide salts, including acid salts, esters, amides, and N-acyl derivatives of an amino group can be prepared using techniques known to one skilled in the art.

As disclosed herein, the TALE DNA binding domain comprises a sequence complimentary to a target sequence in a retrovirus. The retrovirus can be a human immunodeficiency virus (e.g., HIV-1 or HIV-2). For example, the target sequence can be an HIV sequence including a long terminal repeat (LTR) sequence, a protein coding sequence, or a regulatory sequence. The HIV-1 LTR region contains identical DNA sequences of about 640 base pairs in length and is further subdivided into the U3, R, and U5 regions. LTRs contain all of the required signals for gene expression and play a part in the integration of a provirus into the genome of a host cell. The U3 region contains a core promoter, a core enhancer and a modulatory region while the R region contains the transactivation response element (TAR). The U5 region of HIV-1 contains the following sub-regions, a TAR that is important for transcriptional activation; poly(A) which is involved in dimerization and genome packaging; a primer binding site that is involved in the initiation of reverse transcription; a Psi packaging element involved in packaging of the viral genome into the capsid; and a dimer initiation site involved encapsidation. In an aspect, the TALE DNA binding domain comprises a sequence targeting a conserved sequence in the TAR of a human immunodeficiency virus.

An example of a target sequence or region encompassing TAR (e.g., encompassing HIVB5LTR) for the 5' HT-TALEN and 5' NS-TALEN binding sites involve nucleotide positions 459-478 (HIV-1 HXB2 accession number K03455; SEQ ID NO: 1), while the 3' HT-TALEN binding site encompasses nucleotide positions 499-515 (HIV HXB2 accession number K03455; SEQ ID NO: 2). In an aspect, the 5' HT-TALEN binding site is SEQ ID NO: 1. In an aspect, the 3' HT-TALEN binding site has the sequence of SEQ ID NO: 3. A target sequence can comprise, for example, the sequence of: SEQ ID NOs: 1-7.

The TALE DNA binding domain consists of a series of repeated amino acids sequences or segments that are referred to as TAL repeats. The TAL repeats are highly conserved sequences wherein each segment contains about 33-34 amino acids. Each of the TAL repeats also contains two highly variable amino acid acids at the $12^{th}$ and $13^{th}$ positions that encode DNA nucleotide binding specificity. These highly variable amino acids of the TAL repeats are commonly referred to as repeat variable diresidues (RVDs). The TALE DNA binding domain can include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more TAL repeats. In an aspect, the TALE DNA binding domain includes between 15 and 25 TAL repeats. Accordingly, the TALE DNA binding domain can thereby specifically recognize and bind to a nucleic acid sequence consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more continuous nucleotides. In an aspect, the TALE DNA binding domain comprises 20 TAL repeats. The number and composition of the TAL repeats can be varied within the TALE DNA binding domain. The TAL repeats can also be selected or varied to modulate TALEN specificity and activity. Examples of TALE DNA binding domain sequences are provided in SEQ ID NOs: 1-7. In an aspect, the TALE DNA binding domain sequences comprise a sequence having at least 80%, 85%, 90%, 95%, or 99% identify to the sequence of any one of SEQ ID NOs: 1-7. The RVDs within the TAL repeats also specifically recognize and bind to a corresponding nucleotide within a target sequence. Thus, a TALE DNA binding domain can be formed or engineered by selecting a combination of TAL repeats containing the relevant RVDs to recognize a specific target sequence. In other words, the RVD determines the single nucleotide that TALE recognizes. For example, the following RVDs recognize the following nucleotides: HD recognizes C; NG recognizes T; NI recognizes A; NN recognizes G or A; NS recognizes A or C or G; HG recognizes T; and IG recognizes T. Other RVDs and the nucleotides they recognize are known to one skilled in the art. In an aspect, the TALE DNA binding domain comprises one or more RVDs. The composition of the RVDs can be varied to modulate TALEN activity. In an aspect, a TALEN comprising the RVD NS is engineered. In an aspect, a TALEN comprising an RVD that recognizes methylated DNA.

HIV with escape mutations can produce resistance to antiretroviral drugs. Incorporation of an RVD into the TALEN can be used to encode predicted potential degenerate positions of a mutation in the target DNA. For example, a TALEN comprising an NS RVD variant can encode degenerate nucleotide recognition and tolerate predicted escape mutants, based on nucleotide conservation. Thus, such TALENs (e.g., NS-TALEN) can allow degenerate recognition of escape mutations and provide an advantage over other GEEN technologies.

The TALENs described herein can include a C-terminal truncated TAL repeat in the TALE DNA binding domain. The C-terminal truncated TAL repeat can be about 34 or few amino acids. For example, the C-terminal truncated TAL repeat can be 33, 32, 31, 30, 29, and so on amino acids in length or less. The C-terminal truncated TAL repeat regardless of length still contains the RVDs for specificity for a nucleotide. In an aspect, the TALE DNA binding domain comprises a C-terminal truncated TAL repeat.

In an aspect, the TALEN can further comprise a nuclear localization signal (NLS) for import into a cell nucleus. NLS sequences are short segments of amino acids comprising positively charged lysines or arginines or a combination thereof. Generally, a NLS contains positively charged residues since it is well-known that positive residues bind importins to gain access into the nucleus of a cell. The NLS can be any sequence from a nuclear encoded protein. The NLS can be of a classical or non-classical type. An example of an NLS is the SV40 NLS. In an aspect, the SV40 NLS comprises PKKKRKV (SEQ ID NO: 8). The NLS can be positioned at the N-terminal or C-terminal end of the TALEN described herein. In an aspect, the NLS is positioned at the N-terminus.

The TALENs described herein can further comprise one or more labels or detection tags (e.g., FLAG™ tag, epitope or protein tags, such as myc tag, 6 His, and fluorescent fusion protein). In an aspect, the label (e.g., FLAG™ tag) is fused to the NLS. In an aspect, the disclosed methods and compositions further comprise a fusion protein, or a polynucleotide encoding the same. In various aspects, the fusion protein comprises at least one epitope-providing amino acid sequence (e.g., "epitope-tag"), wherein the epitope-tag is selected from i) an epitope-tag added to the N- and/or C-terminus of the protein (e.g., TALEN); or ii) an epitope-tag inserted into a region of the protein (e.g., TALEN), and an epitope-tag replacing a number of amino acids in the protein (e.g., TALEN).

Epitope tags are short stretches of amino acids to which a specific antibody can be raised, which in some aspects allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western blotting"), and affinity chromatography. Epitope tags add a known epitope (e.g., antibody binding site) on the subject protein, to provide binding of a known and often high-affinity antibody, and thereby allowing one to specifically identify and track the tagged protein that has been added to a living organism or to cultured cells. Examples of epitope tags include, but are not limited to, myc, T7, GST, GFP, HA (hemagglutinin), V5 and FLAG tags. The first four examples are epitopes derived from existing molecules. In contrast, FLAG is a synthetic epitope tag designed for high antigenicity (see, e.g., U.S. Pat. Nos. 4,703,004 and 4,851,341). Epitope tags can have one or more additional functions, beyond recognition by an antibody.

In an aspect, the disclosed methods and compositions comprise an epitope-tag wherein the epitope-tag has a length of between 6 to 15 amino acids. In an alternative aspect, the epitope-tag has a length of 9 to 11 amino acids. The disclose methods and compositions can also comprise a fusion protein comprising two or more epitope-tags, either spaced apart or directly in tandem. Further, the disclosed methods and composition can comprise 2, 3, 4, 5 or even more epitope-tags, as long as the fusion protein maintains its biological activity/activities (e.g., "functional").

In an aspect, the epitope-tag is a VSV-G tag, CD tag, calmodulin-binding peptide tag, S-tag, Avitag, SF-TAP-tag, strep-tag, myc-tag, FLAG-tag, T7-tag, HA (hemagglutinin)-tag, His-tag, S-tag, GST-tag, or GFP-tag. The sequences of these tags are described in the literature and well known to the person of skill in art.

As described herein, the term "immunologically binding" is a non-covalent form of attachment between an epitope of an antigen (e.g., the epitope-tag) and the antigen-specific part of an antibody or fragment thereof. Antibodies are preferably monoclonal and must be specific for the respective epitope tag(s) as used. Antibodies include murine, human and humanized antibodies. Antibody fragments are known to the person of skill and include, amongst others, single chain Fv antibody fragments (scFv fragments) and Fab-fragments. The antibodies can be produced by regular hybridoma and/or other recombinant techniques. Many antibodies are commercially available.

The construction of fusion proteins from domains of known proteins, or from whole proteins or proteins and peptides, is well known. Generally, a nucleic acid molecule that encodes the desired protein and/or peptide portions are joined using genetic engineering techniques to create a single, operably linked fusion oligonucleotide. Appropriate molecular biological techniques may be found in Sambrook et al. (Molecular Cloning: A laboratory manual Second Edition Cold Spring Harbor Laboratory Press, Cold spring harbor, NY, USA, 1989). Examples of genetically engineered multi-domain proteins, including those joined by various linkers, and those containing peptide tags, can be found in the following patent documents: U.S. Pat. No. 5,994,104 ("Interleukin-12 fusion protein"); U.S. Pat. No. 5,981,177 ("Protein fusion method and construction"); U.S. Pat. No. 5,914,254 ("Expression of fusion polypeptides transported out of the cytoplasm without leader sequences"); U.S. Pat. No. 5,856,456 ("Linker for linked fusion polypeptides"); U.S. Pat. No. 5,767,260 ("Antigen-binding fusion proteins"); U.S. Pat. No. 5,696,237 ("Recombinant antibody-toxin fusion protein"); U.S. Pat. No. 5,587,455 ("Cytotoxic agent against specific virus infection"); U.S. Pat. No. 4,851,341 ("Immunoaffinity purification system"); U.S. Pat. No. 4,703,004 ("Synthesis of protein with an identification peptide"); and WO 98/36087 ("Immunological tolerance to HIV epitopes").

The placement of the functionalizing peptide portion (epitope-tag) within the subject fusion proteins can be influenced by the activity of the functionalizing peptide portion and the need to maintain at least substantial fusion protein, such as TCR, biological activity in the fusion. Two methods for placement of a functionalizing peptide are: N-terminal, and at a location within a protein portion that exhibits amenability to insertions. Though these are not the only locations in which functionalizing peptides can be inserted, they serve as good examples, and will be used as illustrations. Other appropriate insertion locations can be identified by inserting test peptide encoding sequences (e.g., a sequence encoding the FLAG peptide) into a construct at different locations, then assaying the resultant fusion for the appropriate biological activity and functionalizing peptide activity, using assays that are appropriate for the specific portions used to construct the fusion. The activity of the subject proteins can be measured using any of various known techniques, including those described herein.

Spacers. The TALENs described herein can comprise spacer sequences. Spacer sequences are oriented on either side of the TALE DNA binding domain and are sufficiently long enough to permit two FokI catalytic domains to dimerize and cleave the DNA. In other words, the spacer length should be sufficiently long enough to separate the TALE binding sites to enable the two FokI catalytic domains to efficiently dimerize. The spacer sequence can also be selected or varied to modulate TALEN specificity and activity. As disclosed herein, the TALEN comprises from the N-terminus to the C-terminus, a first spacer sequence, a TALE DNA binding domain, a second spacer sequence, and a FokI nuclease catalytic domain fused to the C-terminus. The spacer sequences can be about 10 to about 200 amino acids in length. Examples of spacer sequences include SEQ ID NOs: 9 and 10.

In an aspect, the first spacer sequence is fused to the NLS. The first spacer sequence can also be fused to one or more labels or detection tags. Further, the first spacer sequence can comprise an N-terminal portion of the coding region for a TALE, for example, the first space sequence can be derived from N-terminal portion of a *Xanthomonas* TALE. In an aspect, the second spacer sequence comprises part of a C-terminal TALE domain. In some aspects, the second spacer comprises a truncated C-terminal TALE domain. The second spacer can also be fused to the NLS and/or to one or more labels or detection tags.

Nuclease catalytic domain. As used herein, the term "nuclease" refers to an exonuclease or an endonuclease. Endonucleases are enzymes that cleave or hydrolyze the bond between nucleotides in an RNA or DNA molecules. An example of an endonuclease is FokI, naturally found in *Flavobacterium okeanokoites*. As described herein, the TALENs can also include a FokI nuclease catalytic domain. Examples of a FokI include SEQ ID NOs: 11-12 (nucleotides) and SEQ ID NOs: 13-14 (amino acids). In an aspect, the FokI nuclease catalytic domain is an obligate homodimer or an obligate heterodimer. The FokI nuclease catalytic domain dimerizes to form an active nuclease, thus two TALENs (e.g., two TALEN monomers) or a pair of TALENs makes a functional genome-editing endonuclease. For example, for a pair of TALENs, each contain one member of the obligate heterodimer pair binds to the adjacent (e.g., within 10, 11, 12, 13, 14, 15, 16, 17, 18, 19, 20, 21, 22, 23, 24, 25 or more continuous nucleotides) recognition site (i.e., effector binding element) to enable dimerization of the endonuclease for cleavage. In an aspect, each effector binding element of an obligate heterodimer pair can independently be about 10, 11, 12, 13, 14, 15, 16, 17, 18, 19, 20, 21, 22, 23, 24, 25, 26, 27, 28, 29, 30 or more base pairs in length. Each monomer of an obligate dimer pair recognizes one strand of a target double-stranded nucleic acid and the other monomer of the obligate dimer pair recognizes the other strand of a target double-stranded nucleic acid. The effector binding elements are generally sufficiently separated by the first and second spacer components where the DNA cleavage occurs.

The FokI nuclease catalytic domain can be modified. For instance, the modified FokI nuclease catalytic domain can include specific mutations, such as, for example, Sharkey mutations and obligate heterodimer mutations. In an aspect, the FokI nuclease catalytic domain can be engineered such that the mutations replace wild-type Gln (Q) residue at position 486 with a Glu (E), the wild-type Iso (1) residue at position 499 with a Leu (L) residue and the wild-type Asn (N) residue at position 496 with an Asp (D) (also referred to as "ELD;" numbered relative to wild-type FokI). In an aspect, the FokI nuclease catalytic domain can be engineered such that the mutations replace wild-type Glu (E) residue at position 490 with a Lys (K), the wild-type Iso (I) residue at position 538 with a Lys (K) residue and the wild-type His (N) residue at position 537 with an Arg (R) (also referred to as "KKR;" numbered relative to wild-type FokI).

In an aspect, the present disclosure provides a pair of TALENs that bind to and flank a nucleic acid of interest. In an aspect, a pair of TALEN obligate heterodimers is disclosed such that they flank a nucleic acid region of interest. In some embodiments, the pair of obligate heterodimers bind to and flank a sequence within the transactivation response element of a human immunodeficiency virus.

In some aspects, the catalytic domain can be a nuclease catalytic domain for a nuclease other than FokI.

Polynucleotides. In an aspect, polynucleotides or polynucleotide sequences encoding the engineered TALENs are disclosed. The polynucleotides or polynucleotide sequences can be optimized for expression in a subject (e.g., human). Methods of codon optimization are well-known in the art.

In an aspect, the present disclosure provides mRNAs encoding any of the TALENs described herein. For example, the mRNA can be obtained via in vitro or in vivo transcription. Such mRNA can be used for the translation into TALENs in a host cell. Examples of administering the mRNA to a host cell include injection, or transfection using polyethylenimine, lipid, or calcium phosphate, or electroporation. The mRNA can also be fused to a translocation domain that is useful for translocation across a cell membrane. Once the mRNA is present inside the host cell, TALEN synthesis can begin.

Vectors. Vectors comprising nucleic acids or polynucleotides as described herein are also provided. As used herein, a "vector" refers a carrier molecule into which another DNA segment can be inserted to initiate replication of the inserted segment. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, and viruses (e.g., bacteriophage, animal viruses, and plant viruses), and artificial chromosomes (e.g., YACs). Vectors can comprise targeting molecules. A targeting molecule is one that directs the desired nucleic acid to a particular organ, tissue, cell, or other location in a subject's body. A vector, generally, brings about replication when it is associated with the proper control elements (e.g., a promoter, a stop codon, and a polyadenylation signal). Examples of vectors that are routinely used in the art include plasmids and viruses. The term "vector" includes expression vectors and refers to a vector containing a nucleic acid sequence coding for at least part of a gene product capable of being transcribed. A variety of ways can be used to introduce an expression vector into cells. In an aspect, the expression vector comprises a virus or an engineered vector derived from a viral genome. As used herein, "expression vector" is a vector that includes a regulatory region. A variety of host/expression vector combinations can be used to express the nucleic acid sequences disclosed herein. Examples of expression vectors include but are not limited to plasmids and viral vectors derived from, for example, bacteriophages, retroviruses (e.g., lentiviruses), and other viruses (e.g., adenoviruses, poxviruses, herpesviruses and adeno-associated viruses). Vectors and expression systems are commercially available and known to one skilled in the art.

The vectors disclosed herein can also include detectable labels. Such detectable labels can include a tag sequence designed for detection (e.g., purification or localization) of an expressed polypeptide. Tag sequences include, for example, green fluorescent protein, glutathione S-transferase, polyhistidine, c-myc, hemagglutinin, or Flag™ tag, and can be fused with the encoded polypeptide and inserted anywhere within the polypeptide, including at either the carboxyl or amino terminus.

The term "expression cassette" as used herein refers to a nucleic acid construct. The expression cassette can be produced either through recombinant techniques or synthetically that will result in the transcription of a certain polynucleotide sequence in a host cell. The expression cassette can be part of a plasmid, viral genome or nucleic acid fragment. Generally, the expression cassette includes a polynucleotide operably linked to a promoter. In an aspect, an expression cassette comprises a promoter and the polynucleotide or polynucleotide sequence encoding any of the engineered TALENs described herein. The expression cassette can further comprise a coding sequence for a nuclear localization signal fused to the N- or C-terminus of the TALEN and a polyadenylation signal. The expression cassette can further encode a detection or purification label or tag, fused to the N- or C-terminus of the TALEN. In an aspect, the expression cassette is a plasmid. Useful commercially available kits include the Voytas/Bogdanove TALEN kit and Dr. Keith Joung's lab TALEN kit, both available through Addgene. Plasmids that are useful include JDS70, JDS71, JDS74 and JDS78. The expression cassette can be adapted for expression in a specific type of host cell (e.g., using a specific type of promoter). The expression cassette can also comprise other components such as polyadenylation signals, enhancer elements or any other component that results in the expression of an engineered TALEN disclosed herein in a specific type of host cell.

As used herein, the term "operably linked" refers to the position of a regulatory region and a sequence to be transcribed in a nucleic acid to facilitate transcription or translation of the sequence. The choice of promoters depends on several factors including but not limited to efficiency, selectability, inducibility, desired expression level, and cell- or tissue-preferential expression. One skilled in the art is capable of appropriately selecting and positioning promoters and other regulatory regions relative to the coding sequence.

Vectors include, for example, viral vectors (such as adenoviruses ("Ad"), adeno-associated viruses (AAV), and retroviruses, including lentiviruses), liposomes and other lipid-containing complexes, and other macromolecular complexes capable of mediating delivery of a polynucleotide to a host cell. Vectors can also comprise other components to further modulate TALEN delivery and/or TALEN expression, or that otherwise provides beneficial properties to the targeted cells. A wide variety of vectors is known to those skilled in the art and is generally available. Other suitable complexes capable of mediating delivery of any of the engineered TALENs described herein include retroviruses (e.g., lentivirus), vaults, cell penetrating peptides and biolistic particle guns. Cell penetrating peptides are capable of transporting or translocating proteins across a plasma membrane; thus, cell penetrating peptides act as delivery vehicles. Examples include but are not limited to labels (e.g., GFP, MRI contrast agents, quantum dots), Tat (a protein made by HIV), and ANT (from *Drosophila* Antennepedia).

A host cell can be selected depending on the nature of the transfection vector. In an aspect, the host cell comprises an expression cassette comprising a promoter and polynucleotide or polynucleotide sequence encoding any of the engineered TALENs described herein. The promoter can be operably linked to the polynucleotide sequence encoding the engineered TALEN. The cell can be examined using a variety of different physiologic assays. Such assays and methods are known to one skilled in the art.

Nucleic acids. The present disclosure also includes a nucleic acid comprising a sequence encoding a TALEN, wherein the TALEN comprises from the N-terminus to the C-terminus, a first spacer sequence a TALE DNA binding domain, a second spacer sequence, and a FokI nuclease catalytic domain fused to the C-terminus. In an aspect, the TALE DNA binding domain is specific for a target sequence in HIV proviral DNA. As described above, the TALEN can comprise a sequence that is optimized for expression in a cell or organism (e.g., human). The nucleic acid sequence can be codon optimized for efficient expression in mammalian cells (i.e., "humanized"). The target sequence can comprise a sequence within a transactivation response element of HIV. In as aspect, the target sequence within the TAR of HIV can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to SEQ ID NOs: 1-7. As used herein, "percent sequence identity" means the degree of identity between two sequences, such as a query sequence an a subject sequence. For example, a naturally occurring TALE sequence can be the query sequence and a fragment thereof (e.g, TALE protein) can be the subject sequence. The computer program ClustalΩ (default parameters) can be used to determine the sequence identify of any nucleic acid or amino acid sequences for comparison.

The term "exogenous" as used herein refers to a nucleic acid or polypeptide that is a part of, or encoded by, a recombinant nucleic acid construct. An exogenous nucleic acid can be a sequence from one species that is introduced into another species, generally through a recombinant nucleic acid construct. Alternatively, an exogenous nucleic acid can be a native sequence that is reintroduced into the cells of that same organism. An exogenous nucleic acid sequence can comprise both naturally occurring sequences and non-naturally occurring sequences (e.g., regulatory sequences flanking a naturally occurring sequence in a recombinant nucleic acid construct).

Recombinant constructs are also disclosed herein. Recombinant sequences can be useful to transform cells to express any one or both of the TALENs comprising sequences complementary to a target sequence in HIV. For example, a recombinant nucleic acid construct comprises TALEN, operably linked to a regulatory region for expressing the TALEN complementary to a target sequence in HIV in a cell. Codons in the coding sequence for TALEN can be modified for optimal expression in a particular organism.

The term "recombinant viral vector" as used herein refers to a viral vector comprising one or more heterologous gene products or sequences. Generally, the heterologous gene products or sequences are introduced by replacing one or more regions of the viral genome.

Examples of promoters that can be useful for gene expression include, but are not limited to, Rous sarcoma virus (RSV), SV40, herpes thymidine kinase promoter, β-lactamase promoter, the tac promoter, Gal 4 promoter, alcohol dehydrogenase promoter, phosphoglycerol kinase promoter, elongation factor-1 alpha promoter, cytomegalovirus promoter, and alkaline phosphatase promoter.

The term "isolated nucleic acid" as used herein refers to a naturally-occurring DNA molecule or a fragment thereof such that the isolated nucleic acid includes a DNA molecule that exists as separate molecule, independent of other sequences. An isolated nucleic acid molecule can be incorporated into a vector, plasmid, or virus. The isolated nucleic acid can include an engineered nucleic acid. Isolated nucleic acid molecules can be produced by standard techniques (e.g., polymerase chain reaction) and are known to one skilled in the art.

Pharmaceutical Compositions

As disclosed herein, are pharmaceutical compositions, comprising a vector encoding a one or more TALEN monomers, wherein the one or more TALEN monomers comprises from the N-terminus to the C-terminus, a first spacer sequence, a TALE DNA binding domain, a second spacer sequence, and a FokI nuclease catalytic domain fused to the C-terminus. In an aspect, the pharmaceutical compositions further comprise a pharmaceutically acceptable carrier. As used herein, the term "pharmaceutically acceptable carrier" refers to solvents, dispersion media, coatings, antibacterial, isotonic and absorption delaying agents, buffers, excipients, binders, lubricants, gels, surfactants that can be used as media for a pharmaceutically acceptable substance. The pharmaceutically acceptable carriers can be lipid-based or a polymer-based colloid. Examples of colloids include liposomes, hydrogels, microparticles, nanoparticles and micelles. The compositions can be formulated for administration by any of a variety of routes of administration, and can include one or more physiologically acceptable excipients, which can vary depending on the route of administration. Any of the nucleic acids and vectors described herein can be administered in the form of a pharmaceutical composition. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed. The compositions can also include additional agents (e.g., preservatives).

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Paternal administration can be in the form of a single bolus dose, or may be, for example, by a continuous pump. Topical administration includes ophthalmic and to mucous membranes including intranasal, vaginal and rectal delivery. Aerosol inhalation can also be used to deliver the TALENs or any of the nucleic acids, polypeptide sequences and vectors described herein. Pulmonary administration includes inhalation or insufflation of powders or aerosols, including by nebulizer; intratracheal, intranasal, epidermal and transdermal. Thus, compositions can be prepared for parenteral administration that includes dissolving or suspending the TALENs, nucleic acids, polypeptide sequences or vectors in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment. The compositions can also be formulated as powders, elixirs, suspensions, emulsions, solutions, syrups, aerosols, lotions, creams, ointments, gels, suppositories, sterile injectable solutions and sterile packaged powders.

The active ingredient can be nucleic acids or vectors described herein in combination with one or more pharmaceutically acceptable carriers. As used herein "pharmaceutically acceptable" means molecules and compositions that do not produce or lead to an untoward reaction (i.e., adverse, negative or allergic reaction) when administered to a subject as intended (i.e., as appropriate).

In an aspect, the nucleic acid sequences as disclosed herein can be delivered to a cell of the subject. Such action can be achieved, for example, by using polymeric, biodegradable microparticle or microcapsule delivery vehicle, sized to optimize phagocytosis by phagocytic cells (e.g., macrophages).

Methods of Treatment

The methods disclosed herein are useful for the treatment of a subject having a retroviral infection (e.g., HIV infection). The method is effective for targeting any HIV, (e.g., HIV-1, HIV-2, and any circulating recombinant form thereof). The method can also include the step of administering a therapeutic effective amount of a pair of engineered TALENs comprising from the N-terminus to the C-terminus, a first spacer sequence, a TALE DNA binding domain, a second spacer sequence, and a FokI nuclease catalytic domain fused to the C-terminus. The method can further include the step of identifying a subject (e.g., a human patient) who has an HIV infection and then providing to the subject a composition comprising a nucleic acid encoding a pair of TALENs. The subject can be identified using standard clinical tests known to those skilled in the art. Examples of tests for diagnosing HIV in a subject include immunoassays to detect the presence of HIV antibodies in the subject's serum. As described above, the therapeutically effective amount can be the amount of the composition administered to a subject that leads to a full resolution of the symptoms of the infection, a reduction in the severity of the symptoms of the infection, or a slowing of the progression of symptoms of the infection. The methods described herein can also include a monitoring step to optimize dosing and detect the onset of drug resistance. In some cases, a clinician can determine whether a subject has a latent HIV infection.

The methods can also include the step of determining the nucleic acid sequence of the specific HIV present in a subject's serum and then design the TALENs to comprise specific TALE DNA binding domain sequences. Accordingly, in an aspect, the present disclosure includes a method comprising a TALE DNA binding domain comprising a sequence that targets a sequence in the HIV infecting the subject. For example, one skilled in the art can determine the nucleic acid sequence of a subject's TAR region and then design one or more pairs of TALENs to be specific and complementary to the patient's sequences. Further, the method described herein, also includes TALENs engineered to comprise RVDs within the TAL repeats to specifically recognize and bind to a corresponding nucleotide within a target sequence. Thus, a TALE DNA binding domain can be formed or engineered by selecting a combination of TAL repeats containing the relevant RVDs to recognize a specific target sequence.

The compositions described herein can be administered as a prophylactic treatment (i.e., a subject at risk for having a retroviral infection, e.g., an HIV infection). Examples of a subject at risk for having an HIV infection include but are not limited to any sexually active individual engaging in unprotected sex (e.g., engaging in sexual activity without the use of a condom), having a sexually transmitted infection, an intravenous drug user, or using needles for piercing or tattooing that are not sterile. Subjects at risk for having an HIV infection can be, for example, an inmate in a correction setting or an individual that uses sexual activity for income or non-monetary items, or health care worker or first responder (i.e., an individual whose occupation brings him/her into contact with an HIV-infected individual or sample). The compositions described herein can also be administered to a pregnant or lactating woman having an HIV infection for the purpose of reducing the risk of transmitting HIV to the child. Since HIV can be transmitted transplacentally in utero, at the time of delivery or following delivery and through breast milk, the compositions described herein can be administered to a woman (e.g., mother) having an HIV infection prenatally, perinatally or postnatally encompassing the time duration of breast feeding, or any combination thereof. The compositions can also be administered to the child (e.g., infant) immediately following birth and at various intervals thereafter.

The compositions described herein can also be administered as a prophylactic treatment to suppress new infections in subjects having an HIV infection and/or currently undergoing HAART therapy and/or treatment with one or more anti-retroviral agents. In some instances, the subject has a latent HIV infection.

The compositions disclosed herein can also be co-administered with another therapeutic agent, for example, an anti-retroviral agent including any agents that are routinely used in HAART therapy. Examples of anti-retroviral agents include reverse transcriptase inhibitors (e.g., nucleoside/nucleotide reverse transcriptase inhibitors, such as zidovudine, emtricitibine, lamivudine and tenofivir; and non-nucleoside reverse transcriptase inhibitors (e.g., efavarenz, nevirapine, rilpivirine); protease inhibitors (e.g., tipiravir, darunavir, indinavir); entry inhibitors (e.g., maraviroc); fusion inhibitors (e.g., enfuviritide); or integrase inhibitors (e.g., raltegrivir, dolutegravir). Anti-retroviral agents can also include multi-class combination agents for example, combinations of emtricitabine, efavarenz, and tenofivir; combinations of emtricitabine; rilpivirine, and tenofivir; or combinations of elvitegravir, cobicistat, emtricitabine and tenofivir. Co-administration of two or more therapeutic agents refers to the administration of the agents at the same time, at different times such that the time period of their therapeutic effect overlaps, or by the same route. Administration can be simultaneous or sequential, including on different days or weeks.

The dosage to be administered depends on many factors including, for example, the route of administration, the formulation, the severity of the patient's illness/disease, previous treatments, the patient's size, weight, surface area, age, and gender, other drugs being administered, and the overall general health of the patient including the presence or absence of other diseases, disorders or illnesses. Dosage levels can be adjusted using standard empirical methods for optimization known by one skilled in the art. Administrations of the compositions described herein can be single or multiple (e.g., 2- or 3-, 4-, 6-, 8-, 10-, 20-, 50-, 100-, 150-, or more fold). Further, encapsulation of the compositions in a suitable delivery vehicle (e.g., polymeric microparticles or implantable devices) can improve the efficiency of delivery.

The therapeutically effective amount of the compositions described herein can include a single treatment or a series of treatments (i.e., multiple treatments or administered multiple times). Treatment duration using any of compositions disclosed herein can be any length of time, such as, for example, one day to as long as the life span of the subject (e.g., many years). For instance, the composition can be administered daily, weekly, monthly, yearly for a period of 5 years, ten years, or longer. The frequency of treatment can vary. For example, the compositions described herein can be administered once (or twice, three times, etc.) daily, weekly, monthly, or yearly for a period of 5 years, ten years, or longer.

In an aspect, the methods disclosed herein also include inactivating a retrovirus. The method can include the steps of inactivating a retrovirus in a mammalian cell. Further, the method can include exposing the cell to a composition comprising an isolated nucleic acid encoding a gene editing complex comprising a TALEN, wherein the TALEN comprises a TALE DNA binding domain wherein the TALE DNA binding domain provides sequence-specific binding to a predetermined nucleotide sequence to target a nucleic acid sequence in the retrovirus. The retrovirus can be a lentivirus including HIV, simian immunodeficiency virus, a feline immunodeficiency or a bovine immunodeficiency virus. The HIV can be HIV-1 or HIV-2. The mammalian cell can be any cell type infected by HIV, including, but not limited to CD4+ lymphocytes, macrophages, fibroblasts, monocytes, T lymphocytes, B lymphocytes, natural killer cells, dendritic cells such as Langerhans cells and follicular dendritic cells, hematopoietic stem cells, endothelial cells, brain microglial cells, and gastrointestinal epithelial cells (e.g., gut-associated lymphoid cell). These cell types also include cell types that make up latent HIV reservoirs or the latently infected cell. The exposing step above can occur in vivo (i.e., administration of the compounds directly to the subject) or ex vivo. For exposing the cell to any of the compositions described herein in an ex vivo situation, a cell or a plurality of cells or a tissue explant is removed from the subject having an infection (e.g., HIV) and placed in culture. Next, the cells in culture are contacted with a composition comprising isolated nucleic acid encoding a gene editing complex comprising a TALEN, wherein the TALEN comprises a TALE DNA binding domain wherein the TALE DNA binding domain provides sequence-specific binding to a predetermined nucleotide sequence to target a nucleic acid sequence in the retrovirus.

In an aspect, a cell or a plurality of cells are removed from a subject having an infection (e.g., HIV), exposed to any of the compositions described herein in an ex vivo situation, and then returned to the subject via dialysis, re-infusion or re-implantation of the cells into the subject, generally, after selection for cells which have incorporated any of the TALENs described herein. A cell or plurality of cells can also be removed via a dialysis system and transferred to a culture. Once the cells are placed in culture, they can be exposed to any of the compositions described herein (e.g., composition comprising isolated nucleic acid encoding a gene editing complex comprising one or more TALENs, wherein the one or more TALEN comprises a TALE DNA binding domain wherein the TALE DNA binding domain provides sequence-specific binding to a predetermined nucleotide sequence to target a nucleic acid sequence in the retrovirus), and then returned to the subject through the dialysis system.

In an aspect, the HIV comprises integrated proviral DNA. Proviral DNA means a virus genome that is integrated into the DNA of the host cell. The HIV genome is RNA, thus, proviral as used herein can also refer to a DNA version of the genome. It is during this stage that the virus is likely replicating. The method described above can comprise a gene editing system that introduces one or more indel mutations in the proviral DNA, wherein the indel mutation inactivates viral replication or viral gene expression. The term "indel" as used herein refers to an insertion or the deletion of bases in the DNA of an organism. The indel can lead to a frame shift wherein the encoded protein or RNA is longer or shorter than the wild-type gene product. In an aspect, the indel is a deletion, an insertion and/or a point mutation. The indel can be located in regulatory sequences or structural gene sequences resulting in defective production of HIV. The size of a deletion or insertion, for example, can be from a single nucleotide base pair to about 10,000 base pairs. In an aspect, the deletion or insertion comprises about one to twenty base pairs of proviral DNA. The indel can also be a point mutation (i.e., the replacement of a single nucleotide with another nucleotide).

In an aspect, the method of inactivating a retrovirus in a mammalian cell can also comprise an isolated nucleic acid encoding the gene editing system that further comprises a nuclear localization signal.

In an aspect, the method of inactivating a retrovirus in a mammalian cell can also comprise an isolated nucleic acid encoding the gene editing system that is operably linked to an expression vector. The expression vector can be, for example, an adenoviral vector.

In an aspect, the method of inactivating a retrovirus in a mammalian cell can also comprise a composition comprising a pharmaceutically acceptable carrier.

The present disclosure also includes methods of reducing risk of HIV infection in a subject at risk for an HIV infection, the method comprising administering to the subject a therapeutically effective amount of a pharmaceutical composition comprising a vector encoding a TALEN, wherein the TALEN comprises from the N-terminus to the C-terminus, a first spacer sequence, a TALE DNA-binding domain, a second spacer sequence, and a FokI nuclease catalytic domain fused to the C-terminus.

The present disclosure also features methods of treating a subject having an HIV infection, the method comprising: determining the nucleic acid sequence of the HIV; and administering to the subject a pharmaceutical composition comprising a nucleic acid sequence encoding a TALEN, wherein the TALEN comprises from the N-terminus to the C-terminus, a first spacer, a TALE DNA binding domain, a second spacer sequence, and a FokI nuclease catalytic domain fused to the C-terminus. In an aspect, the TALEN is optimized for expression in a human cell. Further, the method includes a TALE DNA binding domain comprising a protein sequence specific for binding to a target nucleotide sequence. In an aspect, the target sequence comprises a sequence within the transactivation response element. The target sequence can have the sequence of SEQ ID NOs: 1, 4-7. In an aspect, the TALE DNA binding domain sequences comprise a sequence having at least 80%, 85%, 90%, 95%, or 99% identify to the sequence of SEQ ID NOs: 1, 4-7.

Kits

The kits described herein can include any combination of the compositions described above and suitable instructions (e.g., written and/or provided as audio-, visual-, or audio-visual material). In an aspect, the kit comprises a predetermined amount of a composition comprising an isolated nucleic acid sequence comprising a sequence encoding a TALEN, wherein the TALEN comprises a TALE DNA binding domain providing a sequence-specific binding to a target nucleotide sequence in HIV. The kit can further comprise one or more of the following: instructions, sterile fluid, syringes, a sterile container, delivery devices, and buffers or other control reagents.

The kits can also include one or more anti-retroviral agents, including, for example, a reverse transcriptase inhibitor, or a protease inhibitor. These agents can be packaged together in the same container as the compositions described herein and above or they can be packaged separately. The one or more anti-retroviral agents can be combined with compositions described herein before use or administered separately.

EXAMPLES

Example 1: Selection of TALEN Target Sites and Design of TALENs

TALENs can be designed and used to target a conserved sequence in the transactivation response element (TAR) of the HIV-1 proviral DNA. For this, the following methods were used.

Bioinformatics Analysis of HIV-1 Genome. HIV-1 subtype B DNA sequences for the complete genome and the 5'LTR, 5'LTR(R), 5'LTR(U3), 5'LTR(U5), GAGPOL, RRE, RT, TAR, ENV regions of the genome were downloaded from the Los Alamos HIV Sequence Database (www.hiv.lanl.gov/) and converted into comma-delimited files using a custom script. The files were then loaded, aligned with ClustalK (Sievers et al. (2011) Mol Syst Biol, 7:539), and positional conservation was calculated with Microsoft Excel. Regions with stretches of bases that held the most positional conservation were selected as target regions. The strongest target region, encompassing TAR, was obtained from analysis of the 226 sequences encompassing the HIVB5LTR. The 5' HT-TALEN and 5' NS-TALEN binding sites encompass nucleotide positions 459-478 (HIV-1 HXB2 accession number K03455), while the 3' HT-TALEN binding site encompasses nucleotide positions 499-515 (HIV-1 HXB2 accession number K03455).

Design and Construction of TALEN plasmids. A FASTA file for the HIV-1 Sub-type B 5'LTR HXB2 DNA sequence (accession number K03455) was input into the ZiFiT Webtool (http://zifit.partners.org/ZiFiT/) to retrieve a schematic for building TALEN constructs using the REAL Assembly Kit (Miller et al. (2011) Nat Biotechnol 29: 143-148).

Plasmid DNA constructs for the HT-TALENs were built using the Joung Lab REAL Assembly TALEN kit (Add-Gene), following the REAL Assembly method as described (Miller et al. (2011) Nat Biotechnol 29: 143-148). Identity of correct HT-TALEN DNA clones was confirmed by sequence analysis (Beckman Coulter Genomics).

Using the methods described above, a conserved target region of the HIV-1 proviral DNA genome was identified that was less likely to produce TALEN resistant HIV strains. HIV-1 subtype B DNA sequences from the Los Alamos HIV sequence database were aligned by region and nucleotide conservation was determined. Of the alignments performed, the HIV long terminal repeat (LTR) region (226 DNA sequences) comprised conserved nucleotide stretches (Sievers et al. (2011) Mol Syst Biol, 7: 539). These regions encompassed the trans-activation response element (TAR) of the 5' LTR (FIG. 1). See, also FIG. 15, for a listing of useful constructs and sequences.

BLAST analysis searching for these sequences in the GRCh38 assembly showed no identical sequences in the human genome. The most similar positions were a matched stretch of 17/20 nucleotides to an intergenic region in chromosome 13 (NC_000013) for the 5' HT-TALEN, and the next closest were regions with stretches of 14/20 nucleotides, two intergenic and one in the coding region of the Glypican 6 gene. For the 3' HT-TALEN, the most similar match was a stretch of 16/20 nucleotides, matched to an intergenic region in chromosome 11 (NC_000011) and no other stretches with more than 13/22 nucleotides were observed.

Most positions targeted by these TALENs were highly conserved (FIG. 1D) and both sites were also conserved in laboratory strain NL4-3, but not in all subtype B strains. Mutations that disrupt the TAR stem, in different regions have been shown to abolish viral production, reflecting the high level of sequence conservation (Das et al. (2007) J Virol 81: 7742-7748). The conserved TAR region was selected because this target would be less likely to mutate and produce viable TALEN-resistant escape mutants. The TALE binding sites in the 5' LTR were nearly identical in the 3' LTRs, permitting damage to each site with the same set of TALENs.

Even though a bioinformatic analysis was carried out to select highly conserved sites as TALEN targets; no sites in HIV-1 are completely conserved. For example, positions such as the $6^{th}$, $9^{th}$ and $20^{th}$ positions in the 5' HT-TALEN binding site contain residues that are 67-95% conserved, whereas the remainder of the TALEN binding site is >98% conserved (FIG. 1D). HIV with escape mutations can produce resistance to ARV drugs, which can limit the potential use of GEEN for targeting integrated proviral DNAs derived from reverse transcription. The TALEN gene editing technology, thus has the advantage over other GEEN technologies in that a NS repeat variable di-residue (RVD) variant encodes degenerate nucleotide recognition. This can be used to design custom TALENs that encode predicted degenerate positions (Boch et al. (2009) Science 326: 1509-1512); and Scholze and Boch (2010) Virulence 1: 428-432). Thus, TALENs can be engineered to tolerate predicted escape mutants based on nucleotide conservation.

Target Selection. Recent reviews discussing the use of a GEEN strategy to target the HIV proviral DNA have suggested targeting the coding region of HIV (Stone et al. (2013) Curr Opin HIV AIDS 8: 217-223; and Weber et al. (2013) Mol Ther J Am Soc Gene Ther 21: 1819-1820). In considering the possibility of escape mutations, we and others performed bioinformatic analyses to select the region of HIV-1 with the highest conserved nucleotide stretches (Qu et al. (2013) Nucleic Acids Res 41: 7771-7782; and Ebina et al. (2013) Sci Rep 3:2510). The region with the highest conservation encompassed the TAR region in the LTR (Qu et al. (2013) Nucleic Acids Res 41: 7771-7782; and Ebina et al. (2013) Sci Rep 3:2510). One concern with targeting this region was that it might not be accessible due to histone and DNA modification, and DNA packaging. TALEN-mediated editing of the TAR site; however, was observed. Improved TALEN delivery systems may increase TALEN editing efficiency in individual cells, resulting in both TALEN target sites in the 5' and 3' HIV proviral LTRs being cleaved. This in turn could result in the deletion of the majority of the ~9.6 kb HIV-1 proviral DNA. Large deletions of up to 18 kb have previously been observed with TALENs targeting two local genomic sites (Beumer et al. (2013) G3 Bethesda Md. 3: 1717-1725; Ma et al. (2014) Biotechnol Lett 36(3):471-9; and Ma et al. (2013) PloS One 8(5): e65259). An assay for this deletion was not carried out because the HIV-1 proviral insertion site in HeLa/LAV cells is currently unknown.

While the TALEN target in the TAR region is not known to be methylated, two CpG islands flanking the transcription start site are close and could affect TALEN binding and cleavage of latent HIV-1 proviral DNA (Kauder et al. (2009) Epigenetic regulation of HIV-1 latency by cytosine methylation. PLoS Pathog 5:e1000495). One of the advantages of using TALENs is that new tools are rapidly becoming available. If methylation is an issue, TALEN variants have been developed to bind methylated cytosines. These TALENs™ contain RVD regions mutated from "NX" to "N", which allows recognition of 5-methylated cytosine (Valton et al. (2012) J Biol Chem 287: 38427-38432).

Types of DNA Repair. The repair of genome editing technologies is thought to occur by low fidelity non-homologous end joining (NHEJ). In editing of the HIV-1 LTR, small insertions, short deletions, and deletions with insertions were observed. Since DNA Pol μ or λ, are part of this pathway, these polymerases can generate inserts in a template independent manner (Aza et al. (2013) Nucleic Acids Res 41: 253-263; and Martin et al. (2013) Nucleic Acids Res 41:9105-9116), thus may be responsible for the short inserts we observed (2-6 bp) in three clones; this is an editing signature for classical NHEJ (Dueva and Iliakis G (2013) Transl Cancer Res 2:163-177). Short deletions of 6-13 bp were observed and are likely due to the exonuclease activity of either Artemis in the classical NHEJ pathway (C-NHEJ), or exonuclease 1 in the alternative NHEJ pathway (A-NHEJ). Overexpression of exonuclease 1 was recently shown to increase TALEN-induced mutation efficiency 30%, suggesting that both NHEJ pathways may be involved in editing of TALEN induced double strand breaks. Cells using only the A-NHEJ pathway (generated by XRCC4 or Ku80 nulls that block the C-NHEJ pathway) typically yield small deletions of 4-25 bp, similar to that we observed with our TALEN pairs (Guirouilh-Barbat et al. (2007) Proc Natl Acad Sci USA 104: 20902-20907; and Grabarz et al. (2012) Am J Cancer Res 2: 249-268). The clones having an insertion with deletion are typically observed in other TALEN studies and may represent multiple editing events (e.g., Beumer et al. (2013) G3 Bethesda Md. 3:1717-1725; and Liu et al. (2012) J Genet Genomics 36:209-215). It is noteworthy that improper repair of the targeted TAR region, such as introduction of inserts, deletions, and indels, could negatively affect multiple steps of the viral replication cycle. The 5' untranslated region (UTR) of the 5'LTR is packed with a variety of RNA regulatory elements with functions that are dependent on proper folding. Insertions and deletions, depending on size, could exert severe effects on the ability of the transcribed RNA to achieve necessary secondary structures crucial for transcription.

Example 2: TALEN Pairs Cleave the HIV-1 Target DNA In Vitro

The NS-TALENs described above were used to test whether the wild type and different triple mutant target templates containing predicted escape mutations could be cleaved. In addition to the 5' TALEN that is designed to recognize the canonical 5' TALE binding site, another 5' TALEN construct was designed with NS-TALE monomers positioned to recognize the three less conserved positions in the 5' TALE binding site. This approach was tested for addressing the degenerate positions (FIG. 2A). To differentiate the TALEN pairs described herein, based on the 5' TALEN recognition sequence, the pair containing the canonical 5' TALEN was designated as HT-TALENS and the other pair containing the 5' NS-TALEN was designated as the NS-TALENs.

In vitro Transcription/translation of HT- and NS-TALENs and Cleavage Reactions. The target template DNA to be used in cleavage reactions was synthesized by PCR (HotStarTaq Plus Master Mix, Qiagen) using forward primer U3BamH175F (CAGCTGGATCCTGATTGGCAG; SEQ ID NO: 15) and reverse primer GagSal1804Rev (GGGTGCGAGAGCGTCGACGACGG; SEQ ID NO: 16) to amplify a 747 bp product from plai.2 proviral DNA (NIH AIDS Reagent Program, catalog no. 2532). To generate a mutant target template, overlap extension of two PCR products was performed, followed by a PCR using a forward primer (U3BamHI75F) and a reverse primer (GagSal1804Rev). PCR product 1 (520 bp) was generated using plai.2 (a full-length HIV proviral DNA) as a template, U3BamHIFor and a randomized reverse primer (Random 5'siteRev: CAGGCTCNNATCTGGTCNNNCNA; SEQ ID NO: 17). PCR product 2 (355 bp) was generated using plai.2 as a template, a randomized forward primer (Random 5'siteFor: CTCTNGNNNGACCAGATNNGAGC; SEQ ID NO: 18), and GagSal804Rev. The generated insert was ligated into Sal/BamHI digested pGEX6P3 (GE Healthcare Sciences). In vitro transcription/translation reactions were performed using the TnT® Quick Coupled Transcription/Translation System (Promega). Reactions comprising 500 ng of each HT-TALEN pair DNA plasmid, 20 μL of TNT® T7 Quick Master Mix, 0.5 μL Methionine (1 mM), 500 ng target template DNA, and 2.5 μL H$_2$O. The reactions were incubated at 30° C. for 2 hours. Aliquots were analyzed by Western blot and to the remaining reaction (20 μL) was added to 100 μL of cleavage reaction buffer (Bedell et al. (2012) Nature, 491:114-118). Available: www.ncbi.nlm.nih.gov/pubmed/23000899_; and (Mahfouz et al. (2011) PNAS 108: 2623-2628). The samples were then incubated for an additional 3 hours at 30° C. followed by Rnase A (20 μg) treatment for 15 minutes. DNA from the samples was purified (Wizard® SV Gel and PCR Clean-Up System) and ethanol precipitated to concentrate the samples. Concentrated samples were then run on a 1% 1×TAE agarose gel to visualize the target template and cleaved product DNAs. ImageJ software was used to quantify bands to determine cleavage efficiency (Schneider et al (2012) Nat Methods 9: 671-675). These experiments were repeated 2-3 times.

Figure 2B:
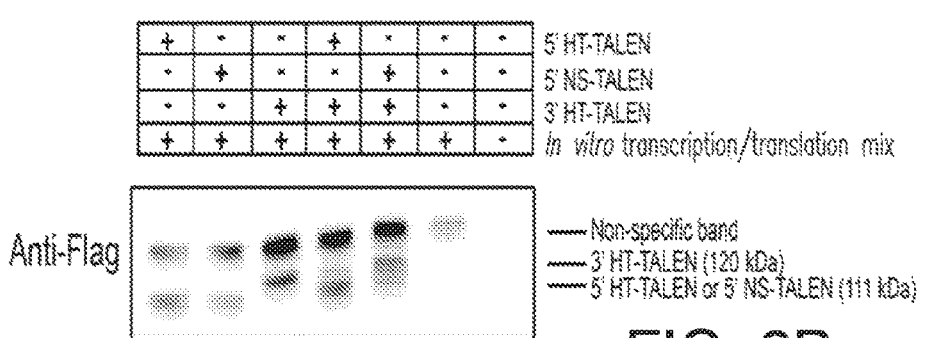
Figure 3A:
Figure 3B:
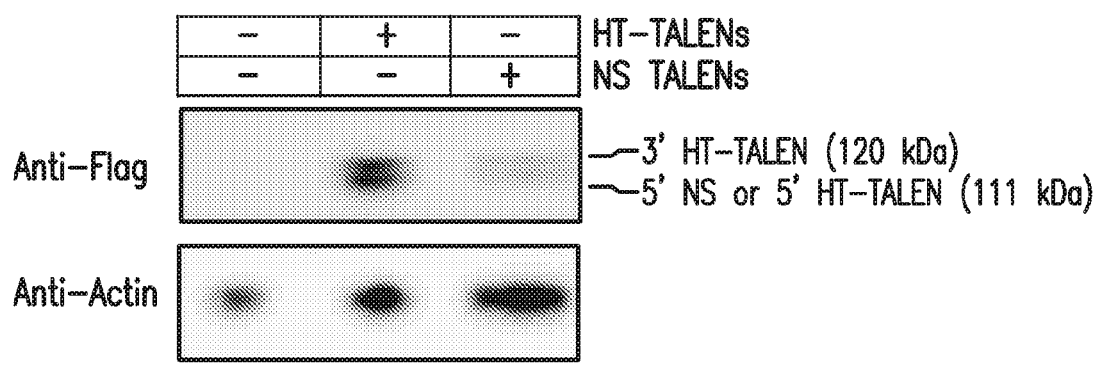
Figure 3C:
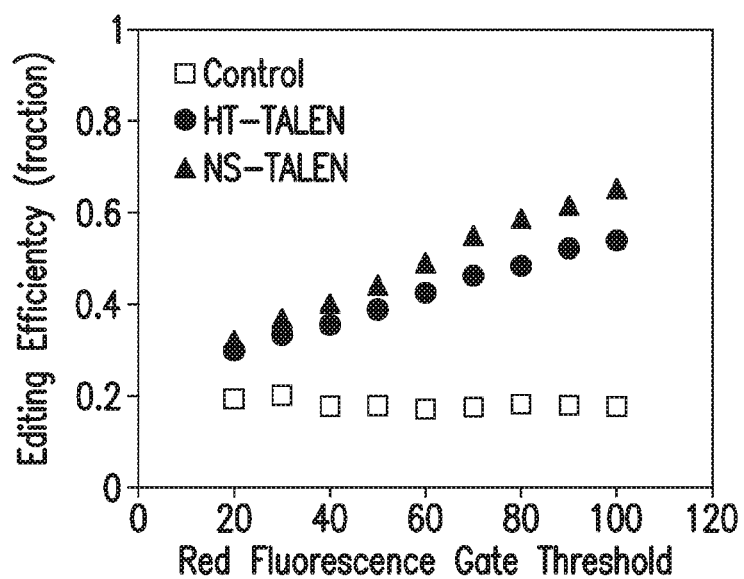

The results show that using the REAL assembly kit, recombinant plasmids that encoded the 5' and 3' HT-TALEN and the 5' NS-TALEN proteins recognizing and cleaving the cognate target LTR sequences were constructed (Reyon et al. (2012) Curr Protoc Mol Biol Ed Frederick M Ausubel A1 Chapter 12: Unit 12.15). The architecture of the repeats and their recognition sequence are shown in FIG. 2A. Expression of the Flag epitope-tagged TALENs was verified by in vitro transcription/translation reactions and Western blot analysis with a Flag antibody (FIGS. 2B, 3). TALEN protein expression of the expected molecular mass was observed in samples containing the TALEN plasmids, but not in extracts lacking the plasmids. The 3' HT-TALEN was expressed as a 120 kDa protein while the 5' HT-TALEN and the 5' NS-TALEN were expressed as 111 kDa proteins. No smaller sized bands were observed, indicating that these proteins are not degraded in vitro (FIG. 3). A higher molecular mass non-specific immunoreactive band was observed in all in vitro transcription/translation samples regardless of TALEN plasmid presence.

Figure 2C:
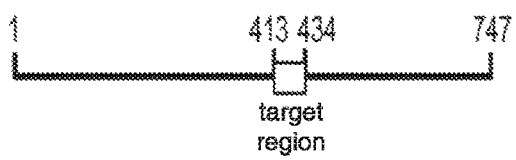
Figure 2D:
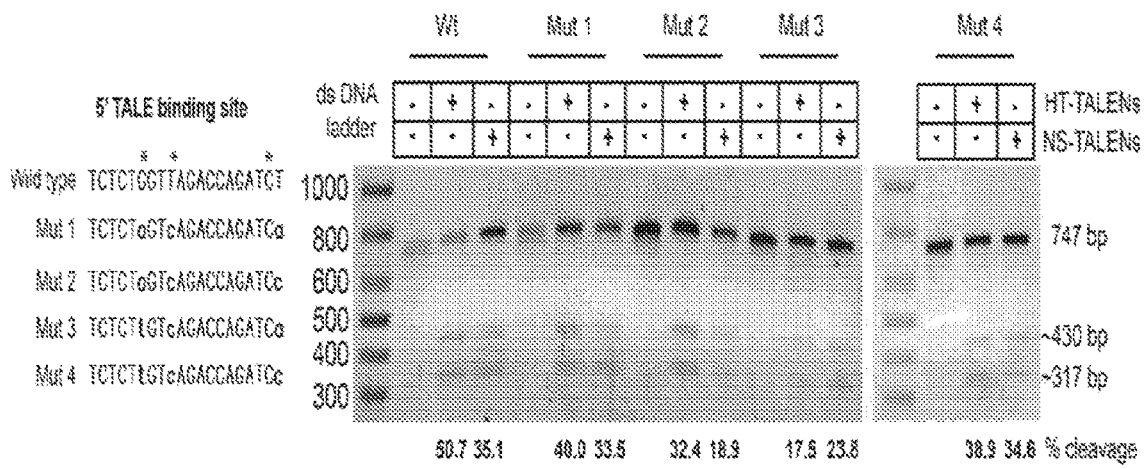

The endonuclease activity of the TALEN pairs was tested on a 747 base pair HIV-1 proviral DNA PCR product fragment comprising the TALEN target sites, as well as HIV-1 proviral DNA PCR product fragments comprising predicted mutations at the $6^{th}$, $9^{th}$ and $20^{th}$ positions of the 5' TALE binding site (FIG. 2C). This DNA was used as a target template to detect TALEN endonuclease activity in cleavage reactions comprising the HT-TALEN or the NS-TALEN pair proteins produced by in vitro transcription/translation reactions. The HIV-1 DNA target template was cleaved into fragments of the expected sizes when incubated with either TALEN pair, but not when incubated with control extracts lacking the TALEN proteins. The results show that both TALEN protein pairs cleave the HIV-1 DNA fragment specifically at the target cleavage site. A cleavage efficiency of approximately 42% for both TALEN pairs was observed.

TALEN DNA target templates comprising mutations in the 5' TALE binding site were also tested. Four mutant templates with substitutions at three sites ($6^{th}$, $9^{th}$ and $20^{th}$) in the 5' TALE binding site were analyzed. The mutant DNA target templates encoded the second most common nucleotide for each position. Both the HT-TALEN and NS-TALEN pairs were shown to cleave all mutant sequences in vitro with similar efficiencies (FIG. 2C). Cleavage of the mutant templates by the HT-TALENs can be explained by some degenerate recognition by some monomers in HT-TALENs or by the fact that the template and TALEN expression can be higher than that of cells. These results demonstrate that the NS-TALENs can cleave wild type and mutant HIV-1 DNA templates.

Example 3: TALEN Pairs Damage Target DNA in Live Cells

Next, the TALEN protein pairs were assessed for their ability to cleave the TALEN target site in living cultured cells. The following methods were used.

Cell Culture and Transfection. HeLa-tat-III/LTR/d1EGFP cells (Parent et al. (2005) J Biol Chem 280: 448-457) were maintained in Dulbecco's modified Eagle's medium (DMEM) supplemented with 10% Fetal Bovine Serum (Fisher Scientific), 1% penicillin and streptomycin (Sigma) and 1 mg/mL G418 (Fisher Scientific). HeLa/LAV cells and pEAK Rapid cells (derived from HEK293 cells, Edge Biosystems) were maintained in Dulbecco's modified Eagle's medium (DMEM) supplemented with 10% Fetal Bovine Serum (Fisher Scientific), and 1% penicillin and streptomycin (Sigma). Transient transfections of both HeLa-tat-II/LTR/d1EGFP and HeLa/LAV cells was performed using the Trans-IT HeLa-MONSTER transfection kit (Mirus). Transient transfection of pEAK Rapid cells was performed using the Trans-IT 2020 transfection kit (Mirus). Cells were harvested 48 hours post-transfection.

Flow Cytometry. Cytotoxicity was determined for transiently transfected HeLa/LAV (pRSET.mCherry expression vector, HT-TALEN pair, NS-TALEN pair) samples in addition to control samples. Samples were harvested for Annexin V staining 72 hours post-transfection (FITC Annexin V Apoptosis Detection Kit, BD). Each sample-type was performed in triplicate. Cells were trypsinized (0.25% Trypsin), resuspended in 1 mL of phosphate buffered saline (PBS), and then centrifuged at 156×g for 5 minutes. Samples were then gently resuspended in 1 mL HEPES buffer and centrifuged at 156×g. for 5 minutes. Samples were gently resuspended in 50 µL HEPES buffer and 3 µL Annexin V was added to each sample, excluding the negative controls. Samples were incubated on ice for 20 minutes in the dark. Samples were centrifuged at 156×g for 5 minutes, followed by a 1 mL ice cold HEPES buffer wash. Samples were resuspended in a 4% paraformaldehyde solution and incubated at room temperature in the dark for 3 hours. Samples were centrifuged at 156×g for 5 minutes. Samples were then washed in 1 mL PBS and then gently resuspended in 300 µL PBS to prepare them for flow analysis.

TALEN damage efficiency was determined by number of mCherry/Green Fluorescent Protein (GFP) vs. mCherry-only positive cells recorded 72 hours post-transfection in transiently transfected HeLa-tat-III/LTR/d1EGFP cells (pRSET.mCherry expression vector, co-transfected HT-TALEN pair and pRSET.mCherry expression vector, co-transfected NS-TALEN pair and pRSET.mCherry expression vector). Each sample-type was performed in triplicate. Wells were trypsinized (0.25% Trypsin), resuspended in 1 mL PBS, and then centrifuged at 156×g for 5 minutes. Samples were fixed in 4% paraformaldehyde, washed once with PBS and then resuspended in 500 µL PBS prior to flow analysis.

Flow cytometry data was acquired using a FACSCalibur Flow cytometer (Becton Dickinson). The blue laser (488 nm) was used for detecting GFP while the red laser (635 nm) was used for mCherry. 10,000 events were acquired for each sample. Flow cytometry analysis was performed using FlowJo (Tree Star) software. Non-fluorescent samples were used to determine thresholds. mCherry-positive samples and GFP-positive samples were used to set gating thresholds. Dose-response curves were generated by counting cells using different mCherry thresholds. Statistical analysis for cytotoxicity experiments was performed using ANOVA and statistical differences in slopes from TALEN dose-response curves were determined with a one-tailed t-test.

Figure 4A:
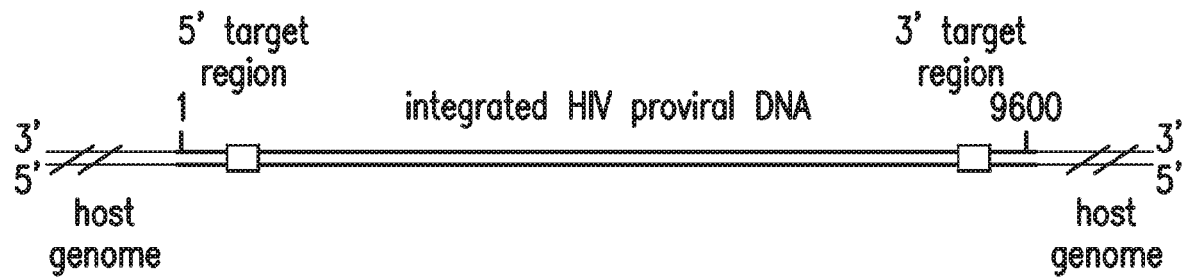
FIGS. 4A-4E show TALEN targeting integrated complete HIV-1 proviral DNA in cell culture. A. Schematic diagram of the complete HIV-1 proviral DNA to be targeted by the HT-TALEN pair or the NS-TALEN pair. The target region is found in both the 5' and 3'LTRs. The host genome is indicated in grey. B. Western blot analysis of HeLa/LAV cells transfected with a HT-TALEN plasmid pair or the NS-TALEN pair. The blot was probed with anti-Flag and anti-Actin as a loading control. C. Bar graph showing quantitation of flow cytometry analysis of cytotoxicity. Transiently transfected HeLa/LAV cells were analyzed by flow cytometry (n=3) to identify Annexin V positive cells. Standard deviations are indicated by error bars with no statistical significance (NS) $p>0.05$ in cytotoxicity between the control and the TALEN pairs. D. Sequences (SEQ ID NOs: 45-55 corresponding to WT through HL2H-04) of clones containing mutated target regions represented as in FIG. 3. E. A schematic of the 5' target region of wild type plai.2 HIV-1 proviral DNA (SEQ ID NO: 45) and the mutated plai.2 HIV-1 proviral DNA (SEQ ID NO: 48). The mutated proviral DNA was designed based on the sequence from HeLa/LAV clone HL-16 (FIG. 4D). The Gag coding region (containing capsid) is indicated. Western blot analysis of cell lysates harvested from pEAK Rapid cells transfected with mutant or wild type plai.2 proviral DNA. The blot was probed with anti-Capsid qingto detect Gag production and anti-Actin as a loading control.
Figure 4B:
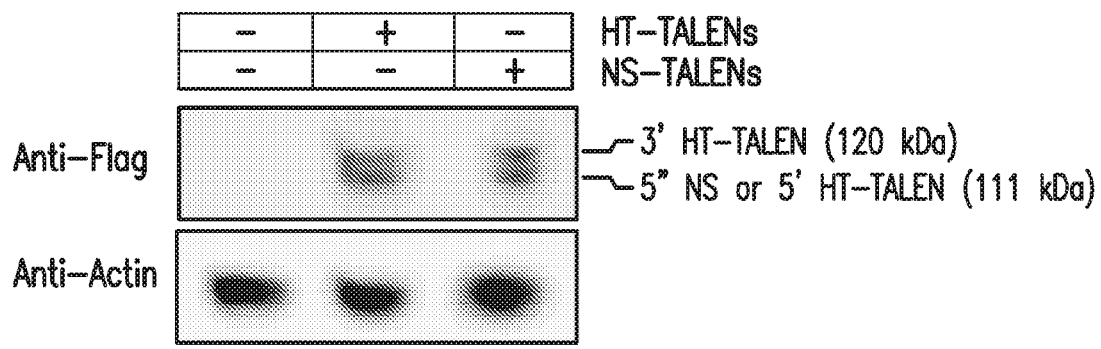
Figure 5:
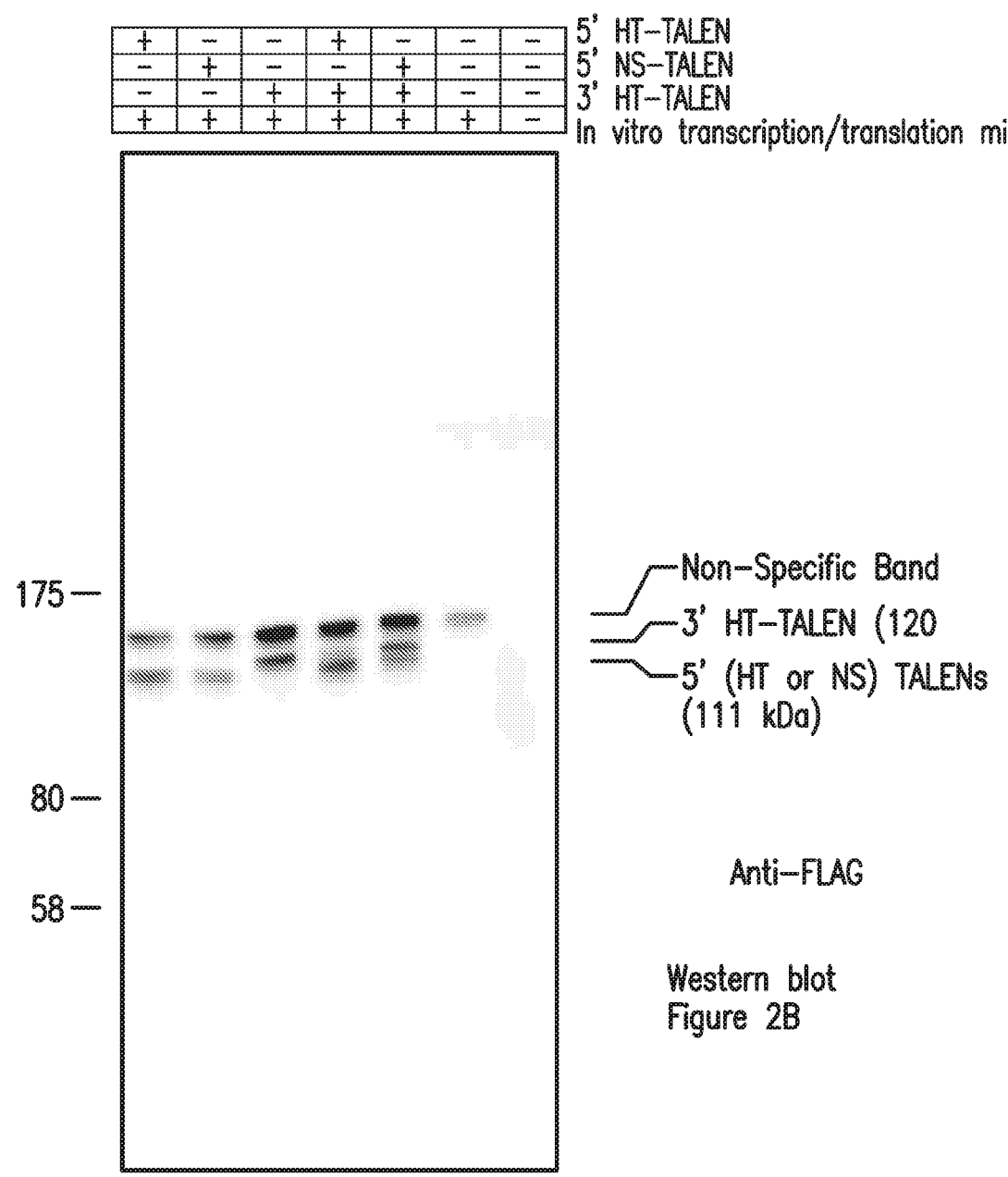
FIG. 5 shows the expression of TALENs in vitro. The Western blot from in vitro transcription/translation reactions in FIG. 2B, showing the full gel.

The results show that HeLa-tat-III/LTR/d1EGFP cells stably express a construct comprising the HIV-1 5' LTR (comprising the HT-TALEN target site) fused upstream of a d1EGFP coding region (FIG. 4A) (Parent et al. (2005) J Biol Chem 280: 448-457). GFP is constitutively expressed in these cells and expression is driven by the HIV-1 5' LTR. These cells were transiently co-transfected with constructs for each TALEN pair and cell lysates were analyzed by Western blot. Expression of the ectopic proteins of the expected molecular masses was observed; however, the NS-TALENs exhibited lower expression (FIGS. 4B, 5).

Figure 6:
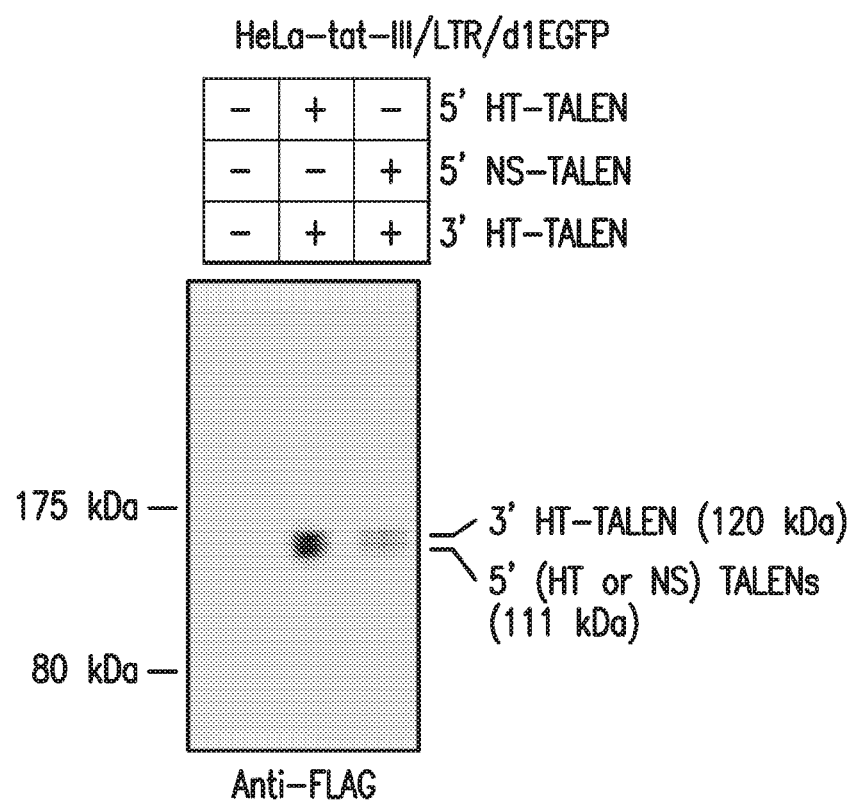
FIG. 6 illustrates the expression of TALENs in HeLa-tat-III/LTR/d1EGFP cells. The Western blot of extracts from transiently transfected HeLa-tat-III/LTR/d1EGFP cells in FIG. 3B, showing the full gel. The blot was probed with anti-Flag.
Figure 7:
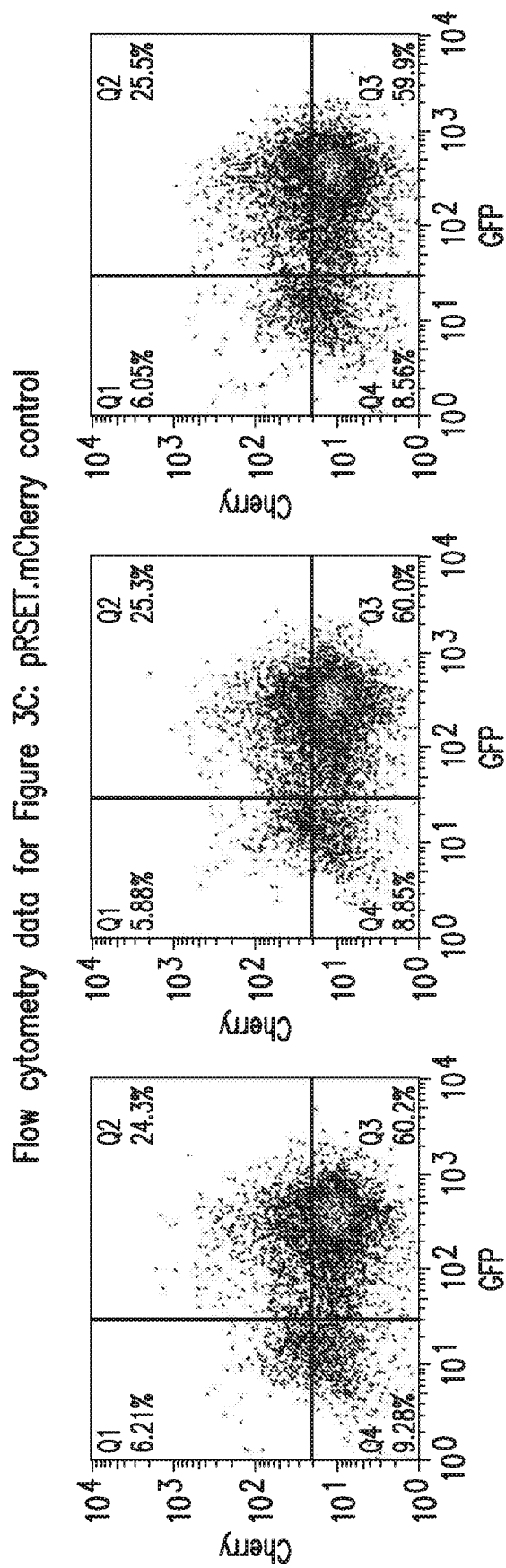
FIG. 7 shows the results of flow cytometry analysis of pRSET.mCherry transfected Hela-tat-III/LTR/d1EGFP cells. Flow cytometry analysis of GFP reporter expression analyzed to create FIG. 3C. HeLa-tat-III/LTR/d1EGFP samples were analyzed for GFP and mCherry expression. Cells comprising the functional HIV-1 LTR fused d1EGFP reporter expressed GFP (n=3).
Figure 8:
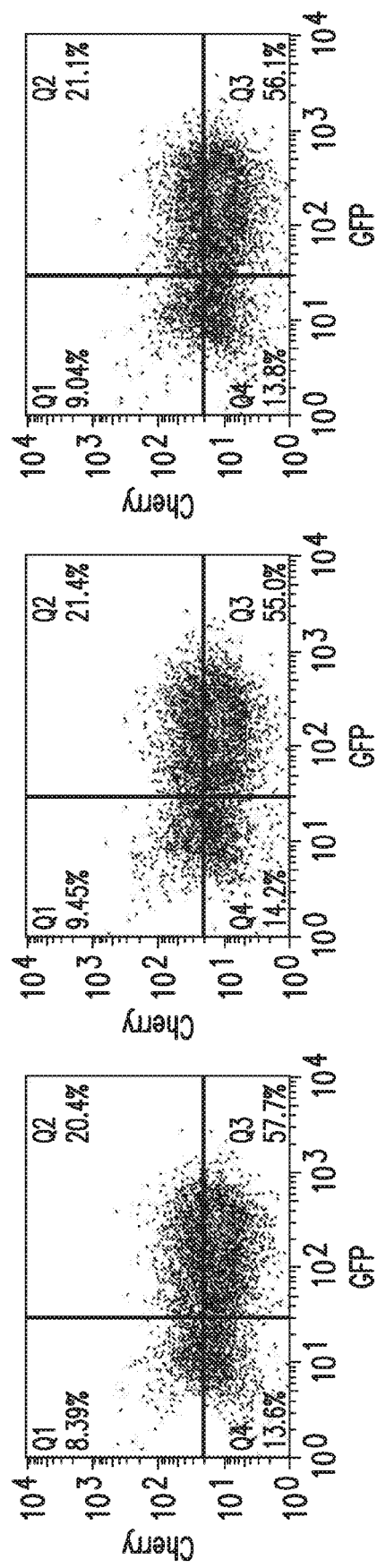
FIG. 8 shows the results of flow analysis of HT-TALEN transfected HeLa-tat-III/LTR/d1 EGFP cells. Flow cytometry analysis of GFP reporter expression analyzed to create FIG. 3C. Transiently transfected HeLa-tat-III/LTR/d1EGFP samples were analyzed for GFP and mCherry expression. Cells with mCherry comprised the transfected mCherry plasmid and the HT-TALEN pair. Cells comprising the functional HIV-1 LTR fused to the d1EGFP reporter expressed GFP (n=3).

The next set of experiments were carried out to test whether the TALEN pairs damaged the HIV-1 TAR element in cells using loss of GFP expression as a read out detected by flow cytometry. In addition to non-transfected controls, HeLa-tat-III/LTR/d1EGFP cells were either transfected with pRSET.mCherry alone or pRSET.mCherry co-transfected with constructs for each TALEN pair (FIGS. 6-8). Transfection of either of the TALEN pairs can result in damage to the HIV-1 LTR, thereby reducing GFP expression. The transfected cell population comprising pRSET.mCherry was analyzed using flow cytometry to determine the levels of GFP expression 72 hours post-transfection. A significant difference in the mCherry cell populations was dependent on the presence of either TALEN pair compared to the pRSET.mCherry control. The cleavage efficiency is estimated at approximately 30% for both HT-TALEN and NS-TALEN pairs.

Figure 4C:
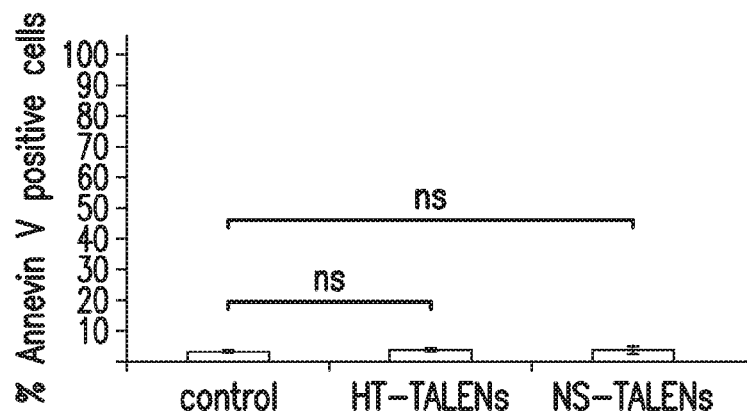

The effect of TALENs on GFP reporter expression was examined to determine if it was dose-dependent by analyzing the flow cytometry data varying the gating threshold for red fluorescence. The HT-TALEN and NS-TALEN pairs both showed a generally linear dose dependent increase in editing efficiency that was significantly different than control cells (FIG. 4C; $p<10^{-6}$). Although it appeared that the NS-TALENs might have a higher editing efficiency, this finding was not statistically significant. Notably, these plots did not show saturation of editing efficiency, suggesting that higher TALEN expression can increase editing of the proviral DNA. An editing efficiency of 55-60% was observed for the cells expressing the highest levels of TALEN pairs.

Figures 4D, 4E:
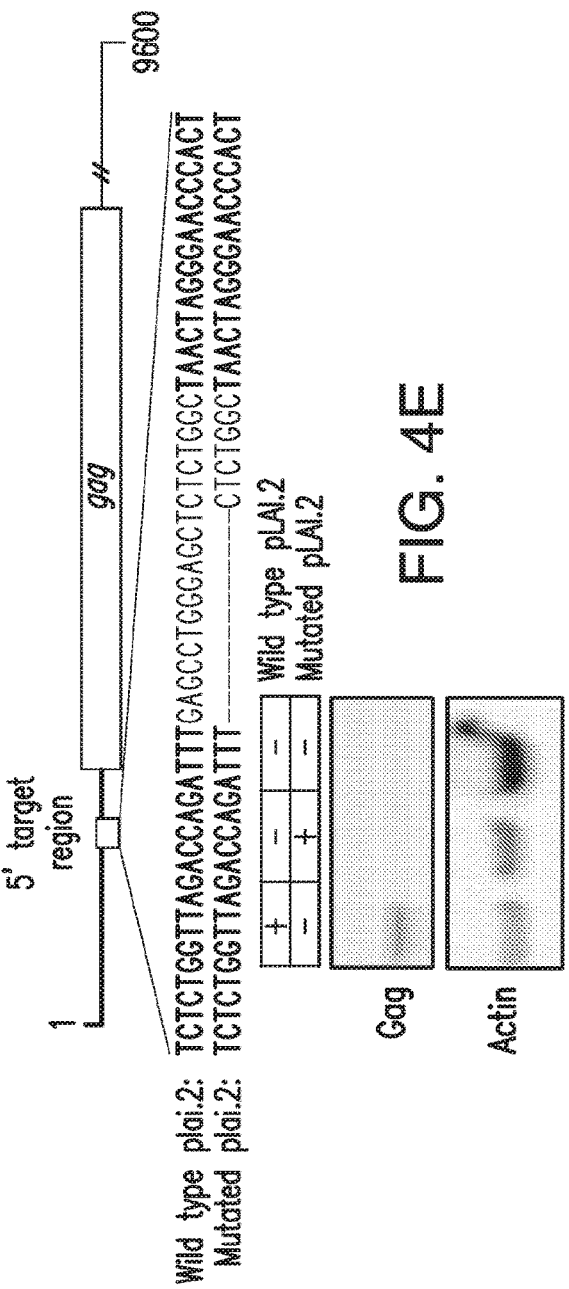

To determine if the targeted region in the LTR comprised mutations, the TALEN target region was amplified from DNA isolated from transfected and control non-transfected cells by PCR using primers flanking the target site. Resulting PCR products were subcloned into the pBluescript II SK (–) plasmid and several clones were sequenced. Clones having both deletions and insertions, as well as clones with deletions were observed. Deletion sizes ranged from 6 to 22 bp in the target region (FIG. 4D). Insertion sizes ranged from 1 to 13 bp in the target region. No mutations were observed in 12 sequenced clones of cells transfected with the control pRSET.mCherry vector, while 8 of 29 had mutations for the HT-TALENs, and 2 of 23 were observed for NS-TALENs. These data support the conclusion that HT-TALENs and NS-TALENs can cleave the HIV-1 target DNA site in live cells.

Example 4: TALEN Pairs Damage the Integrated Complete HIV-1 Genome

Experiments were carried out to determine if the TALEN pairs can edit the full-length integrated HIV-1 proviral DNA in HIV-infected cells. For these experiments, the following methods were used.

Protein Analysis. Cells were washed and lysed in PBS. One-half of the cell lysate was used for genomic DNA purification (see below), while the other half was combined with 2×SDS protein buffer for protein analysis. The protein samples were freeze/thawed three times, boiled at 95° C. for 5 minutes, then loaded onto a 4-12% Bis tris protein gel (Nupage, Life Technologies). Proteins in the gel were transferred onto a PVDF membrane (Immobilon-P, Millipore), blocked with 5% milk/PBS, and then probed with select primary antibodies. The primary antibodies used comprised: mouse anti-actin, mouse anti-Flag-HRP conjugate (SLBD 9930, Sigma Aldrich), mouse anti-capsid, and rabbit anti-Flag (A1113, Santa Cruz). Secondary antibodies used comprised: goat anti-rabbit HRP and rabbit anti-mouse HRP conjugates (GE Life Sciences formerly Amersham Biosciences). Proteins were visualized using chemiluminescence (Super Signal West Pico Chemiluminescent Substrate, Thermo Scientific) on an Automated Biospectrum Imaging System (UVP). All Western analyses were repeated 2-3 times.

Genomic DNA Analysis. Genomic DNA was purified from cell lysates using a PureLink Genomic DNA kit (Life Technologies). PCRs (HotStar High Fidelity Polymerase kit, Qiagen) were performed on the purified genomic DNA to produce products for cloning and for T7 assays. For cloning purposes, primers pBSNY5For (GG-CATGCTCGAGCTCAGATGCTGCATAT; SEQ ID NO: 19) and pBSNY5Rev (CATGCCTCTAGAAGTGGGTTCCCTAGC; SEQ ID NO: 20) were used with the genomic DNA to produce a 114 bp insert for the XhoI/XbaI digested pBlueScript 11 SK(−) vector. Clones produced were sequenced with M13Reverse primer.

Construction of Mutated HIV Proviral Plasmid. To engineer a mutant HIV-1 proviral DNA based on a sequence identified as a genomic edit induced by TALEN cleavage, overlap extension of two PCR products was performed, followed by a PCR using a forward primer (pLAI.28For) and a reverse primer (pLAI.2888Rev). PCR product 1 (7-553) was generated using plai.2 (a full-length HIV proviral DNA) as a template, pLAI.28For and a mutagenic reverse primer (pLai.2Mut1Rev) comprising a deletion of 13 nucleotides (positions 531 to 543). PCR product 2 (517-888) was generated using plai.2 as a template, a mutagenic forward primer (pLai.2Mut1For), and plai.2888Rev. The generated insert was ligated into XbaI/ClaI digested plai.2. The mutated region contained within the full length HIV proviral DNA plasmid was confirmed via DNA sequencing.

Figure 9:
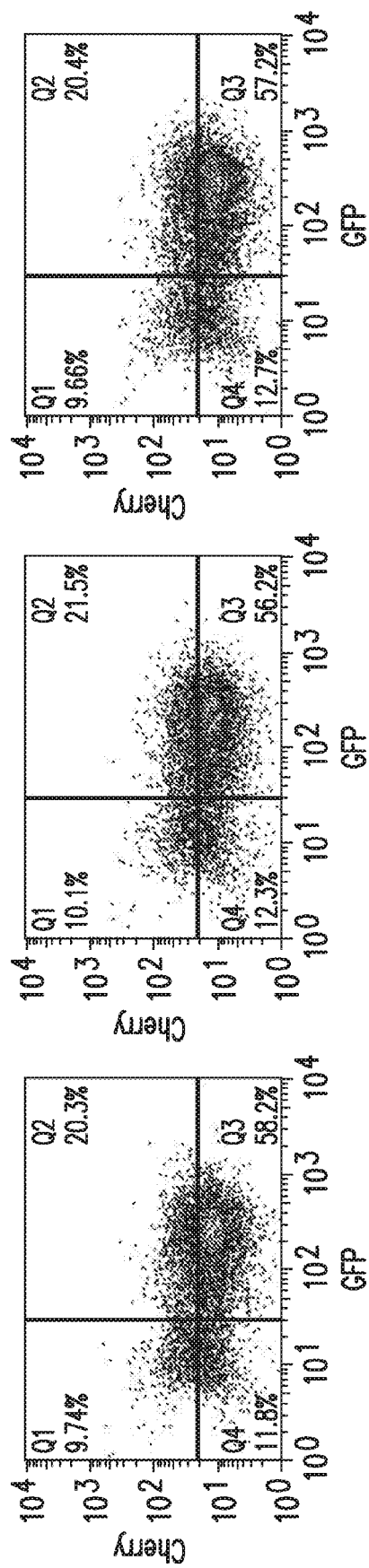
FIG. 9 shows the results of flow analysis of NS-TALEN transfected HeLa-tat-III/LTR/d1EGFP cells. Flow cytometry analysis of GFP reporter expression analyzed to 30 create FIG. 3C. Transiently transfected HeLa-tat-III/LTR/d1EGFP samples were analyzed for GFP and mCherry expression. Cells with mCherry comprised the transfected mCherry plasmid and the NS-TALEN pair. Cells comprising the functional HIV-1 LTR fused to the d1EGFP reporter expressed GFP (n=3).
Figure 10:
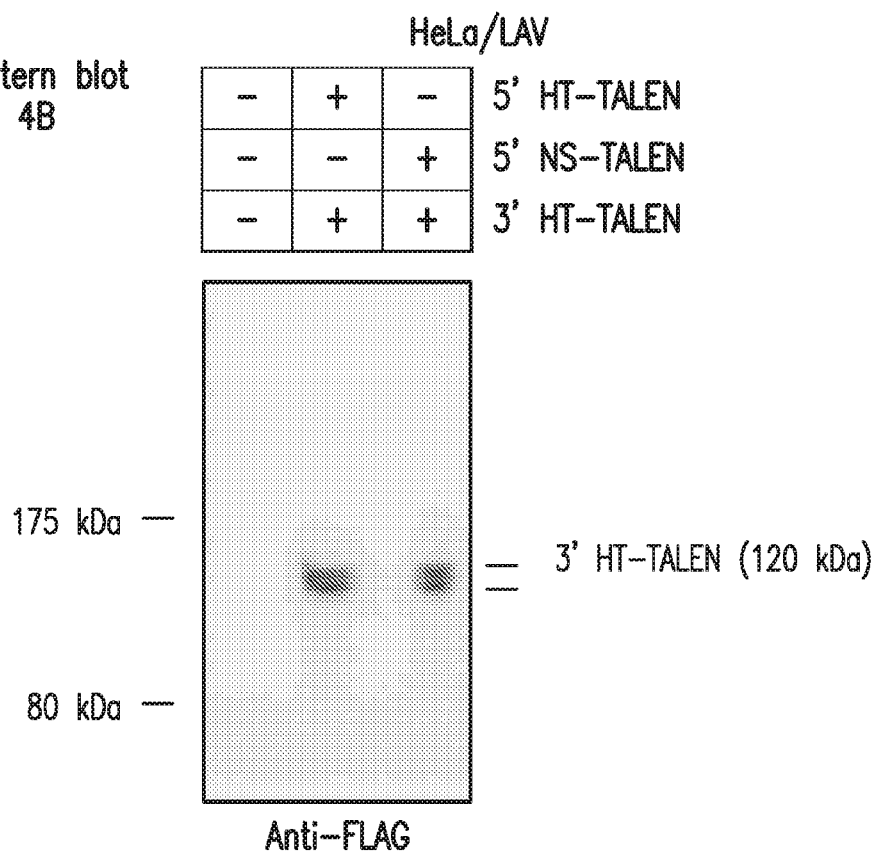
FIG. 10 illustrates the expression of TALENs in HeLa/LAV cells. The Western blot from HeLa/LAV cells transfected with either the HT-TALEN pair or NS-TALEN pair in FIG. 4B showing the full gel. The blot was probes with anti-Flag.

The results show that HeLa/LAV cells harbor integrated HIV-1 proviral DNA (FIG. 9A) and produce active virus (FIG. 9A) (Berg et al. (1991) J Virol Methods 34:173-180). HeLa/LAV cells were separately and transiently transfected with either TALEN construct pair and harvested 48 hours post-transfection. Expression of both ectopic TALEN protein pairs was apparent in harvested cell extracts (FIGS. 9B, 10).

Transfection of TALEN constructs can result in cytotoxicity. Therefore, transfection experiments were carried out to assess cytotoxicity measured by Annexin V staining (FIGS. 9C, 11-13). Triplicate samples analyzed by flow cytometry revealed no significant difference in the number of Annexin V positive cells ($p<0.01$) when transfected TALENs were compared to control. These results demonstrate the TALENs are not significantly cytotoxic to these cells.

Specific editing of the integrated HIV proviral DNA was assessed by amplifying the TALEN target sites from purified genomic DNA, sub-cloning the resulting PCR product into the pBluescript II SK (−) vector, and DNA sequencing of individual clones. Eleven of the 50 sequenced clones comprised mutations. Indels were detected with some clones containing both insertions and deletions. Deletion sizes ranged from 6 to 33 bp while insertion sizes ranged from 1 to 6 bp (FIG. 9D). This editing profile is typical of that observed in other studies using TALENs, e.g., Chen et al. (2013) Nucleic Acids Res 41: 2769-2778; Frank et al. (2013) BMC Genomics 14: 773; and Gaj et al. (2012) Nat Methods 9:805-807. These results demonstrate that cleavage by the TALEN pairs induced mutagenesis of the integrated HIV-1 proviral DNA genome. These findings demonstrate that the TALEN pairs can edit integrated HIV-1 proviral DNA in live cells.

Figure 11:
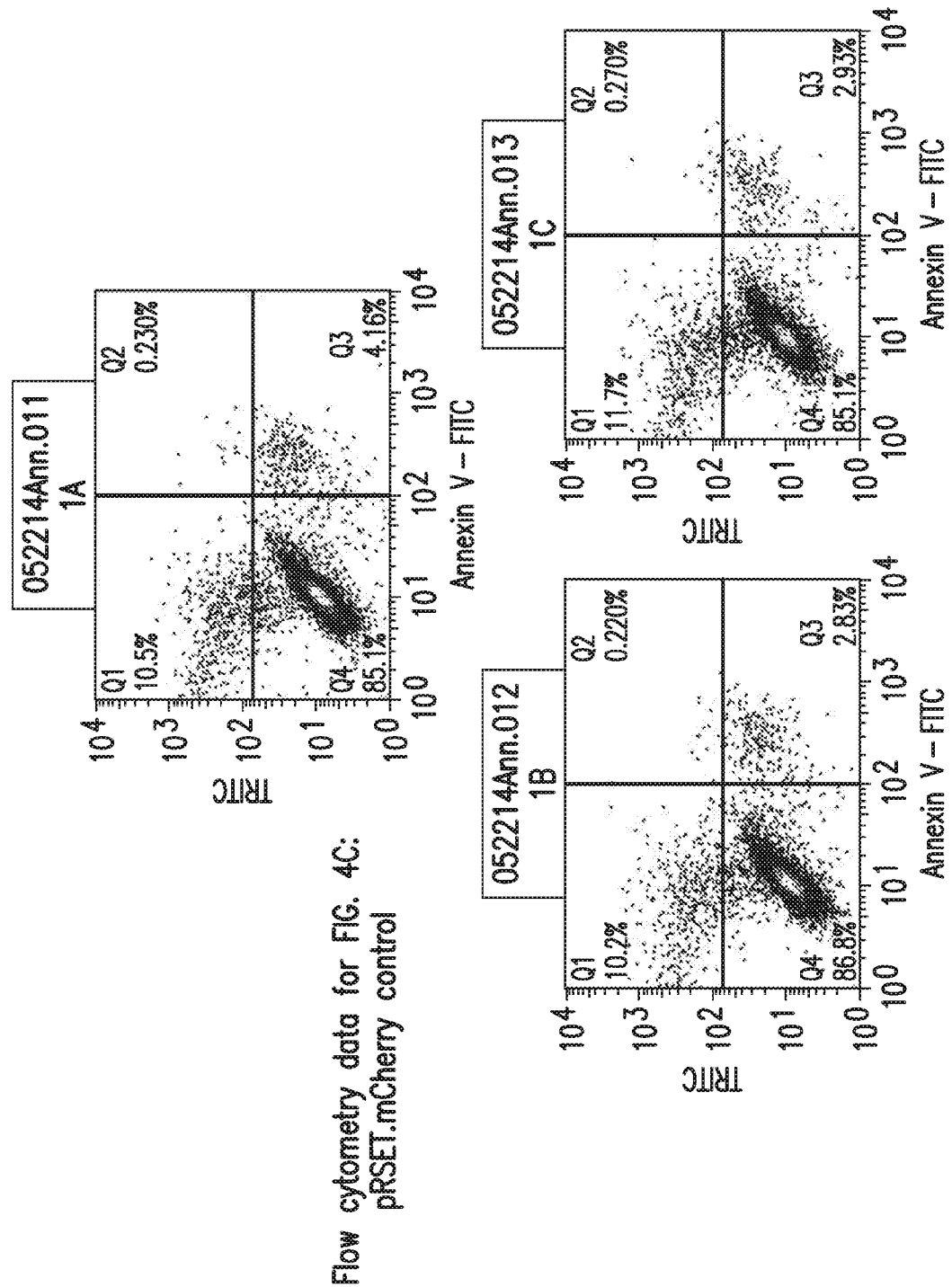
FIG. 11 shows the results of flow cytometry analysis of pRSET.mCherry transfected HeLa/LAV cells following Annexin V staining. Flow cytometry analysis of HeLa/LAV cells transiently transfected with pRSET.mcherry and immunostained with an Annexin V antibody (GFP channel) to create FIG. 4C (n=3).
Figure 12:
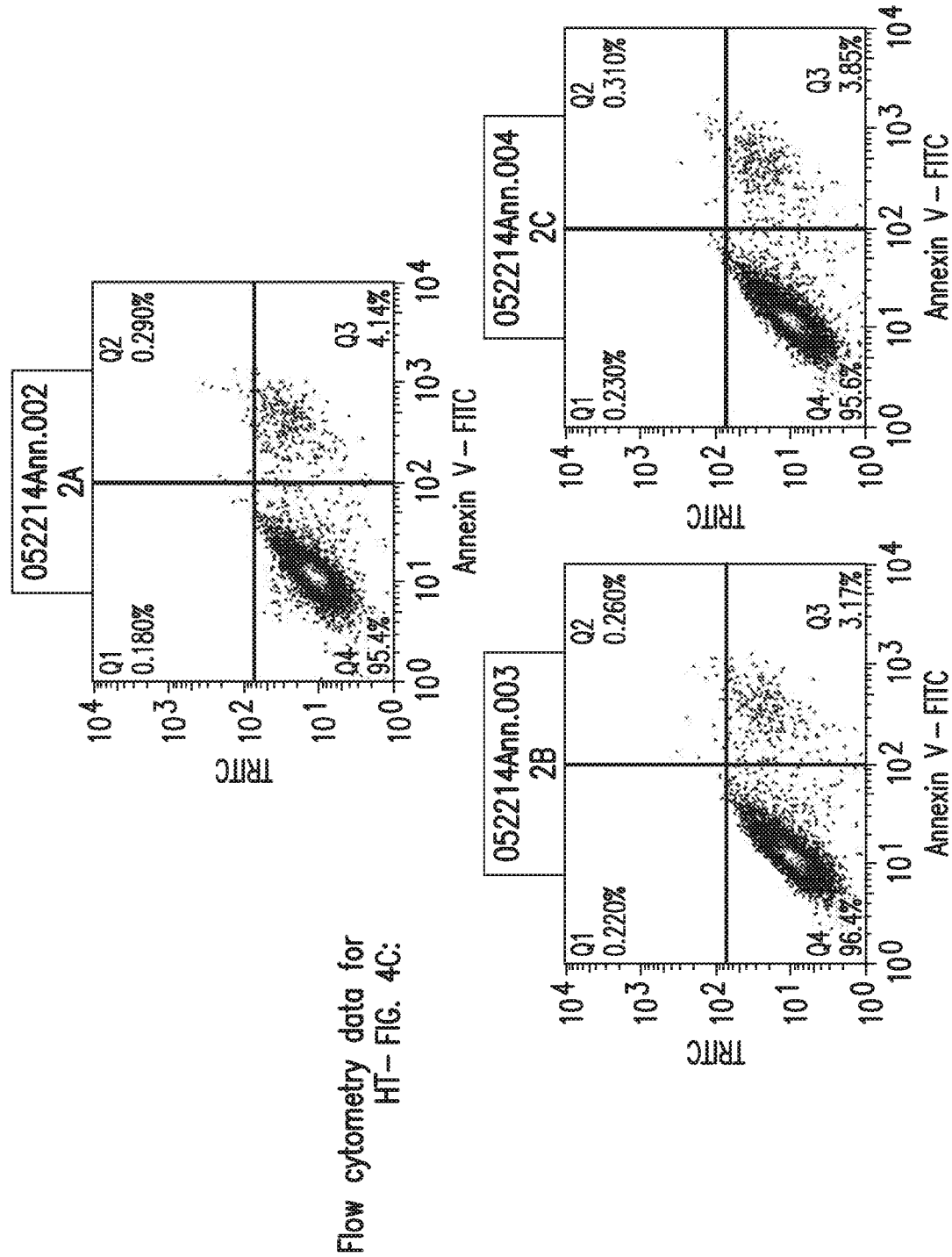
FIG. 12 shows the results of flow cytometry analysis of HT-TALEN transfected HeLa/LAV cells following Annexin V staining. Flow cytometry analysis of HeLa/LAV cells transiently transfected with HT-TALENs and immunostained with an Annexin V antibody (GFP channel) to create FIG. 4C (n=3).
Figure 13:
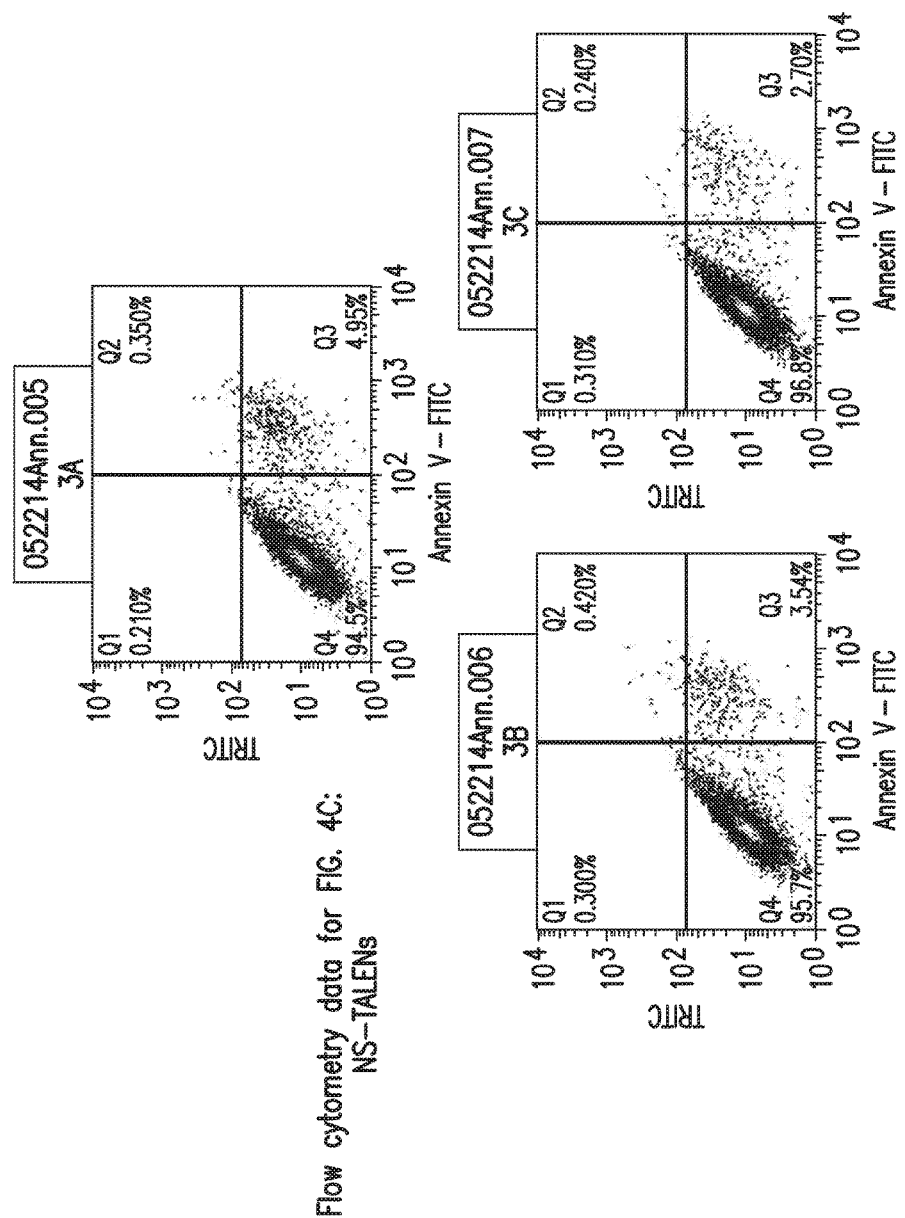
FIG. 13 shows the results of flow cytometry analysis of NS-TALEN transfected HeLa/LAV cells following Annexin V staining. Flow cytometry analysis of HeLa/LAV cells transiently transfected with NS-TALENs and immunostained with an Annexin V antibody (GFP channel) to create FIG. 4C (n=3).
Figure 14:
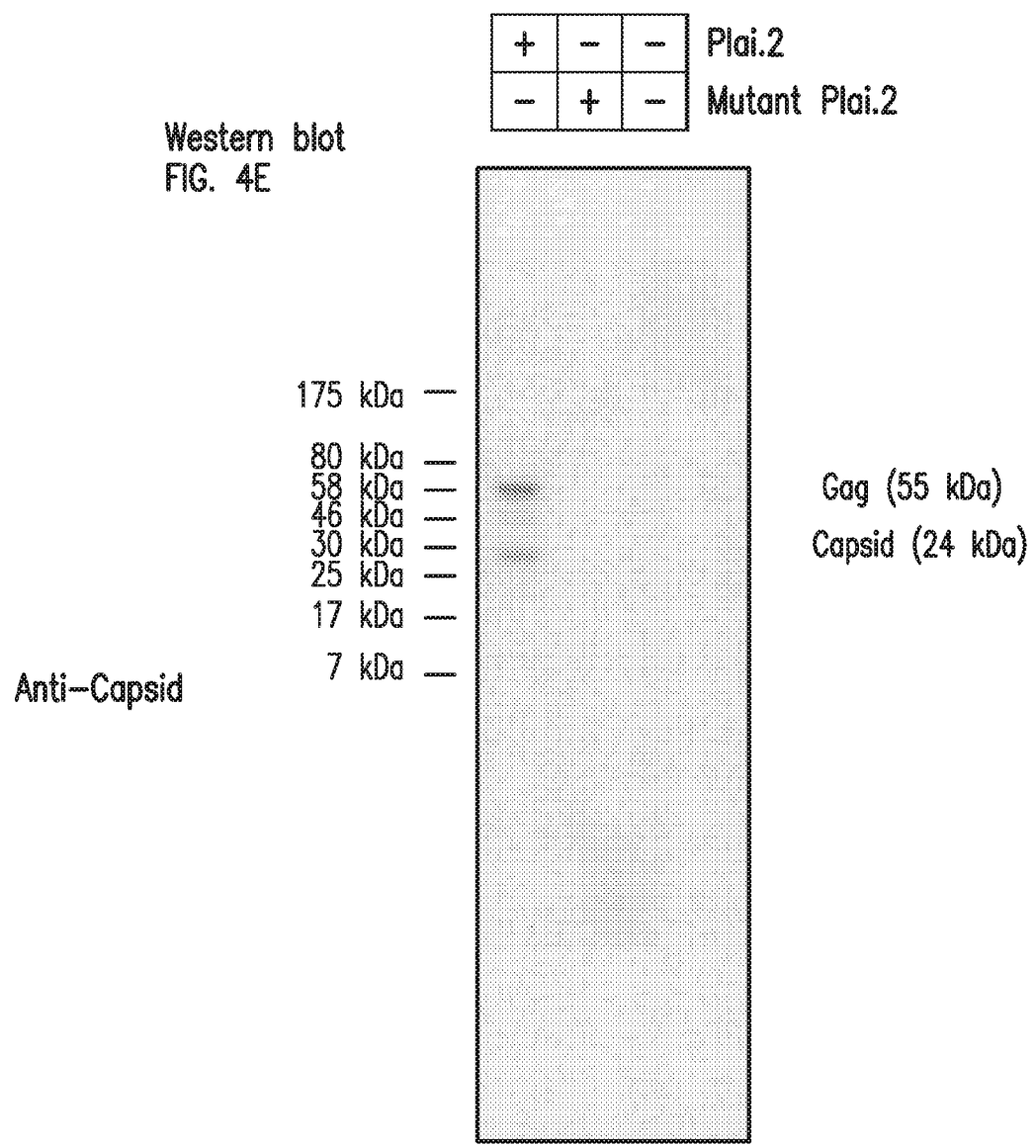
FIG. 14 illustrates the expression of Gag and Actin in transiently transfected pEAK Rapid cells. The western blot from pEAK Rapid cells transfected with either mutant or wild type plai.2 proviral DNA in FIG. 4E, showing the full gel. The blot was probed with anti-Capsid to detect Gag production.

The target region in the LTR of HIV-1 is conserved and mutations in this region abolish viral production. To assess if mutations resulting from TALEN cleavage of HIV-1 proviral DNA abrogate or limit virus production, a sequence from one of the clones (FIG. 9D; HL16) was subcloned into a construct for expression of the full-length HIV-1 proviral DNA. HL16 was selected because it has an indel that deletes the critical stem-loop region of TAR, typical for the majority of other indels observed in these studies. Constructs for the wild type plai.2 and mutant plai.2 HIV-1 full-length proviral DNA were transfected into pEAK Rapid cells (FIG. 9E). As an indicator of viral fitness, expression of a key structural virus poly-protein, Gag, was examined. Western blot analysis of cell lysates was performed and a Gag band was observed in samples from cells transfected with wild type plai.2 HIV proviral DNA, but not in cells transfected with the mutant HIV-1 plai.2 proviral DNA (FIGS. 9E, 11). Western blot analysis with a loading control antibody to Actin shows similar Actin levels in each sample. These results indicate that at least one of the indels introduced by the TALEN pairs can markedly reduce expression of a key viral poly-protein that is important for virion production.

---

What is claimed is:

1. An engineered transcription activator like effector nuclease (TALEN) comprising from the N-terminus to the C-terminus, a first spacer sequence, a TALE DNA binding domain, a second spacer sequence, and a FokI nuclease catalytic domain fused to the C-terminus, wherein the TALE DNA binding domain comprises TAL repeats, wherein the TALE DNA binding domain is specific for binding to a nucleic acid sequence having at least 90% identity to a sequence of SEQ ID NOs: 4, 5, 6 or 7; and wherein the TALE DNA binding domain comprises a C-terminal truncated TAL repeat.

2. The TALEN of claim 1, wherein the TALE DNA binding domain comprises 20 TAL repeats.

3. The TALEN of claim 1, wherein TAL repeats each comprise a repeat-variable-di-residue.

4. The TALEN of claim 3, wherein the repeat-variable-di-residue of at least one TAL repeat is NS.

5. The TALEN of claim 1, wherein the FokI nuclease catalytic domain has the sequence of SEQ ID NO: 13 or SEQ ID NO: 14.

6. An isolated polynucleotide sequence encoding the engineered TALEN of claim 1.

7. A pharmaceutical composition comprising a vector comprising a nucleic acid capable of encoding the engineered TALEN of claim 1.

8. A method of cleaving a target nucleic acid sequence in a genome of a mammalian cell, the method comprising introducing into the cell at least one pair of mRNA encoding a pair of TALENs of claim 1, wherein each member of the pair of TALENs comprises a different FokI nuclease catalytic domain.

9. The method of claim 8, wherein two pairs of mRNA encoding four TALENs are introduced into the cell.

10. The TALEN of claim 1, wherein TALE DNA binding domain is specific for binding to a nucleic acid sequence having at least 95% identity to a sequence of SEQ ID NOs: 4, 5, 6 or 7.

11. The TALEN of claim 1, wherein TALE DNA binding domain is specific for binding to a nucleic acid sequence having the sequence of SEQ ID NOs: 4, 5, 6 or 7.

* * * * *